(12) United States Patent
Watson et al.

(10) Patent No.: US 8,198,024 B2
(45) Date of Patent: Jun. 12, 2012

(54) GENE EXPRESSION MARKERS FOR COLORECTAL CANCER PROGNOSIS

(75) Inventors: Drew Watson, Los Altos, CA (US); Soonmyung Paik, Pittsburgh, PA (US); Wayne Cowens, Tiburon, CA (US); Joffre B. Baker, Montara, CA (US); Kim Clark, Sunnyvale, CA (US); James Hackett, San Jose, CA (US)

(73) Assignees: Genomic Health, Inc., Redwood City, CA (US); NSABP Foundation, Inc., Pittsburgh, PA (US)

( * ) Notice: Subject to any disclaimer, the term of this patent is extended or adjusted under 35 U.S.C. 154(b) by 0 days.

(21) Appl. No.: 13/009,733

(22) Filed: Jan. 19, 2011

(65) Prior Publication Data

US 2011/0111421 A1 May 12, 2011

Related U.S. Application Data

(62) Division of application No. 12/696,934, filed on Jan. 29, 2010, which is a division of application No. 11/653,102, filed on Jan. 11, 2007, now Pat. No. 7,695,913.

(60) Provisional application No. 60/758,392, filed on Jan. 11, 2006, provisional application No. 60/800,277, filed on May 12, 2006, provisional application No. 60/810,077, filed on May 31, 2006.

(51) Int. Cl.
*C12Q 1/68* (2006.01)

(52) U.S. Cl. .................................. 435/6.1; 435/6.12

(58) Field of Classification Search ........................ None
See application file for complete search history.

(56) References Cited

U.S. PATENT DOCUMENTS

| | | | |
|---|---|---|---|
| 6,692,916 B2 | 2/2004 | Bevilacqua et al. | |
| 6,960,439 B2 | 11/2005 | Bevilacqua et al. | |
| 6,964,850 B2 | 11/2005 | Bevilacqua et al. | |
| 7,767,391 B2 | 8/2010 | Scott et al. | |
| 2001/0044414 A1 | 11/2001 | Clark et al. | |
| 2002/0150922 A1 | 10/2002 | Stolk et al. | |
| 2002/0172987 A1 | 11/2002 | Terstappen et al. | |
| 2003/0077568 A1 | 4/2003 | Gish et al. | |
| 2003/0109690 A1 | 6/2003 | Ruben et al. | |
| 2003/0148314 A1 | 8/2003 | Berger et al. | |
| 2003/0148410 A1* | 8/2003 | Berger et al. | 435/7.23 |
| 2003/0166064 A1 | 9/2003 | King et al. | |
| 2003/0198970 A1 | 10/2003 | Roberts | |
| 2003/0219760 A1 | 11/2003 | Gordon et al. | |
| 2003/0225526 A1 | 12/2003 | Golub et al. | |
| 2004/0053317 A1 | 3/2004 | Glinskii et al. | |
| 2005/0014165 A1 | 1/2005 | Lee et al. | |
| 2006/0195269 A1 | 8/2006 | Yeatman et al. | |
| 2006/0211036 A1 | 9/2006 | Chou et al. | |
| 2007/0105133 A1 | 5/2007 | Clarke et al. | |
| 2007/0166704 A1 | 7/2007 | Huang et al. | |
| 2009/0258795 A1 | 10/2009 | Cowens et al. | |
| 2009/0305277 A1 | 12/2009 | Baker | |
| 2010/0285980 A1 | 11/2010 | Shak | |
| 2010/0291573 A1 | 11/2010 | Cowens | |

FOREIGN PATENT DOCUMENTS

| | | |
|---|---|---|
| EP | 1522594 | 4/2005 |
| EP | 1 274 865 B1 | 2/2007 |
| WO | WO99/64626 | 12/1999 |
| WO | WO99/64627 | 12/1999 |
| WO | WO00/24940 | 5/2000 |
| WO | WO01/41815 | 6/2001 |
| WO | WO02/12280 | 2/2002 |
| WO | WO02/12328 | 2/2002 |
| WO | WO02/24956 | 3/2002 |
| WO | WO03050243 A2 | 6/2003 |
| WO | WO03/062395 | 7/2003 |
| WO | WO2004/110345 | 12/2004 |
| WO | WO2005/000087 | 1/2005 |
| WO | WO2005/015236 | 2/2005 |
| WO | WO2005/076005 | 8/2005 |
| WO | WO 2005/100593 | 10/2005 |
| WO | WO2006/010150 | 1/2006 |
| WO | WO2006/081248 | 8/2006 |
| WO | WO2006/110581 | 10/2006 |
| WO | WO2007/061876 | 5/2007 |
| WO | WO2007/070621 | 6/2007 |
| WO | WO 2007/073220 | 6/2007 |
| WO | WO2007/112330 | 10/2007 |

OTHER PUBLICATIONS

Backus, H.H.J. et al., "Differential Expression of Cell Cycle and Apoptosis Related Proteins in Colorectal Mucosa, Primary Colon Tumours, and Liver Metastases," J. Clin. Path. 55:206-211 (2002).
Barrier, A. et al., "Colon Cancer Prognosis Prediction by Gene Expression Profiling," Oncogene 24:6155-6164 (2005).
Bertucci, F. et al., "Gene Expression Profiling of Colon Cancer by DNA microarrays and Correlation with Histoclinical Parameters," Oncogene 23:1377-1391 (2004).
Compton, C. et al., "The Staging of Colorectal Cancer: 2004 and Beyond," CA Cancer J. Clin. 54:295-308 (2004).
Eschrich, S. et al., "Molecular Staging for Survival Prediction of Colorectal Cancer Patients," J. Clin. Oncol. 23:3526-3535 (2005).
Ogawa, S. et al., "The Breakdown of Apoptotic Mechanism in the Development and Progression of Colorectal Carcinoma," Anticancer Research 24:1569-1580 (2004).
Wang, Y. et al., "Gene Expression Profiles and Molecular Markers to Predict Recurrence of Dukes' B Colon Cancer," J. Clin. Oncol. 22:1564-1571 (2004).
U.S. Appl. No. 12/696,934, filed Jan. 29, 2010, Wayne Cowens.
U.S. Appl. No. 12/911,519, filed Oct. 25, 2010, Wayne Cowens.
U.S. Appl. No. 12/911,526, filed Oct. 25, 2010, Wayne Cowens.
U.S. Appl. No. 12/911,532, filed Oct. 25, 2010, Wayne Cowens.
U.S. Appl. No. 12/911,544, filed Oct. 25, 2010, Wayne Cowens.
U.S. Appl. No. 12/911,551, filed Oct. 25, 2010, Wayne Cowens.
Alain et al., "Gene expression profiling of nonneoplastic mucosa may predict clinical outcome of colon cancer patients", Diseases of the Colon and Rectum, 2005, 48(12):2238-2248.
Arango et al., "Gene-expression profiling predicts recurrence in Dukes' C colorectal cancer", Gastroenterology, 2005, 129(3):874-884.

(Continued)

Primary Examiner — James Martinell
(74) Attorney, Agent, or Firm — Paula A. Borden; Bozicevic, Field & Francis LLP

(57) ABSTRACT

A method of predicting clinical outcome in a subject diagnosed with colorectal cancer comprising determining evidence of the expression of one or more predictive RNA transcripts or their expression products in a biological sample of cancer cells obtained from the subject.

16 Claims, 1 Drawing Sheet

OTHER PUBLICATIONS

Bertucci et al., "Gene expression profiling of primary breast carcinomas using arrays of candidate genes", Human Molecular Genetics, 2000, 9(20):2981-2991.

Callagy et al., "Bcl-2 is a prognostic marker in breast cancer independently of the Nottingham Prognostic Index," Clin. Cancer Res., 2006, 12(8):2468-2475.

Kononen J. et al., "Tissue microarrays for high-throughput molecular profiling of tumor specimens", Nature Medicine, 1998, 4(7):844-847.

Lee M. O. et al., "Differential effects of retinoic acid on growth and apoptosis in human colon cancer cell lines associated with the induction of retinoic acid receptor beta", Biochemical Pharmacology, 2000, 59(5):485-496.

Modlich, O. et al., "Predictors of primary breast cancers responsiveness to preoperative Epirubicin/Cyclophosphamide-4 based chemotherapy: transition of microarray data into clinically useful predictive signatures," Journal of Translational Medicine, 2005, 3:32.

Nakopoulou, L. et al., "Stromelysin-3 protein expression in invasive breast cancer: Relation to proliferation, cell survival and patients' outcome," Modern Pathology, 2002, 15(11):1154-1161.

Nessling et al., "Candidate genes in breast cancer revealed by microarray-based comparative genomic hybridization of archived tissue," Cancer Res., 2005, 65(2):439-447.

Rosati et al., "Thymidylate synthase expression p53 bcl-2 K1-67 and p27 in colorectal cancer: Relationships with tumor recurrence and survival", Tumor Biology Karger Basel CH, 2004, 25(5-6):258-263.

Sarela A. I. et al., "Expression of the antiapoptosis gene surviving predicts death from recurrent colorectal carcinoma", Gut British Medical Association, 2000, 46(5):645-650.

Sun, "Retinoic acid receptor beta and colon cancer", Cancer Biology and Therapy, 2004, 3(1):87-88.

Urruticoechea, A. et al., "Proliferation marker in Ki-67 in early breast cancer," Journal of Clinical Oncology, 2005, 23(28):7212-7220.

Wildi S. et al., "Overexpression of activin A in stage IV colorectal cancer", Gut British Medical Association, 2001, 49:409-417.

Youssef E.M. et al., "Methylation and regulation of expression of different retinoic acid receptor beta isoforms in human colon cancer", Cancer Biology and Therapy, 2004, 3(1):82-86.

Augenlicht et al., Low-level c-myc amplification in human colonic carcinoma cell lines and tumors: A frequent, p53-independent mutation associated with improved outcome in a randomized multi-institutional trial. Cancer Research 1997; 57:1769-1775.

Avvisato et al., Mechanical force modulates global gene expression and β-catenin signaling in colon cancer cells. Journal of Cell Science 2007; 120(Pt 15):2672-2682.

Collett et al., Overexpression of p65/ReIA potentiates curcumin-induced apoptosis in HCT116 human colon cancer cells. Carcinogenesis 2006; 27(6):1285-1291.

Traka et al., Transcriptome analysis of human colon caco-2 cells exposed to sulforaphane. Journal of Nutrition 2005; 135(8):1865-1872.

Qui et al., Down-regulation of growth arrest DNA damage-inducible gene 45β expression is associated with human hepatocellular carcinoma. American Journal of Pathology 2003; 162(6):1961-1974.

Bertucci F. et al., "Gene Expression Profiling of Colon Cancer by DNA Microarrays and Correlation with Histoclinical Parameters," Oncogene 23:1377-1391 (2004) and Supplemental Tables 1 and 2.

EP Examination Report in EP App. No. 10177406.5, 10 pages, Sep. 19, 2011.

Anjomshoaa, A. et al., "Reduced expression of a gene proliferation signature is associated with enhanced malignancy in colon cancer," *British Journal of Cancer*, 99:966-973 (2008).

O'Connell, Michael J. et al., "Relationship between tumor gene expression and recurrence in four independent studies of patients with stage II/III colon cancer treated with surgery alone or surgery plus adjuvant fluorouracil plus leucovorin," *Journal of Clinical Oncology*, 28:3937-3944 (2010).

Batlle E. et al., "EphB receptor activity suppresses colorectal cancer progression," Nature, 2005, vol. 435, pp. 1126-1130.

Extended European Search Report for EP Patent App. No. 10194719, Dec. 19, 2011, 10 pgs.

Jubb A.M. et al., "EphB2 is a prognostic factor in colorectal cancer," Clinical Cancer Research, 2005, vol. 11, pp. 5181-5187.

Liu W. et al., "Coexpression of ephrin-B2 and their receptors in colon carcinoma," Cancer, 2002, vol. 94, pp. 934-939.

Liu W. et al., "Effects of overexpression of ephrin-B2 on tumour growth in human colorectal cancer," British Journal of Cancer, 2004, vol. 90, pp. 1620-1626.

\* cited by examiner

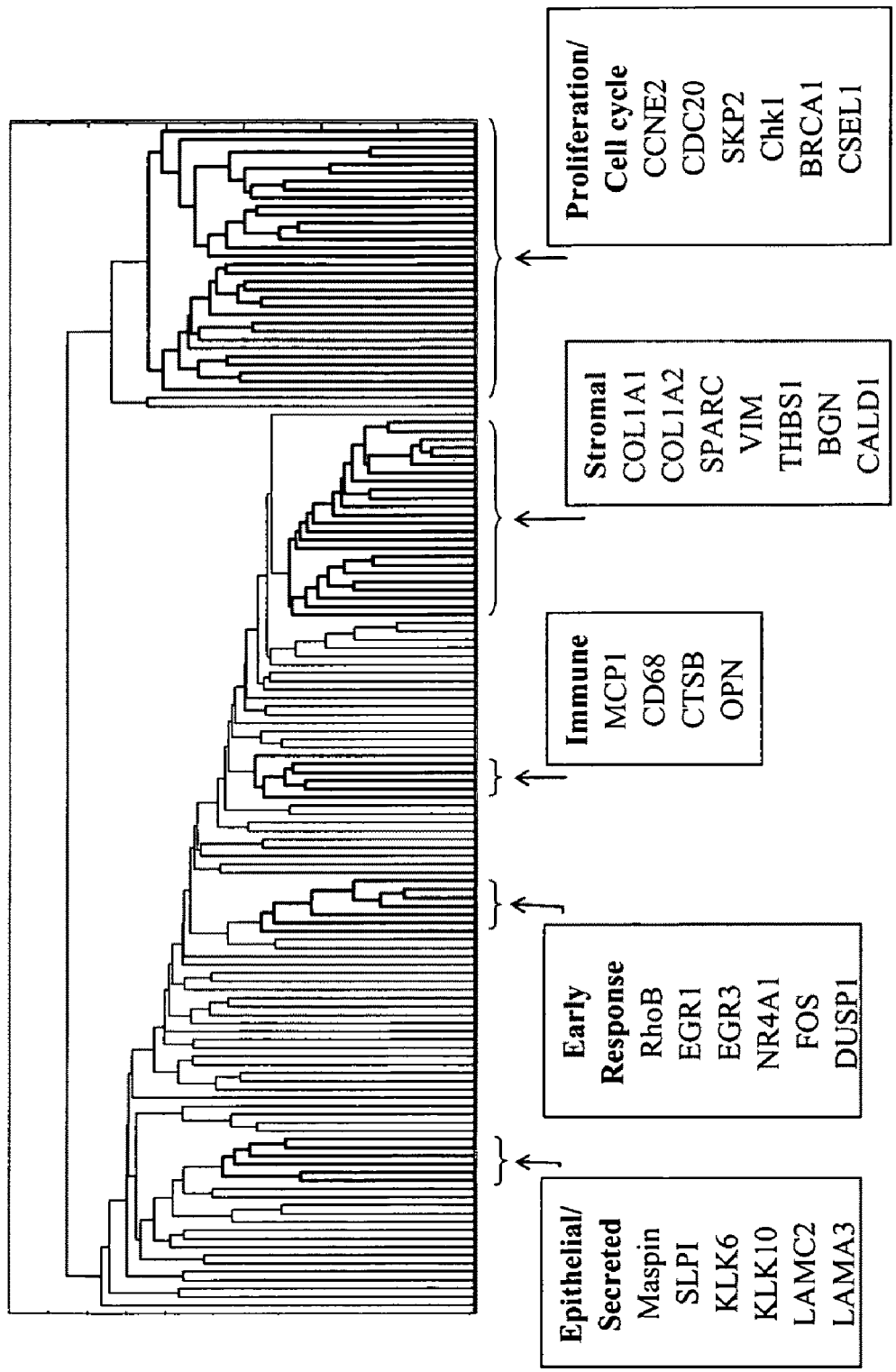

GENE EXPRESSION MARKERS FOR COLORECTAL CANCER PROGNOSIS

CROSS-REFERENCE TO RELATED APPLICATIONS

This application is a divisional of U.S. application Ser. No. 12/696,934, filed Jan. 29, 2010, now pending, which application is a divisional of U.S. application Ser. No. 11/653,102, filed, Jan. 11, 2007, now U.S. Pat. No. 7,695,913, issued Apr. 13, 2010, which application claims priority benefit of provisional U.S. Application Ser. No. 60/758,392 filed Jan. 11, 2006, and which application also claims priority benefit of provisional U.S. Application Ser. No. 60/800,277 filed May 12, 2006, and which application also claims priority benefit of provisional U.S. Application Ser. No. 60/810,077 filed May 31, 2006, all of which are incorporated herein by reference in their entirety.

BACKGROUND OF THE INVENTION

1. Field of the Invention

The present invention provides genes and gene sets, the expression levels of which are useful for predicting outcome of colorectal cancer.

2. Description of Related Art

Colorectal cancer is the number two cause of cancer-related death in the United States and the European Union, accounting for 10% of all cancer-related deaths. Although colon cancer and rectal cancer may represent identical or similar disease at the molecular level, surgery for rectal cancer is complicated by anatomical issues. Possibly for this reason, the rate of local recurrence for rectal cancer is significantly higher than for colon cancer, and so the treatment approach is significantly different. Approximately 100,000 colon cancers are newly diagnosed each year in the United States, with about 65% of these being diagnosed as stage II/III colorectal cancer as discussed below.

Refining a diagnosis of colorectal cancer involves evaluating the progression status of the cancer using standard classification criteria. Two classification systems have been widely used in colorectal cancer, the modified Duke's or Astler-Coller staging system (Stages A-D) (Astler V B, Coller F A., *Ann Surg* 1954; 139:846-52), and more recently TNM staging (Stages I-IV) as developed by the American Joint Committee on Cancer (*AJCC Cancer Staging Manual,* 6th Edition, Springer-Verlag, New York, 2002). Both systems apply measures of the spread of the primary tumor through layers of colon or rectal wall to the adjacent organs, lymph nodes and distant sites to evaluate tumor progression. Estimates of recurrence risk and treatment decisions in colon cancer are currently based primarily on tumor stage.

There are approximately 33,000 newly diagnosed Stage II colorectal cancers each year in the United States. Nearly all of these patients are treated by surgical resection of the tumor and, in addition, about 40% are currently treated with chemotherapy based on 5-fluorouracil (5-FU). The decision whether to administer adjuvant chemotherapy is not straightforward. The five-year survival rate for Stage II colon cancer patients treated with surgery alone is approximately 80%. Standard adjuvant treatment with 5-FU+leucovorin (folinic acid) demonstrates an absolute benefit of only 2-4% in this population and shows significant toxicity, including a rate of toxic death from chemotherapy as high as 1%. Thus, a large number of patients receive toxic therapy from which only a few benefit.

A test capable of prognosis after surgery in Stage II colorectal cancer patients would be of great benefit for guiding treatment decisions for these patients.

The benefit of chemotherapy in Stage III colon cancer is more evident than it is in Stage II. A large proportion of the 31,000 patients annually diagnosed with Stage III colon cancer receive 5-FU-based adjuvant chemotherapy, and the absolute benefit of 5-FU+leucovorin in this setting is around 18-24%, depending on the particular regimen employed. Current standard-of-care chemotherapy treatment for Stage III colon cancer patients (5-FU+leucovorin or 5-FU+leucovorin+oxaliplatin) is moderately effective, achieving an improvement in 5-yr survival rate from about 50% (surgery alone) to about 65% (5-FU+leucovorin) or 70% (5-FU+leucovorin+oxaliplatin). Treatment with 5-FU+leucovorin alone or in combination with oxaliplatin is accompanied by a range of adverse side-effects, including toxic death in approximately 1% of patients treated. Furthermore, the three-year survival rate for Stage III colon cancer patients treated with surgery alone is about 47% and it has not been established whether a subset of Stage III patients exists for which recurrence risk resembles that observed for Stage II patients.

A test that would quantify recurrence risk based on molecular markers rather than tumor stage alone would be useful for identifying a subset of Stage III patients that may not require adjuvant therapy to achieve acceptable outcomes.

Staging of rectal tumors is carried out based on similar criteria as for colon tumor staging, although there are some differences resulting for example from differences in the arrangement of the draining lymph nodes. As a result, Stage II/III rectal tumors bear a reasonable correlation to Stage II/III colon tumors as to their state of progression. As noted above, the rate of local recurrence and other aspects of prognosis differ between rectal cancer and colon cancer, and these differences may arise from difficulties in accomplishing total resection of rectal tumors. Nevertheless, there is no compelling evidence that there is a difference between colon cancer and rectal cancer as to the molecular characteristics of the respective tumors. Prognostic tests for rectal cancer would have utility similar in nature as described for colon cancer prognostic tests and the same prognostic markers might well apply to both cancer types.

In addition, there is a clear need for safer and more efficacious drugs for the treatment of colon cancer. Current chemotherapy for colon cancer is based on the relatively crude approach of administering drugs that generally interfere with the proliferation of dividing cells. Recent clinical studies have demonstrated the feasibility of developing improved drugs based on detailed molecular understanding of particular cancer types and subtypes. For example, the HER2 (ERBB2) gene is amplified and the HER2 protein is overexpressed in a subset of breast cancers; HERCEPTIN® (Genentech, Inc.) a drug developed to target HER2, is indicated only for those patients who have an higher than normal copy number of HER2 as demonstrated by fluorescent in situ hybridization (FISH) or a high level of HER2 expression as demonstrated by immunohistochemistry. Genes, whose expression is associated with clinical outcome in human cancer patients, are a valuable resource for selection of targets for drug compound screening and further drug development activities.

Molecularly targeted drugs, such as HERCEPTIN® (Genentech, Inc.) can be developed and commercialized in conjunction with a diagnostic test that can identify patients who are likely to benefit from the drug; one aspect of such a test is the identification of those patients likely to have a positive outcome without any treatment other than surgery. For example, 80% of Stage II colon cancer patients survive five years or more when treated with surgery alone. Gene markers that identify patients more likely to be among the 20% whose cancer will recur without additional treatment are useful in drug development, for example in screening patients for inclusion in a clinical trial.

SUMMARY OF THE INVENTION

In one aspect, the present invention concerns a method for predicting the clinical outcome in a subject diagnosed with colorectal cancer following surgical resection of said cancer, comprising determining the expression level of one or more predictive RNA transcripts listed in Tables 1A-B, 2A-B, 3A-B, 4A-B, 5A-B, 6 and/or 7, or their expression products, in a biological sample comprising cancer cells obtained from said subject wherein: (a) evidence of increased expression of one or more of the genes listed in Table 1A, 2A, 3A, 4A, and/or 5A, or the corresponding expression product, indicates a decreased likelihood of a positive clinical outcome; and (b) evidence of increased expression of one or more of the genes listed in Table 1B, 2B, 3B, 4B and/or 5B, or the corresponding expression product, indicates an increased likelihood of a positive clinical outcome. It is contemplated that if the likelihood of positive clinical outcome is predicted to be decreased said patient is subjected to further therapy following said surgical removal. It is further contemplated that the therapy is chemotherapy and/or radiation therapy.

The clinical outcome of the method of the invention may be expressed, for example, in terms of Recurrence-Free Interval (RFI), Overall Survival (OS), Disease-Free Survival (DFS), or Distant Recurrence-Free Interval (DRFI).

In one embodiment, the cancer is Dukes B (stage II) or Dukes C (stage III) colorectal cancer.

In another aspect, the invention concerns a method of predicting the duration of Recurrence-Free Interval (RFI) in a subject diagnosed with Dukes B (stage II) or Dukes C (stage III) colorectal cancer following surgical resection of said cancer, comprising determining the expression level of one or more predictive RNA transcripts listed in Tables 1A, 5A, 1B, and/or 5B, or their expression products, in a biological sample comprising cancer cells obtained from said subject, wherein: (a) evidence of increased expression of one or more of the genes listed in Table 1A or 5A, or the corresponding expression product, indicates that said RFI is predicted to be shorter; and (b) evidence of increased expression of one or more of the genes listed in Table 1B, or 5B, or the corresponding expression product, indicates that said RFI is predicted to be longer.

In another aspect, the invention concerns a method of predicting Overall Survival (OS) in a subject diagnosed with Dukes B (stage II) or Dukes C (stage III) colon cancer following surgical resection of said cancer, comprising determining the expression level of one or more predictive RNA transcripts listed in Tables 2A and/or 2B, or their expression products, in a biological sample comprising cancer cells obtained from said subject, wherein: (a) evidence of increased expression of one or more of the genes listed in Table 2A, or the corresponding expression product, indicates that said OS is predicted to be shorter; and (b) evidence of increased expression of one or more of the genes listed in Table 2B, or the corresponding expression product, indicates that said OS is predicted to be longer.

In another aspect, the invention concerns a method of predicting Disease-Free Survival (DFS) in a subject diagnosed with Dukes B (stage II) or Dukes C (stage III) colon cancer following surgical resection of said cancer, comprising determining the expression level of one or more predictive RNA transcripts listed in Tables 3A, and/or 3B, or their expression products, in a biological sample comprising cancer cells obtained from said subject, wherein: (a) evidence of increased expression of one or more of the genes listed in Table 3A, or the corresponding expression product, indicates that said DFS is predicted to be shorter; and (b) evidence of increased expression of one or more of the genes listed in Table 3B, or the corresponding expression product, indicates that said DFS is predicted to be longer.

In another aspect, the invention concerns a method of predicting the duration of Distant Recurrence-Free Interval (DRFI) in a subject diagnosed with Dukes B (stage II) or Dukes C (stage III) colon cancer following surgical resection of said cancer, comprising determining the expression level of one or more predictive RNA transcripts listed in Tables 4A and/or 4B, or their expression products, in a biological sample comprising cancer cells obtained from said subject, wherein: (a) evidence of increased expression of one or more of the genes listed in Table 4A, or the corresponding expression product, indicates that said DRFI is predicted to be shorter; and (b) evidence of increased expression of one or more of the genes listed in Table 4B, or the corresponding expression product, indicates that said DRFI is predicted to be longer.

In another aspect, the invention concerns a method of predicting clinical outcome for a subject diagnosed with colorectal cancer following surgical resection of said cancer, comprising determining evidence of the expression level of one or more predictive RNA transcripts listed in Tables 1.2A-B, 2.2A-B, 3.2A-B, 4.2A-B, 5.2A-B, 6.2 and/or 7.2, or their expression products, in a biological sample comprising cancer cells obtained from said subject, wherein (a) evidence of increased expression of one or more of the genes listed in Table 1.2A, 2.2A, 3.2A, 4.2A and/or 5.2A, or the corresponding expression product, indicates a decreased likelihood of a positive clinical outcome; and (b) evidence of increased expression of one or more of the genes listed in Table 1.2B, 2.2B, 3.2B, 4.2B and/or 5.2B, or the corresponding expression product, indicates an increased likelihood of a positive clinical outcome.

In another aspect, the invention concerns a method of predicting the duration of Recurrence-Free Interval (RFI) in a subject diagnosed with Dukes B (stage II) or Dukes C (stage III) colorectal cancer following surgical resection of said cancer, comprising determining the expression level of one or more predictive RNA transcripts listed in Tables 1.2A, 1.2B, 5.2A and/or 5.2B, or their expression products, in a biological sample comprising cancer cells obtained from said subject, wherein (a) evidence of increased expression of one or more of the genes listed in Table 1.2A or 5.2A, or the corresponding expression product, indicates that said RFI is predicted to be shorter; and (b) evidence of increased expression of one or more of the genes listed in Table 1.2B or 5.2B, or the corresponding expression product, indicates that said RFI is predicted to be longer.

In another aspect, the invention concerns a method of predicting Overall Survival (OS) in a subject diagnosed with Dukes B (stage II) or Dukes C (stage III) colon cancer following surgical resection of said cancer, comprising determining the expression level of one or more predictive RNA transcripts listed in Tables 2.2A and/or 2.2B, or their expression products, in a biological sample comprising cancer cells obtained from said subject, wherein (a) evidence of increased expression of one or more of the genes listed in Table 2.2A, or the corresponding expression product, indicates that said OS is predicted to be shorter; and (b) evidence of increased expression of one or more of the genes listed in Table 2.2B, or the corresponding expression product, indicates that said OS is predicted to be longer.

In another aspect, the invention concerns a method of predicting Disease-Free Survival (DFS) in a subject diagnosed with Dukes B (stage II) or Dukes C (stage III) colon cancer following surgical resection of said cancer, comprising determining the expression level of one or more predictive RNA transcripts listed in Tables 3.2A and/or 3.2B, or their expression products, in a biological sample comprising cancer cells obtained from said subject, wherein (a) evidence of increased expression of one or more of the genes listed in Table 3.2A; or the corresponding expression product, indicates that said DFS is predicted to be shorter; and (b) evidence of increased expression of one or more of the genes listed in Table 3.2B, or the corresponding expression product, indicates that said DFS is predicted to be longer.

In another aspect, the invention concerns a method of predicting the duration of Distant Recurrence-Free Interval (DRFI) in a subject diagnosed with Dukes B (stage II) or Dukes C (stage III) colon cancer following surgical resection of said cancer, comprising determining the expression level of one or more predictive RNA transcripts listed in Tables 4.2A and/or 4.2B, or their expression products, in a biological sample comprising cancer cells obtained from said subject, wherein (a) evidence of increased expression of one or more of the genes listed in Table 4.2A, or the corresponding expression product, indicates that said DRFI is predicted to be shorter; and (b) evidence of increased expression of one or more of the genes listed in Table 4.2B, or the corresponding expression product, indicates that said DRFI is predicted to be longer.

In another aspect, the invention concerns a method of predicting clinical outcome for a subject diagnosed with colorectal cancer following surgical resection of said cancer, comprising determining evidence of the expression level of one or more predictive RNA transcripts listed in Tables 1A-B, 1.2A-B, 2A-B, 2.2A-B, 3A-B, 3.2A-B, 4A-B, 4.2A-B, 5A-B, 5.2A-B, 6, 6.2, 7 and/or 7.2, or their expression products, in a biological sample comprising cancer cells obtained from said subject, wherein (a) evidence of increased expression of one or more of the genes listed in Table 1A, 1.2A, 2A, 2.2A, 3A, 3.2A, 4A, 4.2A, 5A and/or 5.2A, or the corresponding expression product, indicates a decreased likelihood of a positive clinical outcome; and (b) evidence of increased expression of one or more of the genes listed in Table 1B, 1.2B, 2B, 2.2B, 3B, 3.2B, 4B, 4.2B, 5B and/or 5.2B, or the corresponding expression product, indicates an increased likelihood of a positive clinical outcome.

In another aspect, the invention concerns a method of predicting the duration of Recurrence-Free Interval (RFI) in a subject diagnosed with Dukes B (stage II) or Dukes C (stage III) colorectal cancer following surgical resection of said cancer, comprising determining the expression level of one or more predictive RNA transcripts listed in Tables 1A, 1.2A, 1B, 1.2B, 5A, 5.2A, 5B and/or 5.2B, or their expression products, in a biological sample comprising cancer cells obtained from said subject, wherein (a) evidence of increased expression of one or more of the genes listed in Table 1A, 1.2A, 5A and/or 5.2A, or the corresponding expression product, indicates that said RFI is predicted to be shorter; and (b) evidence of increased expression of one or more of the genes listed in Table 1B, 1.2B, 5B and/or 5.2B, or the corresponding expression product, indicates that said RFI is predicted to be longer.

In another aspect, the invention concerns a method of predicting Overall Survival (OS) in a subject diagnosed with Dukes B (stage II) or Dukes C (stage III) colon cancer following surgical resection of said cancer, comprising determining the expression level of one or more predictive RNA transcripts listed in Tables 2A, 2.2A, 2B and/or 2.2B, or their expression products, in a biological sample comprising cancer cells obtained from said subject, wherein (a) evidence of increased expression of one or more of the genes listed in Table 2A and/or 2.2A, or the corresponding expression product, indicates that said OS is predicted to be shorter; and (b) evidence of increased expression of one or more of the genes listed in Table 2B and/or 2.2B, or the corresponding expression product, indicates that said OS is predicted to be longer.

In another aspect, the invention concerns a method of predicting Disease-Free Survival (DFS) in a subject diagnosed with Dukes B (stage II) or Dukes C (stage III) colon cancer following surgical resection of said cancer, comprising determining the expression level of one or more predictive RNA transcripts listed in Tables 3A, 3.2A, 3B and/or 3.2B, or their expression products, in a biological sample comprising cancer cells obtained from said subject, wherein (a) evidence of increased expression of one or more of the genes listed in Table 3A and/or 3.2A, or the corresponding expression product, indicates that said DFS is predicted to be shorter; and (b) evidence of increased expression of one or more of the genes listed in Table 3B and/or 3.2B, or the corresponding expression product, indicates that said DFS is predicted to be longer.

In another aspect, the invention concerns a method of predicting the duration of Distant Recurrence-Free Interval (DRFI) in a subject diagnosed with Dukes B (stage II) or Dukes C (stage III) colon cancer following surgical resection of said cancer, comprising determining the expression level of one or more predictive RNA transcripts listed in Tables 4A, 4.2A, 4B and/or 4.2B, or their expression products, in a biological sample comprising cancer cells obtained from said subject, wherein (a) evidence of increased expression of one or more of the genes listed in Table 4A and/or 4.2A, or the corresponding expression product, indicates that said DRFI is predicted to be shorter; and (b) evidence of increased expression of one or more of the genes listed in Table 4B and/or 4.2B, or the corresponding expression product, indicates that said DRFI is predicted to be longer.

In another aspect, the invention concerns a method of predicting clinical outcome in a subject diagnosed with Dukes B (stage II) colorectal cancer following surgical resection of said cancer, comprising determining the expression level of one or more predictive RNA transcripts selected from the group consisting of ALCAM, CD24, CDH11, CENPE, CLTC, CYR61, EMR3, ICAM2, LOX, MADH2, MGAT5, MT3, NUFIP1, PRDX6, SIR2, SOS1, STAT5B, TFF3, TMSB4X, TP53BP1, WIF, CAPG, CD28, CDC20, CKS1B, DKK1, HSD17B2, and MMP7, or their expression products, in a biological sample comprising cancer cells obtained from said subject, wherein: (a) evidence of increased expression of one or more of the genes selected from the group consisting of ALCAM, CD24, CDH11, CENPE, CLTC, CYR61, EMR3, ICAM2, LOX, MADH2, MGAT5, MT3, NUFIP1, PRDX6, SIR2, SOS1, STAT5B, TFF3, TMSB4X, TP53BP1, and WIF, or the corresponding expression product, indicates a decreased likelihood of positive clinical outcome; and (b) evidence of increased expression of one or more of the genes selected from the group consisting of CAPG, CD28, CDC20, CKS1B, DKK1, HSD17B2, and MMP7, or the corresponding expression product, indicates an increased likelihood of positive clinical outcome.

In another aspect, the invention concerns a method of predicting clinical outcome in a subject diagnosed with Dukes C (stage III) colorectal cancer following surgical resection of said cancer, comprising determining the expression level of one or more predictive RNA transcripts selected from the group consisting of CAPG, CD28, CKS1B, CYR61, DKK1, HSD17B2, LOX, MMP7, SIR2, ALCAM, CD24, CDC20, CDH11, CENPE, CLTC, EMR3, ICAM2, MADH2, MGAT5, MT3, NUFIP1, PRDX6, SOS1, STAT5B, TFF3, TMSB4X, TP53BP1, and WIF, or their expression products, in a biological sample comprising cancer cells obtained from said subject, wherein: (a) evidence of increased expression of one or more of the genes selected from the group consisting of CAPG, CD28, CKS1B, CYR61, DKK1, HSD17B2, LOX, MMP7, and SIR2, or the corresponding expression product, indicates a decreased likelihood of positive clinical outcome; and (b) evidence of increased expression of one or more of the genes selected from the group consisting of ALCAM, CD24, CDC20, CDH11, CENPE, CLTC, EMR3, ICAM2, MADH2, MGAT5, MT3, NUFIP1, PRDX6, SOS1, STAT5B, TFF3, TMSB4X, TP53BP1, and WIF, or the corresponding expression product, indicates an increased likelihood of positive clinical outcome.

For all aspects of the method of the invention, determining the expression level of one or more genes may be obtained, for example, by a method of gene expression profiling. The method of gene expression profiling may be, for example, a PCR-based method.

For all aspects of the invention, the expression levels of the genes may be normalized relative to the expression levels of one or more reference genes, or their expression products.

For all aspects of the invention, the subject preferably is a human patient.

For all aspects of the invention, the method may further comprise determining evidence of the expression levels of at least two of said genes, or their expression products. It is further contemplated that the method of the invention may further comprise determining evidence of the expression levels of at least three of said genes, or their expression products. It is also contemplated that the method of the invention may further comprise determining evidence of the expression levels of at least four of said genes, or their expression products. It is also contemplated that the method of the invention may further comprise determining evidence of the expression levels of at least five of said genes, or their expression products.

For all, aspects of the invention, the method may further comprise the step of creating a report summarizing said prediction.

For all aspects of the invention, it is contemplated that for every increment of an increase in the level of one or more predictive RNA transcripts or their expression products, the patient is identified to show an incremental increase in clinical outcome.

For all aspects of the invention, the determination of expression levels may occur more than one time. For all aspects of the invention, the determination of expression levels may occur before the patient is subjected to any therapy following surgical resection.

In a different aspect the invention is directed to a report comprising the predicted clinical outcome in a subject diagnosed with colorectal cancer following surgical resection of said cancer, comprising a prediction of clinical outcome based on information comprising the expression level of one or more predictive RNA transcripts listed in Tables 1A-B, 2A-B, 3A-B, 4A-B, 5A-B, 6 and/or 7, or their expression products, in a biological sample comprising cancer cells obtained from said subject wherein: (a) evidence of increased expression of one or more of the genes listed in Table 1A, 2A, 3A, 4A, and/or 5A, or the corresponding expression product, indicates a decreased likelihood of a positive clinical outcome; and (b) evidence of increased expression of one or more of the genes listed in Table 1B, 2B, 3B, 4B and/or 5B, or the corresponding expression product, indicates an increased likelihood of a positive clinical outcome. The clinical outcome of the report of the invention may be expressed, for example, in terms of Recurrence-Free Interval (RFI), Overall Survival (OS), Disease-Free Survival (DFS), or Distant Recurrence-Free Interval (DRFI). In one embodiment that cancer is Dukes B (stage II) or Dukes C (stage III) colorectal cancer. The prediction of clinical outcome may comprise an estimate of the likelihood of a particular clinical outcome for a subject or may comprise the classification of a subject into a risk group based on said estimate.

In another aspect the invention is directed to a report predicting clinical outcome for a subject diagnosed with colorectal cancer following surgical resection of said cancer, comprising a prediction of clinical outcome based on information comprising the expression level of one or more predictive RNA transcripts listed in Tables 1.2A-B, 2.2A-B, 3.2A-B, 4.2A-B, 5.2A-B, 6.2 and/or 7.2, or their expression products, in a biological sample comprising cancer cells obtained from said subject, wherein (a) evidence of increased expression of one or more of the genes listed in Table 1.2A, 2.2A, 3.2A, 4.2A and/or 5.2A, or the corresponding expression product, indicates a decreased likelihood of a positive clinical outcome; and (b) evidence of increased expression of one or more of the genes listed in Table 1.2B, 2.2B, 3.2B, 4.2B and/or 5.2B, or the corresponding expression product, indicates an increased likelihood of a positive clinical outcome. The clinical outcome of the report of the invention may be expressed, for example, in terms of Recurrence-Free Interval (RFI), Overall Survival (OS), Disease-Free Survival (DFS), or Distant Recurrence-Free Interval (DRFI). In one embodiment that cancer is Dukes B (stage II) or Dukes C (stage III) colorectal cancer. The prediction of clinical outcome may comprise an estimate of the likelihood of a particular clinical outcome for a subject or may comprise the classification of a subject into a risk group based on said estimate.

In another aspect, the invention concerns a report predicting clinical outcome for a subject diagnosed with colorectal cancer following surgical resection of said cancer, comprising a prediction of clinical outcome based on information comprising the expression level of one or more predictive RNA transcripts listed in Tables 1A-B, 1.2A-B, 2A-B, 2.2A-B, 3A-B, 3.2A-B, 4A-B, 4.2A-B, 5A-B, 5.2A-B, 6, 6.2, 7 and/or 7.2, or their expression products, in a biological sample comprising cancer cells obtained from said subject, wherein (a) evidence of increased expression of one or more of the genes listed in Table 1A, 1.2A, 2A, 2.2A, 3A, 3.2A, 4A, 4.2A, 5A and/or 5.2A, or the corresponding expression product, indicates a decreased likelihood of a positive clinical outcome; and (b) evidence of increased expression of one or more of the genes listed in Table 1B, 1.2B, 2B, 2.2B, 3B, 3.2B, 4B, 4.2B, 5B and/or 5.2B, or the corresponding expression product, indicates an increased likelihood of a positive clinical outcome. The prediction of clinical outcome may comprise an estimate of the likelihood of a particular clinical outcome for a subject or may comprise the classification of a subject into a risk group based on said estimate.

In another aspect the invention is directed to a report predicting clinical outcome in a subject diagnosed with Dukes B (stage II) colorectal cancer following surgical resection of said cancer, comprising a prediction of clinical outcome based on information comprising the expression level of one or more predictive RNA transcripts selected from the group consisting of ALCAM, CD24, CDH11, CENPE, CLTC, CYR61, EMR3, ICAM2, LOX, MADH2, MGAT5, MT3, NUFIP1, PRDX6, SIR2, SOS1, STAT5B, TFF3, TMSB4X, TP53BP1, WIF, CAPG, CD28, CDC20, CKS1B, DKK1, HSD17B2, and MMP7, or their expression products, in a biological sample comprising cancer cells obtained from said subject, wherein: (a) evidence of increased expression of one or more of the genes selected from the group consisting of ALCAM, CD24, CDH11, CENPE, CLTC, CYR61, EMR3, ICAM2, LOX, MADH2, MGAT5, MT3, NUFIP1, PRDX6, SIR2, SOS1, STAT5B, TFF3, TMSB4X, TP53BP1, and WIF, or the corresponding expression product, indicates a decreased likelihood of positive clinical outcome; and (b) evidence of increased expression of one or more of the genes selected from the group consisting of CAPG, CD28, CDC20, CKS1B, DKK1, HSD17B2, and MMP7, or the corresponding expression product, indicates an increased likelihood of positive clinical outcome. The prediction of clinical outcome may comprise an estimate of the likelihood of a particular clinical outcome for a subject or may comprise the classification of a subject into a risk group based on said estimate.

In another aspect the invention is directed to a report predicting clinical outcome in a subject diagnosed with Dukes C (stage III) colorectal cancer following surgical resection of said cancer, comprising a prediction of clinical outcome based on information comprising the expression level of one or more predictive RNA transcripts selected from the group consisting of CAPG, CD28, CKS1B, CYR61, DKK1, HSD17B2, LOX, MMP7, SIR2, ALCAM, CD24, CDC20, CDH11, CENPE, CLTC, EMR3, ICAM2, MADH2, MGAT5, MT3, NUFIP1, PRDX6, SOS1, STAT5B, TFF3, TMSB4X, TP53BP1, and WIF, or their expression products, in a biological sample comprising cancer cells obtained from said subject, wherein: (a) evidence of increased expression of one or more of the genes selected from the group consisting of CAPG, CD28, CKS1B, CYR61, DKK1, HSD17B2, LOX, MMP7, and SIR2, or the corresponding expression product, indicates a decreased likelihood of positive clinical outcome; and (b) evidence of increased expression of one or more of the genes selected from the group consisting of ALCAM, CD24, CDC20, CDH11, CENPE, CLTC, EMR3, ICAM2, MADH2, MGAT5, MT3, NUFIP1, PRDX6, SOS1, STAT5B, TFF3, TMSB4X, TP53BP1, and WIF, or the corresponding expression product, indicates an increased likelihood of positive clinical outcome. The prediction of clinical outcome may comprise an estimate of the likelihood of a particular clinical outcome for a subject or may comprise the classification of a subject into a risk group based on said estimate.

In a different aspect the invention concerns a kit comprising one or more of (1) extraction buffer/reagents and protocol; (2) reverse transcription buffer/reagents and protocol; and (3) qPCR buffer/reagents and protocol suitable for performing the methods of this invention. The kit may comprise data retrieval and analysis software.

BRIEF DESCRIPTION OF DRAWINGS

FIG. 1 shows a dendrogram representing the expression clustering of 142 genes that were statistically significantly related to recurrence-free interval (Tables 1.2A and 1.2B) in the univariate Cox proportional hazards analysis. The cluster analysis used the unweighted pair-group average amalgamation method and 1-Pearson r as the distance measure. The identities of particular genes in clusters of interest are indicated along the x-axis.

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, breast cancer, ovarian cancer, colon cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The term "colorectal cancer" is used in the broadest sense and refers to (1) all stages and all forms of cancer arising from epithelial cells of the large intestine and/or rectum and/or (2) all stages and all forms of cancer affecting the lining of the large intestine and/or rectum. In the staging systems used for classification of colorectal cancer, the colon and rectum are treated as one organ.

According to the tumor, node, metastatis (TNM) staging system of the American Joint Committee on Cancer (AJCC) (Greene et al. (eds.), AJCC Cancer Staging Manual. 6th Ed. New York, N.Y.: Springer; 2002), the various stages of colorectal cancer are defined as follows:

Tumor: T1: tumor invades submucosa; T2: tumor invades muscularis propria; T3: tumor invades through the muscularis propria into the subserose, or into the pericolic or perirectal tissues; T4: tumor directly invades other organs or structures, and/or perforates.

Node: N0: no regional lymph node metastasis; N1: metastasis in 1 to 3 regional lymph nodes; N2: metastasis in 4 or more regional lymph nodes.

Metastasis: M0: mp distant metastasis; M1: distant metastasis present.

Stage groupings: Stage I: T1 N0 M0; T2 N0 M0; Stage II: T3 N0 M0; T4 N0 M0; Stage III: any T, N1-2; M0; Stage 1V: any T, any N, M1.

According to the Modified Duke Staging System, the various stages of colorectal cancer are defined as follows:

Stage A: the tumor penetrates into the mucosa of the bowel wall but not further. Stage B: tumor penetrates into and through the muscularis propria of the bowel wall; Stage C: tumor penetrates into but not through muscularis propria of the bowel wall, there is pathologic evidence of colorectal cancer in the lymph nodes; or tumor penetrates into and through the muscularis propria of the bowel wall, there is pathologic evidence of cancer in the lymph nodes; Stage D: tumor has spread beyond the confines of the lymph nodes, into other organs, such as the liver, lung or bone.

Prognostic factors are those variables related to the natural history of colorectal cancer, which influence the recurrence rates and outcome of patients once they have developed colorectal cancer. Clinical parameters that have been associated with a worse prognosis include, for example, lymph node involvement, and high grade tumors. Prognostic factors are frequently used to categorize patients into subgroups with different baseline relapse risks.

The term "prognosis" is used herein to refer to the prediction of the likelihood of cancer-attributable death or progression, including recurrence, metastatic spread, and drug resistance, of a neoplastic disease, such as colon cancer.

The term "prediction" is used herein to refer to the likelihood that a patient will have a particular clinical outcome, whether positive or negative, following surgical removal of the primary tumor. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention. The prediction may include prognostic factors.

The term "positive clinical outcome" means an improvement in any measure of patient status, including those measures ordinarily used in the art, such as an increase in the duration of Recurrence-Free interval (RFI), an increase in the time of Overall Survival (OS), an increase in the time of Disease-Free Survival (DFS), an increase in the duration of Distant Recurrence-Free Interval (DRFI), and the like. An increase in the likelihood of positive clinical outcome corresponds to a decrease in the likelihood of cancer recurrence.

The term "risk classification" means the level of risk or the prediction that a subject will experience a particular clinical outcome. A subject may be classified into a risk group or classified at a level of risk based on the predictive methods of the present invention. A "risk group" is a group of subjects or individuals with a similar level of risk for a particular clinical outcome.

The term "long-term" survival is used herein to refer to survival for at least 3 years, more preferably for at least 5 years.

The term "Recurrence-Free Interval (RFI)" is used herein to refer to time in years to first colon cancer recurrence censoring for second primary cancer as a first event or death without evidence of recurrence.

The term "Overall Survival (OS)" is used herein to refer to time in years from surgery to death from any cause.

The term "Disease-Free Survival (DFS)" is used herein to refer to time in years to colon cancer recurrence or death from any cause.

The term "Distant Recurrence-Free Interval (DRFI)" is used herein to refer to the time (in years) from surgery to the first anatomically distant cancer recurrence.

The calculation of the measures listed above in practice may vary from study to study depending on the definition of events to be either censored or not considered.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as colon cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

The term "over-expression" with regard to an RNA transcript is used to refer to the level of the transcript determined by normalization to the level of reference mRNAs, which might be all measured transcripts in the specimen or a particular reference set of mRNAs.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide, followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of the present invention, reference to "at least one," "at least two," "at least five," etc. of the genes listed in any particular gene set means any one or any and all combinations of the genes listed.

The term "node negative" cancer, such as "node negative" colon cancer, is used herein to refer to cancer that has not spread to the lymph nodes.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product (B. Lewin. *Genes IV* Cell Press, Cambridge Mass. 1990). In theory the term "intron" refers to any segment of DNA that is transcribed but removed from within the transcript by splicing together the exons on either side of it. Operationally, exon sequences occur in the mRNA sequence of a gene as defined by Ref. SEQ ID numbers. Operationally, intron sequences are the intervening sequences within the genomic DNA of a gene, bracketed by exon sequences and having GT and AG splice consensus sequences at their 5' and 3' boundaries.

The term "expression cluster" is used herein to refer to a group of genes which demonstrate similar expression patterns when studied within samples from a defined set of patients. As used herein, the genes within an expression cluster show similar expression patterns when studied within samples from patients with Stage II and/or Stage III cancers of the colon and/or rectum.

B.1 General Description of the Invention

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Based on evidence of differential expression of RNA transcripts in normal and cancer cells, the present invention provides prognostic gene markers for colorectal cancer. Thus, in a particular aspect, the invention provides prognostic gene markers of Stage II and/or Stage III colorectal cancer, including markers that are specifically prognostic to the outcome of either Stage II or Stage III disease and those that have prognostic value at both stages, reflecting underlying differences in tumor cells in the two stages and/or in the extent of tumor progression. The prognostic markers and associated information provided by the present invention allow physicians to make more intelligent treatment decisions, and to customize the treatment of colorectal cancer to the needs of individual patients, thereby maximizing the benefit of treatment and minimizing the exposure of patients to unnecessary treatments, which do not provide any significant benefits and often carry serious risks due to toxic side-effects.

Disruptions in the normal functioning of various physiological processes, including proliferation, apoptosis, angiogenesis and invasion, have been implicated in the pathology in cancer. The relative contribution of dysfunctions in particular physiological processes to the pathology of particular cancer types is not well characterized. Any physiological process integrates the contributions of numerous gene products expressed by the various cells involved in the process. For example, tumor cell invasion of adjacent normal tissue and intravasation of the tumor cell into the circulatory system are effected by an array of proteins that mediate various cellular characteristics, including cohesion among tumor cells, adhesion of tumor cells to normal cells and connective tissue, ability of the tumor cell first to alter its morphology and then to migrate through surrounding tissues, and ability of the tumor cell to degrade surrounding connective tissue structures.

Multi-analyte gene expression tests can measure the expression level of one or more genes involved in each of several relevant physiologic processes or component cellular characteristics. In some instances the predictive power of the test, and therefore its utility, can be improved by using the expression values obtained for individual genes to calculate a score which is more highly correlated with outcome than is the expression value of the individual genes. For example, the calculation of a quantitative score (recurrence score) that predicts the likelihood of recurrence in estrogen receptor-positive, node-negative breast cancer is describe in a co-pending U.S. patent application (Publication Number 20050048542). The equation used to calculate such a recurrence score may group genes in order to maximize the predictive value of the recurrence score. The grouping of genes may be performed at least in part based on knowledge of their contribution to physiologic functions or component cellular characteristics such as discussed above. The formation of groups, in addition, can facilitate the mathematical weighting of the contribution of various expression values to the recurrence score. The weighting of a gene group representing a physiological process or component cellular characteristic can reflect the contribution of that process or characteristic to the pathology of the cancer and clinical outcome. Accordingly, in an important aspect, the present invention also provides specific groups of the prognostic genes identified herein, that together are more reliable and powerful predictors of outcome than the individual genes or random combinations of the genes identified.

In addition, based on the determination of a recurrence score, one can choose to partition patients into subgroups at any particular value(s) of the recurrence score, where all patients with values in a given range can be classified as belonging to a particular risk group. Thus, the values chosen will define subgroups of patients with respectively greater or lesser risk.

The utility of a gene marker in predicting colon cancer outcome may not be unique to that marker. An alternative marker having a expression pattern that is closely similar to a particular test marker may be substituted for or used in addition to a test marker and have little impact on the overall predictive utility of the test. The closely similar expression patterns of two genes may result from involvement of both genes in a particular process and/or being under common regulatory control in colon tumor cells. The present invention specifically includes and contemplates the use of such substitute genes or gene sets in the methods of the present invention.

The prognostic markers and associated information provided by the present invention predicting the clinical outcome in Stage II and/or Stage III cancers of the colon and/or rectum has utility in the development of drugs to treat Stage II and/or Stage III cancers of the colon and/or rectum.

The prognostic markers and associated information provided by the present invention predicting the clinical outcome in Stage II and/or Stage III cancers of the colon and/or rectum also have utility in screening patients for inclusion in clinical trials that test the efficacy of drug compounds for the treatment of patients with Stage II and/or Stage III cancers of the colon and/or rectum. In particular the prognostic markers may be used on samples collected from patients in a clinical trial and the results of the test used in conjunction with patient outcomes in order to determine whether subgroups of patients are more or less likely to show a response to the drug than the whole group or other subgroups.

The prognostic markers and associated information provided by the present invention predicting the clinical outcome in Stage II and/or Stage III cancers of the colon and/or rectum are useful as inclusion criterion for a clinical trial. For example, a patient is more likely to be included in a clinical trial if the results of the test indicate a higher likelihood that the patient will have a poor clinical outcome if treated with surgery alone and a patient is less likely to be included in a clinical trial if the results of the test indicate a lower likelihood that the patient will have a poor clinical outcome if treated with surgery alone.

In a particular embodiment, prognostic markers and associated information are used to design or produce a reagent that modulates the level or activity of the gene's transcript or its expression product. Said reagents may include but are not limited to an antisense RNA, a small inhibitory RNA, a ribozyme, a monoclonal or polyclonal antibody.

In a further embodiment, said gene or its transcript, or more particularly, an expression product of said transcript is used in an (screening) assay to identify a drug compound, wherein said drug compounds is used in the development of a drug to treat Stage II and/or Stage III cancers of the colon and/or rectum.

In various embodiments of the inventions, various technological approaches are available for determination of expression levels of the disclosed genes, including, without limitation, RT-PCR, microarrays, serial analysis of gene expression (SAGE) and Gene Expression Analysis by Massively Parallel Signature Sequencing (MPSS), which will be discussed in detail below. In particular embodiments, the expression level of each gene may be determined in relation to various features of the expression products of the gene including exons, introns, protein epitopes and protein activity. In other embodiments, the expression level of a gene may be inferred from analysis of the structure of the gene, for example from the analysis of the methylation pattern of gene's promoter(s).

B.2 Gene Expression Profiling

Methods of gene expression profiling include methods based on hybridization analysis of polynucleotides, methods based on sequencing of polynucleotides, and proteomics-based methods. The most commonly used methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and PCR-based methods, such as reverse transcription polymerase chain reaction (RT-PCR) (Weis et al., Trends in Genetics 8:263-264 (1992)). Alternatively, antibodies may be employed that can recognize sequence-specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

a. Reverse Transcriptase PCR (RT-PCR)

Of the techniques listed above, the most sensitive and most flexible quantitative method is RT-PCR, which can be used to determine mRNA levels in various samples. The results can be used to compare gene expression patterns between sample sets, for example in normal and tumor tissues and in patients with or without drug treatment.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include Master-Pure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

The steps of a representative protocol for profiling gene expression using fixed, paraffin-embedded tissues as the RNA source, including mRNA isolation, purification, primer extension and amplification are given in various published journal articles (for example: T. E. Godfrey et al. J. Molec. Diagnostics 2: 84-91 (2000); K. Specht et al., Am. J. Pathol. 158: 419-29 (2001)). Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR.

b. MassARRAY System

In the MassARRAY-based gene expression profiling method, developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derives PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details see, e.g. Ding and Cantor, Proc. Natl. Acad. Sci. USA 100:3059-3064 (2003).

c. Other PCR-based Methods

Further PCR-based techniques include, for example, differential display (Liang and Pardee, Science 257:967-971 (1992)); amplified fragment length polymorphism (iAFLP) (Kawamoto et al., Genome Res. 12:1305-1312 (1999)); BeadArray™ technology (Illumina, San Diego, Calif.; Oliphant et al., Discovery of Markers for Disease (Supplement to Biotechniques), June 2002; Ferguson et al., Analytical Chemistry 72:5618 (2000)); BeadsArray for Detection of Gene Expression (BADGE), using the commercially available Luminex100 LabMAP system and multiple color-coded microspheres (Luminex Corp., Austin, Tex.) in a rapid assay for gene expression (Yang et al., Genome Res. 11:1888-1898 (2001)); and high coverage expression profiling (HiCEP) analysis (Fukumura et al., Nucl. Acids. Res. 31(16) e94 (2003)).

d. Microarrays

Differential gene expression can also be identified, or confirmed using the microarray technique. Thus, the expression profile of colon cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pair wise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

e. Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484-487 (1995); and Velculescu et al., Cell 88:243-51 (1997).

f. Gene Expression Analysis by Massively Parallel Signature Sequencing (MPSS)

This method, described by Brenner et al., Nature Biotechnology 18:630-634 (2000), is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

g. Immunohistochemistry

Immunohistochemistry methods are also suitable for detecting the expression levels of the prognostic markers of the present invention. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

h. Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable supplements to other methods of gene expression profiling, and can be used, alone or in combination with other methods, to detect the products of the prognostic markers of the present invention.

i. Promoter Methylation Analysis

A number of methods for quantization of RNA transcripts (gene expression analysis) or their protein translation products are discussed herein. The expression level of genes may also be inferred from information regarding chromatin structure, such as for example the methylation status of gene promoters and other regulatory elements and the acetylation status of histones.

In particular, the methylation status of a promoter influences the level of expression of the gene regulated by that promoter. Aberrant methylation of particular gene promoters has been implicated in expression regulation, such as for example silencing of tumor suppressor genes. Thus, examination of the methylation status of a gene's promoter can be utilized as a surrogate for direct quantization of RNA levels.

Several approaches for measuring the methylation status of particular DNA elements have been devised, including methylation-specific PCR (Herman J. G. et al. (1996) Methylation-specific PCR: a novel PCR assay for methylation status of CpG islands. Proc. Natl Acad. Sci. USA. 93, 9821-9826.) and bisulfite DNA sequencing (Frommer M. et al. (1992) A genomic sequencing protocol that yields a positive display of 5-methylcytosine residues in individual DNA strands. Proc. Natl Acad. Sci. USA. 89, 1827-1831.). More recently, microarray-based technologies have been used to characterize promoter methylation status (Chen C. M. (2003) Methylation target array for rapid analysis of CpG island hypermethylation in multiple tissue genomes. Am. J. Pathol. 163, 37-45.).

j. Coexpression of Genes

A further aspect of the invention is the identification of gene expression clusters. Gene expression clusters can be identified by analysis of expression data using statistical analyses known in the art, including pairwise analysis of correlation based on Pearson correlation coefficients (Pearson K. and Lee A. (1902) Biometrika 2, 357).

In one embodiment, an expression cluster identified herein includes BGN, CALD1, COL1A1, COL1A2, SPARC, VIM and other genes which are known to be synthesized predominantly by stromal cells and to be involved in remodeling extracellular matrix. This expression cluster is referred to herein as the Extracellular Matrix Remodeling/Stromal cluster.

In another embodiment, an expression cluster identified herein includes ANXA2, KLK6, KLK10, LAMA3, LAMC2, MASPIN, SLPI, and other genes encoding epithelial cell secreted products, most of which are secreted predominantly by epithelial cells but which may be secreted by other cell types. This expression cluster is referred to herein as the Epithelial/Secreted cluster.

In still another embodiment, an expression cluster identified herein includes DUSP1, EGR1, EGR3, FOS, NR4A1, RHOB, and other genes whose transcription is upregulated early after exposure of cells to certain stimuli. A variety of stimuli trigger transcription of early response genes, e.g. exposure to growth factor s, which enables cells to quickly increase their motility and their ability to transport nutrients such as glucose. This expression cluster is referred to herein as the Early Response cluster.

In yet another embodiment, an expression cluster identified herein includes MCP1, CD68, CTSB, OPN, and other genes encoding proteins usually associated with cells of the immune system. This expression cluster is referred to herein as the Immune cluster.

In a further embodiment, an expression cluster identified herein includes CCNE2, CDC20, SKP2, CHK1, BRCA1, CSEL1 and other genes implicated in cell proliferation and regulation of the cell cycle. This expression cluster is referred to herein as the Proliferation/Cell Cycle cluster.

k. General Description of the mRNA Isolation, Purification and Amplification

The steps of a representative protocol for profiling gene expression using fixed, paraffin-embedded tissues as the RNA source, including mRNA isolation, purification, primer extension and amplification are provided in various published journal articles (for example: T. E. Godfrey et al., J. Molec. Diagnostics 2: 84-91 (2000); K. Specht et al., Am. J. Pathol. 158: 419-29 (2001)). Briefly, a representative process starts with cutting about 10 µm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined, dependent on the predicted likelihood of cancer recurrence.

l. Colon Cancer Gene Set, Assayed Gene Subsequences, and Clinical Application of Gene Expression Data An important aspect of the present invention is to use the measured expression of certain genes by colon cancer tissue to provide prognostic information. For this purpose it is necessary to correct for (normalize away) both differences in the amount of RNA assayed and variability in the quality of the RNA used. Therefore, the assay typically measures and incorporates the expression of certain normalizing genes, including well known housekeeping genes, such as GAPDH and Cyp1. Alternatively, normalization can be based on the mean or median signal (Ct) of all of the assayed genes or a large subset thereof (global normalization approach). On a gene-by-gene basis, measured normalized amount of a patient tumor mRNA is compared to the amount found in a colon cancer tissue reference set. The number (N) of colon cancer tissues in this reference set should be sufficiently high to ensure that different reference sets (as a whole) behave essentially the same way. If this condition is met, the identity of the individual colon cancer tissues present in a particular set will have no significant impact on the relative amounts of the genes assayed. Usually, the colon cancer tissue reference set consists of at least about 30, preferably at least about 40 different FPE colon cancer tissue specimens. Unless noted otherwise, normalized expression levels for each mRNA/tested tumor/patient will be expressed as a percentage of the expression level measured in the reference set. More specifically, the reference set of a sufficiently high number (e.g. 40) of tumors yields a distribution of normalized levels of each mRNA species. The level measured in a particular tumor sample to be analyzed falls at some percentile within this range, which can be determined by methods well known in the art. Below, unless noted otherwise, reference to expression levels of a gene assume normalized expression relative to the reference set although this is not always explicitly stated.

m. Design of Intron-Based PCR Primers and Probes

According to one aspect of the present invention, PCR primers and probes are designed based upon intron sequences present in the gene to be amplified. Accordingly, the first step in the primer/probe design is the delineation of intron sequences within the genes. This can be done by publicly available software, such as the DNA BLAT software developed by Kent, W. J., *Genome Res.* 12(4):656-64 (2002), or by the BLAST software including its variations. Subsequent steps follow well established methods of PCR primer and probe design.

In order to avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386).

The most important factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. Primerselect: Primer and probe design. *Methods Mol. Biol.* 70:520-527 (1997), the entire disclosures of which are hereby expressly incorporated by reference.

n. Kits of the Invention

The materials for use in the methods of the present invention are suited for preparation of kits produced in accordance with well known procedures. The invention thus provides kits comprising agents, which may include gene-specific or gene-selective probes and/or primers, for quantitating the expression of the disclosed genes for predicting prognostic outcome or response to treatment. Such kits may optionally contain reagents for the extraction of RNA from tumor samples, in particular fixed paraffin-embedded tissue samples and/or reagents for RNA amplification. In addition, the kits may optionally comprise the reagent(s) with an identifying description or label or instructions relating to their use in the methods of the present invention. The kits may comprise containers (including microtiter plates suitable for use in an automated implementation of the method), each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention (e.g., appropriate length poly(T) or random primers linked to a promoter reactive with the RNA polymerase). Mathematical algorithms used to estimate or quantify prognostic or predictive information are also properly potential components of kits.

o. Reports of the Invention

The methods of this invention, when practiced for commercial diagnostic purposes generally produce a report or summary of the normalized expression levels of one or more of the selected genes. The methods of this invention will produce a report comprising a prediction of the clinical outcome of a subject diagnosed with colorectal cancer following surgical resection of said cancer. The methods and reports of this invention can further include storing the report in a database. Alternatively, the method can further create a record in a database for the subject and populate the record with data. In one embodiment the report is a paper report, in another embodiment the report is an auditory report, in another embodiment the report is an electronic record. It is contemplated that the report is provided to a physician and/or the patient. The receiving of the report can further include establishing a network connection to a server computer that includes the data and report and requesting the data and report from the server computer.

The methods provided by the present invention may also be automated in whole or in part.

All aspects of the present invention may also be practiced such that a limited number of additional genes that are co-expressed with the disclosed genes, for example as evidenced by high Pearson correlation coefficients, are included in a prognostic or predictive test in addition to and/or in place of disclosed genes.

Having described the invention, the same will be more readily understood through reference to the following Example, which is provided by way of illustration, and is not intended to limit the invention in any way.

EXAMPLES

A Study to Explore Relationships Between Genomic Tumor Expression Profiles and the Likelihood of Recurrence in Dukes' B and Duke's C Patients Treated with Resection of the Colon The primary objective of this study was to determine whether there is a significant relationship between the expression of each of 757 amplicons identified in Table B and clinical outcome in stage II and stage III colon cancer patients who receive colon resection (surgery) without chemotherapy.

Study Design

This was an exploratory study using tissue and outcome data from National Surgical Adjuvant Breast and Bowel Project (NSABP) Studies C-01 and C-02 in up to 400 Dukes B (stage II) and Dukes C (stage III) patients who received colon resection (surgery) only or surgery and postoperative Bacillus Calmette-Guerin (BCG).

Inclusion Criteria

Patients enrolled in either NSABP Study C-01: "A Clinical Trial To Evaluate Postoperative Immunotherapy And Postoperative Systemic Chemotherapy In The Management Of Resectable Colon Cancer" or NSABP Study C-02: "A Protocol To Evaluate The Postoperative Portal Vein Infusion Of 5-Flourouracil And Heparin In Adenocarcinoma Of The Colon" Details of C-01 and C-02 can be found on the NSABP Website at the following URL:

http://www.nsabp.pittedu/
NSABP_Protocols.htm#treatment %20closed

Tissue samples from the surgery only and surgery+postoperative BCG arms of NSABP C01 and from the surgery only arm of NSABP C02 surgery were combined into one sample set.

Exclusion Criteria

Patients enrolled in NSABP Study C-01 or NSABP Study C-02 were excluded from the present study if one or more of the following applied:

No tumor block available from initial diagnosis in the NSABP archive.

Insufficient tumor in block as assessed by examination of hematoxylin and eosin (H&E) slide Insufficient RNA (<700 ng) recovered from tissue sections for RT-PCR analysis.

Of 1943 patients enrolled in NSABP Study C-01 or NSABP Study C-02, 270 patient samples were available after application of exclusion criteria and used in the gene expression study disclosed herein. The overall demographic and clinical characteristics of the 270 included samples were similar to the original NSABP combined cohorts.

Gene Panel

Seven hundred sixty-one genes, including seven reference genes, were chosen for expression analysis. These genes are listed in Table A together with the sequences of primers and probes used in qRT-PCR to determine expression level.

Experimental Materials and Methods

The expression of 750 cancer-related genes and 7 genes designated for use as reference genes was quantitatively assessed for each patient using TaqMan® RT-PCR, which was performed in singlet with RNA input at 1 nanogram per reaction.

Data Analysis Methods

Reference Normalization

For normalization of extraneous effects, cycle threshold ($C_T$) measurements obtained by RT-PCR were normalized relative to the mean expression of a set of six reference genes. The resulting reference-normalized expression measurements typically range from 0 to 15, where a one unit increase generally reflects a 2-fold increase in RNA quantity.

Comparison of Study Cohort to Original NSABP Study Populations

We compared the distribution of clinical and demographic variables for the current study cohort of evaluable tissue blocks versus the original NSABP C-01 and C-02 study populations. There were no clinically meaningful differences in the distributions.

Univariate Analysis

For each of the 757 amplicons under study, we used the Cox proportional hazard model to examine the relationship between gene expression and recurrence free interval (RFI). The likelihood ratio was used as the test of statistical significance. The method of Benjamini and Hochberg (Benjamini, Y. and Hochberg, Y. (1995). Controlling the false discovery rate: a practical and powerful approach to multiple testing. J. R. Statist. Soc. B 57, 289-300.), as well as resampling and permutation based methods (Tusher V G, Tibshirani R, Chu G (2001) Significance analysis of microarrays applied to the ionizing radiation response. Proc Natl Acad Sci USA, 98:5116-5121.; Storey J D, Tibshirani R (2001) Estimating false discovery rates under dependence, with applications to DNA microarrays. Stanford: Stanford University, Department of Statistics; Report No.: Technical Report 2001-28; Korn E L, Troendle J, McShane L, Simon R (2001) Controlling the number of false discoveries: Application to high-dimensional genomic data. Technical Report 003. 2001. National Cancer Institute.) were applied to the resulting set of p-values to estimate false discovery rates. All analyses were repeated for each of the alternative endpoints: distant recurrence free interval (DRFI), overall survival (OS), and disease free survival (DFS).

Multivariate Analysis

For each of the 757 amplicons under study, we used the Cox proportional hazard model to examine the relationship between gene expression and RFI, while controlling for the effects of other standard clinical covariates (including tumor location, surgery type, tumor grade, number of lymph nodes examined, and number of positive lymph nodes. The difference in the log likelihoods of the (reduced) model including only the standard clinical covariates and the (full) model including the standard clinical covariates plus gene expression was used as the test of statistical significance.

Non-Linear Analysis

For each of the 757 amplicons under study, we explored alternative functional relationships between gene expression and recurrence using several different methods. For each amplicon, we fit a Cox proportional hazards model of RFI as a function of gene expression using a 2 degree-of-freedom (DF) natural spline (Stone C, Koo C. (1985) In Proceedings of the Statistical Computing Section ASA. Washington, D.C., 45-48). Statistical significance was assessed by the 2 DF likelihood ratio test for the model. Functional relationships were also explored by examining the pattern of (smoothed) Martingale residuals derived from univariate Cox proportional hazards models of RFI as a strictly linear function of gene expression (Gray RJ (1992) Flexible methods for analyzing survival data using splines, with applications to breast cancer prognosis. Journal of the American Statistical Association, 87:942-951; Gray RJ (1994) Spline-based tests in survival analysis. Biometrics, 50:640-652; Gray R J (1990) Some diagnostic methods for Cox regression models through hazard smoothing. Biometrics, 46:93-102.). Additionally, cumulative sums of Martingale residuals from each the same Cox proportional hazards models were used to detect departures from linearity (Lin D, Wei L, Ying Z. (1993) Checking the Cox Model with Cumulative Sums of Martingale-Based Residuals. Vol. 80, No. 3, 557-572).

Interaction with Stage

We determined whether there is a significantly different relationship between gene expression and RFI in stage II and stage III patients. For each of the 757 amplicons, we tested the hypothesis that there is a significant difference between the (reduced) proportional hazards model for gene expression and tumor stage versus the (full) proportional hazards model based on gene expression, tumor stage, and their interaction. The difference in the log likelihoods of the reduced and full models was used as the test of statistical significance.

Table A shows qRT-PCR probe and primer sequences for all genes included in the study described in the Example.

Table B shows target amplicons for all genes included in the study described in the Example.

First Analysis Study Results

Reference Gene set for the first analysis was CLTC, FZD6, NEDD8, RPLPO, RPS13, UBB, UBC.

Table 1A shows associations for those genes whose increased expression is predictive of shorter Recurrence-Free Interval (RFI) based on univariate proportional hazards analysis.

Table 1B shows associations for those genes whose increased expression is predictive of longer Recurrence-Free Interval (RFI) based on univariate proportional hazards analysis.

Table 2A shows associations for those genes whose increased expression is predictive of decreased rate of Overall Survival (OS) based on univariate proportional hazards analysis.

Table 2B shows associations for those genes whose increased expression is predictive of increased rate of Overall Survival (OS) based on univariate proportional hazards analysis.

Table 3A shows associations for those genes whose increased expression is predictive of decreased rate of Disease Free Survival (DFS) based on univariate proportional hazards analysis.

Table 3B shows associations for those genes whose increased expression is predictive of increased rate of Disease Free Survival (DFS) based on univariate proportional hazards analysis.

Table 4A shows associations for those genes whose increased expression is predictive of shorter Distant Recurrence-Free Interval (DRFI) based on univariate proportional hazards analysis.

Table 4B shows associations for those genes whose increased expression is predictive of longer Distant Recurrence-Free Interval (DRFI) based on univariate proportional hazards analysis.

Table 5A shows associations between gene expression and RFI for those genes whose increased expression is predictive of shorter Recurrence-Free Interval (RFI), based on a multivariate analysis controlling for particular demographic and clinical characteristics of patients included in the analysis.

Table 5B shows associations between gene expression and RFI for those genes whose increased expression is predictive of longer Recurrence-Free Interval (RFI), based on a multivariate analysis controlling for particular demographic and clinical characteristics of patients included in the analysis.

Table 6 shows genes for which an association between gene expression and clinical outcome was identified based on a nonlinear proportional hazards analysis, using a 2 degree-of-freedom natural spline.

Table 7 shows all genes exhibiting an interaction (p-value<0.05) with tumor stage.

Table 1A shows associations between clinical outcome and gene expression for those genes which demonstrated a Hazard Ratio>1.0 and for which p<0.1. Univariate Cox Proportional Hazards Regression analysis was applied in combined Stage II (Duke's B) and Stage III (Duke's C) patients using RFI as the metric for clinical outcome.

TABLE 1A

| Gene | Hazard Ratio | P Value | Official Symbol | Accession Number |
|---|---|---|---|---|
| RARB | 2.13 | 0.0252 | RARB | NM_016152 |
| ITGB1 | 1.94 | 0.0002 | ITGB1 | NM_002211 |
| ALDOA | 1.92 | 0.0853 | ALDOA | NM_000034 |
| ANXA2 | 1.90 | <.0001 | ANXA2 | NM_004039 |
| CYP3A4 | 1.81 | 0.0038 | CYP3A4 | NM_017460 |
| KRAS2 | 1.64 | 0.0043 | KRAS | NM_004985 |
| COX2 | 1.62 | 0.0521 | PTGS2 | NM_000963 |
| RhoC | 1.61 | 0.0054 | RHOC | NM_175744 |
| TJP1 | 1.60 | 0.0554 | TJP1 | NM_003257 |
| RhoB | 1.57 | 0.0001 | RHOB | NM_004040 |
| KIAA0125 | 1.56 | 0.0940 | KIAA0125 | NM_014792 |
| TIMP1 | 1.52 | <.0001 | TIMP1 | NM_003254 |
| UBC | 1.49 | 0.0031 | UBC | NM_021009 |

TABLE 1A-continued

| Gene | Hazard Ratio | P Value | Official Symbol | Accession Number |
|---|---|---|---|---|
| ANXA5 | 1.49 | 0.0084 | ANXA5 | NM_001154 |
| NTN1 | 1.49 | 0.0386 | NTN1 | NM_004822 |
| AKT3 | 1.47 | <.0001 | AKT3 | NM_005465 |
| CALD1 | 1.46 | 0.0007 | CALD1 | NM_004342 |
| IGFBP7 | 1.46 | 0.0019 | IGFBP7 | NM_001553 |
| VEGFC | 1.45 | 0.0092 | VEGFC | NM_005429 |
| BGN | 1.44 | 0.0002 | BGN | NM_001711 |
| CYP1B1 | 1.44 | 0.0180 | CYP1B1 | NM_000104 |
| DLC1 | 1.43 | 0.0012 | DLC1 | NM_006094 |
| SI | 1.43 | 0.0063 | SI | NM_001041 |
| CCNE2 variant 1 | 1.43 | 0.0506 | CCNE2 | NM_057749 |
| LAMC2 | 1.42 | 0.0003 | LAMC2 | NM_005562 |
| TIMP2 | 1.42 | 0.0018 | TIMP2 | NM_003255 |
| CDC42BPA | 1.42 | 0.0029 | CDC42BPA | NM_003607 |
| p21 | 1.41 | 0.0062 | CDKN1A | NM_000389 |
| HB-EGF | 1.40 | 0.0105 | HBEGF | NM_001945 |
| TLN1 | 1.40 | 0.0260 | TLN1 | NM_006289 |
| DUSP1 | 1.39 | <.0001 | DUSP1 | NM_004417 |
| ROCK1 | 1.39 | 0.0121 | ROCK1 | NM_005406 |
| CTSB | 1.39 | 0.0307 | CTSB | NM_001908 |
| ITGAV | 1.38 | 0.0020 | ITGAV | NM_002210 |
| HSPG2 | 1.38 | 0.0215 | HSPG2 | NM_005529 |
| GADD45B | 1.37 | 0.0002 | GADD45B | NM_015675 |
| VCL | 1.37 | 0.0201 | VCL | NM_003373 |
| SBA2 | 1.37 | 0.0250 | WSB2 | NM_018639 |
| Maspin | 1.36 | <.0001 | SERPINB5 | NM_002639 |
| CGB | 1.36 | 0.0018 | CGB | NM_000737 |
| TIMP3 | 1.36 | 0.0024 | TIMP3 | NM_000362 |
| VIM | 1.36 | 0.0073 | VIM | NM_003380 |
| S100A1 | 1.36 | 0.0247 | S100A1 | NM_006271 |
| INHBA | 1.35 | 0.0008 | INHBA | NM_002192 |
| SIR2 | 1.35 | 0.0039 | SIRT1 | NM_012238 |
| TMSB10 | 1.35 | 0.0469 | TMSB10 | NM_021103 |
| CD68 | 1.34 | 0.0036 | CD68 | NM_001251 |
| RBX1 | 1.34 | 0.0469 | RBX1 | NM_014248 |
| INHBB | 1.34 | 0.0514 | INHBB | NM_002193 |
| PKR2 | 1.34 | 0.0628 | PKM2 | NM_002654 |
| FOS | 1.33 | 0.0006 | FOS | NM_005252 |
| FYN | 1.33 | 0.0036 | FYN | NM_002037 |
| LOXL2 | 1.33 | 0.0064 | LOXL2 | NM_002318 |
| STC1 | 1.33 | 0.0101 | STC1 | NM_003155 |
| DKK1 | 1.33 | 0.0208 | DKK1 | NM_012242 |
| IGFBP5 | 1.32 | 0.0064 | IGFBP5 | NM_000599 |
| EPAS1 | 1.32 | 0.0270 | EPAS1 | NM_001430 |
| UNC5C | 1.32 | 0.0641 | UNC5C | NM_003728 |
| FAP | 1.31 | 0.0017 | FAP | NM_004460 |
| IGFBP3 | 1.31 | 0.0041 | IGFBP3 | NM_000598 |
| SNAI2 | 1.31 | 0.0055 | SNAI2 | NM_003068 |
| PRKCA | 1.31 | 0.0065 | PRKCA | NM_002737 |
| FST | 1.31 | 0.0399 | FST | NM_006350 |
| KCNH2 iso a/b | 1.31 | 0.0950 | KCNH2 | NM_000238 |
| CTHRC1 | 1.30 | 0.0017 | CTHRC1 | NM_138455 |
| PDGFC | 1.30 | 0.0034 | PDGFC | NM_016205 |
| EGR1 | 1.30 | 0.0048 | EGR1 | NM_001964 |
| TAGLN | 1.30 | 0.0058 | TAGLN | NM_003186 |
| SPARC | 1.30 | 0.0104 | SPARC | NM_003118 |
| KLF6 | 1.30 | 0.0514 | KLF6 | NM_001300 |
| GRIK1 | 1.30 | 0.0753 | GRIK1 | NM_000830 |
| CYR61 | 1.29 | 0.0018 | CYR61 | NM_001554 |
| SLPI | 1.29 | 0.0026 | SLPI | NM_003064 |
| COL1A2 | 1.29 | 0.0076 | COL1A2 | NM_000089 |
| MAPK14 | 1.29 | 0.0916 | MAPK14 | NM_139012 |
| LAMA3 | 1.28 | 0.0020 | LAMA3 | NM_000227 |
| THBS1 | 1.28 | 0.0053 | THBS1 | NM_003246 |
| NRP2 | 1.28 | 0.0120 | NRP2 | NM_003872 |
| LOX | 1.27 | 0.0028 | LOX | NM_002317 |
| S100A4 | 1.27 | 0.0067 | S100A4 | NM_002961 |
| CXCR4 | 1.27 | 0.0083 | CXCR4 | NM_003467 |
| CEBPB | 1.27 | 0.0943 | CEBPB | NM_005194 |
| AKAP12 | 1.26 | 0.0044 | AKAP12 | NM_005100 |
| ADAMTS12 | 1.26 | 0.0100 | ADAMTS12 | NM_030955 |
| CRYAB | 1.25 | 0.0038 | CRYAB | NM_001885 |
| Grb10 | 1.25 | 0.0108 | GRB10 | NM_005311 |
| MCP1 | 1.25 | 0.0118 | CCL2 | NM_002982 |
| COL1A1 | 1.25 | 0.0167 | COL1A1 | NM_000088 |
| EFNB2 | 1.25 | 0.0241 | EFNB2 | NM_004093 |
| ANXA1 | 1.25 | 0.0292 | ANXA1 | NM_000700 |

TABLE 1A-continued

| Gene | Hazard Ratio | P Value | Official Symbol | Accession Number |
|---|---|---|---|---|
| ANGPT2 | 1.25 | 0.0485 | ANGPT2 | NM_001147 |
| EphB6 | 1.25 | 0.0825 | EPHB6 | NM_004445 |
| HSPA1A | 1.24 | 0.0018 | HSPA1A | NM_005345 |
| TGFB3 | 1.24 | 0.0081 | TGFB3 | NM_003239 |
| PTGER3 | 1.24 | 0.0306 | PTGER3 | NM_000957 |
| FXYD5 | 1.24 | 0.0367 | FXYD5 | NM_014164 |
| CAPG | 1.24 | 0.0604 | CAPG | NM_001747 |
| PDGFB | 1.23 | 0.0157 | PDGFB | NM_002608 |
| ANTXR1 | 1.23 | 0.0164 | ANTXR1 | NM_032208 |
| TGFBI | 1.23 | 0.0191 | TGFBI | NM_000358 |
| CTGF | 1.23 | 0.0233 | CTGF | NM_001901 |
| PDGFA | 1.23 | 0.0274 | | NM_002607 |
| P14ARF | 1.23 | 0.0362 | | S78535 |
| KLK10 | 1.22 | 0.0005 | KLK10 | NM_002776 |
| ITGA5 | 1.22 | 0.0178 | ITGA5 | NM_002205 |
| GBP2 | 1.22 | 0.0201 | GBP2 | NM_004120 |
| SIAT4A | 1.22 | 0.0231 | ST3GAL1 | NM_003033 |
| GJB2 | 1.22 | 0.0271 | GJB2 | NM_004004 |
| LAT | 1.22 | 0.0306 | LAT | NM_014387 |
| CTSL | 1.22 | 0.0331 | CTSL | NM_001912 |
| DAPK1 | 1.22 | 0.0384 | DAPK1 | NM_004938 |
| SKP1A | 1.22 | 0.0542 | SKP1A | NM_006930 |
| NDRG1 | 1.22 | 0.0712 | NDRG1 | NM_006096 |
| ITGB5 | 1.22 | 0.0991 | ITGB5 | NM_002213 |
| KLK6 | 1.21 | 0.0034 | KLK6 | NM_002774 |
| SFRP2 | 1.21 | 0.0037 | SFRP2 | NM_003013 |
| TMEPAI | 1.21 | 0.0173 | TMEPAI | NM_020182 |
| ID4 | 1.21 | 0.0530 | ID4 | NM_001546 |
| SFRP4 | 1.20 | 0.0077 | SFRP4 | NM_003014 |
| HOXB7 | 1.20 | 0.0274 | HOXB7 | NM_004502 |
| GJA1 | 1.20 | 0.0311 | GJA1 | NM_000165 |
| CDH11 | 1.20 | 0.0662 | CDH11 | NM_001797 |
| PAI1 | 1.19 | 0.0060 | SERPINE1 | NM_000602 |
| S100P | 1.19 | 0.0119 | S100P | NM_005980 |
| EGR3 | 1.19 | 0.0164 | EGR3 | NM_004430 |
| EMP1 | 1.19 | 0.0460 | EMP1 | NM_001423 |
| ABCC5 | 1.19 | 0.0536 | ABCC5 | NM_005688 |
| FZD1 | 1.19 | 0.0701 | FZD1 | NM_003505 |
| MAD | 1.19 | 0.0811 | MXD1 | NM_002357 |
| EFNA1 | 1.19 | 0.0920 | EFNA1 | NM_004428 |
| OPN_osteopontin | 1.18 | 0.0028 | SPP1 | NM_000582 |
| ALDH1A1 | 1.18 | 0.0246 | ALDH1A1 | NM_000689 |
| NR4A1 | 1.18 | 0.0277 | NR4A1 | NM_002135 |
| SIAT7B | 1.18 | 0.0301 | ST6GALNAC2 | NM_006456 |
| p16-INK4 | 1.18 | 0.0439 | | L27211 |
| TUBB | 1.18 | 0.0761 | TUBB2 | NM_001069 |
| IL6 | 1.18 | 0.0939 | IL6 | NM_000600 |
| RAB32 | 1.18 | 0.0948 | RAB32 | NM_006834 |
| TULP3 | 1.18 | 0.0953 | TULP3 | NM_003324 |
| F3 | 1.17 | 0.0561 | F3 | NM_001993 |
| PLK3 | 1.16 | 0.0792 | PLK3 | NM_004073 |
| EPHA2 | 1.16 | 0.0962 | EPHA2 | NM_004431 |
| SLC2A1 | 1.15 | 0.0745 | SLC2A1 | NM_006516 |
| CXCL12 | 1.14 | 0.0911 | CXCL12 | NM_000609 |
| S100A2 | 1.13 | 0.0287 | S100A2 | NM_005978 |
| FABP4 | 1.13 | 0.0340 | FABP4 | NM_001442 |
| STMY3 | 1.13 | 0.0517 | MMP11 | NM_005940 |
| BCAS1 | 1.13 | 0.0939 | BCAS1 | NM_003657 |
| REG4 | 1.11 | 0.0026 | REG4 | NM_032044 |
| pS2 | 1.09 | 0.0605 | TFF1 | NM_003225 |
| MUC2 | 1.06 | 0.0626 | MUC2 | NM_002457 |

Table 1B shows associations between clinical outcome and gene expression for those genes which demonstrated a Hazard Ratio<1.0 and for which p<0.1. Univariate Cox Proportional Hazards Regression analysis was applied in combined Stage II (Duke's B) and Stage III (Duke's C) patients using RFI as the metric for clinical outcome.

TABLE 1B

| Gene | Hazard Ratio | P Value | Official Symbol | Accession Number |
|---|---|---|---|---|
| ORC1L | 0.42 | 0.0728 | ORC1L | NM_004153 |
| HSPA8 | 0.62 | 0.0430 | HSPA8 | NM_006597 |
| E2F1 | 0.64 | 0.0009 | E2F1 | NM_005225 |
| RAD54L | 0.65 | 0.0026 | RAD54L | NM_003579 |
| RPLPO | 0.67 | 0.0150 | RPLPO | NM_001002 |
| BRCA1 | 0.68 | 0.0001 | BRCA1 | NM_007295 |
| DHFR | 0.69 | 0.0096 | DHFR | NM_000791 |
| SLC25A3 | 0.69 | 0.0110 | SLC25A3 | NM_213611 |
| PPM1D | 0.71 | 0.0033 | PPM1D | NM_003620 |
| SKP2 | 0.71 | 0.0098 | SKP2 | NM_005983 |
| FASN | 0.72 | 0.0071 | FASN | NM_004104 |
| HNRPD | 0.72 | 0.0686 | HNRPD | NM_031370 |
| ENO1 | 0.73 | 0.0418 | ENO1 | NM_001428 |
| RPS13 | 0.75 | 0.0786 | RPS13 | NM_001017 |
| DDB1 | 0.75 | 0.0804 | DDB1 | NM_001923 |
| C20 orf1 | 0.76 | 0.0122 | TPX2 | NM_012112 |
| KIF22 | 0.76 | 0.0137 | KIF22 | NM_007317 |
| Chk1 | 0.76 | 0.0174 | CHEK1 | NM_001274 |
| TCF-1 | 0.77 | 0.0021 | TCF1 | NM_000545 |
| ST14 | 0.77 | 0.0446 | ST14 | NM_021978 |
| RRM1 | 0.77 | 0.0740 | RRM1 | NM_001033 |
| BRCA2 | 0.77 | 0.0800 | BRCA2 | NM_000059 |
| LMNB1 | 0.78 | 0.0513 | LMNB1 | NM_005573 |
| CMYC | 0.79 | 0.0086 | MYC | NM_002467 |
| CDC20 | 0.79 | 0.0290 | CDC20 | NM_001255 |
| CSE1L | 0.79 | 0.0344 | CSE1L | NM_001316 |
| Bax | 0.79 | 0.0662 | BAX | NM_004324 |
| NME1 | 0.79 | 0.0742 | NME1 | NM_000269 |
| c-myb (MYB official) | 0.80 | 0.0077 | MYB | NM_005375 |
| CDCA7 v2 | 0.80 | 0.0159 | CDCA7 | NM_145810 |
| EFP | 0.80 | 0.0405 | TRIM25 | NM_005082 |
| UBE2M | 0.80 | 0.0437 | UBE2M | NM_003969 |
| RRM2 | 0.81 | 0.0168 | RRM2 | NM_001034 |
| ABCC6 | 0.81 | 0.0373 | ABCC6 | NM_001171 |
| SURV | 0.81 | 0.0584 | BIRC5 | NM_001168 |
| CKS2 | 0.81 | 0.0753 | CKS2 | NM_001827 |
| RAF1 | 0.81 | 0.0899 | RAF1 | NM_002880 |
| EPHB2 | 0.82 | 0.0190 | EPHB2 | NM_004442 |
| NOTCH1 | 0.82 | 0.0232 | NOTCH1 | NM_017617 |
| UMPS | 0.82 | 0.0456 | UMPS | NM_000373 |
| CCNE2 | 0.82 | 0.0544 | CCNE2 | NM_057749 |
| PI3KC2A | 0.82 | 0.0916 | PIK3C2A | NM_002645 |
| CD80 | 0.82 | 0.0954 | CD80 | NM_005191 |
| AREG | 0.83 | 0.0014 | AREG | NM_001657 |
| EREG | 0.83 | 0.0062 | EREG | NM_001432 |
| MYBL2 | 0.83 | 0.0259 | MYBL2 | NM_002466 |
| ABCB1 | 0.83 | 0.0322 | ABCB1 | NM_000927 |
| HRAS | 0.83 | 0.0760 | HRAS | NM_005343 |
| SLC7A5 | 0.84 | 0.0585 | SLC7A5 | NM_003486 |
| MAD2L1 | 0.84 | 0.0590 | MAD2L1 | NM_002358 |
| Ki-67 | 0.85 | 0.0620 | MKI67 | NM_002417 |
| MCM2 | 0.85 | 0.0700 | MCM2 | NM_004526 |
| ING5 | 0.85 | 0.0947 | ING5 | NM_032329 |
| Cdx2 | 0.88 | 0.0476 | CDX2 | NM_001265 |
| PTPRO | 0.89 | 0.0642 | PTPRO | NM_030667 |
| cripto (TDGF1 official) | 0.90 | 0.0803 | TDGF1 | NM_003212 |

Table 2A shows associations between clinical outcome and gene expression for those genes which demonstrated a Hazard Ratio>1.0 and for which p<0.1. Univariate Cox Proportional Hazards Regression analysis was applied in combined Stage II (Duke's B) and Stage III (Duke's C) patients using OS as the metric for clinical outcome.

TABLE 2A

| Gene | Hazard Ratio | P Value | Official Symbol | Accession Number |
|---|---|---|---|---|
| RARB | 1.75 | 0.0820 | RARB | NM_016152 |
| RhoC | 1.70 | 0.0001 | RHOC | NM_175744 |
| ANXA2 | 1.64 | 0.0002 | ANXA2 | NM_004039 |

TABLE 2A-continued

| Gene | Hazard Ratio | P Value | Official Symbol | Accession Number |
| --- | --- | --- | --- | --- |
| CYP3A4 | 1.58 | 0.0064 | CYP3A4 | NM_017460 |
| p21 | 1.54 | <.0001 | CDKN1A | NM_000389 |
| ITGB1 | 1.54 | 0.0058 | ITGB1 | NM_002211 |
| UBC | 1.50 | 0.0003 | UBC | NM_021009 |
| TNF | 1.46 | 0.0859 | TNF | NM_000594 |
| VEGFC | 1.44 | 0.0049 | VEGFC | NM_005429 |
| HMLH | 1.44 | 0.0435 | MLH1 | NM_000249 |
| RhoB | 1.37 | 0.0015 | RHOB | NM_004040 |
| TGFBR1 | 1.37 | 0.0127 | TGFBR1 | NM_004612 |
| SPINT2 | 1.37 | 0.0235 | SPINT2 | NM_021102 |
| PFN1 | 1.37 | 0.0842 | PFN1 | NM_005022 |
| HSPG2 | 1.36 | 0.0115 | HSPG2 | NM_005529 |
| TIMP1 | 1.35 | 0.0008 | TIMP1 | NM_003254 |
| INHBB | 1.35 | 0.0190 | INHBB | NM_002193 |
| VCL | 1.34 | 0.0099 | VCL | NM_003373 |
| KCNH2 iso a/b | 1.33 | 0.0362 | KCNH2 | NM_000238 |
| LAMC2 | 1.32 | 0.0005 | LAMC2 | NM_005562 |
| FXYD5 | 1.31 | 0.0021 | FXYD5 | NM_014164 |
| HLA-G | 1.31 | 0.0458 | HLA-G | NM_002127 |
| GADD45B | 1.30 | 0.0002 | GADD45B | NM_015675 |
| CDC42 | 1.30 | 0.0120 | CDC42 | NM_001791 |
| LAMB3 | 1.30 | 0.0163 | LAMB3 | NM_000228 |
| DKK1 | 1.30 | 0.0209 | DKK1 | NM_012242 |
| UNC5C | 1.30 | 0.0452 | UNC5C | NM_003728 |
| UBL1 | 1.29 | 0.0171 | SUMO1 | NM_003352 |
| HB-EGF | 1.29 | 0.0262 | HBEGF | NM_001945 |
| KRAS2 | 1.29 | 0.0726 | KRAS | NM_004985 |
| ID3 | 1.28 | 0.0023 | ID3 | NM_002167 |
| LOXL2 | 1.28 | 0.0039 | LOXL2 | NM_002318 |
| EphB6 | 1.28 | 0.0322 | EPHB6 | NM_004445 |
| DUSP1 | 1.27 | 0.0003 | DUSP1 | NM_004417 |
| BGN | 1.27 | 0.0040 | BGN | NM_001711 |
| CALD1 | 1.27 | 0.0119 | CALD1 | NM_004342 |
| CDC42BPA | 1.27 | 0.0151 | CDC42BPA | NM_003607 |
| SBA2 | 1.27 | 0.0373 | WSB2 | NM_018639 |
| INHBA | 1.26 | 0.0018 | INHBA | NM_002192 |
| NRP1 | 1.26 | 0.0113 | NRP1 | NM_003873 |
| TIMP2 | 1.26 | 0.0123 | TIMP2 | NM_003255 |
| KLF6 | 1.26 | 0.0444 | KLF6 | NM_001300 |
| KLK10 | 1.25 | <.0001 | KLK10 | NM_002776 |
| TIMP3 | 1.25 | 0.0083 | TIMP3 | NM_000362 |
| CAPG | 1.25 | 0.0170 | CAPG | NM_001747 |
| IGFBP7 | 1.25 | 0.0249 | IGFBP7 | NM_001553 |
| S100A1 | 1.25 | 0.0529 | S100A1 | NM_006271 |
| SHC1 | 1.25 | 0.0605 | SHC1 | NM_003029 |
| CTSB | 1.25 | 0.0766 | CTSB | NM_001908 |
| ANXA5 | 1.25 | 0.0787 | ANXA5 | NM_001154 |
| PKR2 | 1.25 | 0.0800 | PKM2 | NM_002654 |
| HSPA1A | 1.24 | 0.0003 | HSPA1A | NM_005345 |
| CGB | 1.24 | 0.0148 | CGB | NM_000737 |
| DLC1 | 1.24 | 0.0231 | DLC1 | NM_006094 |
| TMSB10 | 1.24 | 0.0890 | TMSB10 | NM_021103 |
| LAMA3 | 1.23 | 0.0017 | LAMA3 | NM_000227 |
| FOS | 1.23 | 0.0028 | FOS | NM_005252 |
| SNAI2 | 1.23 | 0.0123 | SNAI2 | NM_003068 |
| SPARC | 1.23 | 0.0134 | SPARC | NM_003118 |
| SIR2 | 1.23 | 0.0173 | SIRT1 | NM_012238 |
| KRT19 | 1.23 | 0.0217 | KRT19 | NM_002276 |
| CTSD | 1.23 | 0.0395 | CTSD | NM_001909 |
| EPAS1 | 1.23 | 0.0409 | EPAS1 | NM_001430 |
| GAGE4 | 1.23 | 0.0468 | GAGE4 | NM_001474 |
| BMP4 | 1.22 | 0.0024 | BMP4 | NM_001202 |
| PLK3 | 1.22 | 0.0056 | PLK3 | NM_004073 |
| Grb10 | 1.22 | 0.0059 | GRB10 | NM_005311 |
| FYN | 1.22 | 0.0120 | FYN | NM_002037 |
| STC1 | 1.22 | 0.0409 | STC1 | NM_003155 |
| G-Catenin | 1.22 | 0.0661 | JUP | NM_002230 |
| HK1 | 1.22 | 0.0872 | HK1 | NM_000188 |
| MADH4 | 1.22 | 0.0956 | SMAD4 | NM_005359 |
| KLK6 | 1.21 | 0.0011 | KLK6 | NM_002774 |
| CTHRC1 | 1.21 | 0.0065 | CTHRC1 | NM_138455 |
| LAT | 1.21 | 0.0146 | LAT | NM_014387 |
| IGFBP3 | 1.21 | 0.0149 | IGFBP3 | NM_000598 |
| AKT3 | 1.21 | 0.0212 | AKT3 | NM_005465 |
| HSPA1B | 1.21 | 0.0262 | HSPA1B | NM_005346 |
| THY1 | 1.21 | 0.0278 | THY1 | NM_006288 |
| ANXA1 | 1.21 | 0.0322 | ANXA1 | NM_000700 |
| LOX | 1.20 | 0.0067 | LOX | NM_002317 |
| CD68 | 1.20 | 0.0223 | CD68 | NM_001251 |
| EFNB2 | 1.20 | 0.0268 | EFNB2 | NM_004093 |
| DYRK1B | 1.20 | 0.0473 | DYRK1B | NM_004714 |
| PTK2 | 1.20 | 0.0889 | PTK2 | NM_005607 |
| THBS1 | 1.19 | 0.0203 | THBS1 | NM_003246 |
| TAGLN | 1.19 | 0.0263 | TAGLN | NM_003186 |
| TULP3 | 1.19 | 0.0334 | TULP3 | NM_003324 |
| SR-A1 | 1.19 | 0.0387 | SR-A1 | NM_021228 |
| APC | 1.19 | 0.0433 | APC | NM_000038 |
| ERK1 | 1.19 | 0.0488 | | Z11696 |
| VIM | 1.19 | 0.0661 | VIM | NM_003380 |
| CREBBP | 1.19 | 0.0802 | CREBBP | NM_004380 |
| ANGPT2 | 1.19 | 0.0860 | ANGPT2 | NM_001147 |
| Maspin | 1.18 | 0.0029 | SERPINB5 | NM_002639 |
| PDGFB | 1.18 | 0.0252 | PDGFB | NM_002608 |
| S100A4 | 1.18 | 0.0270 | S100A4 | NM_002961 |
| EGR1 | 1.18 | 0.0334 | EGR1 | NM_001964 |
| IGFBP5 | 1.18 | 0.0526 | IGFBP5 | NM_000599 |
| NOTCH2 | 1.18 | 0.0527 | NOTCH2 | NM_024408 |
| PAI1 | 1.17 | 0.0036 | SERPINE1 | NM_000602 |
| NR4A1 | 1.17 | 0.0110 | NR4A1 | NM_002135 |
| BCAS1 | 1.17 | 0.0137 | BCAS1 | NM_003657 |
| BRK | 1.17 | 0.0137 | PTK6 | NM_005975 |
| AKAP12 | 1.17 | 0.0195 | AKAP12 | NM_005100 |
| EMP1 | 1.17 | 0.0291 | EMP1 | NM_001423 |
| SIAT4A | 1.17 | 0.0304 | ST3GAL1 | NM_003033 |
| MRP3 | 1.17 | 0.0334 | ABCC3 | NM_003786 |
| COL1A1 | 1.17 | 0.0399 | COL1A1 | NM_000088 |
| Upa | 1.17 | 0.0588 | PLAU | NM_002658 |
| UNC5B | 1.17 | 0.0986 | UNC5B | NM_170744 |
| PDGFC | 1.16 | 0.0355 | PDGFC | NM_016205 |
| MCP1 | 1.16 | 0.0449 | CCL2 | NM_002982 |
| CTGF | 1.16 | 0.0576 | CTGF | NM_001901 |
| COL1A2 | 1.16 | 0.0612 | COL1A2 | NM_000089 |
| RAB32 | 1.16 | 0.0645 | RAB32 | NM_006834 |
| SIN3A | 1.16 | 0.0787 | SIN3A | NM_015477 |
| SKP1A | 1.16 | 0.0837 | SKP1A | NM_006930 |
| EFNA1 | 1.16 | 0.0957 | EFNA1 | NM_004428 |
| S100A2 | 1.15 | 0.0040 | S100A2 | NM_005978 |
| MMP7 | 1.15 | 0.0374 | MMP7 | NM_002423 |
| HOXB7 | 1.15 | 0.0405 | HOXB7 | NM_004502 |
| FAP | 1.15 | 0.0455 | FAP | NM_004460 |
| ANTXR1 | 1.15 | 0.0482 | ANTXR1 | NM_032208 |
| TGFBI | 1.15 | 0.0553 | TGFBI | NM_000358 |
| TMEPAI | 1.14 | 0.0435 | TMEPAI | NM_020182 |
| CYR61 | 1.14 | 0.0490 | CYR61 | NM_001554 |
| SLPI | 1.14 | 0.0724 | SLPI | NM_003064 |
| TP53I3 | 1.14 | 0.0831 | TP53I3 | NM_004881 |
| PDGFA | 1.14 | 0.0845 | | NM_002607 |
| SFRP2 | 1.13 | 0.0255 | SFRP2 | NM_003013 |
| S100A8 | 1.13 | 0.0693 | S100A8 | NM_002964 |
| F3 | 1.13 | 0.0708 | F3 | NM_001993 |
| Bcl2 | 1.13 | 0.0962 | BCL2 | NM_000633 |
| OPN_osteopontin | 1.12 | 0.0097 | SPP1 | NM_000582 |
| FZD6 | 1.12 | 0.0692 | FZD6 | NM_003506 |
| OSM | 1.11 | 0.0744 | OSM | NM_020530 |
| EGLN3 | 1.11 | 0.0884 | EGLN3 | NM_022073 |
| SIAT7B | 1.11 | 0.0938 | ST6GALNAC2 | NM_006456 |
| FABP4 | 1.10 | 0.0454 | FABP4 | NM_001442 |
| EFNA3 | 1.10 | 0.0958 | EFNA3 | NM_004952 |
| MMP2 | 1.10 | 0.0969 | MMP2 | NM_004530 |
| GSTT1 | 1.09 | 0.0737 | GSTT1 | NM_000853 |
| REG4 | 1.07 | 0.0286 | REG4 | NM_032044 |

Table 2B shows associations between clinical outcome and gene expression for those genes which demonstrated a Hazard Ratio<1.0 and for which p<0.1. Univariate Cox Proportional Hazards Regression analysis was applied in combined Stage II (Duke's B) and Stage III (Duke's C) patients using OS as the metric for clinical outcome.

TABLE 2B

| Gene | Hazard Ratio | P Value | Official Symbol | Accession Number |
|---|---|---|---|---|
| HSPA8 | 0.62 | 0.0145 | HSPA8 | NM_006597 |
| SKP2 | 0.70 | 0.0010 | SKP2 | NM_005983 |
| DHFR | 0.74 | 0.0085 | DHFR | NM_000791 |
| PRDX4 | 0.74 | 0.0197 | PRDX4 | NM_006406 |
| RRM1 | 0.75 | 0.0162 | RRM1 | NM_001033 |
| SLC25A3 | 0.75 | 0.0342 | SLC25A3 | NM_213611 |
| RPLPO | 0.75 | 0.0416 | RPLP0 | NM_001002 |
| E2F1 | 0.78 | 0.0190 | E2F1 | NM_005225 |
| SURV | 0.79 | 0.0086 | BIRC5 | NM_001168 |
| c-myb (MYB official) | 0.80 | 0.0020 | MYB | NM_005375 |
| BRCA1 | 0.80 | 0.0077 | BRCA1 | NM_007295 |
| Chk1 | 0.80 | 0.0186 | CHEK1 | NM_001274 |
| ST14 | 0.80 | 0.0407 | ST14 | NM_021978 |
| TCF-1 | 0.81 | 0.0045 | TCF1 | NM_000545 |
| CCNE2 | 0.81 | 0.0112 | CCNE2 | NM_057749 |
| PPM1D | 0.81 | 0.0194 | PPM1D | NM_003620 |
| CDC20 | 0.81 | 0.0213 | CDC20 | NM_001255 |
| EI24 | 0.81 | 0.0585 | EI24 | NM_004879 |
| C20 orf1 | 0.82 | 0.0348 | TPX2 | NM_012112 |
| DUT | 0.83 | 0.0396 | DUT | NM_001948 |
| CD44E | 0.83 | 0.0439 | | X55150 |
| KIF22 | 0.83 | 0.0506 | KIF22 | NM_007317 |
| PPID | 0.83 | 0.0615 | PPID | NM_005038 |
| UBE2M | 0.83 | 0.0805 | UBE2M | NM_003969 |
| LMNB1 | 0.83 | 0.0868 | LMNB1 | NM_005573 |
| MCM2 | 0.84 | 0.0207 | MCM2 | NM_004526 |
| CDC6 | 0.84 | 0.0218 | CDC6 | NM_001254 |
| MRPL40 | 0.84 | 0.0769 | MRPL40 | NM_003776 |
| EPHB2 | 0.85 | 0.0253 | EPHB2 | NM_004442 |
| CMYC | 0.85 | 0.0371 | MYC | NM_002467 |
| AURKB | 0.85 | 0.0375 | AURKB | NM_004217 |
| CDCA7 v2 | 0.85 | 0.0421 | CDCA7 | NM_145810 |
| ABCB1 | 0.86 | 0.0390 | ABCB1 | NM_000927 |
| SMARCA3 | 0.86 | 0.0601 | SMARCA3 | NM_003071 |
| Cdx2 | 0.88 | 0.0166 | CDX2 | NM_001265 |
| PPARG | 0.88 | 0.0645 | PPARG | NM_005037 |
| MYBL2 | 0.88 | 0.0647 | MYBL2 | NM_002466 |
| EREG | 0.89 | 0.0411 | EREG | NM_001432 |
| AREG | 0.90 | 0.0235 | AREG | NM_001657 |

Table 3A shows associations between clinical outcome and gene expression for those genes which demonstrated a Hazard Ratio>1.0 and for which p<0.1. Univariate Cox Proportional Hazards Regression analysis was applied in combined Stage II (Duke's B) and Stage III (Duke's C) patients using DFS as the metric for clinical outcome.

TABLE 3A

| Gene | Hazard Ratio | P Value | Official Symbol | Accession Number |
|---|---|---|---|---|
| ANXA2 | 1.74 | <.0001 | ANXA2 | NM_004039 |
| CYP3A4 | 1.69 | 0.0020 | CYP3A4 | NM_017460 |
| RhoC | 1.53 | 0.0009 | RHOC | NM_175744 |
| TJP1 | 1.45 | 0.0787 | TJP1 | NM_003257 |
| UBC | 1.43 | 0.0007 | UBC | NM_021009 |
| p21 | 1.42 | 0.0004 | CDKN1A | NM_000389 |
| HB-EGF | 1.39 | 0.0032 | HBEGF | NM_001945 |
| SPINT2 | 1.37 | 0.0154 | SPINT2 | NM_021102 |
| HMLH | 1.36 | 0.0711 | MLH1 | NM_000249 |
| VEGFC | 1.35 | 0.0157 | VEGFC | NM_005429 |
| PKR2 | 1.34 | 0.0187 | PKM2 | NM_002654 |
| LAMC2 | 1.33 | 0.0002 | LAMC2 | NM_005562 |
| ITGB1 | 1.33 | 0.0499 | ITGB1 | NM_002211 |
| TIMP1 | 1.32 | 0.0007 | TIMP1 | NM_003254 |
| VCL | 1.31 | 0.0114 | VCL | NM_003373 |
| INHBB | 1.31 | 0.0624 | INHBB | NM_002193 |
| GADD45B | 1.30 | <.0001 | GADD45B | NM_015675 |
| RhoB | 1.30 | 0.0053 | RHOB | NM_004040 |
| DUSP1 | 1.28 | <.0001 | DUSP1 | NM_004417 |
| HK1 | 1.28 | 0.0297 | HK1 | NM_000188 |
| GRIK1 | 1.28 | 0.0364 | GRIK1 | NM_000830 |

TABLE 3A-continued

| Gene | Hazard Ratio | P Value | Official Symbol | Accession Number |
|---|---|---|---|---|
| FOS | 1.27 | 0.0002 | FOS | NM_005252 |
| CGB | 1.27 | 0.0126 | CGB | NM_000737 |
| KLF6 | 1.27 | 0.0288 | KLF6 | NM_001300 |
| ANXA5 | 1.27 | 0.0504 | ANXA5 | NM_001154 |
| KRAS2 | 1.27 | 0.0724 | KRAS | NM_004985 |
| INHBA | 1.26 | 0.0009 | INHBA | NM_002192 |
| DLC1 | 1.26 | 0.0096 | DLC1 | NM_006094 |
| IGFBP7 | 1.26 | 0.0116 | IGFBP7 | NM_001553 |
| BGN | 1.25 | 0.0039 | BGN | NM_001711 |
| LOXL2 | 1.25 | 0.0076 | LOXL2 | NM_002318 |
| STC1 | 1.25 | 0.0135 | STC1 | NM_003155 |
| CTSD | 1.25 | 0.0208 | CTSD | NM_001909 |
| HSPG2 | 1.25 | 0.0485 | HSPG2 | NM_005529 |
| KCNH2 iso a/b | 1.25 | 0.0832 | KCNH2 | NM_000238 |
| TIMP3 | 1.24 | 0.0057 | TIMP3 | NM_000362 |
| FXYD5 | 1.24 | 0.0070 | FXYD5 | NM_014164 |
| A-Catenin | 1.24 | 0.0447 | CTNNA1 | NM_001903 |
| LOX | 1.23 | 0.0013 | LOX | NM_002317 |
| EGR1 | 1.23 | 0.0037 | EGR1 | NM_001964 |
| CAPG | 1.23 | 0.0191 | CAPG | NM_001747 |
| LAMB3 | 1.23 | 0.0377 | LAMB3 | NM_000228 |
| GAGE4 | 1.23 | 0.0402 | GAGE4 | NM_001474 |
| SHC1 | 1.23 | 0.0640 | SHC1 | NM_003029 |
| MVP | 1.23 | 0.0726 | MVP | NM_017458 |
| VEGF | 1.22 | 0.0250 | VEGF | NM_003376 |
| UNC5B | 1.22 | 0.0256 | UNC5B | NM_170744 |
| CDC42BPA | 1.22 | 0.0297 | CDC42BPA | NM_003607 |
| SBA2 | 1.22 | 0.0614 | WSB2 | NM_018639 |
| DKK1 | 1.22 | 0.0689 | DKK1 | NM_012242 |
| EphB6 | 1.22 | 0.0763 | EPHB6 | NM_004445 |
| IGFBP3 | 1.21 | 0.0078 | IGFBP3 | NM_000598 |
| HSPA1B | 1.21 | 0.0167 | HSPA1B | NM_005346 |
| CALD1 | 1.21 | 0.0277 | CALD1 | NM_004342 |
| TIMP2 | 1.21 | 0.0309 | TIMP2 | NM_003255 |
| NR4A1 | 1.20 | 0.0023 | NR4A1 | NM_002135 |
| LAMA3 | 1.20 | 0.0028 | LAMA3 | NM_000227 |
| SIAT4A | 1.20 | 0.0082 | ST3GAL1 | NM_003033 |
| PDGFB | 1.20 | 0.0084 | PDGFB | NM_002608 |
| EMP1 | 1.20 | 0.0107 | EMP1 | NM_001423 |
| THBS1 | 1.20 | 0.0126 | THBS1 | NM_003246 |
| CD68 | 1.20 | 0.0143 | CD68 | NM_001251 |
| FYN | 1.20 | 0.0151 | FYN | NM_002037 |
| TULP3 | 1.20 | 0.0213 | TULP3 | NM_003324 |
| EFNA1 | 1.20 | 0.0254 | EFNA1 | NM_004428 |
| SIR2 | 1.20 | 0.0255 | SIRT1 | NM_012238 |
| G-Catenin | 1.20 | 0.0689 | JUP | NM_002230 |
| S100A1 | 1.20 | 0.0998 | S100A1 | NM_006271 |
| Maspin | 1.19 | 0.0013 | SERPINB5 | NM_002639 |
| HSPA1A | 1.19 | 0.0013 | HSPA1A | NM_005345 |
| SPARC | 1.19 | 0.0359 | SPARC | NM_003118 |
| PTHR1 | 1.19 | 0.0801 | PTHR1 | NM_000316 |
| SNAI2 | 1.18 | 0.0353 | SNAI2 | NM_003068 |
| KRT19 | 1.18 | 0.0419 | KRT19 | NM_002276 |
| ERK1 | 1.18 | 0.0459 | | Z11696 |
| KLK10 | 1.17 | 0.0007 | KLK10 | NM_002776 |
| BMP4 | 1.17 | 0.0121 | BMP4 | NM_001202 |
| CYR61 | 1.17 | 0.0127 | CYR61 | NM_001554 |
| Grb10 | 1.17 | 0.0216 | GRB10 | NM_005311 |
| PLK3 | 1.17 | 0.0242 | PLK3 | NM_004073 |
| EFNB2 | 1.17 | 0.0403 | EFNB2 | NM_004093 |
| P14ARF | 1.17 | 0.0439 | | S78535 |
| ID3 | 1.17 | 0.0446 | ID3 | NM_002167 |
| IGFBP5 | 1.17 | 0.0503 | IGFBP5 | NM_000599 |
| THY1 | 1.17 | 0.0574 | THY1 | NM_006288 |
| VIM | 1.17 | 0.0858 | VIM | NM_003380 |
| EPAS1 | 1.17 | 0.0897 | EPAS1 | NM_001430 |
| PAI1 | 1.16 | 0.0039 | SERPINE1 | NM_000602 |
| F3 | 1.16 | 0.0172 | F3 | NM_001993 |
| CTHRC1 | 1.16 | 0.0181 | CTHRC1 | NM_138455 |
| ANTXR1 | 1.16 | 0.0237 | ANTXR1 | NM_032208 |
| FAP | 1.16 | 0.0289 | FAP | NM_004460 |
| ADAMTS12 | 1.16 | 0.0350 | ADAMTS12 | NM_030955 |
| CTGF | 1.16 | 0.0424 | CTGF | NM_001901 |
| PTGER3 | 1.16 | 0.0569 | PTGER3 | NM_000957 |
| ANXA1 | 1.16 | 0.0699 | ANXA1 | NM_000700 |
| NRP1 | 1.16 | 0.0797 | NRP1 | NM_003873 |
| NDRG1 | 1.16 | 0.0856 | NDRG1 | NM_006096 |

TABLE 3A-continued

| Gene | Hazard Ratio | P Value | Official Symbol | Accession Number |
| --- | --- | --- | --- | --- |
| KLK6 | 1.15 | 0.0092 | KLK6 | NM_002774 |
| EGR3 | 1.15 | 0.0153 | EGR3 | NM_004430 |
| HOXB7 | 1.15 | 0.0345 | HOXB7 | NM_004502 |
| PDGFC | 1.15 | 0.0363 | PDGFC | NM_016205 |
| Herstatin | 1.15 | 0.0403 | | AF177761 |
| MCP1 | 1.15 | 0.0409 | CCL2 | NM_002982 |
| TGFBI | 1.15 | 0.0437 | TGFBI | NM_000358 |
| TP53I3 | 1.15 | 0.0438 | TP53I3 | NM_004881 |
| SLPI | 1.15 | 0.0457 | SLPI | NM_003064 |
| PLAUR | 1.15 | 0.0471 | PLAUR | NM_002659 |
| GJB2 | 1.15 | 0.0610 | GJB2 | NM_004004 |
| COL1A1 | 1.15 | 0.0647 | COL1A1 | NM_000088 |
| IL6 | 1.15 | 0.0790 | IL6 | NM_000600 |
| APC | 1.15 | 0.0821 | APC | NM_000038 |
| S100A2 | 1.14 | 0.0048 | S100A2 | NM_005978 |
| TMEPAI | 1.14 | 0.0300 | TMEPAI | NM_020182 |
| PDGFA | 1.14 | 0.0644 | | NM_002607 |
| S100A4 | 1.14 | 0.0680 | S100A4 | NM_002961 |
| TAGLN | 1.14 | 0.0820 | TAGLN | NM_003186 |
| Upa | 1.14 | 0.0823 | PLAU | NM_002658 |
| COL1A2 | 1.14 | 0.0856 | COL1A2 | NM_000089 |
| OSM | 1.13 | 0.0299 | OSM | NM_020530 |
| BRK | 1.13 | 0.0479 | PTK6 | NM_005975 |
| SEMA3B | 1.13 | 0.0525 | SEMA3B | NM_004636 |
| OPN_osteopontin | 1.12 | 0.0084 | SPP1 | NM_000582 |
| S100P | 1.12 | 0.0283 | S100P | NM_005980 |
| SFRP2 | 1.12 | 0.0291 | SFRP2 | NM_003013 |
| EGLN3 | 1.12 | 0.0465 | EGLN3 | NM_022073 |
| SIAT7B | 1.12 | 0.0570 | ST6GALNAC2 | NM_006456 |
| MMP7 | 1.12 | 0.0743 | MMP7 | NM_002423 |
| FABP4 | 1.11 | 0.0195 | FABP4 | NM_001442 |
| AKAP12 | 1.11 | 0.0899 | AKAP12 | NM_005100 |
| EFNA3 | 1.10 | 0.0684 | EFNA3 | NM_004952 |
| SFRP4 | 1.10 | 0.0684 | SFRP4 | NM_003014 |
| CRYAB | 1.10 | 0.0987 | CRYAB | NM_001885 |
| GSTT1 | 1.09 | 0.0457 | GSTT1 | NM_000853 |
| REG4 | 1.08 | 0.0074 | REG4 | NM_032044 |
| pS2 | 1.08 | 0.0302 | TFF1 | NM_003225 |
| MUC5B | 1.08 | 0.0401 | MUC5B | XM_039877 |
| IGFBP2 | 1.08 | 0.0873 | IGFBP2 | NM_000597 |

Table 3B shows associations between clinical outcome and gene expression for those genes which demonstrated a Hazard Ratio<1.0 and for which p<0.1. Univariate Cox Proportional Hazards Regression analysis was applied in combined Stage II (Duke's B) and Stage III (Duke's C) patients using DFS as the metric for clinical outcome.

TABLE 3B

| Gene | Hazard Ratio | P Value | Official Symbol | Accession Number |
| --- | --- | --- | --- | --- |
| HSPA8 | 0.70 | 0.0487 | HSPA8 | NM_006597 |
| SLC25A3 | 0.71 | 0.0084 | SLC25A3 | NM_213611 |
| E2F1 | 0.73 | 0.0019 | E2F1 | NM_005225 |
| SKP2 | 0.73 | 0.0038 | SKP2 | NM_005983 |
| PPM1D | 0.75 | 0.0008 | PPM1D | NM_003620 |
| RRM1 | 0.76 | 0.0161 | RRM1 | NM_001033 |
| RPLPO | 0.76 | 0.0388 | RPLPO | NM_001002 |
| NPM1 | 0.78 | 0.0223 | NPM1 | NM_002520 |
| DDB1 | 0.78 | 0.0673 | DDB1 | NM_001923 |
| PRDX4 | 0.79 | 0.0526 | PRDX4 | NM_006406 |
| BRCA1 | 0.80 | 0.0051 | BRCA1 | NM_007295 |
| Chk1 | 0.80 | 0.0114 | CHEK1 | NM_001274 |
| SURV | 0.81 | 0.0155 | BIRC5 | NM_001168 |
| C20 orf1 | 0.81 | 0.0195 | TPX2 | NM_012112 |
| EI24 | 0.81 | 0.0382 | EI24 | NM_004879 |
| RAD54L | 0.81 | 0.0501 | RAD54L | NM_003579 |
| DHFR | 0.81 | 0.0530 | DHFR | NM_000791 |
| c-myb (MYB official) | 0.82 | 0.0029 | MYB | NM_005375 |
| CCNE2 | 0.82 | 0.0109 | CCNE2 | NM_057749 |
| KIF22 | 0.82 | 0.0235 | KIF22 | NM_007317 |

TABLE 3B-continued

| Gene | Hazard Ratio | P Value | Official Symbol | Accession Number |
| --- | --- | --- | --- | --- |
| HMGB1 | 0.82 | 0.0849 | HMGB1 | NM_002128 |
| LMNB1 | 0.83 | 0.0665 | LMNB1 | NM_005573 |
| CDCA7 v2 | 0.84 | 0.0224 | CDCA7 | NM_145810 |
| CDC20 | 0.84 | 0.0461 | CDC20 | NM_001255 |
| FASN | 0.84 | 0.0797 | FASN | NM_004104 |
| ABCB1 | 0.85 | 0.0157 | ABCB1 | NM_000927 |
| MCM2 | 0.85 | 0.0183 | MCM2 | NM_004526 |
| DUT | 0.85 | 0.0469 | DUT | NM_001948 |
| KIF2C | 0.85 | 0.0786 | KIF2C | NM_006845 |
| MCM6 | 0.85 | 0.0791 | MCM6 | NM_005915 |
| EIF4E | 0.85 | 0.0863 | EIF4E | NM_001968 |
| EPHB2 | 0.86 | 0.0271 | EPHB2 | NM_004442 |
| RCC1 | 0.86 | 0.0444 | RCC1 | NM_001269 |
| EFP | 0.86 | 0.0760 | TRIM25 | NM_005082 |
| AREG | 0.87 | 0.0029 | AREG | NM_001657 |
| CMYC | 0.87 | 0.0483 | MYC | NM_002467 |
| GCLC | 0.87 | 0.0824 | GCLC | NM_001498 |
| TCF-1 | 0.88 | 0.0520 | TCF1 | NM_000545 |
| MYBL2 | 0.88 | 0.0527 | MYBL2 | NM_002466 |
| EREG | 0.89 | 0.0237 | EREG | NM_001432 |
| Cdx2 | 0.90 | 0.0353 | CDX2 | NM_001265 |
| PTPRO | 0.92 | 0.0896 | PTPRO | NM_030667 |
| cripto (TDGF1 official) | 0.92 | 0.0913 | TDGF1 | NM_003212 |
| HLA-DRB1 | 0.93 | 0.0536 | HLA-DRB1 | NM_002124 |

Table 4A shows associations between clinical outcome and gene expression for those genes which demonstrated a Hazard Ratio>1.0 and for which p<0.1. Univariate Cox Proportional Hazards Regression analysis was applied in combined Stage II (Duke's B) and Stage III (Duke's C) patients using DRFI as the metric for clinical outcome.

TABLE 4A

| Gene | Hazard Ratio | P Value | Official Symbol | Accession Number |
| --- | --- | --- | --- | --- |
| ALDOA | 3.37 | 0.0106 | ALDOA | NM_000034 |
| DCK | 2.74 | 0.0130 | DCK | NM_000788 |
| ITGB1 | 2.50 | <0.0001 | ITGB1 | NM_002211 |
| COX2 | 2.15 | 0.0128 | PTGS2 | NM_000963 |
| TJP1 | 2.12 | 0.0072 | TJP1 | NM_003257 |
| STAT3 | 1.98 | 0.0062 | STAT3 | NM_003150 |
| HMLH | 1.93 | 0.0087 | MLH1 | NM_000249 |
| CYP3A4 | 1.90 | 0.0092 | CYP3A4 | NM_017460 |
| RhoC | 1.89 | 0.0033 | RHOC | NM_175744 |
| ANXA2 | 1.87 | 0.0025 | ANXA2 | NM_004039 |
| TIMP1 | 1.83 | <0.0001 | TIMP1 | NM_003254 |
| WWOX | 1.81 | 0.0288 | WWOX | NM_016373 |
| ANXA5 | 1.80 | 0.0029 | ANXA5 | NM_001154 |
| FUS | 1.79 | 0.0179 | FUS | NM_004960 |
| PADI4 | 1.78 | 0.0168 | PADI4 | NM_012387 |
| RBX1 | 1.71 | 0.0082 | RBX1 | NM_014248 |
| CRIP2 | 1.71 | 0.0343 | CRIP2 | NM_001312 |
| HB-EGF | 1.69 | 0.0013 | HBEGF | NM_001945 |
| KCNH2 iso a/b | 1.69 | 0.0070 | KCNH2 | NM_000238 |
| SBA2 | 1.68 | 0.0066 | WSB2 | NM_018639 |
| RhoB | 1.67 | 0.0010 | RHOB | NM_004040 |
| VIM | 1.66 | 0.0010 | VIM | NM_003380 |
| LILRB3 | 1.66 | 0.0227 | LILRB3 | NM_006864 |
| UBC | 1.64 | 0.0051 | UBC | NM_021009 |
| p21 | 1.63 | 0.0032 | CDKN1A | NM_000389 |
| CCNE2 variant 1 | 1.62 | 0.0363 | CCNE2 | NM_057749 |
| RAB6C | 1.61 | 0.0107 | RAB6C | NM_032144 |
| MSH3 | 1.61 | 0.0213 | MSH3 | NM_002439 |
| AKT3 | 1.59 | 0.0003 | AKT3 | NM_005465 |
| PI3K | 1.58 | 0.0552 | PIK3C2B | NM_002646 |
| RAP1GDS1 | 1.57 | 0.0154 | RAP1GDS1 | NM_021159 |
| CTSB | 1.57 | 0.0250 | CTSB | NM_001908 |
| PRDX6 | 1.57 | 0.0770 | PRDX6 | NM_004905 |
| NRP2 | 1.56 | 0.0005 | NRP2 | NM_003872 |
| DLC1 | 1.56 | 0.0026 | DLC1 | NM_006094 |
| BGN | 1.55 | 0.0006 | BGN | NM_001711 |

TABLE 4A-continued

| Gene | Hazard Ratio | P Value | Official Symbol | Accession Number |
|---|---|---|---|---|
| SIR2 | 1.55 | 0.0016 | SIRT1 | NM_012238 |
| CALD1 | 1.53 | 0.0046 | CALD1 | NM_004342 |
| YWHAH | 1.53 | 0.0429 | YWHAH | NM_003405 |
| CDC42 | 1.52 | 0.0207 | CDC42 | NM_001791 |
| ITGA5 | 1.51 | 0.0004 | ITGA5 | NM_002205 |
| KLF6 | 1.51 | 0.0197 | KLF6 | NM_001300 |
| TLN1 | 1.51 | 0.0414 | TLN1 | NM_006289 |
| LAMC2 | 1.49 | 0.0017 | LAMC2 | NM_005562 |
| STC1 | 1.49 | 0.0040 | STC1 | NM_003155 |
| CDC42BPA | 1.49 | 0.0109 | CDC42BPA | NM_003607 |
| RBM5 | 1.49 | 0.0184 | RBM5 | NM_005778 |
| INHBB | 1.49 | 0.0310 | INHBB | NM_002193 |
| TGFBR1 | 1.49 | 0.0502 | TGFBR1 | NM_004612 |
| ADAM10 | 1.49 | 0.0819 | ADAM10 | NM_001110 |
| CEBPB | 1.48 | 0.0399 | CEBPB | NM_005194 |
| AKT1 | 1.48 | 0.0846 | AKT1 | NM_005163 |
| FYN | 1.47 | 0.0036 | FYN | NM_002037 |
| ARG | 1.47 | 0.0067 | ABL2 | NM_005158 |
| HIF1A | 1.47 | 0.0221 | HIF1A | NM_001530 |
| S100A1 | 1.47 | 0.0293 | S100A1 | NM_006271 |
| KRAS2 | 1.47 | 0.0958 | KRAS | NM_004985 |
| CTHRC1 | 1.46 | 0.0008 | CTHRC1 | NM_138455 |
| IGFBP7 | 1.46 | 0.0173 | IGFBP7 | NM_001553 |
| ROCK1 | 1.46 | 0.0326 | ROCK1 | NM_005406 |
| VEGFC | 1.46 | 0.0516 | VEGFC | NM_005429 |
| EPAS1 | 1.45 | 0.0316 | EPAS1 | NM_001430 |
| DUSP1 | 1.44 | 0.0008 | DUSP1 | NM_004417 |
| FST | 1.44 | 0.0340 | FST | NM_006350 |
| GADD45B | 1.43 | 0.0013 | GADD45B | NM_015675 |
| FLT4 | 1.43 | 0.0663 | FLT4 | NM_002020 |
| PTEN | 1.43 | 0.0760 | PTEN | NM_000314 |
| FAP | 1.42 | 0.0017 | FAP | NM_004460 |
| PDGFC | 1.42 | 0.0033 | PDGFC | NM_016205 |
| LOXL2 | 1.42 | 0.0115 | LOXL2 | NM_002318 |
| Pak1 | 1.42 | 0.0846 | PAK1 | NM_002576 |
| Grb10 | 1.41 | 0.0020 | GRB10 | NM_005311 |
| INHBA | 1.41 | 0.0036 | INHBA | NM_002192 |
| GJA1 | 1.41 | 0.0039 | GJA1 | NM_000165 |
| CTGF | 1.41 | 0.0053 | CTGF | NM_001901 |
| COL1A2 | 1.41 | 0.0057 | COL1A2 | NM_000089 |
| PTK2 | 1.40 | 0.0496 | PTK2 | NM_005607 |
| THBS1 | 1.39 | 0.0059 | THBS1 | NM_003246 |
| RANBP9 | 1.39 | 0.0333 | RANBP9 | NM_005493 |
| RANBP2 | 1.39 | 0.0988 | RANBP2 | NM_006267 |
| ITGAV | 1.38 | 0.0210 | ITGAV | NM_002210 |
| TIMP2 | 1.38 | 0.0285 | TIMP2 | NM_003255 |
| PTHR1 | 1.38 | 0.0297 | PTHR1 | NM_000316 |
| GADD45 | 1.38 | 0.0340 | GADD45A | NM_001924 |
| c-abl | 1.38 | 0.0526 | ABL1 | NM_005157 |
| EGR1 | 1.37 | 0.0097 | EGR1 | NM_001964 |
| NCAM1 | 1.37 | 0.0657 | NCAM1 | NM_000615 |
| VCL | 1.37 | 0.0845 | VCL | NM_003373 |
| LOX | 1.36 | 0.0026 | LOX | NM_002317 |
| SNAI2 | 1.36 | 0.0178 | SNAI2 | NM_003068 |
| SPARC | 1.36 | 0.0198 | SPARC | NM_003118 |
| CDH11 | 1.36 | 0.0233 | CDH11 | NM_001797 |
| NFKBp50 | 1.36 | 0.0767 | NFKB1 | NM_003998 |
| CYR61 | 1.35 | 0.0065 | CYR61 | NM_001554 |
| S100A4 | 1.35 | 0.0104 | S100A4 | NM_002961 |
| TAGLN | 1.35 | 0.0168 | TAGLN | NM_003186 |
| PCAF | 1.34 | 0.0327 | PCAF | NM_003884 |
| NOTCH2 | 1.34 | 0.0390 | NOTCH2 | NM_024408 |
| LRP5 | 1.34 | 0.0722 | LRP5 | NM_002335 |
| SI | 1.34 | 0.0787 | SI | NM_001041 |
| GBP2 | 1.33 | 0.0139 | GBP2 | NM_004120 |
| Bcl2 | 1.33 | 0.0143 | BCL2 | NM_000633 |
| MCP1 | 1.33 | 0.0159 | CCL2 | NM_002982 |
| EPHA2 | 1.33 | 0.0184 | EPHA2 | NM_004431 |
| PRKCA | 1.33 | 0.0329 | PRKCA | NM_002737 |
| TIMP3 | 1.33 | 0.0337 | TIMP3 | NM_000362 |
| ANGPT2 | 1.33 | 0.0476 | ANGPT2 | NM_001147 |
| CTSD | 1.33 | 0.0766 | CTSD | NM_001909 |
| SEMA3F | 1.33 | 0.0931 | SEMA3F | NM_004186 |
| BCAS1 | 1.32 | 0.0044 | BCAS1 | NM_003657 |
| ANXA1 | 1.32 | 0.0458 | ANXA1 | NM_000700 |
| KRT19 | 1.32 | 0.0535 | KRT19 | NM_002276 |
| PTPRJ | 1.32 | 0.0618 | PTPRJ | NM_002843 |
| CAPG | 1.32 | 0.0641 | CAPG | NM_001747 |
| FOS | 1.31 | 0.0129 | FOS | NM_005252 |
| COL1A1 | 1.31 | 0.0236 | COL1A1 | NM_000088 |
| CXCR4 | 1.31 | 0.0251 | CXCR4 | NM_003467 |
| TUBB | 1.31 | 0.0354 | TUBB2 | NM_001069 |
| PIM1 | 1.31 | 0.0373 | PIM1 | NM_002648 |
| IGFBP5 | 1.31 | 0.0477 | IGFBP5 | NM_000599 |
| AP-1 (JUN official) | 1.31 | 0.0519 | JUN | NM_002228 |
| GCNT1 | 1.31 | 0.0534 | GCNT1 | NM_001490 |
| MAX | 1.31 | 0.0650 | MAX | NM_002382 |
| PAI1 | 1.30 | 0.0017 | SERPINE1 | NM_000602 |
| SLPI | 1.30 | 0.0176 | SLPI | NM_003064 |
| IGFBP3 | 1.30 | 0.0320 | IGFBP3 | NM_000598 |
| DAPK1 | 1.30 | 0.0402 | DAPK1 | NM_004938 |
| ID3 | 1.30 | 0.0442 | ID3 | NM_002167 |
| EFNA1 | 1.30 | 0.0623 | EFNA1 | NM_004428 |
| AKAP12 | 1.29 | 0.0162 | AKAP12 | NM_005100 |
| PDGFB | 1.29 | 0.0242 | PDGFB | NM_002608 |
| CD68 | 1.29 | 0.0524 | CD68 | NM_001251 |
| FGFR1 | 1.29 | 0.0709 | FGFR1 | NM_023109 |
| GSK3B | 1.29 | 0.0765 | GSK3B | NM_002093 |
| CXCL12 | 1.28 | 0.0129 | CXCL12 | NM_000609 |
| DPYD | 1.28 | 0.0186 | DPYD | NM_000110 |
| LAMA3 | 1.28 | 0.0193 | LAMA3 | NM_000227 |
| MRP3 | 1.28 | 0.0384 | ABCC3 | NM_003786 |
| ABCC5 | 1.28 | 0.0402 | ABCC5 | NM_005688 |
| PDGFA | 1.28 | 0.0482 | | NM_002607 |
| XPA | 1.28 | 0.0740 | XPA | NM_000380 |
| NDRG1 | 1.28 | 0.0786 | NDRG1 | NM_006096 |
| FES | 1.27 | 0.0458 | FES | NM_002005 |
| CTSL | 1.27 | 0.0485 | CTSL | NM_001912 |
| IL6 | 1.27 | 0.0606 | IL6 | NM_000600 |
| SFRP2 | 1.26 | 0.0085 | SFRP2 | NM_003013 |
| Maspin | 1.26 | 0.0096 | SERPINB5 | NM_002639 |
| TGFBI | 1.26 | 0.0470 | TGFBI | NM_000358 |
| NOS3 | 1.26 | 0.0978 | NOS3 | NM_000603 |
| HSPA1A | 1.25 | 0.0161 | HSPA1A | NM_005345 |
| S100A8 | 1.25 | 0.0180 | S100A8 | NM_002964 |
| HOXB7 | 1.25 | 0.0396 | HOXB7 | NM_004502 |
| P14ARF | 1.25 | 0.0697 | | S78535 |
| WISP1 | 1.25 | 0.0712 | WISP1 | NM_003882 |
| ID4 | 1.25 | 0.0883 | ID4 | NM_001546 |
| SFRP4 | 1.24 | 0.0200 | SFRP4 | NM_003014 |
| FZD6 | 1.24 | 0.0220 | FZD6 | NM_003506 |
| EGR3 | 1.24 | 0.0237 | EGR3 | NM_004430 |
| ALDH1A1 | 1.24 | 0.0258 | ALDH1A1 | NM_000689 |
| CRYAB | 1.23 | 0.0394 | CRYAB | NM_001885 |
| TGFB3 | 1.23 | 0.0541 | TGFB3 | NM_003239 |
| ANTXR1 | 1.23 | 0.0661 | ANTXR1 | NM_032208 |
| KLK6 | 1.22 | 0.0211 | KLK6 | NM_002774 |
| ILT-2 | 1.22 | 0.0676 | LILRB1 | NM_006669 |
| EMP1 | 1.22 | 0.0871 | EMP1 | NM_001423 |
| PLAUR | 1.22 | 0.0943 | PLAUR | NM_002659 |
| S100A2 | 1.20 | 0.0100 | S100A2 | NM_005978 |
| MMP7 | 1.19 | 0.0810 | MMP7 | NM_002423 |
| OPN_osteopontin | 1.17 | 0.0231 | SPP1 | NM_000582 |
| FABP4 | 1.17 | 0.0325 | FABP4 | NM_001442 |
| KLK10 | 1.17 | 0.0452 | KLK10 | NM_002776 |
| PS2 | 1.16 | 0.0140 | TFF1 | NM_003225 |
| STMY3 | 1.15 | 0.0850 | MMP11 | NM_005940 |
| REG4 | 1.14 | 0.0042 | REG4 | NM_032044 |
| MUC2 | 1.09 | 0.0370 | MUC2 | NM_002457 |

Table 4B shows associations between clinical outcome and gene expression for those genes which demonstrated a Hazard Ratio<1.0 and for which p<0.1. Univariate Cox Proportional Hazards Regression analysis was applied in combined Stage II (Duke's B) and Stage III (Duke's C) patients using DRFI as the metric for clinical outcome.

| Gene | Hazard Ratio | P Value | Official Symbol | Accession Number |
|---|---|---|---|---|
| HSPA8 | 0.51 | 0.0261 | HSPA8 | NM_006597 |
| RPS13 | 0.58 | 0.0089 | RPS13 | NM_001017 |
| RPLPO | 0.63 | 0.0324 | RPLP0 | NM_001002 |
| NDUFS3 | 0.66 | 0.0142 | NDUFS3 | NM_004551 |
| LMNB1 | 0.67 | 0.0202 | LMNB1 | NM_005573 |
| ST14 | 0.67 | 0.0206 | ST14 | NM_021978 |
| BRCA1 | 0.68 | 0.0032 | BRCA1 | NM_007295 |
| TMSB4X | 0.68 | 0.0075 | TMSB4X | NM_021109 |
| DHFR | 0.68 | 0.0356 | DHFR | NM_000791 |
| SKP2 | 0.69 | 0.0248 | SKP2 | NM_005983 |
| TCF-1 | 0.70 | 0.0015 | TCF1 | NM_000545 |
| CDC20 | 0.70 | 0.0067 | CDC20 | NM_001255 |
| SLC25A3 | 0.70 | 0.0418 | SLC25A3 | NM_213611 |
| NME1 | 0.72 | 0.0503 | NME1 | NM_000269 |
| RRM1 | 0.72 | 0.0850 | RRM1 | NM_001033 |
| MCM2 | 0.76 | 0.0168 | MCM2 | NM_004526 |
| ABCC6 | 0.76 | 0.0445 | ABCC6 | NM_001171 |
| CKS2 | 0.76 | 0.0869 | CKS2 | NM_001827 |
| EPHB2 | 0.77 | 0.0174 | EPHB2 | NM_004442 |
| C20 orf1 | 0.77 | 0.0716 | TPX2 | NM_012112 |
| CSEL1 | 0.77 | 0.0725 | CSE1L | NM_001316 |
| NFKBp65 | 0.78 | 0.0957 | RELA | NM_021975 |
| AURKB | 0.79 | 0.0742 | AURKB | NM_004217 |
| CMYC | 0.82 | 0.0901 | MYC | NM_002467 |
| Cdx2 | 0.85 | 0.0510 | CDX2 | NM_001265 |
| EREG | 0.85 | 0.0730 | EREG | NM_001432 |
| AREG | 0.86 | 0.0365 | AREG | NM_001657 |

Table 5A shows associations between gene expression and RFI, controlling for particular demographic and clinical characteristics of patients included in the analysis. All genes are listed whose expression correlates with RFI (p<0.1) and which demonstrated a Hazard Ratio>1 in a multivariate analysis including the following variables: tumor location, surgery, tumor grade, nodes examined, and number of positive nodes.

TABLE 5A

| Gene | HR | LR Chi-Square | DF | P-Value |
|---|---|---|---|---|
| RARB | 2.06780 | 4.23265 | 1 | 0.03965 |
| CYP3A4 | 1.85387 | 7.99462 | 1 | 0.00469 |
| ANXA2 | 1.80012 | 10.84166 | 1 | 0.00099 |
| COX2 | 1.79051 | 4.52307 | 1 | 0.03344 |
| RhoC | 1.73986 | 9.97133 | 1 | 0.00159 |
| MAPK14 | 1.68382 | 8.04253 | 1 | 0.00457 |
| UBC | 1.67323 | 11.69444 | 1 | 0.00063 |
| RhoB | 1.66612 | 15.92497 | 1 | 0.00007 |
| ITGB1 | 1.65796 | 8.18638 | 1 | 0.00422 |
| KRAS2 | 1.63873 | 6.80447 | 1 | 0.00909 |
| NTN1 | 1.61833 | 5.43469 | 1 | 0.01974 |
| ATP5E | 1.60990 | 4.93660 | 1 | 0.02629 |
| G-Catenin | 1.58482 | 9.24422 | 1 | 0.00236 |
| STC1 | 1.58163 | 11.10757 | 1 | 0.00086 |
| SPINT2 | 1.52653 | 6.17276 | 1 | 0.01297 |
| Claudin 4 | 1.50290 | 12.29943 | 1 | 0.00045 |
| IGFBP7 | 1.48789 | 9.62569 | 1 | 0.00192 |
| NCAM1 | 1.48294 | 5.11428 | 1 | 0.02373 |
| TIMP1 | 1.46045 | 9.98492 | 1 | 0.00158 |
| CEBPB | 1.46025 | 5.23659 | 1 | 0.02212 |
| KCNH2 iso a/b | 1.44616 | 3.97304 | 1 | 0.04623 |
| TMSB10 | 1.43107 | 4.65463 | 1 | 0.03097 |
| VEGFC | 1.41860 | 4.66918 | 1 | 0.03071 |
| HB-EGF | 1.41757 | 7.00399 | 1 | 0.00813 |
| FST | 1.41061 | 5.59674 | 1 | 0.01799 |
| LAMC2 | 1.40860 | 11.33997 | 1 | 0.00076 |
| GADD45B | 1.40671 | 12.26323 | 1 | 0.00046 |
| AKT3 | 1.40161 | 10.13028 | 1 | 0.00146 |
| EFNA1 | 1.40048 | 8.86645 | 1 | 0.00290 |
| p21 | 1.39939 | 5.42981 | 1 | 0.01980 |
| INHBA | 1.38204 | 11.03909 | 1 | 0.00089 |
| CALD1 | 1.38009 | 6.93406 | 1 | 0.00846 |
| DUSP1 | 1.36464 | 13.04379 | 1 | 0.00030 |
| HSPG2 | 1.36387 | 4.11749 | 1 | 0.04244 |
| GJB2 | 1.36358 | 8.42204 | 1 | 0.00371 |
| EPAS1 | 1.36323 | 4.74318 | 1 | 0.02941 |
| BGN | 1.35821 | 7.66947 | 1 | 0.00562 |
| TIMP2 | 1.35571 | 5.78791 | 1 | 0.01614 |
| A-Catenin | 1.35566 | 4.35623 | 1 | 0.03687 |
| LOXL2 | 1.35470 | 7.23663 | 1 | 0.00714 |
| DKK1 | 1.35126 | 3.88504 | 1 | 0.04872 |
| ITGAV | 1.34899 | 8.03554 | 1 | 0.00459 |
| CGB | 1.34840 | 7.06221 | 1 | 0.00787 |
| EGR1 | 1.33424 | 8.41855 | 1 | 0.00371 |
| TIMP3 | 1.33197 | 6.28550 | 1 | 0.01217 |
| VIM | 1.33196 | 4.92198 | 1 | 0.02652 |
| TGFBI | 1.32511 | 8.30278 | 1 | 0.00396 |
| FXYD5 | 1.32500 | 6.22751 | 1 | 0.01258 |
| VEGF | 1.32291 | 4.93825 | 1 | 0.02627 |
| ADAMTS12 | 1.31794 | 7.46749 | 1 | 0.00628 |
| SLPI | 1.31565 | 8.38324 | 1 | 0.00379 |
| DLC1 | 1.30862 | 5.51638 | 1 | 0.01884 |
| HOXB7 | 1.30822 | 8.04076 | 1 | 0.00457 |
| TMEPAI | 1.30395 | 8.43736 | 1 | 0.00368 |
| IGFBP5 | 1.30260 | 5.44022 | 1 | 0.01968 |
| CDC42BPA | 1.30167 | 4.20771 | 1 | 0.04024 |
| PDGFA | 1.29760 | 5.54964 | 1 | 0.01848 |
| GSTp | 1.29594 | 3.96268 | 1 | 0.04652 |
| FOS | 1.29427 | 8.42847 | 1 | 0.00369 |
| PDGFC | 1.28813 | 6.81737 | 1 | 0.00903 |
| IGFBP3 | 1.28701 | 6.33625 | 1 | 0.01183 |
| LOX | 1.28433 | 8.15598 | 1 | 0.00429 |
| SPARC | 1.28260 | 4.75876 | 1 | 0.02915 |
| EFNB2 | 1.27720 | 4.71247 | 1 | 0.02994 |
| Maspin | 1.27645 | 10.57657 | 1 | 0.00115 |
| THBS1 | 1.27619 | 6.61087 | 1 | 0.01014 |
| TAGLN | 1.26904 | 5.15123 | 1 | 0.02323 |
| VEGF_altsplice1 | 1.26734 | 5.29282 | 1 | 0.02141 |
| S100P | 1.26586 | 9.88713 | 1 | 0.00166 |
| HSPA1A | 1.26209 | 8.59704 | 1 | 0.00337 |
| MAD | 1.26112 | 3.96163 | 1 | 0.04655 |
| ANGPT2 | 1.25701 | 3.91148 | 1 | 0.04796 |
| PRKCA | 1.24853 | 4.69452 | 1 | 0.03026 |
| F3 | 1.24848 | 5.06788 | 1 | 0.02437 |
| FAP | 1.24657 | 5.19589 | 1 | 0.02264 |
| BRK | 1.24507 | 5.44048 | 1 | 0.01968 |
| CD68 | 1.23943 | 4.02530 | 1 | 0.04482 |
| NR4A1 | 1.23772 | 7.09548 | 1 | 0.00773 |
| CTHRC1 | 1.23465 | 5.21100 | 1 | 0.02244 |
| SLC2A1 | 1.22967 | 5.22364 | 1 | 0.02228 |
| Grb10 | 1.22209 | 4.12811 | 1 | 0.04218 |
| p16-INK4 | 1.21325 | 4.44296 | 1 | 0.03505 |
| MDK | 1.21116 | 5.25025 | 1 | 0.02194 |
| CYR61 | 1.19995 | 4.14452 | 1 | 0.04177 |
| LAMA3 | 1.19794 | 4.33073 | 1 | 0.03743 |
| FOXO3A | 1.19557 | 4.20079 | 1 | 0.04041 |
| EFNA3 | 1.19439 | 5.51728 | 1 | 0.01883 |
| CRYAB | 1.17514 | 3.90435 | 1 | 0.04816 |
| CEACAM6 | 1.16804 | 3.96486 | 1 | 0.04646 |
| OPN_osteopontin | 1.16112 | 5.50891 | 1 | 0.01892 |
| KLK10 | 1.15851 | 5.65625 | 1 | 0.01739 |
| SFRP2 | 1.15773 | 4.02893 | 1 | 0.04473 |
| KLK6 | 1.15163 | 4.65953 | 1 | 0.03088 |
| S100A2 | 1.14185 | 3.94284 | 1 | 0.04707 |
| REG4 | 1.09037 | 4.16995 | 1 | 0.04115 |

Table 5B shows associations between gene expression and RFI, controlling for particular demographic and clinical characteristics of patients included in the analysis. All genes are listed whose expression correlates with RFI (p<0.1) and which demonstrated a Hazard Ratio<1 in a multivariate analysis including the following variables: tumor location, surgery, tumor grade, nodes examined, and number of positive nodes.

TABLE 5B

| Gene | HR | LR Chi-Square | DF | P-Value |
|---|---|---|---|---|
| BFGF | 0.46674 | 6.95233 | 1 | 0.00837 |
| Fasl | 0.47324 | 4.08714 | 1 | 0.04321 |
| KLRK1 | 0.63331 | 10.28820 | 1 | 0.00134 |
| DHFR | 0.64947 | 7.64434 | 1 | 0.00570 |
| BRCA1 | 0.65247 | 15.21566 | 1 | 0.00010 |
| SLC25A3 | 0.67480 | 5.72977 | 1 | 0.01668 |
| RAD54L | 0.68215 | 5.38684 | 1 | 0.02029 |
| PPM1D | 0.68777 | 10.02879 | 1 | 0.00154 |
| CD80 | 0.69347 | 8.70087 | 1 | 0.00318 |
| ATP5A1 | 0.70467 | 4.06718 | 1 | 0.04372 |
| PRKCB1 | 0.73152 | 5.21950 | 1 | 0.02234 |
| KIF22 | 0.73945 | 5.13202 | 1 | 0.02349 |
| Chk1 | 0.75865 | 4.38139 | 1 | 0.03633 |
| TRAIL | 0.76430 | 4.12533 | 1 | 0.04225 |
| CDC20 | 0.77071 | 5.04557 | 1 | 0.02469 |
| DUT | 0.78196 | 4.13381 | 1 | 0.04203 |
| ABCB1 | 0.79434 | 5.33783 | 1 | 0.02087 |
| UMPS | 0.80011 | 4.65425 | 1 | 0.03098 |
| ING5 | 0.80230 | 4.04085 | 1 | 0.04441 |
| CMYC | 0.80757 | 4.26709 | 1 | 0.03886 |
| GBP1 | 0.83015 | 3.98302 | 1 | 0.04596 |
| AREG | 0.86091 | 4.94239 | 1 | 0.02621 |

Table 6 shows associations between gene expression and clinical outcome based on a nonlinear proportional hazards analysis, using a 2 degree-of-freedom natural spline. All genes are listed which demonstrated a departure from a strictly linear relationship (p<0.05) with RFI in combined Stage II (Duke's B) and Stage III (Duke's C) patients. The relationship between gene expression and RFI was not constant throughout the observed range of expression values in the study, e.g. increases in gene expression may have been related to increases in duration of RFI in one portion of the observed range and with decreases in duration of RFI in a different portion of the range.

TABLE 6

| Gene | P-Value | Official Symbol | Accession Number |
|---|---|---|---|
| PTHLH | 0.001 | PTHLH | NM_002820 |
| CDCA7 v2 | 0.002 | CDCA7 | NM_145810 |
| CREBBP | 0.002 | CREBBP | NM_004380 |
| KLF5 | 0.002 | KLF5 | NM_001730 |
| LAMB3 | 0.004 | LAMB3 | NM_000228 |
| TGFBR1 | 0.005 | TGFBR1 | NM_004612 |
| NR4A1 | 0.005 | NR4A1 | NM_002135 |
| Upa | 0.005 | PLAU | NM_002658 |
| Cad17 | 0.007 | CDH17 | NM_004063 |
| S100A4 | 0.008 | S100A4 | NM_002961 |
| A-Catenin | 0.008 | CTNNA1 | NM_001903 |
| EPHB2 | 0.009 | EPHB2 | NM_004442 |
| Axin 2 | 0.011 | AXIN2 | NM_004655 |
| PTPRJ | 0.011 | PTPRJ | NM_002843 |
| CAPN1 | 0.012 | CAPN1 | NM_005186 |
| CEGP1 | 0.013 | SCUBE2 | NM_020974 |
| APOC1 | 0.013 | APOC1 | NM_001645 |
| GBP1 | 0.015 | GBP1 | NM_002053 |
| SKP2 | 0.016 | SKP2 | NM_005983 |
| ATP5E | 0.016 | ATP5E | NM_006886 |
| GRIK1 | 0.017 | GRIK1 | NM_000830 |
| PRKR | 0.018 | EIF2AK2 | NM_002759 |
| FUT6 | 0.020 | FUT6 | NM_000150 |
| PFN2 | 0.020 | PFN2 | NM_053024 |
| ITGB4 | 0.021 | ITGB4 | NM_000213 |
| MADH7 | 0.021 | SMAD7 | NM_005904 |
| RALBP1 | 0.021 | RALBP1 | NM_006788 |
| AKT1 | 0.022 | AKT1 | NM_005163 |
| KLK6 | 0.022 | KLK6 | NM_002774 |
| PLK | 0.023 | PLK1 | NM_005030 |
| CYP2C8 | 0.025 | CYP2C8 | NM_000770 |
| BTF3 | 0.026 | BTF3 | NM_001207 |
| CCNE2 variant 1 | 0.026 | CCNE2 | NM_057749 |
| STMY3 | 0.030 | MMP11 | NM_005940 |
| NRP1 | 0.030 | NRP1 | NM_003873 |
| SIAT4A | 0.031 | ST3GAL1 | NM_003033 |
| SEMA3B | 0.033 | SEMA3B | NM_004636 |
| TRAG3 | 0.033 | CSAG2 | NM_004909 |
| HSPE1 | 0.035 | HSPE1 | NM_002157 |
| SBA2 | 0.036 | WSB2 | NM_018639 |
| TK1 | 0.036 | TK1 | NM_003258 |
| CCNB2 | 0.037 | CCNB2 | NM_004701 |
| TMEPAI | 0.037 | TMEPAI | NM_020182 |
| SPRY2 | 0.037 | SPRY2 | NM_005842 |
| AGXT | 0.038 | AGXT | NM_000030 |
| ALCAM | 0.038 | ALCAM | NM_001627 |
| HSPCA | 0.038 | HSPCA | NM_005348 |
| TIMP3 | 0.038 | TIMP3 | NM_000362 |
| DET1 | 0.039 | DET1 | NM_017996 |
| tusc4 | 0.040 | TUSC4 | NM_006545 |
| SNAI2 | 0.040 | SNAI2 | NM_003068 |
| CD28 | 0.040 | CD28 | NM_006139 |
| RNF11 | 0.041 | RNF11 | NM_014372 |
| PAI1 | 0.042 | SERPINE1 | NM_000602 |
| XRCC1 | 0.042 | XRCC1 | NM_006297 |
| EGLN1 | 0.044 | EGLN1 | NM_022051 |
| EGFR | 0.044 | EGFR | NM_005228 |
| HES6 | 0.044 | HES6 | NM_018645 |
| KCNK4 | 0.045 | KCNK4 | NM_016611 |
| CXCR4 | 0.047 | CXCR4 | NM_003467 |
| PTP4A3 | 0.048 | PTP4A3 | NM_007079 |
| p27 | 0.048 | CDKN1B | NM_004064 |
| MADH4 | 0.049 | SMAD4 | NM_005359 |
| ICAM1 | 0.049 | ICAM1 | NM_000201 |

Table 7 shows all genes exhibiting an interaction (p-value<0.05) with tumor stage. The data were modeled using a proportional hazards model of RFI with gene expression, tumor stage, and their interaction as predictors.

TABLE 7

| Gene | HR Stage II | HR Stage III | P-value for Interaction |
|---|---|---|---|
| ICAM2 | 1.49 | 0.68 | 0.0019 |
| CD24 | 1.26 | 0.84 | 0.0054 |
| PRDX6 | 2.29 | 0.73 | 0.0058 |
| HSD17B2 | 0.62 | 1.29 | 0.0072 |
| ALCAM | 1.61 | 0.94 | 0.0088 |
| SIR2 | 2.02 | 1.09 | 0.0089 |
| NUFIP1 | 1.32 | 0.79 | 0.0093 |
| EMR3 | 2.14 | 0.57 | 0.0127 |
| CDC20 | 0.56 | 0.98 | 0.0130 |
| MT3 | 1.37 | 0.79 | 0.0134 |
| CLTC | 1.80 | 0.71 | 0.0144 |
| CYR61 | 1.73 | 1.10 | 0.0145 |
| WIF | 1.34 | 0.78 | 0.0195 |
| TFF3 | 1.23 | 0.90 | 0.0209 |
| SOS1 | 1.46 | 0.79 | 0.0287 |
| TMSB4X | 1.34 | 0.74 | 0.0293 |
| CENPE | 3.05 | 0.85 | 0.0330 |
| CDH11 | 1.49 | 0.96 | 0.0339 |
| CAPG | 0.90 | 1.50 | 0.0348 |
| TP53BP1 | 1.54 | 0.93 | 0.0357 |
| MGAT5 | 1.25 | 0.73 | 0.0362 |
| MADH2 | 1.36 | 0.70 | 0.0393 |
| LOX | 1.58 | 1.11 | 0.0396 |
| DKK1 | 0.87 | 1.55 | 0.0415 |
| CKS1B | 0.31 | 1.75 | 0.0467 |
| MMP7 | 0.92 | 1.28 | 0.0471 |
| STAT5B | 1.28 | 0.86 | 0.0471 |
| CD28 | 0.69 | 1.25 | 0.0472 |

Second Analysis Study Results

Reference Gene Set for the second analysis was ATP5E, CLTC, GPX1, NEDD8, PGK1, UBB.

Table 1.2A shows associations for those genes whose increased expression is predictive of shorter Recurrence-Free Interval (RFI) based on univariate proportional hazards analysis.

Table 1.2B shows associations for those genes whose increased expression is predictive of longer Recurrence-Free Interval (RFI) based on univariate proportional hazards analysis.

Table 2.2A shows associations for those genes whose increased expression is predictive of decreased rate of Overall Survival (OS) based on univariate proportional hazards analysis.

Table 2.2B shows associations for those genes whose increased expression is predictive of increased rate of Overall Survival (OS) based on univariate proportional hazards analysis.

Table 3.2A shows associations for those genes whose increased expression is predictive of decreased rate of Disease Free Survival (DFS) based on univariate proportional hazards analysis.

Table 3.2B shows associations for those genes whose increased expression is predictive of increased rate of Disease Free Survival (DFS) based on univariate proportional hazards analysis.

Table 4.2A shows associations for those genes whose increased expression is predictive of shorter Distant Recurrence-Free Interval (DRFI) based on univariate proportional hazards analysis.

Table 4.2B shows associations for those genes whose increased expression is predictive of longer Distant Recurrence-Free Interval (DRFI) based on univariate proportional hazards analysis.

Table 5.2A shows associations between gene expression and RFI for those genes whose increased expression is predictive of shorter Recurrence-Free Interval (RFI), based on a multivariate analysis controlling for particular demographic and clinical characteristics of patients included in the analysis.

Table 5.2B shows associations between gene expression and RFI for those genes whose increased expression is predictive of longer Recurrence-Free Interval (RFI), based on a multivariate analysis controlling for particular demographic and clinical characteristics of patients included in the analysis.

Table 6.2 shows genes for which an association between gene expression and clinical outcome was identified based on a nonlinear proportional hazards analysis, using a 2 degree-of-freedom natural spline.

Table 7.2 shows all genes exhibiting an interaction (p-value<0.05) with tumor stage.

Table 1.2A shows associations between clinical outcome and gene expression for those genes which demonstrated a Hazard Ratio>1.0 and for which p<0.1. Univariate Cox Proportional Hazards Regression analysis was applied in combined Stage II (Duke's B) and Stage III (Duke's C) patients using RFI as the metric for clinical outcome.

| Gene | Hazard Ratio | P Value | Official Symbol | Accession Number |
|---|---|---|---|---|
| RARB | 2.22 | 0.0294 | RARB | NM_016152 |
| ITGB1 | 2.04 | 0.0002 | ITGB1 | NM_002211 |
| ANXA2 | 1.78 | 0.0003 | ANXA2 | NM_004039 |
| CYP3A4 | 1.68 | 0.0075 | CYP3A4 | NM_017460 |
| COX2 | 1.64 | 0.0604 | PTGS2 | NM_000963 |
| KRAS2 | 1.62 | 0.0064 | KRAS | NM_004985 |

-continued

| Gene | Hazard Ratio | P Value | Official Symbol | Accession Number |
|---|---|---|---|---|
| TJP1 | 1.58 | 0.0751 | TJP1 | NM_003257 |
| KIAA0125 | 1.58 | 0.0889 | KIAA0125 | NM_014792 |
| RhoB | 1.57 | 0.0002 | RHOB | NM_004040 |
| RhoC | 1.56 | 0.0059 | RHOC | NM_175744 |
| NTN1 | 1.54 | 0.0336 | NTN1 | NM_004822 |
| ANXA5 | 1.52 | 0.0086 | ANXA5 | NM_001154 |
| TIMP1 | 1.52 | <0.0001 | TIMP1 | NM_003254 |
| AKT3 | 1.50 | <0.0001 | AKT3 | NM_005465 |
| CALD1 | 1.48 | 0.0007 | CALD1 | NM_004342 |
| IGFBP7 | 1.46 | 0.0023 | IGFBP7 | NM_001553 |
| CYP1B1 | 1.45 | 0.0222 | CYP1B1 | NM_000104 |
| BGN | 1.44 | 0.0002 | BGN | NM_001711 |
| VEGFC | 1.44 | 0.0151 | VEGFC | NM_005429 |
| DLC1 | 1.44 | 0.0014 | DLC1 | NM_006094 |
| SI | 1.42 | 0.0086 | SI | NM_001041 |
| TIMP2 | 1.42 | 0.0022 | TIMP2 | NM_003255 |
| CDC42BPA | 1.41 | 0.0038 | CDC42BPA | NM_003607 |
| LAMC2 | 1.40 | 0.0004 | LAMC2 | NM_005562 |
| ITGAV | 1.40 | 0.0019 | ITGAV | NM_002210 |
| CTSB | 1.40 | 0.0357 | CTSB | NM_001908 |
| DUSP1 | 1.39 | <0.0001 | DUSP1 | NM_004417 |
| TLN1 | 1.39 | 0.0335 | TLN1 | NM_006289 |
| CCNE2 variant 1 | 1.39 | 0.0708 | CCNE2 | NM_057749 |
| TIMP3 | 1.38 | 0.0023 | TIMP3 | NM_000362 |
| GHI BRAF mut4 | 1.38 | 0.0537 | | GHI_BRAF_mut4 |
| HB-EGF | 1.38 | 0.0109 | HBEGF | NM_001945 |
| HSPG2 | 1.38 | 0.0258 | HSPG2 | NM_005529 |
| VIM | 1.37 | 0.0077 | VIM | NM_003380 |
| ROCK1 | 1.37 | 0.0168 | ROCK1 | NM_005406 |
| S100A1 | 1.36 | 0.0233 | S100A1 | NM_006271 |
| p21 | 1.36 | 0.0113 | CDKN1A | NM_000389 |
| CGB | 1.36 | 0.0023 | CGB | NM_000737 |
| UBC | 1.36 | 0.0137 | UBC | NM_021009 |
| GADD45B | 1.36 | 0.0003 | GADD45B | NM_015675 |
| INHBA | 1.35 | 0.0010 | INHBA | NM_002192 |
| VCL | 1.34 | 0.0286 | VCL | NM_003373 |
| SIR2 | 1.34 | 0.0049 | SIRT1 | NM_012238 |
| CD68 | 1.34 | 0.0042 | CD68 | NM_001251 |
| Maspin | 1.34 | <0.0001 | SERPINB5 | NM_002639 |
| FST | 1.33 | 0.0326 | FST | NM_006350 |
| EPAS1 | 1.33 | 0.0306 | EPAS1 | NM_001430 |
| LOXL2 | 1.33 | 0.0076 | LOXL2 | NM_002318 |
| STC1 | 1.33 | 0.0119 | STC1 | NM_003155 |
| UNC5C | 1.32 | 0.0642 | UNC5C | NM_003728 |
| IGFBP5 | 1.32 | 0.0080 | IGFBP5 | NM_000599 |
| INHBB | 1.32 | 0.0643 | INHBB | NM_002193 |
| FAP | 1.32 | 0.0017 | FAP | NM_004460 |
| DKK1 | 1.31 | 0.0298 | DKK1 | NM_012242 |
| FYN | 1.31 | 0.0053 | FYN | NM_002037 |
| CTHRC1 | 1.31 | 0.0017 | CTHRC1 | NM_138455 |
| FOS | 1.31 | 0.0010 | FOS | NM_005252 |
| RBX1 | 1.31 | 0.0633 | RBX1 | NM_014248 |
| TAGLN | 1.31 | 0.0058 | TAGLN | NM_003186 |
| SBA2 | 1.31 | 0.0439 | WSB2 | NM_018639 |
| CYR61 | 1.30 | 0.0018 | CYR61 | NM_001554 |
| SPARC | 1.30 | 0.0117 | SPARC | NM_003118 |
| SNAI2 | 1.30 | 0.0076 | SNAI2 | NM_003068 |
| TMSB10 | 1.30 | 0.0757 | TMSB10 | NM_021103 |
| IGFBP3 | 1.30 | 0.0056 | IGFBP3 | NM_000598 |
| PDGFC | 1.29 | 0.0040 | PDGFC | NM_016205 |
| SLPI | 1.29 | 0.0026 | SLPI | NM_003064 |
| COL1A2 | 1.29 | 0.0087 | COL1A2 | NM_000089 |
| NRP2 | 1.29 | 0.0112 | NRP2 | NM_003872 |
| PRKCA | 1.29 | 0.0093 | PRKCA | NM_002737 |
| KLF6 | 1.29 | 0.0661 | KLF6 | NM_001300 |
| THBS1 | 1.28 | 0.0062 | THBS1 | NM_003246 |
| EGR1 | 1.28 | 0.0067 | EGR1 | NM_001964 |
| S100A4 | 1.28 | 0.0070 | S100A4 | NM_002961 |
| CXCR4 | 1.28 | 0.0089 | CXCR4 | NM_003467 |
| LAMA3 | 1.27 | 0.0024 | LAMA3 | NM_000227 |
| LOX | 1.26 | 0.0036 | LOX | NM_002317 |
| AKAP12 | 1.26 | 0.0046 | AKAP12 | NM_005100 |
| ADAMTS12 | 1.26 | 0.0109 | ADAMTS12 | NM_030955 |
| MCP1 | 1.25 | 0.0122 | CCL2 | NM_002982 |
| Grb10 | 1.25 | 0.0107 | GRB10 | NM_005311 |

| Gene | Hazard Ratio | P Value | Official Symbol | Accession Number |
|---|---|---|---|---|
| PTGER3 | 1.25 | 0.0240 | PTGER3 | NM_000957 |
| CRYAB | 1.25 | 0.0035 | CRYAB | NM_001885 |
| ANGPT2 | 1.25 | 0.0566 | ANGPT2 | NM_001147 |
| ANXA1 | 1.25 | 0.0353 | ANXA1 | NM_000700 |
| EphB6 | 1.24 | 0.0960 | EPHB6 | NM_004445 |
| PDGFB | 1.24 | 0.0139 | PDGFB | NM_002608 |
| COL1A1 | 1.24 | 0.0198 | COL1A1 | NM_000088 |
| TGFB3 | 1.23 | 0.0094 | TGFB3 | NM_003239 |
| CTGF | 1.23 | 0.0265 | CTGF | NM_001901 |
| PDGFA | 1.23 | 0.0312 | | NM_002607 |
| HSPA1A | 1.23 | 0.0027 | HSPA1A | NM_005345 |
| EFNB2 | 1.23 | 0.0331 | EFNB2 | NM_004093 |
| CAPG | 1.23 | 0.0724 | CAPG | NM_001747 |
| TGFBI | 1.22 | 0.0231 | TGFBI | NM_000358 |
| SIAT4A | 1.22 | 0.0253 | ST3GAL1 | NM_003033 |
| LAT | 1.22 | 0.0307 | LAT | NM_014387 |
| ITGA5 | 1.22 | 0.0224 | ITGA5 | NM_002205 |
| GBP2 | 1.22 | 0.0225 | GBP2 | NM_004120 |
| ANTXR1 | 1.22 | 0.0204 | ANTXR1 | NM_032208 |
| ID4 | 1.22 | 0.0512 | ID4 | NM_001546 |
| SFRP2 | 1.22 | 0.0039 | SFRP2 | NM_003013 |
| TMEPAI | 1.21 | 0.0170 | TMEPAI | NM_020182 |
| CTSL | 1.21 | 0.0388 | CTSL | NM_001912 |
| KLK10 | 1.21 | 0.0007 | KLK10 | NM_002776 |
| FXYD5 | 1.21 | 0.0547 | FXYD5 | NM_014164 |
| GJB2 | 1.21 | 0.0356 | GJB2 | NM_004004 |
| P14ARF | 1.21 | 0.0451 | | S78535 |
| DAPK1 | 1.21 | 0.0525 | DAPK1 | NM_004938 |
| SKP1A | 1.21 | 0.0663 | SKP1A | NM_006930 |
| SFRP4 | 1.21 | 0.0078 | SFRP4 | NM_003014 |
| KLK6 | 1.20 | 0.0048 | KLK6 | NM_002774 |
| GJA1 | 1.20 | 0.0345 | GJA1 | NM_000165 |
| HOXB7 | 1.20 | 0.0278 | HOXB7 | NM_004502 |
| NDRG1 | 1.20 | 0.0948 | NDRG1 | NM_006096 |
| PAI1 | 1.19 | 0.0061 | SERPINE1 | NM_000602 |
| CDH11 | 1.19 | 0.0762 | CDH11 | NM_001797 |
| EGR3 | 1.19 | 0.0149 | EGR3 | NM_004430 |
| EMP1 | 1.19 | 0.0533 | EMP1 | NM_001423 |
| FZD1 | 1.19 | 0.0671 | FZD1 | NM_003505 |
| ABCC5 | 1.19 | 0.0631 | ABCC5 | NM_005688 |
| S100P | 1.18 | 0.0160 | S100P | NM_005980 |
| OPN, osteopontin | 1.18 | 0.0030 | SPP1 | NM_000582 |
| p16-INK4 | 1.17 | 0.0503 | | L27211 |
| NR4A1 | 1.17 | 0.0332 | NR4A1 | NM_002135 |
| TUBB | 1.17 | 0.0950 | TUBB | NM_001069 |
| SIAT7B | 1.17 | 0.0352 | ST6GALNAC2 | NM_006456 |
| ALDH1A1 | 1.17 | 0.0299 | ALDH1A1 | NM_000689 |
| F3 | 1.16 | 0.0654 | F3 | NM_001993 |
| SLC2A1 | 1.15 | 0.0806 | SLC2A1 | NM_006516 |
| CXCL12 | 1.13 | 0.0986 | CXCL12 | NM_000609 |
| STMY3 | 1.13 | 0.0518 | MMP11 | NM_005940 |
| S100A2 | 1.13 | 0.0303 | S100A2 | NM_005978 |
| FABP4 | 1.13 | 0.0363 | FABP4 | NM_001442 |
| REG4 | 1.11 | 0.0034 | REG4 | NM_032044 |
| pS2 | 1.09 | 0.0690 | TFF1 | NM_003225 |
| MUC2 | 1.06 | 0.0674 | MUC2 | NM_002457 |

Table 1.2B shows associations between clinical outcome and gene expression for those genes which demonstrated a Hazard Ratio<1.0 and for which p<0.1. Univariate Cox Proportional Hazards Regression analysis was applied in combined Stage II (Duke's B) and Stage III (Duke's C) patients using RFI as the metric for clinical outcome.

| Gene | Hazard Ratio | P Value | Official Symbol | Accession Number |
|---|---|---|---|---|
| ORC1L | 0.41 | 0.0623 | ORC1L | NM_004153 |
| E2F1 | 0.63 | 0.0006 | E2F1 | NM_005225 |
| HSPA8 | 0.63 | 0.0346 | HSPA8 | NM_006597 |
| RAD54L | 0.65 | 0.0026 | RAD54L | NM_003579 |
| BRCA1 | 0.68 | 0.0001 | BRCA1 | NM_007295 |
| SLC25A3 | 0.70 | 0.0100 | SLC25A3 | NM_213611 |
| PPM1D | 0.71 | 0.0025 | PPM1D | NM_003620 |
| DHFR | 0.71 | 0.0106 | DHFR | NM_000791 |
| SKP2 | 0.72 | 0.0087 | SKP2 | NM_005983 |
| FASN | 0.73 | 0.0070 | FASN | NM_004104 |
| HNRPD | 0.73 | 0.0611 | HNRPD | NM_031370 |
| ENO1 | 0.74 | 0.0432 | ENO1 | NM_001428 |
| C20 orf1 | 0.74 | 0.0086 | TPX2 | NM_012112 |
| BRCA2 | 0.75 | 0.0515 | BRCA2 | NM_000059 |
| DDB1 | 0.75 | 0.0639 | DDB1 | NM_001923 |
| KIF22 | 0.76 | 0.0127 | KIF22 | NM_007317 |
| RPLPO | 0.76 | 0.0330 | RPLP0 | NM_001002 |
| Chk1 | 0.76 | 0.0164 | CHEK1 | NM_001274 |
| ST14 | 0.77 | 0.0392 | ST14 | NM_021978 |
| Bax | 0.77 | 0.0502 | BAX | NM_004324 |
| TCF-1 | 0.78 | 0.0023 | TCF1 | NM_000545 |
| LMNB1 | 0.78 | 0.0458 | LMNB1 | NM_005573 |
| RRM1 | 0.78 | 0.0693 | RRM1 | NM_001033 |
| CSEL1 | 0.79 | 0.0261 | CSE1L | NM_001316 |
| CDC20 | 0.79 | 0.0274 | CDC20 | NM_001255 |
| PRDX2 | 0.79 | 0.0930 | PRDX2 | NM_005809 |
| RPS13 | 0.79 | 0.0906 | RPS13 | NM_001017 |
| RAF1 | 0.80 | 0.0717 | RAF1 | NM_002880 |
| CMYC | 0.80 | 0.0095 | MYC | NM_002467 |
| UBE2M | 0.80 | 0.0390 | UBE2M | NM_003969 |
| CKS2 | 0.80 | 0.0596 | CKS2 | NM_001827 |
| NME1 | 0.80 | 0.0694 | NME1 | NM_000269 |
| c-myb (MYB official) | 0.80 | 0.0082 | MYB | NM_005375 |
| CD80 | 0.80 | 0.0688 | CD80 | NM_005191 |
| CDCA7 v2 | 0.81 | 0.0164 | CDCA7 | NM_145810 |
| EFP | 0.81 | 0.0387 | TRIM25 | NM_005082 |
| CCNE2 | 0.81 | 0.0405 | CCNE2 | NM_057749 |
| SURV | 0.81 | 0.0573 | BIRC5 | NM_001168 |
| RRM2 | 0.82 | 0.0181 | RRM2 | NM_001034 |
| ABCC6 | 0.82 | 0.0464 | ABCC6 | NM_001171 |
| UMPS | 0.82 | 0.0371 | UMPS | NM_000373 |
| PI3KC2A | 0.82 | 0.0855 | PIK3C2A | NM_002645 |
| NOTCH1 | 0.82 | 0.0222 | NOTCH1 | NM_017617 |
| EIF4E | 0.82 | 0.0928 | EIF4E | NM_001968 |
| EPHB2 | 0.82 | 0.0183 | EPHB2 | NM_004442 |
| AREG | 0.83 | 0.0012 | AREG | NM_001657 |
| EREG | 0.83 | 0.0059 | EREG | NM_001432 |
| MYBL2 | 0.83 | 0.0234 | MYBL2 | NM_002466 |
| ABCB1 | 0.83 | 0.0342 | ABCB1 | NM_000927 |
| HRAS | 0.83 | 0.0708 | HRAS | NM_005343 |
| SLC7A5 | 0.84 | 0.0547 | SLC7A5 | NM_003486 |
| MAD2L1 | 0.84 | 0.0653 | MAD2L1 | NM_002358 |
| ING5 | 0.85 | 0.0920 | ING5 | NM_032329 |
| Ki-67 | 0.85 | 0.0562 | MKI67 | NM_002417 |
| MCM2 | 0.85 | 0.0671 | MCM2 | NM_004526 |
| Cdx2 | 0.88 | 0.0430 | CDX2 | NM_001265 |
| HES6 | 0.89 | 0.0966 | HES6 | NM_018645 |
| PTPRO | 0.89 | 0.0664 | PTPRO | NM_030667 |
| cripto (TDGF1 official) | 0.90 | 0.0781 | TDGF1 | NM_003212 |

Table 2.2A shows associations between clinical outcome and gene expression for those genes which demonstrated a Hazard Ratio>1.0 and for which p<0.1. Univariate Cox Proportional Hazards Regression analysis was applied in combined Stage II (Duke's B) and Stage III (Duke's C) patients using OS as the metric for clinical outcome.

| Gene | Hazard Ratio | P Value | Official Symbol | Accession Number |
|---|---|---|---|---|
| RhoC | 1.66 | 0.0002 | RHOC | NM_175744 |
| ITGB1 | 1.59 | 0.0049 | ITGB1 | NM_002211 |
| ANXA2 | 1.58 | 0.0004 | ANXA2 | NM_004039 |
| CYP3A4 | 1.49 | 0.0114 | CYP3A4 | NM_017460 |
| p21 | 1.49 | <.0001 | CDKN1A | NM_000389 |
| HMLH | 1.42 | 0.0555 | MLH1 | NM_000249 |

| Gene | Hazard Ratio | P Value | Official Symbol | Accession Number |
|---|---|---|---|---|
| VEGFC | 1.41 | 0.0095 | VEGFC | NM_005429 |
| TGFBR1 | 1.40 | 0.0113 | TGFBR1 | NM_004612 |
| UBC | 1.38 | 0.0013 | UBC | NM_021009 |
| RhoB | 1.37 | 0.0016 | RHOB | NM_004040 |
| HSPG2 | 1.37 | 0.0111 | HSPG2 | NM_005529 |
| PFN1 | 1.35 | 0.0987 | PFN1 | NM_005022 |
| TIMP1 | 1.35 | 0.0008 | TIMP1 | NM_003254 |
| VCL | 1.33 | 0.0116 | VCL | NM_003373 |
| INHBB | 1.32 | 0.0265 | INHBB | NM_002193 |
| SPINT2 | 1.32 | 0.0358 | SPINT2 | NM_021102 |
| GHI BRAF mut4 | 1.31 | 0.0822 | | GHI_BRAF_mut4 |
| LAMC2 | 1.31 | 0.0007 | LAMC2 | NM_005562 |
| KCNH2 iso a/b | 1.31 | 0.0474 | KCNH2 | NM_000238 |
| UNC5C | 1.30 | 0.0417 | UNC5C | NM_003728 |
| CDC42 | 1.30 | 0.0122 | CDC42 | NM_001791 |
| UBL1 | 1.29 | 0.0169 | SUMO1 | NM_003352 |
| GADD45B | 1.29 | 0.0003 | GADD45B | NM_015675 |
| KRAS2 | 1.29 | 0.0774 | KRAS | NM_004985 |
| HB-EGF | 1.29 | 0.0219 | HBEGF | NM_001945 |
| DKK1 | 1.28 | 0.0304 | DKK1 | NM_012242 |
| FXYD5 | 1.28 | 0.0035 | FXYD5 | NM_014164 |
| CALD1 | 1.28 | 0.0107 | CALD1 | NM_004342 |
| ANXA5 | 1.27 | 0.0723 | ANXA5 | NM_001154 |
| HLA-G | 1.27 | 0.0732 | HLA-G | NM_002127 |
| DUSP1 | 1.27 | 0.0004 | DUSP1 | NM_004417 |
| LOXL2 | 1.27 | 0.0050 | LOXL2 | NM_002318 |
| CDC42BPA | 1.27 | 0.0155 | CDC42BPA | NM_003607 |
| BGN | 1.27 | 0.0039 | BGN | NM_001711 |
| LAMB3 | 1.27 | 0.0221 | LAMB3 | NM_000228 |
| EphB6 | 1.27 | 0.0373 | EPHB6 | NM_004445 |
| SHC1 | 1.27 | 0.0582 | SHC1 | NM_003029 |
| TIMP2 | 1.26 | 0.0126 | TIMP2 | NM_003255 |
| CTSB | 1.26 | 0.0748 | CTSB | NM_001908 |
| TIMP3 | 1.26 | 0.0072 | TIMP3 | NM_000362 |
| ID3 | 1.26 | 0.0033 | ID3 | NM_002167 |
| CAPG | 1.26 | 0.0162 | CAPG | NM_001747 |
| NRP1 | 1.26 | 0.0135 | NRP1 | NM_003873 |
| INHBA | 1.26 | 0.0021 | INHBA | NM_002192 |
| KLF6 | 1.25 | 0.0477 | KLF6 | NM_001300 |
| IGFBP7 | 1.25 | 0.0251 | IGFBP7 | NM_001553 |
| S100A1 | 1.25 | 0.0528 | S100A1 | NM_006271 |
| EPAS1 | 1.24 | 0.0382 | EPAS1 | NM_001430 |
| DLC1 | 1.24 | 0.0228 | DLC1 | NM_006094 |
| KLK10 | 1.24 | <.0001 | KLK10 | NM_002776 |
| SBA2 | 1.24 | 0.0493 | WSB2 | NM_018639 |
| SPARC | 1.24 | 0.0133 | SPARC | NM_003118 |
| GAGE4 | 1.23 | 0.0475 | GAGE4 | NM_001474 |
| HSPA1A | 1.23 | 0.0004 | HSPA1A | NM_005345 |
| SIR2 | 1.23 | 0.0179 | SIRT1 | NM_012238 |
| CGB | 1.23 | 0.0202 | CGB | NM_000737 |
| Grb10 | 1.22 | 0.0059 | GRB10 | NM_005311 |
| SNAI2 | 1.22 | 0.0145 | SNAI2 | NM_003068 |
| LAMA3 | 1.22 | 0.0019 | LAMA3 | NM_000227 |
| AKT3 | 1.22 | 0.0169 | AKT3 | NM_005465 |
| FYN | 1.22 | 0.0138 | FYN | NM_002037 |
| FOS | 1.22 | 0.0035 | FOS | NM_005252 |
| CTHRC1 | 1.21 | 0.0056 | CTHRC1 | NM_138455 |
| CTSD | 1.21 | 0.0506 | CTSD | NM_001909 |
| THY1 | 1.21 | 0.0290 | THY1 | NM_006288 |
| ANXA1 | 1.21 | 0.0339 | ANXA1 | NM_000700 |
| CD68 | 1.21 | 0.0227 | CD68 | NM_001251 |
| G-Catenin | 1.20 | 0.0789 | JUP | NM_002230 |
| PLK3 | 1.20 | 0.0081 | PLK3 | NM_004073 |
| STC1 | 1.20 | 0.0577 | STC1 | NM_003155 |
| TAGLN | 1.20 | 0.0238 | TAGLN | NM_003186 |
| VIM | 1.20 | 0.0632 | VIM | NM_003380 |
| HSPA1B | 1.20 | 0.0302 | HSPA1B | NM_005346 |
| LAT | 1.20 | 0.0184 | LAT | NM_014387 |
| KRT19 | 1.20 | 0.0309 | KRT19 | NM_002276 |
| IGFBP3 | 1.20 | 0.0167 | IGFBP3 | NM_000598 |
| BMP4 | 1.20 | 0.0035 | BMP4 | NM_001202 |
| KLK6 | 1.20 | 0.0014 | KLK6 | NM_002774 |
| THBS1 | 1.20 | 0.0206 | THBS1 | NM_003246 |
| TULP3 | 1.19 | 0.0344 | TULP3 | NM_003324 |
| ERK1 | 1.19 | 0.0522 | | Z11696 |
| CREBBP | 1.19 | 0.0866 | CREBBP | NM_004380 |
| S100A4 | 1.19 | 0.0259 | S100A4 | NM_002961 |
| PDGFB | 1.19 | 0.0205 | PDGFB | NM_002608 |
| EFNB2 | 1.19 | 0.0299 | EFNB2 | NM_004093 |
| LOX | 1.19 | 0.0104 | LOX | NM_002317 |
| PTK2 | 1.18 | 0.0983 | PTK2 | NM_005607 |
| IGFBP5 | 1.18 | 0.0544 | IGFBP5 | NM_000599 |
| APC | 1.18 | 0.0461 | APC | NM_000038 |
| DYRK1B | 1.18 | 0.0681 | DYRK1B | NM_004714 |
| NOTCH2 | 1.18 | 0.0533 | NOTCH2 | NM_024408 |
| Maspin | 1.18 | 0.0033 | SERPINB5 | NM_002639 |
| AKAP12 | 1.18 | 0.0195 | AKAP12 | NM_005100 |
| COL1A1 | 1.17 | 0.0417 | COL1A1 | NM_000088 |
| EMP1 | 1.17 | 0.0295 | EMP1 | NM_001423 |
| SIAT4A | 1.17 | 0.0311 | ST3GAL1 | NM_003033 |
| PAI1 | 1.17 | 0.0036 | SERPINE1 | NM_000602 |
| NR4A1 | 1.17 | 0.0117 | NR4A1 | NM_002135 |
| EGR1 | 1.17 | 0.0379 | EGR1 | NM_001964 |
| BRK | 1.17 | 0.0156 | PTK6 | NM_005975 |
| UNC5B | 1.17 | 0.0956 | UNC5B | NM_170744 |
| SR-A1 | 1.17 | 0.0512 | SR-A1 | NM_021228 |
| MRP3 | 1.16 | 0.0353 | ABCC3 | NM_003786 |
| hCRA a | 1.16 | 0.0878 | | U78556 |
| Upa | 1.16 | 0.0630 | PLAU | NM_002658 |
| BCAS1 | 1.16 | 0.0147 | BCAS1 | NM_003657 |
| PDGFC | 1.16 | 0.0375 | PDGFC | NM_016205 |
| COL1A2 | 1.16 | 0.0620 | COL1A2 | NM_000089 |
| CTGF | 1.16 | 0.0580 | CTGF | NM_001901 |
| MCP1 | 1.16 | 0.0463 | CCL2 | NM_002982 |
| RAB32 | 1.16 | 0.0686 | RAB32 | NM_006834 |
| SKP1A | 1.16 | 0.0842 | SKP1A | NM_006930 |
| FAP | 1.16 | 0.0443 | FAP | NM_004460 |
| EFNA1 | 1.16 | 0.0990 | EFNA1 | NM_004428 |
| HOXB7 | 1.15 | 0.0378 | HOXB7 | NM_004502 |
| CYR61 | 1.15 | 0.0452 | CYR61 | NM_001554 |
| TGFBI | 1.15 | 0.0591 | TGFBI | NM_000358 |
| TMEPAI | 1.15 | 0.0419 | TMEPAI | NM_020182 |
| SIN3A | 1.15 | 0.0853 | SIN3A | NM_015477 |
| S100A2 | 1.15 | 0.0038 | S100A2 | NM_005978 |
| PDGFA | 1.15 | 0.0840 | | NM_002607 |
| MMP7 | 1.15 | 0.0469 | MMP7 | NM_002423 |
| ANTXR1 | 1.15 | 0.0520 | ANTXR1 | NM_032208 |
| SLPI | 1.14 | 0.0755 | SLPI | NM_003064 |
| SFRP2 | 1.13 | 0.0253 | SFRP2 | NM_003013 |
| S100A8 | 1.13 | 0.0795 | S100A8 | NM_002964 |
| TP53I3 | 1.13 | 0.0973 | TP53I3 | NM_004881 |
| F3 | 1.13 | 0.0735 | F3 | NM_001993 |
| OPN, osteopontin | 1.12 | 0.0100 | SPP1 | NM_000582 |
| EGLN3 | 1.11 | 0.0883 | EGLN3 | NM_022073 |
| FZD6 | 1.11 | 0.0791 | FZD6 | NM_003506 |
| OSM | 1.10 | 0.0913 | OSM | NM_020530 |
| FABP4 | 1.10 | 0.0521 | FABP4 | NM_001442 |
| GSTT1 | 1.09 | 0.0837 | GSTT1 | NM_000853 |
| REG4 | 1.07 | 0.0300 | REG4 | NM_032044 |

Table 2.2B shows associations between clinical outcome and gene expression for those genes which demonstrated a Hazard Ratio<1.0 and for which p<0.1. Univariate Cox Proportional Hazards Regression analysis was applied in combined Stage II (Duke's B) and Stage III (Duke's C) patients using OS as the metric for clinical outcome.

| Gene | Hazard Ratio | P Value | Official Symbol | Accession Number |
|---|---|---|---|---|
| ORC1L | 0.52 | 0.0895 | ORC1L | NM_004153 |
| HSPA8 | 0.64 | 0.0164 | HSPA8 | NM_006597 |
| SKP2 | 0.71 | 0.0012 | SKP2 | NM_005983 |
| PRDX4 | 0.74 | 0.0202 | PRDX4 | NM_006406 |
| DHFR | 0.76 | 0.0111 | DHFR | NM_000791 |
| FGF18 | 0.76 | 0.0915 | FGF18 | NM_003862 |
| SLC25A3 | 0.76 | 0.0391 | SLC25A3 | NM_213611 |
| RRM1 | 0.77 | 0.0218 | RRM1 | NM_001033 |
| E2F1 | 0.78 | 0.0180 | E2F1 | NM_005225 |

-continued

| Gene | Hazard Ratio | P Value | Official Symbol | Accession Number |
|---|---|---|---|---|
| SURV | 0.79 | 0.0098 | BIRC5 | NM_001168 |
| PPM1D | 0.80 | 0.0154 | PPM1D | NM_003620 |
| CCNE2 | 0.80 | 0.0090 | CCNE2 | NM_057749 |
| BRCA1 | 0.80 | 0.0093 | BRCA1 | NM_007295 |
| ST14 | 0.80 | 0.0436 | ST14 | NM_021978 |
| c-myb (MYB official) | 0.81 | 0.0027 | MYB | NM_005375 |
| Chk1 | 0.81 | 0.0220 | CHEK1 | NM_001274 |
| C20 orf1 | 0.81 | 0.0305 | TPX2 | NM_012112 |
| EI24 | 0.81 | 0.0574 | EI24 | NM_004879 |
| CDC20 | 0.82 | 0.0234 | CDC20 | NM_001255 |
| TCF-1 | 0.82 | 0.0061 | TCF1 | NM_000545 |
| PPID | 0.83 | 0.0584 | PPID | NM_005038 |
| KIF22 | 0.83 | 0.0466 | KIF22 | NM_007317 |
| UBE2M | 0.83 | 0.0850 | UBE2M | NM_003969 |
| MRPL40 | 0.83 | 0.0716 | MRPL40 | NM_003776 |
| RPLPO | 0.84 | 0.0987 | RPLP0 | NM_001002 |
| LMNB1 | 0.84 | 0.0910 | LMNB1 | NM_005573 |
| DUT | 0.84 | 0.0401 | DUT | NM_001948 |
| CD44E | 0.84 | 0.0483 | | X55150 |
| MCM2 | 0.85 | 0.0214 | MCM2 | NM_004526 |
| CDC6 | 0.85 | 0.0235 | CDC6 | NM_001254 |
| AURKB | 0.85 | 0.0373 | AURKB | NM_004217 |
| SMARCA3 | 0.86 | 0.0562 | SMARCA3 | NM_003071 |
| CDCA7 v2 | 0.86 | 0.0435 | CDCA7 | NM_145810 |
| EPHB2 | 0.86 | 0.0281 | EPHB2 | NM_004442 |
| CMYC | 0.86 | 0.0441 | MYC | NM_002467 |
| ABCB1 | 0.86 | 0.0352 | ABCB1 | NM_000927 |
| Cdx2 | 0.87 | 0.0156 | CDX2 | NM_001265 |
| PPARG | 0.88 | 0.0655 | PPARG | NM_005037 |
| MYBL2 | 0.88 | 0.0667 | MYBL2 | NM_002466 |
| EREG | 0.89 | 0.0352 | EREG | NM_001432 |
| AREG | 0.90 | 0.0221 | AREG | NM_001657 |

Table 3.2A shows associations between clinical outcome and gene expression for those genes which demonstrated a Hazard Ratio>1.0 and for which p<0.1. Univariate Cox Proportional Hazards Regression analysis was applied in combined Stage II (Duke's B) and Stage III (Duke's C) patients using DFS as the metric for clinical outcome.

| Gene | Hazard Ratio | P Value | Official Symbol | Accession Number |
|---|---|---|---|---|
| ANXA2 | 1.67 | <.0001 | ANXA2 | NM_004039 |
| CYP3A4 | 1.59 | 0.0035 | CYP3A4 | NM_017460 |
| RhoC | 1.52 | 0.0010 | RHOC | NM_175744 |
| TJP1 | 1.44 | 0.0951 | TJP1 | NM_003257 |
| HB-EGF | 1.39 | 0.0023 | HBEGF | NM_001945 |
| p21 | 1.39 | 0.0006 | CDKN1A | NM_000389 |
| HMLH | 1.37 | 0.0678 | MLH1 | NM_000249 |
| ITGB1 | 1.37 | 0.0419 | ITGB1 | NM_002211 |
| UBC | 1.34 | 0.0024 | UBC | NM_021009 |
| VEGFC | 1.33 | 0.0246 | VEGFC | NM_005429 |
| TIMP1 | 1.33 | 0.0007 | TIMP1 | NM_003254 |
| CCNE2 variant 1 | 1.32 | 0.0745 | CCNE2 | NM_057749 |
| SPINT2 | 1.32 | 0.0224 | SPINT2 | NM_021102 |
| LAMC2 | 1.32 | 0.0002 | LAMC2 | NM_005562 |
| VCL | 1.31 | 0.0119 | VCL | NM_003373 |
| RhoB | 1.31 | 0.0049 | RHOB | NM_004040 |
| PKR2 | 1.30 | 0.0258 | PKM2 | NM_002654 |
| ANXA5 | 1.30 | 0.0406 | ANXA5 | NM_001154 |
| GADD45B | 1.30 | 0.0001 | GADD45B | NM_015675 |
| INHBB | 1.29 | 0.0368 | INHBB | NM_002193 |
| DUSP1 | 1.29 | <.0001 | DUSP1 | NM_004417 |
| KRAS2 | 1.28 | 0.0686 | KRAS | NM_004985 |
| KLF6 | 1.28 | 0.0284 | KLF6 | NM_001300 |
| IGFBP7 | 1.27 | 0.0103 | IGFBP7 | NM_001553 |
| GRIK1 | 1.27 | 0.0421 | GRIK1 | NM_000830 |
| DLC1 | 1.27 | 0.0084 | DLC1 | NM_006094 |
| FOS | 1.26 | 0.0003 | FOS | NM_005252 |
| HSPG2 | 1.26 | 0.0443 | HSPG2 | NM_005529 |
| INHBA | 1.26 | 0.0009 | INHBA | NM_002192 |
| TIMP3 | 1.26 | 0.0045 | TIMP3 | NM_000362 |
| BGN | 1.26 | 0.0035 | BGN | NM_001711 |
| CGB | 1.26 | 0.0172 | CGB | NM_000737 |
| HK1 | 1.26 | 0.0352 | HK1 | NM_000188 |
| SHC1 | 1.25 | 0.0562 | SHC1 | NM_003029 |
| STC1 | 1.25 | 0.0161 | STC1 | NM_003155 |
| LOXL2 | 1.24 | 0.0078 | LOXL2 | NM_002318 |
| CAPG | 1.24 | 0.0161 | CAPG | NM_001747 |
| UNC5B | 1.23 | 0.0204 | UNC5B | NM_170744 |
| MVP | 1.23 | 0.0729 | MVP | NM_017458 |
| CTSD | 1.23 | 0.0256 | CTSD | NM_001909 |
| EGR1 | 1.23 | 0.0041 | EGR1 | NM_001964 |
| LOX | 1.23 | 0.0017 | LOX | NM_002317 |
| CDC42BPA | 1.23 | 0.0278 | CDC42BPA | NM_003607 |
| GAGE4 | 1.23 | 0.0425 | GAGE4 | NM_001474 |
| CALD1 | 1.22 | 0.0239 | CALD1 | NM_004342 |
| FXYD5 | 1.22 | 0.0096 | FXYD5 | NM_014164 |
| EphB6 | 1.22 | 0.0825 | EPHB6 | NM_004445 |
| LAMB3 | 1.22 | 0.0444 | LAMB3 | NM_000228 |
| VEGF | 1.21 | 0.0267 | VEGF | NM_003376 |
| PDGFB | 1.21 | 0.0062 | PDGFB | NM_002608 |
| TIMP2 | 1.21 | 0.0292 | TIMP2 | NM_003255 |
| A-Catenin | 1.21 | 0.0598 | CTNNA1 | NM_001903 |
| IGFBP3 | 1.21 | 0.0081 | IGFBP3 | NM_000598 |
| CD68 | 1.21 | 0.0138 | CD68 | NM_001251 |
| S100A1 | 1.21 | 0.0886 | S100A1 | NM_006271 |
| SIAT4A | 1.21 | 0.0076 | ST3GAL1 | NM_003033 |
| HSPA1B | 1.21 | 0.0182 | HSPA1B | NM_005346 |
| DKK1 | 1.20 | 0.0900 | DKK1 | NM_012242 |
| SBA2 | 1.20 | 0.0733 | WSB2 | NM_018639 |
| SIR2 | 1.20 | 0.0250 | SIRT1 | NM_012238 |
| THBS1 | 1.20 | 0.0119 | THBS1 | NM_003246 |
| FYN | 1.20 | 0.0156 | FYN | NM_002037 |
| TULP3 | 1.20 | 0.0205 | TULP3 | NM_003324 |
| LAMA3 | 1.20 | 0.0026 | LAMA3 | NM_000227 |
| NR4A1 | 1.20 | 0.0022 | NR4A1 | NM_002135 |
| EFNA1 | 1.20 | 0.0258 | EFNA1 | NM_004428 |
| EMP1 | 1.20 | 0.0102 | EMP1 | NM_001423 |
| SPARC | 1.19 | 0.0333 | SPARC | NM_003118 |
| G-Catenin | 1.19 | 0.0761 | JUP | NM_002230 |
| CYR61 | 1.19 | 0.0103 | CYR61 | NM_001554 |
| Maspin | 1.19 | 0.0015 | SERPINB5 | NM_002639 |
| HSPA1A | 1.18 | 0.0018 | HSPA1A | NM_005345 |
| PTHR1 | 1.18 | 0.0856 | PTHR1 | NM_000316 |
| EPAS1 | 1.18 | 0.0789 | EPAS1 | NM_001430 |
| Grb10 | 1.18 | 0.0173 | GRB10 | NM_005311 |
| ERK1 | 1.18 | 0.0464 | | Z11696 |
| VIM | 1.18 | 0.0772 | VIM | NM_003380 |
| SNAI2 | 1.18 | 0.0379 | SNAI2 | NM_003068 |
| IGFBP5 | 1.17 | 0.0492 | IGFBP5 | NM_000599 |
| CTHRC1 | 1.17 | 0.0155 | CTHRC1 | NM_138455 |
| THY1 | 1.17 | 0.0562 | THY1 | NM_006288 |
| NRP1 | 1.17 | 0.0747 | NRP1 | NM_003873 |
| PTGER3 | 1.17 | 0.0493 | PTGER3 | NM_000957 |
| ID3 | 1.17 | 0.0437 | ID3 | NM_002167 |
| F3 | 1.17 | 0.0157 | F3 | NM_001993 |
| CTGF | 1.17 | 0.0394 | CTGF | NM_001901 |
| KRT19 | 1.17 | 0.0517 | KRT19 | NM_002276 |
| PAI1 | 1.17 | 0.0033 | SERPINE1 | NM_000602 |
| FAP | 1.17 | 0.0260 | FAP | NM_004460 |
| ANXA1 | 1.16 | 0.0688 | ANXA1 | NM_000700 |
| KLK10 | 1.16 | 0.0009 | KLK10 | NM_002776 |
| EFNB2 | 1.16 | 0.0447 | EFNB2 | NM_004093 |
| P14ARF | 1.16 | 0.0573 | | S78535 |
| MCP1 | 1.16 | 0.0359 | CCL2 | NM_002982 |
| PLK3 | 1.16 | 0.0296 | PLK3 | NM_004073 |
| ANTXR1 | 1.16 | 0.0243 | ANTXR1 | NM_032208 |
| ADAMTS12 | 1.16 | 0.0346 | ADAMTS12 | NM_030955 |
| EGR3 | 1.16 | 0.0109 | EGR3 | NM_004430 |
| APC | 1.16 | 0.0733 | APC | NM_000038 |
| PDGFC | 1.16 | 0.0326 | PDGFC | NM_016205 |
| BMP4 | 1.16 | 0.0151 | BMP4 | NM_001202 |
| HOXB7 | 1.15 | 0.0281 | HOXB7 | NM_004502 |
| NDRG1 | 1.15 | 0.0912 | NDRG1 | NM_006096 |
| Herstatin | 1.15 | 0.0380 | | AF177761 |
| TMEPAI | 1.15 | 0.0268 | TMEPAI | NM_020182 |
| IL6 | 1.15 | 0.0914 | IL6 | NM_000600 |

-continued

| Gene | Hazard Ratio | P Value | Official Symbol | Accession Number |
|---|---|---|---|---|
| PDGFA | 1.15 | 0.0599 | | NM_002607 |
| TGFBI | 1.15 | 0.0439 | TGFBI | NM_000358 |
| Upa | 1.15 | 0.0740 | PLAU | NM_002658 |
| S100A4 | 1.15 | 0.0621 | S100A4 | NM_002961 |
| SLPI | 1.15 | 0.0447 | SLPI | NM_003064 |
| KLK6 | 1.15 | 0.0112 | KLK6 | NM_002774 |
| COL1A1 | 1.15 | 0.0637 | COL1A1 | NM_000088 |
| GJB2 | 1.15 | 0.0604 | GJB2 | NM_004004 |
| PKD1 | 1.15 | 0.0939 | PKD1 | NM_000296 |
| TP53I3 | 1.15 | 0.0450 | TP53I3 | NM_004881 |
| PLAUR | 1.14 | 0.0477 | PLAUR | NM_002659 |
| TAGLN | 1.14 | 0.0739 | TAGLN | NM_003186 |
| COL1A2 | 1.14 | 0.0818 | COL1A2 | NM_000089 |
| S100A2 | 1.14 | 0.0045 | S100A2 | NM_005978 |
| AKT3 | 1.14 | 0.0949 | AKT3 | NM_005465 |
| SEMA3B | 1.13 | 0.0467 | SEMA3B | NM_004636 |
| BRK | 1.13 | 0.0476 | PTK6 | NM_005975 |
| OSM | 1.13 | 0.0344 | OSM | NM_020530 |
| SFRP2 | 1.12 | 0.0279 | SFRP2 | NM_003013 |
| MRP3 | 1.12 | 0.0946 | ABCC3 | NM_003786 |
| EGLN3 | 1.12 | 0.0452 | EGLN3 | NM_022073 |
| SIAT7B | 1.12 | 0.0603 | ST6GALNAC2 | NM_006456 |
| OPN, osteopontin | 1.12 | 0.0082 | SPP1 | NM_000582 |
| S100P | 1.12 | 0.0313 | S100P | NM_005980 |
| AKAP12 | 1.12 | 0.0865 | AKAP12 | NM_005100 |
| MMP7 | 1.11 | 0.0909 | MMP7 | NM_002423 |
| FABP4 | 1.11 | 0.0214 | FABP4 | NM_001442 |
| CRYAB | 1.11 | 0.0960 | CRYAB | NM_001885 |
| SFRP4 | 1.10 | 0.0625 | SFRP4 | NM_003014 |
| EFNA3 | 1.10 | 0.0707 | EFNA3 | NM_004952 |
| GSTT1 | 1.09 | 0.0516 | GSTT1 | NM_000853 |
| pS2 | 1.08 | 0.0313 | TFF1 | NM_003225 |
| REG4 | 1.08 | 0.0080 | REG4 | NM_032044 |
| IGFBP2 | 1.08 | 0.0846 | IGFBP2 | NM_000597 |
| MUC5B | 1.08 | 0.0387 | MUC5B | XM_039877 |

Table 3.2B shows associations between clinical outcome and gene expression for those genes which demonstrated a Hazard Ratio<1.0 and for which p<0.1. Univariate Cox Proportional Hazards Regression analysis was applied in combined Stage II (Duke's B) and Stage III (Duke's C) patients using DFS as the metric for clinical outcome.

| Gene | Hazard Ratio | P Value | Official Symbol | Accession Number |
|---|---|---|---|---|
| HSPA8 | 0.72 | 0.0604 | HSPA8 | NM_006597 |
| SLC25A3 | 0.73 | 0.0126 | SLC25A3 | NM_213611 |
| E2F1 | 0.73 | 0.0019 | E2F1 | NM_005225 |
| IFIT1 | 0.74 | 0.0820 | IFIT1 | NM_001548 |
| PPM1D | 0.74 | 0.0007 | PPM1D | NM_003620 |
| SKP2 | 0.75 | 0.0049 | SKP2 | NM_005983 |
| RRM1 | 0.78 | 0.0224 | RRM1 | NM_001033 |
| DDB1 | 0.79 | 0.0720 | DDB1 | NM_001923 |
| NPM1 | 0.79 | 0.0255 | NPM1 | NM_002520 |
| PRDX4 | 0.80 | 0.0570 | PRDX4 | NM_006406 |
| BRCA1 | 0.80 | 0.0064 | BRCA1 | NM_007295 |
| C20 orf1 | 0.81 | 0.0180 | TPX2 | NM_012112 |
| Chk1 | 0.81 | 0.0148 | CHEK1 | NM_001274 |
| EI24 | 0.81 | 0.0417 | EI24 | NM_004879 |
| CCNE2 | 0.81 | 0.0094 | CCNE2 | NM_057749 |
| HMGB1 | 0.82 | 0.0852 | HMGB1 | NM_002128 |
| SURV | 0.82 | 0.0185 | BIRC5 | NM_001168 |
| KIF22 | 0.82 | 0.0264 | KIF22 | NM_007317 |
| RAD54L | 0.82 | 0.0674 | RAD54L | NM_003579 |
| c-myb (MYB official) | 0.82 | 0.0038 | MYB | NM_005375 |
| DHFR | 0.82 | 0.0669 | DHFR | NM_000791 |
| TNFRSF5 | 0.83 | 0.0855 | CD40 | NM_001250 |
| LMNB1 | 0.83 | 0.0741 | LMNB1 | NM_005573 |
| CDC20 | 0.85 | 0.0538 | CDC20 | NM_001255 |
| CDCA7 v2 | 0.85 | 0.0277 | CDCA7 | NM_145810 |
| FASN | 0.85 | 0.0919 | FASN | NM_004104 |
| MCM2 | 0.85 | 0.0194 | MCM2 | NM_004526 |
| ABCB1 | 0.85 | 0.0169 | ABCB1 | NM_000927 |
| EIF4E | 0.85 | 0.0902 | EIF4E | NM_001968 |
| DUT | 0.86 | 0.0535 | DUT | NM_001948 |
| C20ORF126 | 0.86 | 0.0932 | PDRG1 | NM_030815 |
| MCM6 | 0.86 | 0.0970 | MCM6 | NM_005915 |
| EFP | 0.87 | 0.0850 | TRIM25 | NM_005082 |
| EPHB2 | 0.87 | 0.0314 | EPHB2 | NM_004442 |
| GCLC | 0.87 | 0.0862 | GCLC | NM_001498 |
| RCC1 | 0.87 | 0.0540 | RCC1 | NM_001269 |
| AREG | 0.87 | 0.0028 | AREG | NM_001657 |
| CMYC | 0.88 | 0.0584 | MYC | NM_002467 |
| MYBL2 | 0.88 | 0.0567 | MYBL2 | NM_002466 |
| TCF-1 | 0.88 | 0.0644 | TCF1 | NM_000545 |
| EREG | 0.89 | 0.0232 | EREG | NM_001432 |
| Cdx2 | 0.90 | 0.0354 | CDX2 | NM_001265 |
| PTPRO | 0.92 | 0.0935 | PTPRO | NM_030667 |
| cripto (TDGF1 official) | 0.92 | 0.0950 | TDGF1 | NM_003212 |
| HLA-DRB1 | 0.93 | 0.0521 | HLA-DRB1 | NM_002124 |

Table 4.2A shows associations between clinical outcome and gene expression for those genes which demonstrated a Hazard Ratio>1.0 and for which p<0.1. Univariate Cox Proportional Hazards Regression analysis was applied in combined Stage II (Duke's B) and Stage III (Duke's C) patients using DRFI as the metric for clinical outcome.

| Gene | Hazard Ratio | P Value | Official Symbol | Accession Number |
|---|---|---|---|---|
| ALDOA | 3.21 | 0.0189 | ALDOA | NM_000034 |
| DCK | 2.60 | 0.0248 | DCK | NM_000788 |
| ITGB1 | 2.58 | 0.0002 | ITGB1 | NM_002211 |
| COX2 | 2.16 | 0.0198 | PTGS2 | NM_000963 |
| TJP1 | 2.10 | 0.0122 | TJP1 | NM_003257 |
| STAT3 | 1.87 | 0.0148 | STAT3 | NM_003150 |
| ANXA5 | 1.83 | 0.0043 | ANXA5 | NM_001154 |
| GHI BRAF mut4 | 1.82 | 0.0024 | | GHI_BRAF_mut4 |
| TIMP1 | 1.80 | <.0001 | TIMP1 | NM_003254 |
| hMLH | 1.80 | 0.0242 | MLH1 | NM_000249 |
| PADI4 | 1.74 | 0.0288 | PADI4 | NM_012387 |
| rhoC | 1.74 | 0.0093 | RHOC | NM_175744 |
| CYP3A4 | 1.73 | 0.0219 | CYP3A4 | NM_017460 |
| WWOX | 1.72 | 0.0467 | WWOX | NM_016373 |
| ANXA2 | 1.70 | 0.0081 | ANXA2 | NM_004039 |
| LILRB3 | 1.70 | 0.0295 | LILRB3 | NM_006864 |
| VIM | 1.66 | 0.0015 | VIM | NM_003380 |
| FUS | 1.65 | 0.0432 | FUS | NM_004960 |
| KCNH2 iso a/b | 1.64 | 0.0111 | KCNH2 | NM_000238 |
| RhoB | 1.63 | 0.0019 | RHOB | NM_004040 |
| CRIP2 | 1.62 | 0.0455 | CRIP2 | NM_001312 |
| AKT3 | 1.60 | 0.0004 | AKT3 | NM_005465 |
| RBX1 | 1.60 | 0.0195 | RBX1 | NM_014248 |
| HB-EGF | 1.59 | 0.0032 | HBEGF | NM_001945 |
| NRP2 | 1.55 | 0.0007 | NRP2 | NM_003872 |
| MSH3 | 1.55 | 0.0353 | MSH3 | NM_002439 |
| PI3K | 1.54 | 0.0651 | PIK3C2B | NM_002646 |
| BGN | 1.54 | 0.0009 | BGN | NM_001711 |
| RAB6C | 1.54 | 0.0210 | RAB6C | NM_032144 |
| CTSB | 1.53 | 0.0415 | CTSB | NM_001908 |
| DLC1 | 1.53 | 0.0047 | DLC1 | NM_006094 |
| p21 | 1.53 | 0.0085 | CDKN1A | NM_000389 |
| CCNE2 variant 1 | 1.52 | 0.0647 | CCNE2 | NM_057749 |
| CALD1 | 1.51 | 0.0069 | CALD1 | NM_004342 |
| SBA2 | 1.51 | 0.0202 | WSB2 | NM_018639 |
| SIR2 | 1.51 | 0.0028 | SIRT1 | NM_012238 |
| ITGA5 | 1.50 | 0.0006 | ITGA5 | NM_002205 |
| RAP1GDS1 | 1.50 | 0.0317 | RAP1GDS1 | NM_021159 |
| CTHRC1 | 1.46 | 0.0010 | CTHRC1 | NM_138455 |
| STC1 | 1.46 | 0.0083 | STC1 | NM_003155 |
| KLF6 | 1.46 | 0.0362 | KLF6 | NM_001300 |
| CDC42BPA | 1.45 | 0.0187 | CDC42BPA | NM_003607 |

-continued

| Gene | Hazard Ratio | P Value | Official Symbol | Accession Number |
|---|---|---|---|---|
| CEBPB | 1.45 | 0.0605 | CEBPB | NM_005194 |
| LAMC2 | 1.45 | 0.0031 | LAMC2 | NM_005562 |
| TGFBR1 | 1.45 | 0.0824 | TGFBR1 | NM_004612 |
| TLN1 | 1.45 | 0.0730 | TLN1 | NM_006289 |
| CDC42 | 1.44 | 0.0387 | CDC42 | NM_001791 |
| FYN | 1.43 | 0.0070 | FYN | NM_002037 |
| IGFBP7 | 1.43 | 0.0283 | IGFBP7 | NM_001553 |
| ARG | 1.43 | 0.0119 | ABL2 | NM_005158 |
| HIF1A | 1.42 | 0.0397 | HIF1A | NM_001530 |
| FST | 1.42 | 0.0460 | FST | NM_006350 |
| S100A1 | 1.42 | 0.0473 | S100A1 | NM_006271 |
| FAP | 1.42 | 0.0023 | FAP | NM_004460 |
| DUSP1 | 1.42 | 0.0014 | DUSP1 | NM_004417 |
| EPAS1 | 1.41 | 0.0494 | EPAS1 | NM_001430 |
| Grb10 | 1.41 | 0.0027 | GRB10 | NM_005311 |
| VEGFC | 1.41 | 0.0894 | VEGFC | NM_005429 |
| INHBB | 1.41 | 0.0710 | INHBB | NM_002193 |
| GADD45B | 1.40 | 0.0023 | GADD45B | NM_015675 |
| UBC | 1.40 | 0.0368 | UBC | NM_021009 |
| GJA1 | 1.40 | 0.0053 | GJA1 | NM_000165 |
| COL1A2 | 1.40 | 0.0086 | COL1A2 | NM_000089 |
| RBM5 | 1.40 | 0.0423 | RBM5 | NM_005778 |
| ROCK1 | 1.39 | 0.0604 | ROCK1 | NM_005406 |
| CTGF | 1.39 | 0.0081 | CTGF | NM_001901 |
| FLT4 | 1.39 | 0.0978 | FLT4 | NM_002020 |
| PDGFC | 1.39 | 0.0052 | PDGFC | NM_016205 |
| INHBA | 1.39 | 0.0058 | INHBA | NM_002192 |
| LOXL2 | 1.38 | 0.0209 | LOXL2 | NM_002318 |
| THBS1 | 1.37 | 0.0090 | THBS1 | NM_003246 |
| ITGAV | 1.37 | 0.0298 | ITGAV | NM_002210 |
| NCAM1 | 1.36 | 0.0714 | NCAM1 | NM_000615 |
| PTHR1 | 1.35 | 0.0410 | PTHR1 | NM_000316 |
| TIMP2 | 1.35 | 0.0446 | TIMP2 | NM_003255 |
| LOX | 1.35 | 0.0041 | LOX | NM_002317 |
| SPARC | 1.35 | 0.0292 | SPARC | NM_003118 |
| TAGLN | 1.34 | 0.0222 | TAGLN | NM_003186 |
| CYR61 | 1.34 | 0.0086 | CYR61 | NM_001554 |
| RANBP9 | 1.34 | 0.0553 | RANBP9 | NM_005493 |
| GADD45 | 1.34 | 0.0604 | GADD45A | NM_001924 |
| S100A4 | 1.34 | 0.0141 | S100A4 | NM_002961 |
| SNAI2 | 1.33 | 0.0263 | SNAI2 | NM_003068 |
| EGR1 | 1.33 | 0.0174 | EGR1 | NM_001964 |
| CDH11 | 1.33 | 0.0355 | CDH11 | NM_001797 |
| SI | 1.33 | 0.0967 | SI | NM_001041 |
| PTK2 | 1.33 | 0.0911 | PTK2 | NM_005607 |
| MCP1 | 1.32 | 0.0215 | CCL2 | NM_002982 |
| PCAF | 1.32 | 0.0463 | PCAF | NM_003884 |
| c-abl | 1.32 | 0.0868 | ABL1 | NM_005157 |
| TIMP3 | 1.32 | 0.0455 | TIMP3 | NM_000362 |
| ANGPT2 | 1.31 | 0.0711 | ANGPT2 | NM_001147 |
| NOTCH2 | 1.30 | 0.0645 | NOTCH2 | NM_024408 |
| GBP2 | 1.30 | 0.0218 | GBP2 | NM_004120 |
| PAI1 | 1.30 | 0.0022 | SERPINE1 | NM_000602 |
| CXCR4 | 1.30 | 0.0341 | CXCR4 | NM_003467 |
| BCAS1 | 1.30 | 0.0060 | BCAS1 | NM_003657 |
| COL1A1 | 1.29 | 0.0349 | COL1A1 | NM_000088 |
| PIM1 | 1.29 | 0.0507 | PIM1 | NM_002648 |
| PDGFB | 1.29 | 0.0288 | PDGFB | NM_002608 |
| Bcl2 | 1.29 | 0.0270 | BCL2 | NM_000633 |
| SLPI | 1.29 | 0.0222 | SLPI | NM_003064 |
| IGFBP5 | 1.29 | 0.0676 | IGFBP5 | NM_000599 |
| ANXA1 | 1.29 | 0.0690 | ANXA1 | NM_000700 |
| FGFR1 | 1.28 | 0.0790 | FGFR1 | NM_023109 |
| CAPG | 1.28 | 0.0987 | CAPG | NM_001747 |
| PRKCA | 1.28 | 0.0548 | PRKCA | NM_002737 |
| EPHA2 | 1.28 | 0.0339 | EPHA2 | NM_004431 |
| AKAP12 | 1.28 | 0.0215 | AKAP12 | NM_005100 |
| FOS | 1.28 | 0.0219 | FOS | NM_005252 |
| CXCL12 | 1.27 | 0.0169 | CXCL12 | NM_000609 |
| GCNT1 | 1.27 | 0.0875 | GCNT1 | NM_001490 |
| IGFBP3 | 1.27 | 0.0499 | IGFBP3 | NM_000598 |
| DPYD | 1.27 | 0.0259 | DPYD | NM_000110 |
| CD68 | 1.27 | 0.0752 | CD68 | NM_001251 |
| EFNA1 | 1.27 | 0.0890 | EFNA1 | NM_004428 |
| ABCC5 | 1.26 | 0.0536 | ABCC5 | NM_005688 |
| TUBB | 1.26 | 0.0635 | TUBB2 | NM_001069 |
| PDGFA | 1.26 | 0.0676 | | NM_002607 |
| DAPK1 | 1.26 | 0.0701 | DAPK1 | NM_004938 |
| SFRP2 | 1.25 | 0.0109 | SFRP2 | NM_003013 |
| ID3 | 1.25 | 0.0744 | ID3 | NM_002167 |
| CTSL | 1.25 | 0.0679 | CTSL | NM_001912 |
| LAMA3 | 1.25 | 0.0299 | LAMA3 | NM_000227 |
| KRT19 | 1.25 | 0.0982 | KRT19 | NM_002276 |
| S100A8 | 1.25 | 0.0228 | S100A8 | NM_002964 |
| IL6 | 1.25 | 0.0933 | IL6 | NM_000600 |
| MRP3 | 1.25 | 0.0538 | ABCC3 | NM_003786 |
| FES | 1.25 | 0.0694 | FES | NM_002005 |
| AP-1 (JUN official) | 1.25 | 0.0974 | JUN | NM_002228 |
| WISP1 | 1.24 | 0.0897 | WISP1 | NM_003882 |
| SFRP4 | 1.24 | 0.0250 | SFRP4 | NM_003014 |
| TGFBI | 1.24 | 0.0692 | TGFBI | NM_000358 |
| Maspin | 1.24 | 0.0152 | SERPINB5 | NM_002639 |
| HOXB7 | 1.23 | 0.0541 | HOXB7 | NM_004502 |
| P14ARF | 1.23 | 0.0944 | | S78535 |
| HSPA1A | 1.23 | 0.0259 | HSPA1A | NM_005345 |
| EGR3 | 1.22 | 0.0312 | EGR3 | NM_004430 |
| CRYAB | 1.22 | 0.0483 | CRYAB | NM_001885 |
| ALDH1A1 | 1.22 | 0.0372 | ALDH1A1 | NM_000689 |
| TGFB3 | 1.22 | 0.0673 | TGFB3 | NM_003239 |
| KLK6 | 1.21 | 0.0288 | KLK6 | NM_002774 |
| ANTXR1 | 1.21 | 0.0942 | ANTXR1 | NM_032208 |
| FZD6 | 1.20 | 0.0479 | FZD6 | NM_003506 |
| ILT-2 | 1.20 | 0.0930 | LILRB1 | NM_006669 |
| S100A2 | 1.20 | 0.0116 | S100A2 | NM_005978 |
| MMP7 | 1.18 | 0.0987 | MMP7 | NM_002423 |
| FABP4 | 1.17 | 0.0371 | FABP4 | NM_001442 |
| OPN, osteopontin | 1.17 | 0.0301 | SPP1 | NM_000582 |
| KLK10 | 1.16 | 0.0581 | KLK10 | NM_002776 |
| pS2 | 1.15 | 0.0186 | TFF1 | NM_003225 |
| REG4 | 1.14 | 0.0053 | REG4 | NM_032044 |
| MUC2 | 1.09 | 0.0429 | MUC2 | NM_002457 |

Table 4.2B shows associations between clinical outcome and gene expression for those genes which demonstrated a Hazard Ratio<1.0 and for which p<0.1. Univariate Cox Proportional Hazards Regression analysis was applied in combined Stage II (Duke's B) and Stage III (Duke's C) patients using DRFI as the metric for clinical outcome.

| Gene | Hazard Ratio | P Value | Official Symbol | Accession Number |
|---|---|---|---|---|
| HSPA8 | 0.48 | 0.0114 | HSPA8 | NM_006597 |
| RPS13 | 0.64 | 0.0082 | RPS13 | NM_001017 |
| NDUFS3 | 0.66 | 0.0096 | NDUFS3 | NM_004551 |
| ST14 | 0.66 | 0.0132 | ST14 | NM_021978 |
| LMNB1 | 0.66 | 0.0135 | LMNB1 | NM_005573 |
| TMSB4X | 0.67 | 0.0039 | TMSB4X | NM_021109 |
| DHFR | 0.68 | 0.0260 | DHFR | NM_000791 |
| BRCA1 | 0.68 | 0.0029 | BRCA1 | NM_007295 |
| SKP2 | 0.68 | 0.0151 | SKP2 | NM_005983 |
| SLC25A3 | 0.69 | 0.0265 | SLC25A3 | NM_213611 |
| CDC20 | 0.69 | 0.0048 | CDC20 | NM_001255 |
| RPLPO | 0.70 | 0.0320 | RPLP0 | NM_001002 |
| TCF-1 | 0.70 | 0.0013 | TCF1 | NM_000545 |
| RRM1 | 0.71 | 0.0598 | RRM1 | NM_001033 |
| ATP5A1 | 0.71 | 0.0827 | ATP5A1 | NM_004046 |
| NME1 | 0.73 | 0.0378 | NME1 | NM_000269 |
| CKS2 | 0.74 | 0.0537 | CKS2 | NM_001827 |
| EI24 | 0.74 | 0.0639 | EI24 | NM_004879 |
| C20 orf1 | 0.74 | 0.0435 | TPX2 | NM_012112 |
| SDC1 | 0.74 | 0.0930 | SDC1 | NM_002997 |
| CSEL1 | 0.75 | 0.0443 | CSE1L | NM_001316 |
| ABCC6 | 0.76 | 0.0416 | ABCC6 | NM_001171 |

| Gene | Hazard Ratio | P Value | Official Symbol | Accession Number |
|---|---|---|---|---|
| MCM2 | 0.76 | 0.0136 | MCM2 | NM_004526 |
| NFKBp65 | 0.77 | 0.0672 | RELA | NM_021975 |
| EPHB2 | 0.77 | 0.0133 | EPHB2 | NM_004442 |
| FASN | 0.78 | 0.0980 | FASN | NM_004104 |
| AURKB | 0.78 | 0.0528 | AURKB | NM_004217 |
| VDR | 0.79 | 0.0832 | VDR | NM_000376 |
| UMPS | 0.80 | 0.0721 | UMPS | NM_000373 |
| UBE2C | 0.81 | 0.0860 | UBE2C | NM_007019 |
| CMYC | 0.82 | 0.0742 | MYC | NM_002467 |
| MYBL2 | 0.83 | 0.0780 | MYBL2 | NM_002466 |
| Cdx2 | 0.84 | 0.0392 | CDX2 | NM_001265 |
| MX1 | 0.85 | 0.0786 | MX1 | NM_002462 |
| EREG | 0.85 | 0.0638 | EREG | NM_001432 |
| AREG | 0.85 | 0.0295 | AREG | NM_001657 |

Table 5.2A shows associations between gene expression and RFI, controlling for particular demographic and clinical characteristics of patients included in the analysis. All genes are listed whose expression correlates with RFI (p<0.1) and which demonstrated a Hazard Ratio>1 in a multivariate analysis including the following variables: tumor location, year of surgery, tumor grade, treatment protocol (C-01 or C-02), BCG treatment (yes or no), and classification of patients according to lymph node status as follows: 0 positive nodes and <12 nodes examined, 0 positive nodes and >12 nodes examined, 1-3 positive nodes, and >4 positive nodes.

| Gene | Hazard Ratio | LR Chi-Square | DF | P Value | Official Symbol | Accession Number |
|---|---|---|---|---|---|---|
| RARB | 2.02 | 3.42 | 1 | 0.0644 | RARB | NM_016152 |
| COX2 | 1.69 | 3.13 | 1 | 0.0768 | PTGS2 | NM_000963 |
| RhoC | 1.60 | 8.71 | 1 | 0.0032 | RHOC | NM_175744 |
| CYP3A4 | 1.57 | 5.15 | 1 | 0.0233 | CYP3A4 | NM_017460 |
| RhoB | 1.54 | 12.40 | 1 | 0.0004 | RHOB | NM_004040 |
| ANXA2 | 1.54 | 7.01 | 1 | 0.0081 | ANXA2 | NM_004039 |
| ITGB1 | 1.54 | 5.54 | 1 | 0.0186 | ITGB1 | NM_002211 |
| NTN1 | 1.53 | 3.63 | 1 | 0.0568 | NTN1 | NM_004822 |
| KRAS2 | 1.51 | 4.83 | 1 | 0.0279 | KRAS | NM_004985 |
| IGFBP7 | 1.44 | 8.53 | 1 | 0.0035 | IGFBP7 | NM_001553 |
| TIMP1 | 1.43 | 9.03 | 1 | 0.0027 | TIMP1 | NM_003254 |
| WWOX | 1.43 | 2.73 | 1 | 0.0988 | WWOX | NM_016373 |
| CYP1B1 | 1.39 | 3.69 | 1 | 0.0548 | CYP1B1 | NM_000104 |
| KCNH2 iso a/b | 1.38 | 3.23 | 1 | 0.0723 | KCNH2 | NM_000238 |
| STC1 | 1.37 | 6.55 | 1 | 0.0105 | STC1 | NM_003155 |
| ITGAV | 1.37 | 9.37 | 1 | 0.0022 | ITGAV | NM_002210 |
| VEGFC | 1.37 | 3.62 | 1 | 0.0571 | VEGFC | NM_005429 |
| G-Catenin | 1.36 | 4.78 | 1 | 0.0287 | JUP | NM_002230 |
| S100A1 | 1.34 | 4.12 | 1 | 0.0423 | S100A1 | NM_006271 |
| GADD45B | 1.34 | 9.63 | 1 | 0.0019 | GADD45B | NM_015675 |
| NCAM1 | 1.33 | 3.00 | 1 | 0.0832 | NCAM1 | NM_000615 |
| CALD1 | 1.33 | 6.05 | 1 | 0.0139 | CALD1 | NM_004342 |
| FST | 1.33 | 4.24 | 1 | 0.0396 | FST | NM_006350 |
| INHBA | 1.33 | 9.68 | 1 | 0.0019 | INHBA | NM_002192 |
| BGN | 1.33 | 7.27 | 1 | 0.0070 | BGN | NM_001711 |
| Claudin 4 | 1.33 | 7.13 | 1 | 0.0076 | CLDN4 | NM_001305 |
| CEBPB | 1.33 | 2.96 | 1 | 0.0851 | CEBPB | NM_005194 |
| LAMC2 | 1.32 | 8.62 | 1 | 0.0033 | LAMC2 | NM_005562 |
| SPINT2 | 1.32 | 3.14 | 1 | 0.0762 | SPINT2 | NM_021102 |
| AKT3 | 1.32 | 7.54 | 1 | 0.0060 | AKT3 | NM_005465 |
| TIMP3 | 1.32 | 6.33 | 1 | 0.0119 | TIMP3 | NM_000362 |
| MAPK14 | 1.31 | 2.75 | 1 | 0.0972 | MAPK14 | NM_139012 |
| HB-EGF | 1.31 | 4.74 | 1 | 0.0294 | HBEGF | NM_001945 |
| DUSP1 | 1.30 | 11.34 | 1 | 0.0008 | DUSP1 | NM_004417 |
| EFNA1 | 1.30 | 5.87 | 1 | 0.0154 | EFNA1 | NM_004428 |
| PTK2 | 1.29 | 3.60 | 1 | 0.0576 | PTK2 | NM_005607 |
| DLC1 | 1.29 | 5.19 | 1 | 0.0227 | DLC1 | NM_006094 |
| EPAS1 | 1.28 | 3.30 | 1 | 0.0693 | EPAS1 | NM_001430 |
| THBS1 | 1.28 | 7.51 | 1 | 0.0061 | THBS1 | NM_003246 |
| TIMP2 | 1.28 | 4.20 | 1 | 0.0404 | TIMP2 | NM_003255 |
| TGFBI | 1.27 | 6.68 | 1 | 0.0098 | TGFBI | NM_000358 |
| DKK1 | 1.27 | 3.05 | 1 | 0.0806 | DKK1 | NM_012242 |
| SPARC | 1.26 | 4.37 | 1 | 0.0366 | SPARC | NM_003118 |
| PDGFC | 1.26 | 6.74 | 1 | 0.0094 | PDGFC | NM_016205 |
| RAB6C | 1.26 | 3.27 | 1 | 0.0704 | RAB6C | NM_032144 |
| LOXL2 | 1.26 | 4.48 | 1 | 0.0343 | LOXL2 | NM_002318 |
| CD68 | 1.25 | 4.68 | 1 | 0.0305 | CD68 | NM_001251 |
| LOX | 1.25 | 7.16 | 1 | 0.0075 | LOX | NM_002317 |
| CDC42BPA | 1.25 | 3.35 | 1 | 0.0671 | CDC42BPA | NM_003607 |

| Gene | Hazard Ratio | LR Chi-Square | DF | P Value | Official Symbol | Accession Number |
|---|---|---|---|---|---|---|
| TAGLN | 1.25 | 4.83 | 1 | 0.0279 | TAGLN | NM_003186 |
| CTHRC1 | 1.25 | 5.96 | 1 | 0.0146 | CTHRC1 | NM_138455 |
| PDGFA | 1.25 | 4.63 | 1 | 0.0314 | | NM_002607 |
| TMEPAI | 1.24 | 5.63 | 1 | 0.0176 | TMEPAI | NM_020182 |
| RAB32 | 1.24 | 4.48 | 1 | 0.0343 | RAB32 | NM_006834 |
| HSPA1A | 1.24 | 8.19 | 1 | 0.0042 | HSPA1A | NM_005345 |
| VIM | 1.24 | 2.97 | 1 | 0.0848 | VIM | NM_003380 |
| IGFBP5 | 1.23 | 3.69 | 1 | 0.0549 | IGFBP5 | NM_000599 |
| EGR1 | 1.23 | 5.12 | 1 | 0.0236 | EGR1 | NM_001964 |
| ANGPT2 | 1.23 | 2.96 | 1 | 0.0852 | ANGPT2 | NM_001147 |
| NDRG1 | 1.22 | 2.91 | 1 | 0.0879 | NDRG1 | NM_006096 |
| VEGF_altsplice1 | 1.22 | 4.08 | 1 | 0.0433 | | AF486837 |
| SLPI | 1.22 | 4.94 | 1 | 0.0262 | SLPI | NM_003064 |
| FOS | 1.22 | 5.67 | 1 | 0.0172 | FOS | NM_005252 |
| VEGF | 1.22 | 2.80 | 1 | 0.0942 | VEGF | NM_003376 |
| ADAMTS12 | 1.22 | 4.40 | 1 | 0.0359 | ADAMTS12 | NM_030955 |
| Maspin | 1.22 | 7.60 | 1 | 0.0058 | SERPINB5 | NM_002639 |
| CGB | 1.22 | 3.25 | 1 | 0.0713 | CGB | NM_000737 |
| CYR61 | 1.21 | 5.22 | 1 | 0.0224 | CYR61 | NM_001554 |
| GJB2 | 1.21 | 3.77 | 1 | 0.0522 | GJB2 | NM_004004 |
| IGFBP3 | 1.21 | 4.24 | 1 | 0.0396 | IGFBP3 | NM_000598 |
| PRKCA | 1.21 | 3.81 | 1 | 0.0508 | PRKCA | NM_002737 |
| S100P | 1.21 | 6.98 | 1 | 0.0082 | S100P | NM_005980 |
| NRP2 | 1.21 | 3.25 | 1 | 0.0714 | NRP2 | NM_003872 |
| EFNB2 | 1.21 | 3.00 | 1 | 0.0834 | EFNB2 | NM_004093 |
| COL1A2 | 1.21 | 3.59 | 1 | 0.0581 | COL1A2 | NM_000089 |
| VEGFB | 1.20 | 2.80 | 1 | 0.0942 | VEGFB | NM_003377 |
| HOXB7 | 1.20 | 4.37 | 1 | 0.0367 | HOXB7 | NM_004502 |
| Grb10 | 1.20 | 3.91 | 1 | 0.0480 | GRB10 | NM_005311 |
| FAP | 1.20 | 4.12 | 1 | 0.0425 | FAP | NM_004460 |
| GJA1 | 1.20 | 4.80 | 1 | 0.0285 | GJA1 | NM_000165 |
| CTGF | 1.19 | 3.38 | 1 | 0.0660 | CTGF | NM_001901 |
| NR4A1 | 1.18 | 5.13 | 1 | 0.0235 | NR4A1 | NM_002135 |
| COL1A1 | 1.18 | 2.77 | 1 | 0.0961 | COL1A1 | NM_000088 |
| ABCC5 | 1.17 | 2.80 | 1 | 0.0945 | ABCC5 | NM_005688 |
| EMP1 | 1.17 | 3.06 | 1 | 0.0804 | EMP1 | NM_001423 |
| SFRP2 | 1.17 | 4.89 | 1 | 0.0270 | SFRP2 | NM_003013 |
| SLC2A1 | 1.17 | 3.52 | 1 | 0.0606 | SLC2A1 | NM_006516 |
| F3 | 1.17 | 3.10 | 1 | 0.0783 | F3 | NM_001993 |
| S100A4 | 1.17 | 2.87 | 1 | 0.0900 | S100A4 | NM_002961 |
| BRK | 1.17 | 2.81 | 1 | 0.0935 | PTK6 | NM_005975 |
| CRYAB | 1.17 | 3.77 | 1 | 0.0523 | CRYAB | NM_001885 |
| MDK | 1.16 | 3.84 | 1 | 0.0500 | MDK | NM_002391 |
| OPN, osteopontin | 1.16 | 6.07 | 1 | 0.0138 | SPP1 | NM_000582 |
| SFRP4 | 1.16 | 4.09 | 1 | 0.0432 | SFRP4 | NM_003014 |
| SIAT4A | 1.16 | 2.76 | 1 | 0.0969 | ST3GAL1 | NM_003033 |
| LAMA3 | 1.16 | 3.23 | 1 | 0.0725 | LAMA3 | NM_000227 |
| AKAP12 | 1.15 | 2.74 | 1 | 0.0976 | AKAP12 | NM_005100 |
| KLK10 | 1.15 | 5.23 | 1 | 0.0221 | KLK10 | NM_002776 |
| EGR3 | 1.14 | 3.16 | 1 | 0.0755 | EGR3 | NM_004430 |
| PAI1 | 1.13 | 3.39 | 1 | 0.0655 | SERPINE1 | NM_000602 |
| CEACAM6 | 1.13 | 2.98 | 1 | 0.0845 | CEACAM6 | NM_002483 |
| KLK6 | 1.13 | 3.74 | 1 | 0.0532 | KLK6 | NM_002774 |
| Nkd-1 | 1.11 | 3.34 | 1 | 0.0674 | NKD1 | NM_033119 |
| IGFBP2 | 1.11 | 3.15 | 1 | 0.0758 | IGFBP2 | NM_000597 |
| REG4 | 1.08 | 3.51 | 1 | 0.0610 | REG4 | NM_032044 |

Table 5.2B shows associations between gene expression and RFI, controlling for particular demographic and clinical characteristics of patients included in the analysis. All genes are listed whose expression correlates with RFI (p<0.1) and which demonstrated a Hazard Ratio<1 in a multivariate analysis including the following variables: tumor location, year of surgery, tumor grade, treatment protocol (C-01 or C-02), BCG treatment (yes or no), and classification of patients according to lymph node status as follows: 0 positive nodes and <12 nodes examined, 0 positive nodes and >12 nodes examined, 1-3 positive nodes, and ≧4 positive nodes.

| Gene | Hazard Ratio | LR Chi-Square | DF | P Value | Official Symbol | Accession Number |
|---|---|---|---|---|---|---|
| Fasl | 0.43 | 5.57 | 1 | 0.0183 | FASLG | NM_000639 |
| BFGF | 0.57 | 4.68 | 1 | 0.0306 | NUDT6 | NM_007083 |
| EstR1 | 0.57 | 3.22 | 1 | 0.0726 | ESR1 | NM_000125 |
| IFIT1 | 0.60 | 4.30 | 1 | 0.0381 | IFIT1 | NM_001548 |

| Gene | Hazard Ratio | LR Chi-Square | DF | P Value | Official Symbol | Accession Number |
|---|---|---|---|---|---|---|
| KLRK1 | 0.64 | 10.81 | 1 | 0.0010 | KLRK1 | NM_007360 |
| E2F1 | 0.65 | 7.49 | 1 | 0.0062 | E2F1 | NM_005225 |
| BRCA1 | 0.66 | 16.33 | 1 | <.0001 | BRCA1 | NM_007295 |
| RAD54L | 0.67 | 6.36 | 1 | 0.0117 | RAD54L | NM_003579 |
| ATP5A1 | 0.67 | 5.50 | 1 | 0.0190 | ATP5A1 | NM_004046 |
| MCM3 | 0.68 | 2.84 | 1 | 0.0922 | MCM3 | NM_002388 |
| DHFR | 0.68 | 7.44 | 1 | 0.0064 | DHFR | NM_000791 |
| HSPA8 | 0.68 | 2.96 | 1 | 0.0855 | HSPA8 | NM_006597 |
| APG-1 | 0.71 | 5.86 | 1 | 0.0155 | HSPA4L | NM_014278 |
| BRCA2 | 0.71 | 4.69 | 1 | 0.0304 | BRCA2 | NM_000059 |
| TRAIL | 0.71 | 7.27 | 1 | 0.0070 | TNFSF10 | NM_003810 |
| SLC25A3 | 0.71 | 5.56 | 1 | 0.0184 | SLC25A3 | NM_213611 |
| PPM1D | 0.72 | 8.02 | 1 | 0.0046 | PPM1D | NM_003620 |
| Chk1 | 0.73 | 6.61 | 1 | 0.0102 | CHEK1 | NM_001274 |
| CD80 | 0.73 | 6.85 | 1 | 0.0089 | CD80 | NM_005191 |
| MADH2 | 0.73 | 3.93 | 1 | 0.0476 | SMAD2 | NM_005901 |
| KIF22 | 0.75 | 5.77 | 1 | 0.0163 | KIF22 | NM_007317 |
| TNFRSF5 | 0.76 | 3.52 | 1 | 0.0607 | CD40 | NM_001250 |
| C20 orf1 | 0.76 | 4.82 | 1 | 0.0281 | TPX2 | NM_012112 |
| ENO1 | 0.76 | 2.88 | 1 | 0.0894 | ENO1 | NM_001428 |
| PRKCB1 | 0.77 | 4.25 | 1 | 0.0393 | PRKCB1 | NM_002738 |
| RAF1 | 0.77 | 4.17 | 1 | 0.0412 | RAF1 | NM_002880 |
| RRM1 | 0.78 | 3.07 | 1 | 0.0799 | RRM1 | NM_001033 |
| UBE2M | 0.78 | 4.43 | 1 | 0.0352 | UBE2M | NM_003969 |
| SKP2 | 0.79 | 3.42 | 1 | 0.0644 | SKP2 | NM_005983 |
| DUT | 0.79 | 4.38 | 1 | 0.0364 | DUT | NM_001948 |
| EI24 | 0.80 | 2.85 | 1 | 0.0912 | EI24 | NM_004879 |
| UMPS | 0.80 | 4.96 | 1 | 0.0260 | UMPS | NM_000373 |
| EFP | 0.81 | 3.83 | 1 | 0.0502 | TRIM25 | NM_005082 |
| HRAS | 0.81 | 3.80 | 1 | 0.0513 | HRAS | NM_005343 |
| CDC20 | 0.81 | 3.78 | 1 | 0.0519 | CDC20 | NM_001255 |
| CSF1 | 0.82 | 2.86 | 1 | 0.0910 | CSF1 | NM_000757 |
| CKS2 | 0.82 | 2.90 | 1 | 0.0886 | CKS2 | NM_001827 |
| ABCB1 | 0.82 | 4.02 | 1 | 0.0450 | ABCB1 | NM_000927 |
| CDC6 | 0.83 | 4.23 | 1 | 0.0397 | CDC6 | NM_001254 |
| GBP1 | 0.83 | 4.34 | 1 | 0.0373 | GBP1 | NM_002053 |
| SURV | 0.83 | 2.91 | 1 | 0.0878 | BIRC5 | NM_001168 |
| CCNE2 | 0.83 | 2.75 | 1 | 0.0975 | CCNE2 | NM_057749 |
| RRM2 | 0.83 | 4.19 | 1 | 0.0407 | RRM2 | NM_001034 |
| CMYC | 0.84 | 3.34 | 1 | 0.0677 | MYC | NM_002467 |
| TCF-1 | 0.84 | 3.96 | 1 | 0.0466 | TCF1 | NM_000545 |
| c-myb (MYB official) | 0.84 | 3.72 | 1 | 0.0538 | MYB | NM_005375 |
| NOTCH1 | 0.85 | 3.39 | 1 | 0.0658 | NOTCH1 | NM_017617 |
| MCM2 | 0.85 | 3.30 | 1 | 0.0693 | MCM2 | NM_004526 |
| ING5 | 0.85 | 2.84 | 1 | 0.0922 | ING5 | NM_032329 |
| AREG | 0.88 | 3.72 | 1 | 0.0538 | AREG | NM_001657 |
| HLA-DRB1 | 0.90 | 3.84 | 1 | 0.0500 | HLA-DRB1 | NM_002124 |

Table 6.2 shows associations between gene expression and clinical outcome based on a nonlinear proportional hazards analysis, using a 2 degree-of-freedom natural spline. All genes are listed which demonstrated a departure from a strictly linear relationship (p<0.05) with RFI in combined Stage II (Duke's B) and Stage III (Duke's C) patients. The relationship between gene expression and RFI was not constant throughout the observed range of expression values in the study, e.g. increases in gene expression may have been related to increases in duration of RFI in one portion of the observed range and with decreases in duration of RFI in a different portion of the range.

| Gene | P Value | Official Symbol | Accession Number |
|---|---|---|---|
| PTHLH | <.0001 | PTHLH | NM_002820 |
| TGFBR1 | 0.0011 | TGFBR1 | NM_004612 |
| CDCA7 v2 | 0.0020 | CDCA7 | NM_145810 |
| S100A4 | 0.0034 | S100A4 | NM_002961 |
| CREBBP | 0.0040 | CREBBP | NM_004380 |
| Upa | 0.0040 | PLAU | NM_002658 |
| KLF5 | 0.0048 | KLF5 | NM_001730 |
| CYP2C8 | 0.0070 | CYP2C8 | NM_000770 |
| HES6 | 0.0090 | HES6 | NM_018645 |
| Cad17 | 0.0093 | CDH17 | NM_004063 |
| CEGP1 | 0.0100 | SCUBE2 | NM_020974 |
| GHI k-ras mut3 | 0.0100 | | GHI_k-ras_mut3 |
| AKT1 | 0.0104 | AKT1 | NM_005163 |
| LAMB3 | 0.0111 | LAMB3 | NM_000228 |
| CAPG | 0.0120 | CAPG | NM_001747 |
| FUT6 | 0.0130 | FUT6 | NM_000150 |
| A-Catenin | 0.0141 | CTNNA1 | NM_001903 |
| CAPN1 | 0.0167 | CAPN1 | NM_005186 |
| HSPE1 | 0.0180 | HSPE1 | NM_002157 |
| MADH4 | 0.0180 | SMAD4 | NM_005359 |
| STMY3 | 0.0190 | MMP11 | NM_005940 |
| TRAG3 | 0.0200 | CSAG2 | NM_004909 |
| GBP1 | 0.0200 | GBP1 | NM_002053 |
| EFNA1 | 0.0210 | EFNA1 | NM_004428 |
| SEMA3B | 0.0210 | SEMA3B | NM_004636 |
| CLTC | 0.0216 | CLTC | NM_004859 |

-continued

| Gene | P Value | Official Symbol | Accession Number |
|---|---|---|---|
| BRK | 0.0240 | PTK6 | NM_005975 |
| Fas | 0.0240 | FAS | NM_000043 |
| CCNE2 variant 1 | 0.0243 | CCNE2 | NM_057749 |
| TMEPAI | 0.0246 | TMEPAI | NM_020182 |
| PTPRJ | 0.0260 | PTPRJ | NM_002843 |
| SKP2 | 0.0261 | SKP2 | NM_005983 |
| AGXT | 0.0273 | AGXT | NM_000030 |
| MAP2 | 0.0320 | MAP2 | NM_031846 |
| PFN2 | 0.0330 | PFN2 | NM_053024 |
| ATP5E | 0.0350 | ATP5E | NM_006886 |
| NRP1 | 0.0352 | NRP1 | NM_003873 |
| MYH11 | 0.0360 | MYH11 | NM_002474 |
| cIAP2 | 0.0369 | BIRC3 | NM_001165 |
| INHBA | 0.0370 | INHBA | NM_002192 |
| EGLN1 | 0.0371 | EGLN1 | NM_022051 |
| GRIK1 | 0.0380 | GRIK1 | NM_000830 |
| KDR | 0.0380 | KDR | NM_002253 |
| KLK6 | 0.0388 | KLK6 | NM_002774 |
| APOC1 | 0.0390 | APOC1 | NM_001645 |
| EP300 | 0.0390 | EP300 | NM_001429 |
| DET1 | 0.0390 | DET1 | NM_017996 |
| ITGB4 | 0.0394 | ITGB4 | NM_000213 |

-continued

| Gene | P Value | Official Symbol | Accession Number |
|---|---|---|---|
| CD3z | 0.0400 | CD3Z | NM_000734 |
| MAX | 0.0400 | MAX | NM_002382 |
| PAI1 | 0.0407 | SERPINE1 | NM_000602 |
| MADH7 | 0.0430 | SMAD7 | NM_005904 |
| SIR2 | 0.0440 | SIRT1 | NM_012238 |
| NEDD8 | 0.0440 | NEDD8 | NM_006156 |
| EPHB2 | 0.0445 | EPHB2 | NM_004442 |
| BTF3 | 0.0460 | BTF3 | NM_001207 |
| CD34 | 0.0470 | CD34 | NM_001773 |
| VEGF_altsplice2 | 0.0480 | | AF214570 |
| Wnt-5b | 0.0480 | WNT5B | NM_032642 |
| RXRA | 0.0482 | RXRA | NM_002957 |
| tusc4 | 0.0486 | TUSC4 | NM_006545 |

Table 7.2 shows all genes exhibiting an interaction (p-value<0.1) with tumor stage. The data were modeled using a proportional hazards model of RFI with gene expression, tumor stage, and their interaction as predictors. Patients who had 0 positive nodes but <12 nodes examined were excluded from these analyses.

| Gene | HR Stage II | HR Stage III | P-Value for Interaction | Official Symbol | Accession Number |
|---|---|---|---|---|---|
| SOS1 | 3.35 | 0.81 | 0.0009 | SOS1 | NM_005633 |
| ALCAM | 2.36 | 0.94 | 0.0020 | ALCAM | NM_001627 |
| pS2 | 1.58 | 1.04 | 0.0040 | TFF1 | NM_003225 |
| TGFB2 | 1.83 | 0.95 | 0.0064 | TGFB2 | NM_003238 |
| TFF3 | 1.57 | 0.90 | 0.0066 | TFF3 | NM_003226 |
| KLF6 | 0.35 | 1.34 | 0.0092 | KLF6 | NM_001300 |
| SNRPF | 0.50 | 1.16 | 0.0106 | SNRPF | NM_003095 |
| CENPA | 2.41 | 0.94 | 0.0106 | CENPA | NM_001809 |
| HES6 | 1.69 | 0.86 | 0.0119 | HES6 | NM_018645 |
| CLDN1 | 0.51 | 0.95 | 0.0124 | CLDN1 | NM_021101 |
| FGF2 | 0.19 | 0.97 | 0.0125 | FGF2 | NM_002006 |
| LEF | 1.94 | 0.94 | 0.0141 | LEF1 | NM_016269 |
| MADH2 | 2.70 | 0.74 | 0.0145 | SMAD2 | NM_005901 |
| TP53BP1 | 2.31 | 0.91 | 0.0153 | TP53BP1 | NM_005657 |
| CCR7 | 1.89 | 0.98 | 0.0182 | CCR7 | NM_001838 |
| MRP3 | 2.26 | 1.08 | 0.0204 | ABCC3 | NM_003786 |
| UPP1 | 0.16 | 1.02 | 0.0208 | UPP1 | NM_003364 |
| PTEN | 3.46 | 1.00 | 0.0216 | PTEN | NM_000314 |
| ST14 | 1.64 | 0.66 | 0.0223 | ST14 | NM_021978 |
| FYN | 2.28 | 1.10 | 0.0241 | FYN | NM_002037 |
| CD24 | 1.33 | 0.84 | 0.0260 | CD24 | NM_013230 |
| LMYC | 1.80 | 0.82 | 0.0275 | RLF | NM_012421 |
| CDC42BPA | 2.82 | 1.12 | 0.0315 | CDC42BPA | NM_003607 |
| CAV1 | 2.11 | 0.95 | 0.0364 | CAV1 | NM_001753 |
| CHFR | 1.81 | 0.99 | 0.0382 | CHFR | NM_018223 |
| MGAT5 | 1.59 | 0.72 | 0.0383 | MGAT5 | NM_002410 |
| FPGS | 1.93 | 0.71 | 0.0402 | FPGS | NM_004957 |
| EMR3 | 2.63 | 0.57 | 0.0488 | EMR3 | NM_032571 |
| SIR2 | 2.17 | 1.07 | 0.0538 | SIRT1 | NM_012238 |
| PTK2B | 1.44 | 0.93 | 0.0542 | PTK2B | NM_004103 |
| Axin 2 | 1.38 | 0.90 | 0.0549 | AXIN2 | NM_004655 |
| TRAG3 | 0.46 | 1.12 | 0.0570 | CSAG2 | NM_004909 |
| MMP7 | 0.78 | 1.28 | 0.0608 | MMP7 | NM_002423 |
| PFN2 | 1.33 | 0.84 | 0.0610 | PFN2 | NM_053024 |
| PTPRJ | 2.05 | 1.00 | 0.0632 | PTPRJ | NM_002843 |
| CXCR4 | 1.96 | 1.08 | 0.0644 | CXCR4 | NM_003467 |
| CCNA2 | 1.55 | 0.79 | 0.0661 | CCNA2 | NM_001237 |
| MMP12 | 0.74 | 1.11 | 0.0685 | MMP12 | NM_002426 |
| KRT8 | 0.64 | 1.27 | 0.0694 | KRT8 | NM_002273 |
| ABCC5 | 2.06 | 1.14 | 0.0704 | ABCC5 | NM_005688 |
| PRDX6 | 2.09 | 0.74 | 0.0711 | PRDX6 | NM_004905 |
| WIF | 1.54 | 0.77 | 0.0738 | WIF1 | NM_007191 |
| cdc25A | 2.48 | 0.94 | 0.0769 | CDC25A | NM_001789 |
| KLF5 | 1.87 | 1.03 | 0.0772 | KLF5 | NM_001730 |
| LRP5 | 1.92 | 0.98 | 0.0783 | LRP5 | NM_002335 |
| PTPD1 | 0.54 | 1.00 | 0.0789 | PTPN21 | NM_007039 |
| RALBP1 | 2.20 | 0.91 | 0.0791 | RALBP1 | NM_006788 |

-continued

| Gene | HR Stage II | HR Stage III | P-Value for Interaction | Official Symbol | Accession Number |
|---|---|---|---|---|---|
| TP53BP2 | 1.82 | 1.05 | 0.0819 | TP53BP2 | NM_005426 |
| STAT5B | 1.57 | 0.86 | 0.0822 | STAT5B | NM_012448 |
| PPARG | 1.32 | 0.79 | 0.0844 | PPARG | NM_005037 |
| HB-EGF | 0.50 | 1.38 | 0.0845 | HBEGF | NM_001945 |
| RARA | 1.77 | 0.96 | 0.0848 | RARA | NM_000964 |
| GCNT1 | 1.86 | 1.07 | 0.0883 | GCNT1 | NM_001490 |
| Ki-67 | 1.53 | 0.86 | 0.0885 | MKI67 | NM_002417 |
| EFNB2 | 1.76 | 1.05 | 0.0895 | EFNB2 | NM_004093 |
| LGMN | 0.59 | 1.37 | 0.0900 | LGMN | NM_001008530 |
| DKK1 | 0.68 | 1.51 | 0.0922 | DKK1 | NM_012242 |
| MADH4 | 2.04 | 0.98 | 0.0964 | SMAD4 | NM_005359 |
| BIK | 1.53 | 0.94 | 0.0966 | BIK | NM_001197 |
| CD44v3 | 1.58 | 0.97 | 0.0996 | | AJ251595v3 |

TABLE A

| Gene | Accession | Reagent | Sequence | Sequence ID Number |
|---|---|---|---|---|
| A-Catenin | NM_001903.1 | Forward Primer | CGTTCCGATCCTCTATACTGCAT | SEQ ID NO: 1 |
| | | Probe | ATGCCTACAGCACCCTGATGTCGCA | SEQ ID NO: 2 |
| | | Reverse Primer | AGGTCCCTGTTGGCCTTATAGG | SEQ ID NO: 3 |
| ABCB1 | NM_000927.2 | Forward Primer | AAACACCACTGGAGCATTGA | SEQ ID NO: 4 |
| | | Probe | CTCGCCAATGATGCTGCTCAAGTT | SEQ ID NO: 5 |
| | | Reverse Primer | CAAGCCTGGAACCTATAGCC | SEQ ID NO: 6 |
| ABCC5 | NM_005688.1 | Forward Primer | TGCAGACTGTACCATGCTGA | SEQ ID NO: 7 |
| | | Probe | CTGCACACGGTTCTAGGCTCCG | SEQ ID NO: 8 |
| | | Reverse Primer | GGCCAGCACCATAATCCTAT | SEQ ID NO: 9 |
| ABCC6 | NM_001171.2 | Forward Primer | GGATGAACCTCGACCTGC | SEQ ID NO: 10 |
| | | Probe | CCAGATAGCCTCGTCCGAGTGCTC | SEQ ID NO: 11 |
| | | Reverse Primer | GAGCTGCACCGTCTCCAG | SEQ ID NO: 12 |
| ACP1 | NM_004300.2 | Forward Primer | GCTACCAAGTCCGTGCTGT | SEQ ID NO: 13 |
| | | Probe | TGATCGACAAATGTTACCCAGACACACA | SEQ ID NO: 14 |
| | | Reverse Primer | GAAAACTGCTTCTGCAATGG | SEQ ID NO: 15 |
| ADAM10 | NM_001110.1 | Forward Primer | CCCATCAACTTGTGCCAGTA | SEQ ID NO: 16 |
| | | Probe | TGCCTACTCCACTGCACAGACCCT | SEQ ID NO: 17 |
| | | Reverse Primer | GGTGATGGTTCGACCACTG | SEQ ID NO: 18 |
| ADAM17 | NM_003183.3 | Forward Primer | GAAGTGCCAGGAGGCGATTA | SEQ ID NO: 19 |
| | | Probe | TGCTACTTGCAAAGGCGTGTCCTACTGC | SEQ ID NO: 20 |
| | | Reverse Primer | CGGGCACTCACTGCTATTACC | SEQ ID NO: 21 |
| ADAMTS12 | NM_030955.2 | Forward Primer | GGAGAAGGGTGGAGTGCAG | SEQ ID NO: 22 |
| | | Probe | CGCACAGTCAGAATCCATCTGGGT | SEQ ID NO: 23 |
| | | Reverse Primer | CAGGGTCAGGTCTCTGGATG | SEQ ID NO: 24 |
| ADPRT | NM_001618.2 | Forward Primer | TTGACAACCTGCTGGACATC | SEQ ID NO: 25 |
| | | Probe | CCCTGAGCAGACTGTAGGCCACCT | SEQ ID NO: 26 |
| | | Reverse Primer | ATGGGATCCTTGCTGCTATC | SEQ ID NO: 27 |
| AGXT | NM_000030.1 | Forward Primer | CTTTTCCCTCCAGTGGCA | SEQ ID NO: 28 |
| | | Probe | CTCCTGGAAACAGTCCACTTGGGC | SEQ ID NO: 29 |
| | | Reverse Primer | ATTTGGAAGGCACTGGGTTT | SEQ ID NO: 30 |
| AKAP12 | NM_005100.2 | Forward Primer | TAGAGAGCCCCTGACAATCC | SEQ ID NO: 31 |
| | | Probe | TGGCTCTAGCTCCTGATGAAGCCTC | SEQ ID NO: 32 |
| | | Reverse Primer | GGTTGGTCTTGGAAAGAGGA | SEQ ID NO: 33 |
| AKT1 | NM_005163.1 | Forward Primer | CGCTTCTATGGCGCTGAGAT | SEQ ID NO: 34 |
| | | Probe | CAGCCCTGGACTACCTGCACTCGG | SEQ ID NO: 35 |
| | | Reverse Primer | TCCCGGTACACCACGTTCTT | SEQ ID NO: 36 |
| AKT2 | NM_001626.2 | Forward Primer | TCCTGCCACCCTTCAAACC | SEQ ID NO: 37 |
| | | Probe | CAGGTCACGTCCGAGGTCGACACA | SEQ ID NO: 38 |
| | | Reverse Primer | GGCGGTAAATTCATCATCGAA | SEQ ID NO: 39 |
| AKT3 | NM_005465.1 | Forward Primer | TTGTCTCTGCCTTGGACTATCTACA | SEQ ID NO: 40 |
| | | Probe | TCACGGTACACAATCTTTCCGGA | SEQ ID NO: 41 |
| | | Reverse Primer | CCAGCATTAGATTCTCCAACTTGA | SEQ ID NO: 42 |

TABLE A-continued

| Gene | Accession | Reagent | Sequence | Sequence ID Number |
|---|---|---|---|---|
| AL137428 | AL137428.1 | Forward Primer | CAAGAAGAGGCTCTACCCTGG | SEQ ID NO: 43 |
| | | Probe | ACTGGGAATTTCCAAGGCCACCTT | SEQ ID NO: 44 |
| | | Reverse Primer | AAATGAGCTCTGCGATCCTC | SEQ ID NO: 45 |
| ALCAM | NM_001627.1 | Forward Primer | GAGGAATATGGAATCCAAGGG | SEQ ID NO: 46 |
| | | Probe | CCAGTTCCTGCCGTCTGCTCTTCT | SEQ ID NO: 47 |
| | | Reverse Primer | GTGGCGGAGATCAAGAGG | SEQ ID NO: 48 |
| ALDH1A1 | NM_000689.1 | Forward Primer | GAAGGAGATAAGGAGGATGTTGACA | SEQ ID NO: 49 |
| | | Probe | AGTGAAGGCCGCAAGACAGGCTTTTC | SEQ ID NO: 50 |
| | | Reverse Primer | CGCCACGGAGATCCAATC | SEQ ID NO: 51 |
| ALDOA | NM_000034.2 | Forward Primer | GCCTGTACGTGCCAGCTC | SEQ ID NO: 52 |
| | | Probe | TGCCAGAGCCTCAACTGTCTCTGC | SEQ ID NO: 53 |
| | | Reverse Primer | TCATCGGAGCTTGATCTCG | SEQ ID NO: 54 |
| AMFR | NM_001144.2 | Forward Primer | GATGGTTCAGCTCTGCAAGGA | SEQ ID NO: 55 |
| | | Probe | CGATTTGAATATCTTTCCTTCTCGCCCACC | SEQ ID NO: 56 |
| | | Reverse Primer | TCGACCGTGGCTGCTCAT | SEQ ID NO: 57 |
| ANGPT2 | NM_001147.1 | Forward Primer | CCGTGAAAGCTGCTCTGTAA | SEQ ID NO: 58 |
| | | Probe | AAGCTGACACAGCCCTCCCAAGTG | SEQ ID NO: 59 |
| | | Reverse Primer | TTGCAGTGGGAAGAACAGTC | SEQ ID NO: 60 |
| ANTXR1 | NM_032208.1 | Forward Primer | CTCCAGGTGTACCTCCAACC | SEQ ID NO: 61 |
| | | Probe | AGCCTTCTCCCACAGCTGCCTACA | SEQ ID NO: 62 |
| | | Reverse Primer | GAGAAGGCTGGGAGACTCTG | SEQ ID NO: 63 |
| ANXA1 | NM_000700.1 | Forward Primer | GCCCCTATCCTACCTTCAATCC | SEQ ID NO: 64 |
| | | Probe | TCCTCGGATGTCGCTGCCT | SEQ ID NO: 65 |
| | | Reverse Primer | CCTTTAACCATTATGGCCTTATGC | SEQ ID NO: 66 |
| ANXA2 | NM_004039.1 | Forward Primer | CAAGACACTAAGGGCGACTACCA | SEQ ID NO: 67 |
| | | Probe | CCACCACACAGGTACAGCAGCGCT | SEQ ID NO: 68 |
| | | Reverse Primer | CGTGTCGGGCTTCAGTCAT | SEQ ID NO: 69 |
| ANXA5 | NM_001154.2 | Forward Primer | GCTCAAGCCTGGAAGATGAC | SEQ ID NO: 70 |
| | | Probe | AGTACCCTGAAGTGTCCCCCACCA | SEQ ID NO: 71 |
| | | Reverse Primer | AGAACCACCAACATCCGCT | SEQ ID NO: 72 |
| AP-1 (JUN official) | NM_002228.2 | Forward Primer | GACTGCAAAGATGGAAACGA | SEQ ID NO: 73 |
| | | Probe | CTATGACGATGCCCTCAACGCCTC | SEQ ID NO: 74 |
| | | Reverse Primer | TAGCCATAAGGTCCGCTCTC | SEQ ID NO: 75 |
| APC | NM_000038.1 | Forward Primer | GGACAGCAGGAATGTGTTTC | SEQ ID NO: 76 |
| | | Probe | CATTGGCTCCCCGTGACCTGTA | SEQ ID NO: 77 |
| | | Reverse Primer | ACCCACTCGATTTGTTTCTG | SEQ ID NO: 78 |
| APEX-1 | NM_001641.2 | Forward Primer | GATGAAGCCTTTCGCAAGTT | SEQ ID NO: 79 |
| | | Probe | CTTTCGGGAAGCCAGGCCCTT | SEQ ID NO: 80 |
| | | Reverse Primer | AGGTCTCCACACAGCACAAG | SEQ ID NO: 81 |
| APG-1 | NM_014278.2 | Forward Primer | ACCCCGGCCTGTATATCAT | SEQ ID NO: 82 |
| | | Probe | CCAATGGCTCGAGTTCTTGATCCC | SEQ ID NO: 83 |
| | | Reverse Primer | CTATCTGGCTCTTTGCTGCAT | SEQ ID NO: 84 |
| APN (ANPEP official) | NM_001150.1 | Forward Primer | CCACCTTGGACCAAAGTAAAGC | SEQ ID NO: 85 |
| | | Probe | CTCCCCAACACGCTGAAACCCG | SEQ ID NO: 86 |
| | | Reverse Primer | TCTCAGCGTCACCTGGTAGGA | SEQ ID NO: 87 |
| APOC1 | NM_001645.3 | Forward Primer | GGAAACACACTGGAGGACAAG | SEQ ID NO: 88 |
| | | Probe | TCATCAGCCGCATCAAACAGAGTG | SEQ ID NO: 89 |
| | | Reverse Primer | CGCATCTTGGCAGAAAGTT | SEQ ID NO: 90 |
| AREG | NM_001657.1 | Forward Primer | TGTGAGTGAAATGCCTTCTAGTAGTGA | SEQ ID NO: 91 |
| | | Probe | CCGTCCTCGGGAGCCGACTATGA | SEQ ID NO: 92 |
| | | Reverse Primer | TTGTGGTTCGTTATCATACTCTTCTGA | SEQ ID NO: 93 |
| ARG | NM_005158.2 | Forward Primer | CGCAGTGCAGCTGAGTATCTG | SEQ ID NO: 94 |
| | | Probe | TCGCACCAGGAAGCTGCCATTGA | SEQ ID NO: 95 |
| | | Reverse Primer | TGCCCAGGGCTACTCTCACTT | SEQ ID NO: 96 |

TABLE A-continued

| Gene | Accession | Reagent | Sequence | Sequence ID Number |
|---|---|---|---|---|
| ARHF | NM_019034.2 | Forward Primer | ACTGGCCCACTTAGTCCTCA | SEQ ID NO: 97 |
| | | Probe | CTCCCAACCTGCTGTCCCTCAAG | SEQ ID NO: 98 |
| | | Reverse Primer | CTGAACTCCACAGGCTGGTA | SEQ ID NO: 99 |
| ATOH1 | NM_005172.1 | Forward Primer | GCAGCCACCTGCAACTTT | SEQ ID NO: 100 |
| | | Probe | CAGGCGAGAGAGCATCCCGTCTAC | SEQ ID NO: 101 |
| | | Reverse Primer | TCCAGGAGGGACAGCTCA | SEQ ID NO: 102 |
| ATP5A1 | NM_004046.3 | Forward Primer | GATGCTGCCACTCAACAACT | SEQ ID NO: 103 |
| | | Probe | AGTTAGACGCACGCCACGACTCAA | SEQ ID NO: 104 |
| | | Reverse Primer | TGTCCTTGCTTCAGCAACTC | SEQ ID NO: 105 |
| ATP5E | NM_006886.2 | Forward Primer | CCGCTTTCGCTACAGCAT | SEQ ID NO: 106 |
| | | Probe | TCCAGCCTGTCTCCAGTAGGCCAC | SEQ ID NO: 107 |
| | | Reverse Primer | TGGGAGTATCGGATGTAGCTG | SEQ ID NO: 108 |
| AURKB | NM_004217.1 | Forward Primer | AGCTGCAGAAGAGCTGCACAT | SEQ ID NO: 109 |
| | | Probe | TGACGAGCAGCGAACAGCCACG | SEQ ID NO: 110 |
| | | Reverse Primer | GCATCTGCCAACTCCTCCAT | SEQ ID NO: 111 |
| Axin 2 | NM_004655.2 | Forward Primer | GGCTATGTCTTTGCACCAGC | SEQ ID NO: 112 |
| | | Probe | ACCAGCGCCAACGACAGTGAGATA | SEQ ID NO: 113 |
| | | Reverse Primer | ATCCGTCAGCGCATCACT | SEQ ID NO: 114 |
| axin1 | NM_003502.2 | Forward Primer | CCGTGTGACAGCATCGTT | SEQ ID NO: 115 |
| | | Probe | CGTACTACTTCTGCGGGGAACCCA | SEQ ID NO: 116 |
| | | Reverse Primer | CTCACCAGGGTGCGGTAG | SEQ ID NO: 117 |
| B-Catenin | NM_001904.1 | Forward Primer | GGCTCTTGTGCGTACTGTCCTT | SEQ ID NO: 118 |
| | | Probe | AGGCTCAGTGATGTCTTCCCTGTCACCAG | SEQ ID NO: 119 |
| | | Reverse Primer | TCAGATGACGAAGAGCACAGATG | SEQ ID NO: 120 |
| BAD | NM_032989.1 | Forward Primer | GGGTCAGGTGCCTCGAGAT | SEQ ID NO: 121 |
| | | Probe | TGGGCCCAGAGCATGTTCCAGATC | SEQ ID NO: 122 |
| | | Reverse Primer | CTGCTCACTCGGCTCAAACTC | SEQ ID NO: 123 |
| BAG1 | NM_004323.2 | Forward Primer | CGTTGTCAGCACTTGGAATACAA | SEQ ID NO: 124 |
| | | Probe | CCCAATTAACATGACCCGGCAACCAT | SEQ ID NO: 125 |
| | | Reverse Primer | GTTCAACCTCTTCCTGTGGACTGT | SEQ ID NO: 126 |
| BAG2 | NM_004282.2 | Forward Primer | CTAGGGGCAAAAAGCATGA | SEQ ID NO: 127 |
| | | Probe | TTCCATGCCAGACAGGAAAAAGCA | SEQ ID NO: 128 |
| | | Reverse Primer | CTAAATGCCCAAGGTGACTG | SEQ ID NO: 129 |
| BAG3 | NM_004281.2 | Forward Primer | GAAAGTAAGCCAGGCCCAGTT | SEQ ID NO: 130 |
| | | Probe | CAGAACTCCTCCTGGACACATCCCAA | SEQ ID NO: 131 |
| | | Reverse Primer | ACCTCTTTGCGGATCACTTGA | SEQ ID NO: 132 |
| Bak | NM_001188.1 | Forward Primer | CCATTCCCACCATTCTACCT | SEQ ID NO: 133 |
| | | Probe | ACACCCCAGACGTCCTGGCCT | SEQ ID NO: 134 |
| | | Reverse Primer | GGGAACATAGACCCACCAAT | SEQ ID NO: 135 |
| Bax | NM_004324.1 | Forward Primer | CCGCCGTGGACACAGACT | SEQ ID NO: 136 |
| | | Probe | TGCCACTCGGAAAAAGACCTCTCGG | SEQ ID NO: 137 |
| | | Reverse Primer | TTGCCGTCAGAAAACATGTCA | SEQ ID NO: 138 |
| BBC3 | NM_014417.1 | Forward Primer | CCTGGAGGGTCCTGTACAAT | SEQ ID NO: 139 |
| | | Probe | CATCATGGGACTCCTGCCCTTACC | SEQ ID NO: 140 |
| | | Reverse Primer | CTAATTGGGCTCCATCTCG | SEQ ID NO: 141 |
| BCAS1 | NM_003657.1 | Forward Primer | CCCCGAGACAACGGAGATAA | SEQ ID NO: 142 |
| | | Probe | CTTTCCGTTGGCATCCGCAACAG | SEQ ID NO: 143 |
| | | Reverse Primer | CTCGGGTTTGGCCTCTTTC | SEQ ID NO: 144 |
| Bcl2 | NM_000633.1 | Forward Primer | CAGATGGACCTAGTACCCACTGAGA | SEQ ID NO: 145 |
| | | Probe | TTCCACGCCGAAGGACAGCGAT | SEQ ID NO: 146 |
| | | Reverse Primer | CCTATGATTTAAGGGCATTTTTCC | SEQ ID NO: 147 |
| BCL2L10 | NM_020396.2 | Forward Primer | GCTGGGATGGCTTTTGTCA | SEQ ID NO: 148 |
| | | Probe | TCTTCAGGACCCCCTTTCCACTGGC | SEQ ID NO: 149 |
| | | Reverse Primer | GCCTGGACCAGCTGTTTTCTC | SEQ ID NO: 150 |
| BCL2L11 | NM_138621.1 | Forward Primer | AATTACCAAGCAGCCGAAGA | SEQ ID NO: 151 |
| | | Probe | CCACCCACGAATGGTTATCTTACGACTG | SEQ ID NO: 152 |
| | | Reverse Primer | CAGGCGGACAATGTAACGTA | SEQ ID NO: 153 |

TABLE A-continued

| Gene | Accession | Reagent | Sequence | Sequence ID Number |
|---|---|---|---|---|
| BCL2L12 | NM_138639.1 | Forward Primer | AACCCACCCCTGTCTTGG | SEQ ID NO: 154 |
| | | Probe | TCCGGGTAGCTCTCAAACTCGAGG | SEQ ID NO: 155 |
| | | Reverse Primer | CTCAGCTGACGGGAAAGG | SEQ ID NO: 156 |
| Bclx | NM_001191.1 | Forward Primer | CTTTTGTGGAACTCTATGGGAACA | SEQ ID NO: 157 |
| | | Probe | TTCGGCTCTCGGCTGCTGCA | SEQ ID NO: 158 |
| | | Reverse Primer | CAGCGGTTGAAGCGTTCCT | SEQ ID NO: 159 |
| BCRP | NM_004827.1 | Forward Primer | TGTACTGGCGAAGAATATTTGGTAAA | SEQ ID NO: 160 |
| | | Probe | CAGGGCATCGATCTCTCACCCTGG | SEQ ID NO: 161 |
| | | Reverse Primer | GCCACGTGATTCTTCCACAA | SEQ ID NO: 162 |
| BFGF | NM_007083.1 | Forward Primer | CCAGGAAGAATGCTTAAGATGTGA | SEQ ID NO: 163 |
| | | Probe | TTCGCCAGGTCATTGAGATCCATCCA | SEQ ID NO: 164 |
| | | Reverse Primer | TGGTGATGGGAGTTGTATTTTCAG | SEQ ID NO: 165 |
| BGN | NM_001711.3 | Forward Primer | GAGCTCCGCAAGGATGAC | SEQ ID NO: 166 |
| | | Probe | CAAGGGTCTCCAGCACCTCTACGC | SEQ ID NO: 167 |
| | | Reverse Primer | CTTGTTGTTCACCAGGACGA | SEQ ID NO: 168 |
| BID | NM_001196.2 | Forward Primer | GGACTGTGAGGTCAACAACG | SEQ ID NO: 169 |
| | | Probe | TGTGATGCACTCATCCCTGAGGCT | SEQ ID NO: 170 |
| | | Reverse Primer | GGAAGCCAAACACCAGTAGG | SEQ ID NO: 171 |
| BIK | NM_001197.3 | Forward Primer | ATTCCTATGGCTCTGCAATTGTC | SEQ ID NO: 172 |
| | | Probe | CCGGTTAACTGTGGCCTGTGCCC | SEQ ID NO: 173 |
| | | Reverse Primer | GGCAGGAGTGAATGGCTCTTC | SEQ ID NO: 174 |
| BIN1 | NM_004305.1 | Forward Primer | CCTGCAAAAGGGAACAAGAG | SEQ ID NO: 175 |
| | | Probe | CTTCGCCTCCAGATGGCTCCC | SEQ ID NO: 176 |
| | | Reverse Primer | CGTGGTTGACTCTGATCTCG | SEQ ID NO: 177 |
| BLMH | NM_000386.2 | Forward Primer | GGTTGCTGCCTCCATCAAAG | SEQ ID NO: 178 |
| | | Probe | ACATCACAGCCAAACCACACAGCCTCT | SEQ ID NO: 179 |
| | | Reverse Primer | CCAGCTTGCTATTGAAGTGTTTTC | SEQ ID NO: 180 |
| BMP2 | NM_001200.1 | Forward Primer | ATGTGGACGCTCTTTCAATG | SEQ ID NO: 181 |
| | | Probe | ACCGCAGTCCGTCTAAGAAGCACG | SEQ ID NO: 182 |
| | | Reverse Primer | ACCATGGTCGACCTTTAGGA | SEQ ID NO: 183 |
| BMP4 | NM_001202.2 | Forward Primer | GGGCTAGCCATTGAGGTG | SEQ ID NO: 184 |
| | | Probe | CTCACCTCCATCAGACTCGGACCC | SEQ ID NO: 185 |
| | | Reverse Primer | GCTAATCCTGACATGCTGGC | SEQ ID NO: 186 |
| BMP7 | NM_001719.1 | Forward Primer | TCGTGGAACATGACAAGGAATT | SEQ ID NO: 187 |
| | | Probe | TTCCACCCACGCTACCACCATCG | SEQ ID NO: 188 |
| | | Reverse Primer | TGGAAAGATCAAACCGGAACTC | SEQ ID NO: 189 |
| BMPR1A | NM_004329.2 | Forward Primer | TTGGTTCAGCGAACTATTGC | SEQ ID NO: 190 |
| | | Probe | CAAACAGATTCAGATGGTCCGGCA | SEQ ID NO: 191 |
| | | Reverse Primer | TCTCCATATCGGCCTTTACC | SEQ ID NO: 192 |
| BRAF | NM_004333.1 | Forward Primer | CCTTCCGACCAGCAGATGAA | SEQ ID NO: 193 |
| | | Probe | CAATTTGGGCAACGAGACCGATCCT | SEQ ID NO: 194 |
| | | Reverse Primer | TTTATATGCACATTGGGAGCTGAT | SEQ ID NO: 195 |
| BRCA1 | NM_007295.1 | Forward Primer | TCAGGGGGCTAGAAATCTGT | SEQ ID NO: 196 |
| | | Probe | CTATGGGCCCTTCACCAACATGC | SEQ ID NO: 197 |
| | | Reverse Primer | CCATTCCAGTTGATCTGTGG | SEQ ID NO: 198 |
| BRCA2 | NM_000059.1 | Forward Primer | AGTTCGTGCTTTGCAAGATG | SEQ ID NO: 199 |
| | | Probe | CATTCTTCACTGCTTCATAAAGCTCTGCA | SEQ ID NO: 200 |
| | | Reverse Primer | AAGGTAAGCTGGGTCTGCTG | SEQ ID NO: 201 |
| BRK | NM_005975.1 | Forward Primer | GTGCAGGAAAGGTTCACAAA | SEQ ID NO: 202 |
| | | Probe | AGTGTCTGCGTCCAATACACGCGT | SEQ ID NO: 203 |
| | | Reverse Primer | GCACACACGATGGAGTAAGG | SEQ ID NO: 204 |
| BTF3 | NM_001207.2 | Forward Primer | CAGTGATCCACTTTAACAACCCTAAAG | SEQ ID NO: 205 |
| | | Probe | TCAGGCATCTCTGGCAGCGAACAC | SEQ ID NO: 206 |
| | | Reverse Primer | AGCATGGCCTGTAATGGTGAA | SEQ ID NO: 207 |
| BTRC | NM_033637.2 | Forward Primer | GTTGGGACACAGTTGGTCTG | SEQ ID NO: 208 |
| | | Probe | CAGTCGGCCCAGGACGGTCTACT | SEQ ID NO: 209 |
| | | Reverse Primer | TGAAGCAGTCAGTTGTGCTG | SEQ ID NO: 210 |

TABLE A-continued

| Gene | Accession | Reagent | Sequence | Sequence ID Number |
| --- | --- | --- | --- | --- |
| BUB1 | NM_004336.1 | Forward Primer | CCGAGGTTAATCCAGCACGTA | SEQ ID NO: 211 |
| | | Probe | TGCTGGGAGCCTACACTTGGCCC | SEQ ID NO: 212 |
| | | Reverse Primer | AAGACATGGCGCTCTCAGTTC | SEQ ID NO: 213 |
| BUB1B | NM_001211.3 | Forward Primer | TCAACAGAAGGCTGAACCACTAGA | SEQ ID NO: 214 |
| | | Probe | TACAGTCCCAGCACCGACAATTCC | SEQ ID NO: 215 |
| | | Reverse Primer | CAACAGAGTTTGCCGAGACACT | SEQ ID NO: 216 |
| BUB3 | NM_004725.1 | Forward Primer | CTGAAGCAGATGGTTCATCATT | SEQ ID NO: 217 |
| | | Probe | CCTCGCTTTGTTTAACAGCCCAGG | SEQ ID NO: 218 |
| | | Reverse Primer | GCTGATTCCCAAGAGTCTAACC | SEQ ID NO: 219 |
| c-abl | NM_005157.2 | Forward Primer | CCATCTCGCTGAGATACGAA | SEQ ID NO: 220 |
| | | Probe | GGGAGGGTGTACCATTACAGGATCAACA | SEQ ID NO: 221 |
| | | Reverse Primer | AGACGTAGAGCTTGCCATCA | SEQ ID NO: 222 |
| c-kit | NM_000222.1 | Forward Primer | GAGGCAACTGCTTATGGCTTAATTA | SEQ ID NO: 223 |
| | | Probe | TTACAGCGACAGTCATGGCCGCAT | SEQ ID NO: 224 |
| | | Reverse Primer | GGCACTCGGCTTGAGCAT | SEQ ID NO: 225 |
| c-myb (MYB official) | NM_005375.1 | Forward Primer | AACTCAGACTTGGAAATGCCTTCT | SEQ ID NO: 226 |
| | | Probe | AACTTCCACCCCCCTCATTGGTCACA | SEQ ID NO: 227 |
| | | Reverse Primer | CTGGTCTCTATGAAATGGTGTTGTAAC | SEQ ID NO: 228 |
| c-Src | NM_005417.3 | Forward Primer | TGAGGAGTGGTATTTTGGCAAGA | SEQ ID NO: 229 |
| | | Probe | AACCGCTCTGACTCCCGTCGGTG | SEQ ID NO: 230 |
| | | Reverse Primer | CTCTCGGGTTCTCTGCATTGA | SEQ ID NO: 231 |
| C20 orf1 | NM_012112.2 | Forward Primer | TCAGCTGTGAGCTGCGGATA | SEQ ID NO: 232 |
| | | Probe | CAGGTCCCATTGCCGGGCG | SEQ ID NO: 233 |
| | | Reverse Primer | ACGGTCCTAGGTTTGAGGTTAAGA | SEQ ID NO: 234 |
| C20ORF126 | NM_030815.2 | Forward Primer | CCAGCACTGCTCGTTACTGT | SEQ ID NO: 235 |
| | | Probe | TGGGACCTCAGACCACTGAAGGC | SEQ ID NO: 236 |
| | | Reverse Primer | TTGACTTCACGGCAGTTCATA | SEQ ID NO: 237 |
| C8orf4 | NM_020130.2 | Forward Primer | CTACGAGTCAGCCCATCCAT | SEQ ID NO: 238 |
| | | Probe | CATGGCTACCACTTCGACACAGCC | SEQ ID NO: 239 |
| | | Reverse Primer | TGCCCACGGCTTTCTTAC | SEQ ID NO: 240 |
| CA9 | NM_001216.1 | Forward Primer | ATCCTAGCCCTGGTTTTTGG | SEQ ID NO: 241 |
| | | Probe | TTTGCTGTCACCAGCGTCGC | SEQ ID NO: 242 |
| | | Reverse Primer | CTGCCTTCTCATCTGCACAA | SEQ ID NO: 243 |
| Cad17 | NM_004063.2 | Forward Primer | GAAGGCCAAGAACCGAGTCA | SEQ ID NO: 244 |
| | | Probe | TTATATTCCAGTTTAAGGCCAATCCTC | SEQ ID NO: 245 |
| | | Reverse Primer | TCCCCAGTTAGTTCAAAAGTCACA | SEQ ID NO: 246 |
| CALD1 | NM_004342.4 | Forward Primer | CACTAAGGTTTGAGACAGTTCCAGAA | SEQ ID NO: 247 |
| | | Probe | AACCCAAGCTCAAGACGCAGGACGAG | SEQ ID NO: 248 |
| | | Reverse Primer | GCGAATTAGCCCTCTACAACTGA | SEQ ID NO: 249 |
| CAPG | NM_001747.1 | Forward Primer | GATTGTCACTGATGGGGAGG | SEQ ID NO: 250 |
| | | Probe | AGGACCTGGATCATCTCAGCAGGC | SEQ ID NO: 251 |
| | | Reverse Primer | CCTTCAGAGCAGGCTTGG | SEQ ID NO: 252 |
| CAPN1 | NM_005186.2 | Forward Primer | CAAGAAGCTGTACGAGCTCATCA | SEQ ID NO: 253 |
| | | Probe | CCGCTACTCGGAGCCCGACCTG | SEQ ID NO: 254 |
| | | Reverse Primer | GCAGCAAACGAAATTGTCAAAG | SEQ ID NO: 255 |
| CASP8 | NM_033357.1 | Forward Primer | CCTCGGGGATACTGTCTGAT | SEQ ID NO: 256 |
| | | Probe | CAACAATCACAATTTTGCAAAAGCACG | SEQ ID NO: 257 |
| | | Reverse Primer | GAAGTTTGGGCACTTTCTCC | SEQ ID NO: 258 |
| CASP9 | NM_001229.2 | Forward Primer | TGAATGCCGTGGATTGCA | SEQ ID NO: 259 |
| | | Probe | CACTAGCCCTGGACCAGCCACTGCT | SEQ ID NO: 260 |
| | | Reverse Primer | ACAGGGATCATGGGACACAAG | SEQ ID NO: 261 |
| CAT | NM_001752.1 | Forward Primer | ATCCATTCGATCTCACCAAGGT | SEQ ID NO: 262 |
| | | Probe | TGGCCTCACAAGGACTACCCTCTCATCC | SEQ ID NO: 263 |
| | | Reverse Primer | TCCGGTTTAAGACCAGTTTACCA | SEQ ID NO: 264 |
| CAV1 | NM_001753.3 | Forward Primer | GTGGCTCAACATTGTGTTCC | SEQ ID NO: 265 |
| | | Probe | ATTTCAGCTGATCAGTGGGCCTCC | SEQ ID NO: 266 |
| | | Reverse Primer | CAATGGCCTCCATTTTACAG | SEQ ID NO: 267 |

TABLE A-continued

| Gene | Accession | Reagent | Sequence | Sequence ID Number |
|---|---|---|---|---|
| CBL | NM_005188.1 | Forward Primer | TCATTCACAAACCTGGCAGT | SEQ ID NO: 268 |
| | | Probe | TTCCGGCTGAGCTGTACTCGTCTG | SEQ ID NO: 269 |
| | | Reverse Primer | CATACCCAATAGCCCACTGA | SEQ ID NO: 270 |
| CCL20 | NM_004591.1 | Forward Primer | CCATGTGCTGTACCAAGAGTTTG | SEQ ID NO: 271 |
| | | Probe | CAGCACTGACATCAAAGCAGCCAGGA | SEQ ID NO: 272 |
| | | Reverse Primer | CGCCGCAGAGGTGGAGTA | SEQ ID NO: 273 |
| CCL3 | NM_002983.1 | Forward Primer | AGCAGACAGTGGTCAGTCCTT | SEQ ID NO: 274 |
| | | Probe | CTCTGCTGACACTCGAGCCCACAT | SEQ ID NO: 275 |
| | | Reverse Primer | CTGCATGATTCTGAGCAGGT | SEQ ID NO: 276 |
| CCNA2 | NM_001237.2 | Forward Primer | CCATACCTCAAGTATTTGCCATCAG | SEQ ID NO: 277 |
| | | Probe | ATTGCTGGAGCTGCCTTTCATTTAGCACT | SEQ ID NO: 278 |
| | | Reverse Primer | AGCTTTGTCCCGTGACTGTGTA | SEQ ID NO: 279 |
| CCNB1 | NM_031966.1 | Forward Primer | TTCAGGTTGTTGCAGGAGAC | SEQ ID NO: 280 |
| | | Probe | TGTCTCCATTATTGATCGGTTCATGCA | SEQ ID NO: 281 |
| | | Reverse Primer | CATCTTCTTGGGCACACAAT | SEQ ID NO: 282 |
| CCNB2 | NM_004701.2 | Forward Primer | AGGCTTCTGCAGGAGACTCTGT | SEQ ID NO: 283 |
| | | Probe | TCGATCCATAATGCCAACGCACATG | SEQ ID NO: 284 |
| | | Reverse Primer | GGGAAACTGGCTGAACCTGTAA | SEQ ID NO: 285 |
| CCND1 | NM_001758.1 | Forward Primer | GCATGTTCGTGGCCTCTAAGA | SEQ ID NO: 286 |
| | | Probe | AAGGAGACCATCCCCCTGACGGC | SEQ ID NO: 287 |
| | | Reverse Primer | CGGTGTAGATGCACAGCTTCTC | SEQ ID NO: 288 |
| CCND3 | NM_001760.2 | Forward Primer | CCTCTGTGCTACAGATTATACCTTTGC | SEQ ID NO: 289 |
| | | Probe | TACCCGCCATCCATGATCGCCA | SEQ ID NO: 290 |
| | | Reverse Primer | CACTGCAGCCCCAATGCT | SEQ ID NO: 291 |
| CCNE1 | NM_001238.1 | Forward Primer | AAAGAAGATGATGACCGGGTTTAC | SEQ ID NO: 292 |
| | | Probe | CAAACTCAACGTGCAAGCCTCGGA | SEQ ID NO: 293 |
| | | Reverse Primer | GAGCCTCTGGATGGTGCAAT | SEQ ID NO: 294 |
| CCNE2 | NM_057749.1 | Forward Primer | GGTCACCAAGAAACATCAGTATGAA | SEQ ID NO: 295 |
| | | Probe | CCCAGATAATACAGGTGGCCAACAATTCCT | SEQ ID NO: 296 |
| | | Reverse Primer | TTCAATGATAATGCAAGGACTGATC | SEQ ID NO: 297 |
| CCNE2 variant 1 | NM_057749var1 | Forward Primer | ATGCTGTGGCTCCTTCCTAACT | SEQ ID NO: 298 |
| | | Probe | TACCAAGCAACCTACATGTCAAGAAAGCCC | SEQ ID NO: 299 |
| | | Reverse Primer | ACCCAAATTGTGATATACAAAAAGGTT | SEQ ID NO: 300 |
| CCR7 | NM_001838.2 | Forward Primer | GGATGACATGCACTCAGCTC | SEQ ID NO: 301 |
| | | Probe | CTCCCATCCCAGTGGAGCCAA | SEQ ID NO: 302 |
| | | Reverse Primer | CCTGACATTTCCCTTGTCCT | SEQ ID NO: 303 |
| CD105 | NM_000118.1 | Forward Primer | GCAGGTGTCAGCAAGTATGATCAG | SEQ ID NO: 304 |
| | | Probe | CGACAGGATATTGACCACCGCCTCATT | SEQ ID NO: 305 |
| | | Reverse Primer | TTTTTCCGCTGTGGTGATGA | SEQ ID NO: 306 |
| CD134 (TNFRSF4 official) | NM_003327.1 | Forward Primer | GCCCAGTGCGGAGAACAG | SEQ ID NO: 307 |
| | | Probe | CCAGCTTGATTCTCGTCTCTGCACTTAAGC | SEQ ID NO: 308 |
| | | Reverse Primer | AATCACACGCACCTGGAGAAC | SEQ ID NO: 309 |
| CD18 | NM_000211.1 | Forward Primer | CGTCAGGACCCACCATGTCT | SEQ ID NO: 310 |
| | | Probe | CGCGGCCGAGACATGGCTTG | SEQ ID NO: 311 |
| | | Reverse Primer | GGTTAATTGGTGACATCCTCAAGA | SEQ ID NO: 312 |
| CD24 | NM_013230.1 | Forward Primer | TCCAACTAATGCCACCACCAA | SEQ ID NO: 313 |
| | | Probe | CTGTTGACTGCAGGGCACCACCA | SEQ ID NO: 314 |
| | | Reverse Primer | GAGAGAGTGAGACCACGAAGAGACT | SEQ ID NO: 315 |
| CD28 | NM_006139.1 | Forward Primer | TGTGAAAGGGAAACACCTTTG | SEQ ID NO: 316 |
| | | Probe | CCAAGTCCCCTATTTCCCGGACCT | SEQ ID NO: 317 |
| | | Reverse Primer | AGCACCCAAAAGGGCTTAG | SEQ ID NO: 318 |
| CD31 | NM_000442.1 | Forward Primer | TGTATTTCAAGACCTCTGTGCACTT | SEQ ID NO: 319 |
| | | Probe | TTTATGAACCTGCCCTGCTCCCACA | SEQ ID NO: 320 |
| | | Reverse Primer | TTAGCCTGAGGAATTGCTGTGTT | SEQ ID NO: 321 |

TABLE A-continued

| Gene | Accession | Reagent | Sequence | Sequence ID Number |
|---|---|---|---|---|
| CD34 | NM_001773.1 | Forward Primer | CCACTGCACACACCTCAGA | SEQ ID NO: 322 |
| | | Probe | CTGTTCTTGGGGCCCTACACCTTG | SEQ ID NO: 323 |
| | | Reverse Primer | CAGGAGTTTACCTGCCCCT | SEQ ID NO: 324 |
| CD3z | NM_000734.1 | Forward Primer | AGATGAAGTGGAAGGCGCTT | SEQ ID NO: 325 |
| | | Probe | CACCGCGGCCATCCTGCA | SEQ ID NO: 326 |
| | | Reverse Primer | TGCCTCTGTAATCGGCAACTG | SEQ ID NO: 327 |
| CD44E | X55150 | Forward Primer | ATCACCGACAGCACAGACA | SEQ ID NO: 328 |
| | | Probe | CCCTGCTACCAATATGGACTCCAGTCA | SEQ ID NO: 329 |
| | | Reverse Primer | ACCTGTGTTTGGATTTGCAG | SEQ ID NO: 330 |
| CD44s | M59040.1 | Forward Primer | GACGAAGACAGTCCCTGGAT | SEQ ID NO: 331 |
| | | Probe | CACCGACAGCACAGACAGAATCCC | SEQ ID NO: 332 |
| | | Reverse Primer | ACTGGGGTGGAATGTGTCTT | SEQ ID NO: 333 |
| CD44v3 | AJ251595v3 | Forward Primer | CACACAAAACAGAACCAGGACT | SEQ ID NO: 334 |
| | | Probe | ACCCAGTGGAACCCAAGCCATTC | SEQ ID NO: 335 |
| | | Reverse Primer | CTGAAGTAGCACTTCCGGATT | SEQ ID NO: 336 |
| CD44v6 | AJ251595v6 | Forward Primer | CTCATACCAGCCATCCAATG | SEQ ID NO: 337 |
| | | Probe | CACCAAGCCCAGAGGACAGTTCCT | SEQ ID NO: 338 |
| | | Reverse Primer | TTGGGTTGAAGAAATCAGTCC | SEQ ID NO: 339 |
| CD68 | NM_001251.1 | Forward Primer | TGGTTCCCAGCCCTGTGT | SEQ ID NO: 340 |
| | | Probe | CTCCAAGCCCAGATTCAGATTCGAGTCA | SEQ ID NO: 341 |
| | | Reverse Primer | CTCCTCCACCCTGGGTTGT | SEQ ID NO: 342 |
| CD80 | NM_005191.2 | Forward Primer | TTCAGTTGCTTTGCAGGAAG | SEQ ID NO: 343 |
| | | Probe | TTCTGTGCCCACCATATTCCTCTAGACA | SEQ ID NO: 344 |
| | | Reverse Primer | TTGATCAAGGTCACCAGAGC | SEQ ID NO: 345 |
| CD82 | NM_002231.2 | Forward Primer | GTGCAGGCTCAGGTGAAGTG | SEQ ID NO: 346 |
| | | Probe | TCAGCTTCTACAACTGGACAGACAACGCTG | SEQ ID NO: 347 |
| | | Reverse Primer | GACCTCAGGGCGATTCATGA | SEQ ID NO: 348 |
| CD8A | NM_171827.1 | Forward Primer | AGGGTGAGGTGCTTGAGTCT | SEQ ID NO: 349 |
| | | Probe | CCAACGGCAAGGGAACAAGTACTTCT | SEQ ID NO: 350 |
| | | Reverse Primer | GGGCACAGTATCCCAGGTA | SEQ ID NO: 351 |
| CD9 | NM_001769.1 | Forward Primer | GGGCGTGGAACAGTTTATCT | SEQ ID NO: 352 |
| | | Probe | AGACATCTGCCCCAAGAAGGACGT | SEQ ID NO: 353 |
| | | Reverse Primer | CACGGTGAAGGTTTCGAGT | SEQ ID NO: 354 |
| CDC2 | NM_001786.2 | Forward Primer | GAGAGCGACGCGGTTGTT | SEQ ID NO: 355 |
| | | Probe | TAGCTGCCGCTGCGGCCG | SEQ ID NO: 356 |
| | | Reverse Primer | GTATGGTAGATCCCGGCTTATTATTC | SEQ ID NO: 357 |
| CDC20 | NM_001255.1 | Forward Primer | TGGATTGGAGTTCTGGGAATG | SEQ ID NO: 358 |
| | | Probe | ACTGGCCGTGGCACTGGACAACA | SEQ ID NO: 359 |
| | | Reverse Primer | GCTTGCACTCCACAGGTACACA | SEQ ID NO: 360 |
| cdc25A | NM_001789.1 | Forward Primer | TCTTGCTGGCTACGCCTCTT | SEQ ID NO: 361 |
| | | Probe | TGTCCCTGTTAGACGTCCTCCGTCCATA | SEQ ID NO: 362 |
| | | Reverse Primer | CTGCATTGTGGCACAGTTCTG | SEQ ID NO: 363 |
| CDC25B | NM_021874.1 | Forward Primer | AAACGAGCAGTTTGCCATCAG | SEQ ID NO: 364 |
| | | Probe | CCTCACCGGCATAGACTGGAAGCG | SEQ ID NO: 365 |
| | | Reverse Primer | GTTGGTGATGTTCCGAAGCA | SEQ ID NO: 366 |
| CDC25C | NM_001790.2 | Forward Primer | GGTGAGCAGAAGTGGCCTAT | SEQ ID NO: 367 |
| | | Probe | CTCCCCGTCGATGCCAGAGAACT | SEQ ID NO: 368 |
| | | Reverse Primer | CTTCAGTCTTGGCCTGTTCA | SEQ ID NO: 369 |
| CDC4 | NM_018315.2 | Forward Primer | GCAGTCCGCTGTGTTCAA | SEQ ID NO: 370 |
| | | Probe | TGCTCCACTAACAACCCTCCTGCC | SEQ ID NO: 371 |
| | | Reverse Primer | GGATCCCACACCTTTACCATAA | SEQ ID NO: 372 |
| CDC42 | NM_001791.2 | Forward Primer | TCCAGAGACTGCTGAAAA | SEQ ID NO: 373 |
| | | Probe | CCCGTGACCTGAAGGCTGTCAAG | SEQ ID NO: 374 |
| | | Reverse Primer | TGTGTAAGTGCAGAACAC | SEQ ID NO: 375 |
| CDC42BPA | NM_003607.2 | Forward Primer | GAGCTGAAAGACGCACACTG | SEQ ID NO: 376 |
| | | Probe | AATTCCTGCATGGCCAGTTTCCTC | SEQ ID NO: 377 |
| | | Reverse Primer | GCCGCTCATTGATCTCCA | SEQ ID NO: 378 |

TABLE A-continued

| Gene | Accession | Reagent | Sequence | Sequence ID Number |
|---|---|---|---|---|
| CDC6 | NM_001254.2 | Forward Primer | GCAACACTCCCCATTTACCTC | SEQ ID NO: 379 |
| | | Probe | TTGTTCTCCACCAAAGCAAGGCAA | SEQ ID NO: 380 |
| | | Reverse Primer | TGAGGGGACCATTCTCTTT | SEQ ID NO: 381 |
| CDCA7 v2 | NM_145810.1 | Forward Primer | AAGACCGTGGATGGCTACAT | SEQ ID NO: 382 |
| | | Probe | ATGAAGATGACCTGCCCAGAAGCC | SEQ ID NO: 383 |
| | | Reverse Primer | AGGGTCACGGATGATCTGG | SEQ ID NO: 384 |
| CDH1 | NM_004360.2 | Forward Primer | TGAGTGTCCCCCGGTATCTTC | SEQ ID NO: 385 |
| | | Probe | TGCCAATCCCGATGAAATTGGAAATTT | SEQ ID NO: 386 |
| | | Reverse Primer | CAGCCGCTTTCAGATTTTCAT | SEQ ID NO: 387 |
| CDH11 | NM_001797.2 | Forward Primer | GTCGGCAGAAGCAGGACT | SEQ ID NO: 388 |
| | | Probe | CCTTCTGCCCATAGTGATCAGCGA | SEQ ID NO: 389 |
| | | Reverse Primer | CTACTCATGGGCGGGATG | SEQ ID NO: 390 |
| CDH3 | NM_001793.3 | Forward Primer | ACCCATGTACCGTCCTCG | SEQ ID NO: 391 |
| | | Probe | CCAACCCAGATGAAATCGGCAACT | SEQ ID NO: 392 |
| | | Reverse Primer | CCGCCTTCAGGTTCTCAAT | SEQ ID NO: 393 |
| CDK2 | NM_001798.2 | Forward Primer | AATGCTGCACTACGACCCTA | SEQ ID NO: 394 |
| | | Probe | CCTTGGCCGAAATCCGCTTGT | SEQ ID NO: 395 |
| | | Reverse Primer | TTGGTCACATCCTGGAAGAA | SEQ ID NO: 396 |
| CDX1 | NM_001804.1 | Forward Primer | AGCAACACCAGCCTCCTG | SEQ ID NO: 397 |
| | | Probe | CACCTCCTCTCCAATGCCTGTGAA | SEQ ID NO: 398 |
| | | Reverse Primer | GGGCTATGGCAGAAACTCCT | SEQ ID NO: 399 |
| Cdx2 | NM_001265.2 | Forward Primer | GGGCAGGCAAGGTTTACA | SEQ ID NO: 400 |
| | | Probe | ATCTTAGCTGCCTTTGGCTTCCGC | SEQ ID NO: 401 |
| | | Reverse Primer | GTCTTTGGTCAGTCCAGCTTTC | SEQ ID NO: 402 |
| CEACAM1 | NM_001712.2 | Forward Primer | ACTTGCCTGTTCAGAGCACTCA | SEQ ID NO: 403 |
| | | Probe | TCCTTCCCACCCCCAGTCCTGTC | SEQ ID NO: 404 |
| | | Reverse Primer | TGGCAAATCCGAATTAGAGTGA | SEQ ID NO: 405 |
| CEACAM6 | NM_002483.2 | Forward Primer | CACAGCCTCACTTCTAACCTTCTG | SEQ ID NO: 406 |
| | | Probe | ACCCACCCACCACTGCCAAGCTC | SEQ ID NO: 407 |
| | | Reverse Primer | TTGAATGGCGTGGATTCAATAG | SEQ ID NO: 408 |
| CEBPB | NM_005194.2 | Forward Primer | GCAACCCACGTGTAACTGTC | SEQ ID NO: 409 |
| | | Probe | CCGGGCCCTGAGTAATCGCTTAA | SEQ ID NO: 410 |
| | | Reverse Primer | ACAAGCCCGTAGGAACATCT | SEQ ID NO: 411 |
| CEGP1 | NM_020974.1 | Forward Primer | TGACAATCAGCACACCTGCAT | SEQ ID NO: 412 |
| | | Probe | CAGGCCCTCTTCCGAGCGGT | SEQ ID NO: 413 |
| | | Reverse Primer | TGTGACTACAGCCGTGATCCTTA | SEQ ID NO: 414 |
| CENPA | NM_001809.2 | Forward Primer | TAAATTCACTCGTGGTGTGGA | SEQ ID NO: 415 |
| | | Probe | CTTCAATTGGCAAGCCCAGGC | SEQ ID NO: 416 |
| | | Reverse Primer | GCCTCTTGTAGGGCCAATAG | SEQ ID NO: 417 |
| CENPE | NM_001813.1 | Forward Primer | GGATGCTGGTGACCTCTTCT | SEQ ID NO: 418 |
| | | Probe | TCCCTCACGTTGCAACAGGAATTAA | SEQ ID NO: 419 |
| | | Reverse Primer | GCCAAGGCACCAAGTAACTC | SEQ ID NO: 420 |
| CENPF | NM_016343.2 | Forward Primer | CTCCCGTCAACAGCGTTC | SEQ ID NO: 421 |
| | | Probe | ACACTGGACCAGGAGTGCATCCAG | SEQ ID NO: 422 |
| | | Reverse Primer | GGGTGAGTCTGGCCTTCA | SEQ ID NO: 423 |
| CES2 | NM_003869.4 | Forward Primer | ACTTTGCGAGAAATGGGAAC | SEQ ID NO: 424 |
| | | Probe | AGTGTGGCAGACCCTCGCCATT | SEQ ID NO: 425 |
| | | Reverse Primer | CAGGTATTGCTCCTCCTGGT | SEQ ID NO: 426 |
| CGA (CHGA official) | NM_001275.2 | Forward Primer | CTGAAGGAGCTCCAAGACCT | SEQ ID NO: 427 |
| | | Probe | TGCTGATGTGCCCTCTCCTTGG | SEQ ID NO: 428 |
| | | Reverse Primer | CAAAACCGCTGTGTTTCTTC | SEQ ID NO: 429 |
| CGB | NM_000737.2 | Forward Primer | CCACCATAGGCAGAGGCA | SEQ ID NO: 430 |
| | | Probe | ACACCCTACTCCCTGTGCCTCCAG | SEQ ID NO: 431 |
| | | Reverse Primer | AGTCGTCGAGTGCTAGGGAC | SEQ ID NO: 432 |
| CHAF1B | NM_005441.1 | Forward Primer | GAGGCCAGTGGTGGAAACAG | SEQ ID NO: 433 |
| | | Probe | AGCTGATGAGTCTGCCCTACCGCTG | SEQ ID NO: 434 |
| | | Reverse Primer | TCCGAGGCCACAGCAAAC | SEQ ID NO: 435 |

TABLE A-continued

| Gene | Accession | Reagent | Sequence | Sequence ID Number |
|---|---|---|---|---|
| CHD2 | NM_001271.1 | Forward Primer | CTCTGTGCGAGGCTGTCA | SEQ ID NO: 436 |
| | | Probe | ACCCATCTCGGGATCCCTGATACC | SEQ ID NO: 437 |
| | | Reverse Primer | GGTAAGGACTGTGGGCTGG | SEQ ID NO: 438 |
| CHFR | NM_018223.1 | Forward Primer | AAGGAAGTGGTCCCTCTGTG | SEQ ID NO: 439 |
| | | Probe | TGAAGTCTCCAGCTTTGCCTCAGC | SEQ ID NO: 440 |
| | | Reverse Primer | GACGCAGTCTTTCTGTCTGG | SEQ ID NO: 441 |
| Chk1 | NM_001274.1 | Forward Primer | GATAAATTGGTACAAGGGATCAGCTT | SEQ ID NO: 442 |
| | | Probe | CCAGCCCACATGTCCTGATCATATGC | SEQ ID NO: 443 |
| | | Reverse Primer | GGGTGCCAAGTAACTGACTATTCA | SEQ ID NO: 444 |
| Chk2 | NM_007194.1 | Forward Primer | ATGTGGAACCCCCACCTACTT | SEQ ID NO: 445 |
| | | Probe | AGTCCCAACAGAAACAAGAACTTCAGGCG | SEQ ID NO: 446 |
| | | Reverse Primer | CAGTCCACAGCACGGTTATACC | SEQ ID NO: 447 |
| CIAP1 | NM_001166.2 | Forward Primer | TGCCTGTGGTGGGAAGCT | SEQ ID NO: 448 |
| | | Probe | TGACATAGCATCATCCTTTGGTTCCCAGTT | SEQ ID NO: 449 |
| | | Reverse Primer | GGAAAATGCCTCCGGTGTT | SEQ ID NO: 450 |
| cIAP2 | NM_001165.2 | Forward Primer | GGATATTTCCGTGGCTCTTATTCA | SEQ ID NO: 451 |
| | | Probe | TCTCCATCAAATCCTGTAAACTCCAGAGCA | SEQ ID NO: 452 |
| | | Reverse Primer | CTTCTCATCAAGGCAGAAAAATCTT | SEQ ID NO: 453 |
| CKS1B | NM_001826.1 | Forward Primer | GGTCCCTAAAACCCATCTGA | SEQ ID NO: 454 |
| | | Probe | TGAACGCCAAGATTCCTCCATTCA | SEQ ID NO: 455 |
| | | Reverse Primer | TAATGGACCCATCCCTGACT | SEQ ID NO: 456 |
| CKS2 | NM_001827.1 | Forward Primer | GGCTGGACGTGGTTTTGTCT | SEQ ID NO: 457 |
| | | Probe | CTGCGCCCGCTCTTCGCG | SEQ ID NO: 458 |
| | | Reverse Primer | CGCTGCAGAAAATGAAACGA | SEQ ID NO: 459 |
| Claudin 4 | NM_001305.2 | Forward Primer | GGCTGCTTTGCTGCAACTG | SEQ ID NO: 460 |
| | | Probe | CGCACAGACAAGCCTTACTCCGCC | SEQ ID NO: 461 |
| | | Reverse Primer | CAGAGCGGGCAGCAGAATA | SEQ ID NO: 462 |
| CLDN1 | NM_021101.3 | Forward Primer | TCTGGGAGGTGCCCTACTT | SEQ ID NO: 463 |
| | | Probe | TGTTCCTGTCCCGAAAAACAACC | SEQ ID NO: 464 |
| | | Reverse Primer | TGGATAGGGCCTTGGTGTT | SEQ ID NO: 465 |
| CLDN7 | NM_001307.3 | Forward Primer | GGTCTGCCCTAGTCATCCTG | SEQ ID NO: 466 |
| | | Probe | TGCACTGCTCTCCTGTTCCTGTCC | SEQ ID NO: 467 |
| | | Reverse Primer | GTACCCAGCCTTGCTCTCAT | SEQ ID NO: 468 |
| CLIC1 | NM_001288.3 | Forward Primer | CGGTACTTGAGCAATGCCTA | SEQ ID NO: 469 |
| | | Probe | CGGGAAGAATTCGCTTCCACCTG | SEQ ID NO: 470 |
| | | Reverse Primer | TCGATCTCCTCATCATCTGG | SEQ ID NO: 471 |
| CLTC | NM_004859.1 | Forward Primer | ACCGTATGGACAGCCACAG | SEQ ID NO: 472 |
| | | Probe | TCTCACATGCTGTACCCAAAGCCA | SEQ ID NO: 473 |
| | | Reverse Primer | TGACTACAGGATCAGCGCTTC | SEQ ID NO: 474 |
| CLU | NM_001831.1 | Forward Primer | CCCCAGGATACCTACCACTACCT | SEQ ID NO: 475 |
| | | Probe | CCCTTCAGCCTGCCCCACCG | SEQ ID NO: 476 |
| | | Reverse Primer | TGCGGGACTTGGGAAAGA | SEQ ID NO: 477 |
| cMet | NM_000245.1 | Forward Primer | GACATTTCCAGTCCTGCAGTCA | SEQ ID NO: 478 |
| | | Probe | TGCCTCTCTGCCCCACCCTTTGT | SEQ ID NO: 479 |
| | | Reverse Primer | CTCCGATCGCACACATTTGT | SEQ ID NO: 480 |
| cMYC | NM_002467.1 | Forward Primer | TCCCTCCACTCGGAAGGACTA | SEQ ID NO: 481 |
| | | Probe | TCTGACACTGTCCAACTTGACCCTCTT | SEQ ID NO: 482 |
| | | Reverse Primer | CGGTTGTTGCTGATCTGTCTCA | SEQ ID NO: 483 |
| CNN | NM_001299.2 | Forward Primer | TCCACCCTCCTGGCTTTG | SEQ ID NO: 484 |
| | | Probe | TCCTTTCGTCTTCGCCATGCTGG | SEQ ID NO: 485 |
| | | Reverse Primer | TCACTCCCACGTTCACCTTGT | SEQ ID NO: 486 |
| COL1A1 | NM_000088.2 | Forward Primer | GTGGCCATCCAGCTGACC | SEQ ID NO: 487 |
| | | Probe | TCCTGCGCCTGATGTCCACCG | SEQ ID NO: 488 |
| | | Reverse Primer | CAGTGGTAGGTGATGTTCTGGGA | SEQ ID NO: 489 |
| COL1A2 | NM_000089.2 | Forward Primer | CAGCCAAGAACTGGTATAGGAGCT | SEQ ID NO: 490 |
| | | Probe | TCTCCTAGCCAGACGTGTTTCTTGTCCTTG | SEQ ID NO: 491 |
| | | Reverse Primer | AAACTGGCTGCCAGCATTG | SEQ ID NO: 492 |

TABLE A-continued

| Gene | Accession | Reagent | Sequence | Sequence ID Number |
|---|---|---|---|---|
| COPS3 | NM_003653.2 | Forward Primer | ATGCCCAGTGTTCCTGACTT | SEQ ID NO: 493 |
| | | Probe | CGAAACGCTATTCTCACAGGTTCAGC | SEQ ID NO: 494 |
| | | Reverse Primer | CTCCCCATTACAAGTGCTGA | SEQ ID NO: 495 |
| COX2 | NM_000963.1 | Forward Primer | TCTGCAGAGTTGGAAGCACTCTA | SEQ ID NO: 496 |
| | | Probe | CAGGATACAGCTCCACAGCATCGATGTC | SEQ ID NO: 497 |
| | | Reverse Primer | GCCGAGGCTTTTCTACCAGAA | SEQ ID NO: 498 |
| COX3 | MITO_COX3 | Forward Primer | TCGAGTCTCCCTTCACCATT | SEQ ID NO: 499 |
| | | Probe | CGACGGCATCTACGGCTCAACAT | SEQ ID NO: 500 |
| | | Reverse Primer | GACGTGAAGTCCGTGGAAG | SEQ ID NO: 501 |
| CP | NM_000096.1 | Forward Primer | CGTGAGTACACAGATGCCTCC | SEQ ID NO: 502 |
| | | Probe | TCTTCAGGGCCTCTCTCCTTTCGA | SEQ ID NO: 503 |
| | | Reverse Primer | CCAGGATGCCAAGATGCT | SEQ ID NO: 504 |
| CRBP | NM_002899.2 | Forward Primer | TGGTCTGCAAGCAAGTATTCAAG | SEQ ID NO: 505 |
| | | Probe | TCTGCTTGGGCCTCACTGCACCT | SEQ ID NO: 506 |
| | | Reverse Primer | GCTGATTGGTTGGGACAAGGT | SEQ ID NO: 507 |
| CREBBP | NM_004380.1 | Forward Primer | TGGGAAGCAGCTGTGTACCAT | SEQ ID NO: 508 |
| | | Probe | CCTCGCGATGCTGCCTACTACAGCTATC | SEQ ID NO: 509 |
| | | Reverse Primer | GAAACACTTCTCACAGAAATGATACCTATT | SEQ ID NO: 510 |
| CRIP2 | NM_001312.1 | Forward Primer | GTGCTACGCCACCCTGTT | SEQ ID NO: 511 |
| | | Probe | CCGATGTTCACGCCTTTGGGTC | SEQ ID NO: 512 |
| | | Reverse Primer | CAGGGGCTTCTCGTAGATGT | SEQ ID NO: 513 |
| cripto (TDGF1 official) | NM_003212.1 | Forward Primer | GGGTCTGTGCCCCATGAC | SEQ ID NO: 514 |
| | | Probe | CCTGGCTGCCCAAGAAGTGTTCCCT | SEQ ID NO: 515 |
| | | Reverse Primer | TGACCGTGCCAGCATTTACA | SEQ ID NO: 516 |
| CRK(a) | NM_016823.2 | Forward Primer | CTCCCTAACCTCCAGAATGG | SEQ ID NO: 517 |
| | | Probe | ACTCGCTTCTGGATAACCCTGGCA | SEQ ID NO: 518 |
| | | Reverse Primer | TGTCTTGTCGTAGGCATTGG | SEQ ID NO: 519 |
| CRMP1 | NM_001313.1 | Forward Primer | AAGGTTTTTGGATTGCAAGG | SEQ ID NO: 520 |
| | | Probe | ACCGTCATACATGCCCCTGGAAAC | SEQ ID NO: 521 |
| | | Reverse Primer | GGGTGTAGCTGGTACCTCGT | SEQ ID NO: 522 |
| CRYAB | NM_001885.1 | Forward Primer | GATGTGATTGAGGTGCATGG | SEQ ID NO: 523 |
| | | Probe | TGTTCATCCTGGCGCTCTTCATGT | SEQ ID NO: 524 |
| | | Reverse Primer | GAACTCCCTGGAGATGAAACC | SEQ ID NO: 525 |
| CSEL1 | NM_001316.2 | Forward Primer | TTACGCAGCTCATGCTCTTG | SEQ ID NO: 526 |
| | | Probe | ACGGCTCTTTACTATGCGAGGGCC | SEQ ID NO: 527 |
| | | Reverse Primer | GCAGCTGTAAAGAGAGTGGCAT | SEQ ID NO: 528 |
| CSF1 | NM_000757.3 | Forward Primer | TGCAGCGGCTGATTGACA | SEQ ID NO: 529 |
| | | Probe | TCAGATGGAGACCTCGTGCCAAATTACA | SEQ ID NO: 530 |
| | | Reverse Primer | CAACTGTTCCTGGTCTACAAACTCA | SEQ ID NO: 531 |
| CSK (SRC) | NM_004383.1 | Forward Primer | CCTGAACATGAAGGAGCTGA | SEQ ID NO: 532 |
| | | Probe | TCCCGATGGTCTGCAGCAGCT | SEQ ID NO: 533 |
| | | Reverse Primer | CATCACGTCTCCGAACTCC | SEQ ID NO: 534 |
| CTAG1B | NM_001327.1 | Forward Primer | GCTCTCCATCAGCTCCTGTC | SEQ ID NO: 535 |
| | | Probe | CCACATCAACAGGGAAAGCTGCTG | SEQ ID NO: 536 |
| | | Reverse Primer | AACACGGGCAGAAAGCACT | SEQ ID NO: 537 |
| CTGF | NM_001901.1 | Forward Primer | GAGTTCAAGTGCCCTGACG | SEQ ID NO: 538 |
| | | Probe | AACATCATGTTCTTCTTCATGACCTCGC | SEQ ID NO: 539 |
| | | Reverse Primer | AGTTGTAATGGCAGGCACAG | SEQ ID NO: 540 |
| CTHRC1 | NM_138455.2 | Forward Primer | GCTCACTTCGGCTAAAATGC | SEQ ID NO: 541 |
| | | Probe | ACCAACGCTGACAGCATGCATTTC | SEQ ID NO: 542 |
| | | Reverse Primer | TCAGCTCCATTGAATGTGAAA | SEQ ID NO: 543 |
| CTLA4 | NM_005214.2 | Forward Primer | CACTGAGGTCCGGGTGACA | SEQ ID NO: 544 |
| | | Probe | CACCTGGCTGTCAGCCTGCCG | SEQ ID NO: 545 |
| | | Reverse Primer | GTAGGTTGCCGCACAGACTTC | SEQ ID NO: 546 |

TABLE A-continued

| Gene | Accession | Reagent | Sequence | Sequence ID Number |
|---|---|---|---|---|
| CTNNBIP1 | NM_020248.2 | Forward Primer | GTTTTCCAGGTCGGAGACG | SEQ ID NO: 547 |
| | | Probe | CTTTGCAGCTACTGCCTCCGGTCT | SEQ ID NO: 548 |
| | | Reverse Primer | AGCATCCAGGGTGTTCCA | SEQ ID NO: 549 |
| CTSB | NM_001908.1 | Forward Primer | GGCCGAGATCTACAAAAACG | SEQ ID NO: 550 |
| | | Probe | CCCCGTGGAGGGAGCTTTCTC | SEQ ID NO: 551 |
| | | Reverse Primer | GCAGGAAGTCCGAATACACA | SEQ ID NO: 552 |
| CTSD | NM_001909.1 | Forward Primer | GTACATGATCCCTGTGAGAAGGT | SEQ ID NO: 553 |
| | | Probe | ACCCTGCCCGCGATCACACTGA | SEQ ID NO: 554 |
| | | Reverse Primer | GGGACAGCTTGTAGCCTTTGC | SEQ ID NO: 555 |
| CTSH | NM_004390.1 | Forward Primer | GCAAGTTCCAACCTGGAAAG | SEQ ID NO: 556 |
| | | Probe | TGGCTACATCCTTGACAAAGCCGA | SEQ ID NO: 557 |
| | | Reverse Primer | CATCGCTTCCTCGTCATAGA | SEQ ID NO: 558 |
| CTSL | NM_001912.1 | Forward Primer | GGGAGGCTTATCTCACTGAGTGA | SEQ ID NO: 559 |
| | | Probe | TTGAGGCCCAGAGCAGTCTACCAGATTCT | SEQ ID NO: 560 |
| | | Reverse Primer | CCATTGCAGCCTTCATTGC | SEQ ID NO: 561 |
| CTSL2 | NM_001333.2 | Forward Primer | TGTCTCACTGAGCGAGCAGAA | SEQ ID NO: 562 |
| | | Probe | CTTGAGGACGCGAACAGTCCACCA | SEQ ID NO: 563 |
| | | Reverse Primer | ACCATTGCAGCCCTGATTG | SEQ ID NO: 564 |
| CUL1 | NM_003592.2 | Forward Primer | ATGCCCTGGTAATGTCTGCAT | SEQ ID NO: 565 |
| | | Probe | CAGCCACAAAGCCAGCGTCATTGT | SEQ ID NO: 566 |
| | | Reverse Primer | GCGACCACAAGCCTTATCAAG | SEQ ID NO: 567 |
| CUL4A | NM_003589.1 | Forward Primer | AAGCATCTTCCTGTTCTTGGA | SEQ ID NO: 568 |
| | | Probe | TATGTGCTGCAGAACTCCACGCTG | SEQ ID NO: 569 |
| | | Reverse Primer | AATCCCATATCCCAGATGGA | SEQ ID NO: 570 |
| CXCL12 | NM_000609.3 | Forward Primer | GAGCTACAGATGCCCATGC | SEQ ID NO: 571 |
| | | Probe | TTCTTCGAAAGCCATGTTGCCAGA | SEQ ID NO: 572 |
| | | Reverse Primer | TTTGAGATGCTTGACGTTGG | SEQ ID NO: 573 |
| CXCR4 | NM_003467.1 | Forward Primer | TGACCGCTTCTACCCCAATG | SEQ ID NO: 574 |
| | | Probe | CTGAAACTGGAACACAACCACCCACAAG | SEQ ID NO: 575 |
| | | Reverse Primer | AGGATAAGGCCAACCATGATGT | SEQ ID NO: 576 |
| CYBA | NM_000101.1 | Forward Primer | GGTGCCTACTCCATTGTGG | SEQ ID NO: 577 |
| | | Probe | TACTCCAGCAGGCACACAAACACG | SEQ ID NO: 578 |
| | | Reverse Primer | GTGGAGCCCTTCTTCCTCTT | SEQ ID NO: 579 |
| CYP1B1 | NM_000104.2 | Forward Primer | CCAGCTTTGTGCCTGTCACTAT | SEQ ID NO: 580 |
| | | Probe | CTCATGCCACCACTGCCCAACACCTC | SEQ ID NO: 581 |
| | | Reverse Primer | GGGAATGTGGTAGCCCAAGA | SEQ ID NO: 582 |
| CYP2C8 | NM_000770.2 | Forward Primer | CCGTGTTCAAGAGGAAGCTC | SEQ ID NO: 583 |
| | | Probe | TTTTCTCAACTCCTCCACAAGGCA | SEQ ID NO: 584 |
| | | Reverse Primer | AGTGGGATCACAGGGTGAAG | SEQ ID NO: 585 |
| CYP3A4 | NM_017460.3 | Forward Primer | AGAACAAGGACAACATAGATCCTTACATAT | SEQ ID NO: 586 |
| | | Probe | CACACCCTTTGGAAGTGGACCCAGAA | SEQ ID NO: 587 |
| | | Reverse Primer | GCAAACCTCATGCCAATGC | SEQ ID NO: 588 |
| CYR61 | NM_001554.3 | Forward Primer | TGCTCATTCTTGAGGAGCAT | SEQ ID NO: 589 |
| | | Probe | CAGCACCCTTGGCAGTTTCGAAAT | SEQ ID NO: 590 |
| | | Reverse Primer | GTGGCTGCATTAGTGTCCAT | SEQ ID NO: 591 |
| DAPK1 | NM_004938.1 | Forward Primer | CGCTGACATCATGAATGTTCCT | SEQ ID NO: 592 |
| | | Probe | TCATATCCAAACTCGCCTCCAGCCG | SEQ ID NO: 593 |
| | | Reverse Primer | TCTCTTTCAGCAACGATGTGTCTT | SEQ ID NO: 594 |
| DCC | NM_005215.1 | Forward Primer | AAATGTCCTCCTCGACTGCT | SEQ ID NO: 595 |
| | | Probe | ATCACTGGAACTCCTCGGTCGGAC | SEQ ID NO: 596 |
| | | Reverse Primer | TGAATGCCATCTTTCTTCCA | SEQ ID NO: 597 |
| DCC_exons18-23 | X76132_18-23 | Forward Primer | GGTCACCGTTGGTGTCATCA | SEQ ID NO: 598 |
| | | Probe | CAGCCACGATGACCACTACCAGCACT | SEQ ID NO: 599 |
| | | Reverse Primer | GAGCGTCGGGTGCAAATC | SEQ ID NO: 600 |
| DCC_exons6-7 | X76132_6-7 | Forward Primer | ATGGAGATGTGGTCATTCCTAGTG | SEQ ID NO: 601 |
| | | Probe | TGCTTCCTCCCACTATCTGAAAATAA | SEQ ID NO: 602 |
| | | Reverse Primer | CACCACCCCAAGTATCCGTAAG | SEQ ID NO: 603 |

TABLE A-continued

| Gene | Accession | Reagent | Sequence | Sequence ID Number |
|---|---|---|---|---|
| DCK | NM_000788.1 | Forward Primer<br>Probe<br>Reverse Primer | GCCGCCACAAGACTAAGGAAT<br>AGCTGCCCGTCTTTCTCAGCCAGC<br>CGATGTTCCCTTCGATGGAG | SEQ ID NO: 604<br>SEQ ID NO: 605<br>SEQ ID NO: 606 |
| DDB1 | NM_001923.2 | Forward Primer<br>Probe<br>Reverse Primer | TGCGGATCATCCGGAATG<br>AATTGGAATCCACGAGCATGCCAGC<br>TCCTTTGATGCCTGGTAAGTCA | SEQ ID NO: 607<br>SEQ ID NO: 608<br>SEQ ID NO: 609 |
| DET1 | NM_017996.2 | Forward Primer<br>Probe<br>Reverse Primer | CTTGTGGAGATCACCCAATCAG<br>CTATGCCCGGGACTCGGGCCT<br>CCCGCCTGGATCTCAAACT | SEQ ID NO: 610<br>SEQ ID NO: 611<br>SEQ ID NO: 612 |
| DHFR | NM_000791.2 | Forward Primer<br>Probe<br>Reverse Primer | TTGCTATAACTAAGTGCTTCTCCAAGA<br>CCCAACTGAGTCCCCAGCACCT<br>GTGGAATGGCAGCTCACTGTAG | SEQ ID NO: 613<br>SEQ ID NO: 614<br>SEQ ID NO: 615 |
| DHPS | NM_013407.1 | Forward Primer<br>Probe<br>Reverse Primer | GGGAGAACGGGATCAATAGGAT<br>CTCATTGGGCACCAGCAGGTTTCC<br>GCATCAGCCAGTCCTCAAACT | SEQ ID NO: 616<br>SEQ ID NO: 617<br>SEQ ID NO: 618 |
| DIABLO | NM_019887.1 | Forward Primer<br>Probe<br>Reverse Primer | CACAATGGCGGCTCTGAAG<br>AAGTTACGCTGCGCGACAGCCAA<br>ACACAAACACTGTCTGTACCTGAAGA | SEQ ID NO: 619<br>SEQ ID NO: 620<br>SEQ ID NO: 621 |
| DIAPH1 | NM_005219.2 | Forward Primer<br>Probe<br>Reverse Primer | CAAGCAGTCAAGGAGAACCA<br>TTCTTCTGTCTCCCGCCGCTTC<br>AGTTTTGCTCGCCTCATCTT | SEQ ID NO: 622<br>SEQ ID NO: 623<br>SEQ ID NO: 624 |
| DICER1 | NM_177438.1 | Forward Primer<br>Probe<br>Reverse Primer | TCCAATTCCAGCATCACTGT<br>AGAAAAGCTGTTTGTCTCCCCAGCA<br>GGCAGTGAAGGCGATAAAGT | SEQ ID NO: 625<br>SEQ ID NO: 626<br>SEQ ID NO: 627 |
| DKK1 | NM_012242.1 | Forward Primer<br>Probe<br>Reverse Primer | TGACAACTACCAGCCGTACC<br>AGTGCCGCACTCCTCGTCCTCT<br>GGGACTAGCGCAGTACTCATC | SEQ ID NO: 628<br>SEQ ID NO: 629<br>SEQ ID NO: 630 |
| DLC1 | NM_006094.3 | Forward Primer<br>Probe<br>Reverse Primer | GATTCAGACGAGGATGAGCC<br>AAAGTCCATTTGCCACTGATGGCA<br>CACCTCTTGCTGTCCCTTTG | SEQ ID NO: 631<br>SEQ ID NO: 632<br>SEQ ID NO: 633 |
| DPYD | NM_000110.2 | Forward Primer<br>Probe<br>Reverse Primer | AGGACGCAAGGAGGGTTTG<br>CAGTGCCTACAGTCTCGAGTCTGCCAGTG<br>GATGTCCGCCGAGTCCTTACT | SEQ ID NO: 634<br>SEQ ID NO: 635<br>SEQ ID NO: 636 |
| DR4 | NM_003844.1 | Forward Primer<br>Probe<br>Reverse Primer | TGCACAGAGGGTGTGGGTTAC<br>CAATGCTTCCAACAATTTGTTTGCTTGCC<br>TCTTCATCTGATTTACAAGCTGTACATG | SEQ ID NO: 637<br>SEQ ID NO: 638<br>SEQ ID NO: 639 |
| DR5 | NM_003842.2 | Forward Primer<br>Probe<br>Reverse Primer | CTCTGAGACAGTGCTTCGATGACT<br>CAGACTTGGTGCCCTTTGACTCC<br>CCATGAGGCCCAACTTCCT | SEQ ID NO: 640<br>SEQ ID NO: 641<br>SEQ ID NO: 642 |
| DRG1 | NM_004147.3 | Forward Primer<br>Probe<br>Reverse Primer | CCTGGATCTCCCAGGTATCA<br>ACCTTTCCCATCCTTGGCACCTTC<br>TGCAATGACTTGACGACCTC | SEQ ID NO: 643<br>SEQ ID NO: 644<br>SEQ ID NO: 645 |
| DSP | NM_004415.1 | Forward Primer<br>Probe<br>Reverse Primer | TGGCACTACTGCATGATTGACA<br>CAGGGCCATGACAATCGCCAA<br>CCTGCCGCATTGTTTTCAG | SEQ ID NO: 646<br>SEQ ID NO: 647<br>SEQ ID NO: 648 |
| DTYMK | NM_012145.1 | Forward Primer<br>Probe<br>Reverse Primer | AAATCGCTGGGAACAAGTG<br>CGCCCTGGCTCAACTTTTCCTTAA<br>AATGCGTATCTGTCCACGAC | SEQ ID NO: 649<br>SEQ ID NO: 650<br>SEQ ID NO: 651 |
| DUSP1 | NM_004417.2 | Forward Primer<br>Probe<br>Reverse Primer | AGACATCAGCTCCTGGTTCA<br>CGAGGCCATTGACTTCATAGACTCCA<br>GACAAACACCCTTCCTCCAG | SEQ ID NO: 652<br>SEQ ID NO: 653<br>SEQ ID NO: 654 |
| DUSP2 | NM_004418.2 | Forward Primer<br>Probe<br>Reverse Primer | TATCCCTGTGGAGGACAACC<br>CCTCCTGGAACCAGGCACTGATCT<br>CACCCAGTCAATGAAGCCTA | SEQ ID NO: 655<br>SEQ ID NO: 656<br>SEQ ID NO: 657 |
| DUT | NM_001948.2 | Forward Primer<br>Probe<br>Reverse Primer | ACACATGGAGTGCTTCTGGA<br>ATCAGCCCACTTGACCACCCAGTT<br>CTCTTGCCTGTGCTTCCAC | SEQ ID NO: 658<br>SEQ ID NO: 659<br>SEQ ID NO: 660 |

TABLE A-continued

| Gene | Accession | Reagent | Sequence | Sequence ID Number |
|---|---|---|---|---|
| DYRK1B | NM_004714.1 | Forward Primer | AGCATGACACGGAGATGAAG | SEQ ID NO: 661 |
| | | Probe | CACCTGAAGCGGCACTTCATGTTC | SEQ ID NO: 662 |
| | | Reverse Primer | AATACCAGGCACAGGTGGTT | SEQ ID NO: 663 |
| E2F1 | NM_005225.1 | Forward Primer | ACTCCCTCTACCCTTGAGCA | SEQ ID NO: 664 |
| | | Probe | CAGAAGAACAGCTCAGGGACCCCT | SEQ ID NO: 665 |
| | | Reverse Primer | CAGGCCTCAGTTCCTTCAGT | SEQ ID NO: 666 |
| EDN1 endothelin | NM_001955.1 | Forward Primer | TGCCACCTGGACATCATTTG | SEQ ID NO: 667 |
| | | Probe | CACTCCCGAGCACGTTGTTCCGT | SEQ ID NO: 668 |
| | | Reverse Primer | TGGACCTAGGGCTTCCAAGTC | SEQ ID NO: 669 |
| EFNA1 | NM_004428.2 | Forward Primer | TACATCTCCAAACCCATCCA | SEQ ID NO: 670 |
| | | Probe | CAACCTCAAGCAGCGGTCTTCATG | SEQ ID NO: 671 |
| | | Reverse Primer | TTGCCACTGACAGTCACCTT | SEQ ID NO: 672 |
| EFNA3 | NM_004952.3 | Forward Primer | ACTACATCTCCACGCCCACT | SEQ ID NO: 673 |
| | | Probe | CCTCAGACACTTCCAGTGCAGGTTG | SEQ ID NO: 674 |
| | | Reverse Primer | CAGCAGACGAACACCTTCAT | SEQ ID NO: 675 |
| EFNB1 | NM_004429.3 | Forward Primer | GGAGCCCGTATCCTGGAG | SEQ ID NO: 676 |
| | | Probe | CCCTCAACCCCAAGTTCCTGAGTG | SEQ ID NO: 677 |
| | | Reverse Primer | GGATAGATCACCAAGCCCTTC | SEQ ID NO: 678 |
| EFNB2 | NM_004093.2 | Forward Primer | TGACATTATCATCCCGCTAAGGA | SEQ ID NO: 679 |
| | | Probe | CGGACAGCGTCTTCTGCCCTCACT | SEQ ID NO: 680 |
| | | Reverse Primer | GTAGTCCCCGCTGACCTTCTC | SEQ ID NO: 681 |
| EFP | NM_005082.2 | Forward Primer | TTGAACAGAGCCTGACCAAG | SEQ ID NO: 682 |
| | | Probe | TGATGCTTTCTCCAGAAACTCGAACTCA | SEQ ID NO: 683 |
| | | Reverse Primer | TGTTGAGATTCCTCGCAGTT | SEQ ID NO: 684 |
| EGFR | NM_005228.1 | Forward Primer | TGTCGATGGACTTCCAGAAC | SEQ ID NO: 685 |
| | | Probe | CACCTGGGCAGCTGCCAA | SEQ ID NO: 686 |
| | | Reverse Primer | ATTGGGACAGCTTGGATCA | SEQ ID NO: 687 |
| EGLN1 | NM_022051.1 | Forward Primer | TCAATGGCCGGACGAAAG | SEQ ID NO: 688 |
| | | Probe | CATTGCCCGGATAACAAGCAACCATG | SEQ ID NO: 689 |
| | | Reverse Primer | TTTGGATTATCAACATGACGTACATAAC | SEQ ID NO: 690 |
| EGLN3 | NM_022073.2 | Forward Primer | GCTGGTCCTCTACTGCGG | SEQ ID NO: 691 |
| | | Probe | CCGGCTGGGCAAATACTACGTCAA | SEQ ID NO: 692 |
| | | Reverse Primer | CCACCATTGCCTTAGACCTC | SEQ ID NO: 693 |
| EGR1 | NM_001964.2 | Forward Primer | GTCCCCGCTGCAGATCTCT | SEQ ID NO: 694 |
| | | Probe | CGGATCCTTTCCTCACTCGCCCA | SEQ ID NO: 695 |
| | | Reverse Primer | CTCCAGCTTAGGGTAGTTGTCCAT | SEQ ID NO: 696 |
| EGR3 | NM_004430.2 | Forward Primer | CCATGTGGATGAATGAGGTG | SEQ ID NO: 697 |
| | | Probe | ACCCAGTCTCACCTTCTCCCCACC | SEQ ID NO: 698 |
| | | Reverse Primer | TGCCTGAGAAGAGGTGAGGT | SEQ ID NO: 699 |
| EI24 | NM_004879.2 | Forward Primer | AAAGTGGTGAATGCCATTTG | SEQ ID NO: 700 |
| | | Probe | CCTCAAATGCCAGGTCAGCTATATCCTG | SEQ ID NO: 701 |
| | | Reverse Primer | GTGAGGCTTCCTCCCTGATA | SEQ ID NO: 702 |
| EIF4E | NM_001968.1 | Forward Primer | GATCTAAGATGGCGACTGTCGAA | SEQ ID NO: 703 |
| | | Probe | ACCACCCCTACTCCTAATCCCCGACT | SEQ ID NO: 704 |
| | | Reverse Primer | TTAGATTCCGTTTTCTCCTCTTCTG | SEQ ID NO: 705 |
| EIF4EL3 | NM_004846.1 | Forward Primer | AAGCCGCGGTTGAATGTG | SEQ ID NO: 706 |
| | | Probe | TGACCCTCTCCCTCTCTGGATGGCA | SEQ ID NO: 707 |
| | | Reverse Primer | TGACGCCAGCTTCAATGATG | SEQ ID NO: 708 |
| ELAVL1 | NM_001419.2 | Forward Primer | GACAGGAGGCCTCTATCCTG | SEQ ID NO: 709 |
| | | Probe | CACCCCACCCTCCACCTCAATC | SEQ ID NO: 710 |
| | | Reverse Primer | GTGAGGTAGGTCTGGGGAAG | SEQ ID NO: 711 |
| EMP1 | NM_001423.1 | Forward Primer | GCTAGTACTTTGATGCTCCCTTGAT | SEQ ID NO: 712 |
| | | Probe | CCAGAGAGCCTCCCTGCAGCCA | SEQ ID NO: 713 |
| | | Reverse Primer | GAACAGCTGGAGGCCAAGTC | SEQ ID NO: 714 |
| EMR3 | NM_032571.2 | Forward Primer | TGGCCTACCTCTTCACCATC | SEQ ID NO: 715 |
| | | Probe | TCAACAGCCTCCAAGGCTTCTTCA | SEQ ID NO: 716 |
| | | Reverse Primer | TGAGGAGGCAGTAGACCAAGA | SEQ ID NO: 717 |

TABLE A-continued

| Gene | Accession | Reagent | Sequence | Sequence ID Number |
|---|---|---|---|---|
| EMS1 | NM_005231.2 | Forward Primer | GGCAGTGTCACTGAGTCCTTGA | SEQ ID NO: 718 |
| | | Probe | ATCCTCCCCTGCCCCGCG | SEQ ID NO: 719 |
| | | Reverse Primer | TGCACTGTGCGTCCCAAT | SEQ ID NO: 720 |
| ENO1 | NM_001428.2 | Forward Primer | CAAGGCCGTGAACGAGAAGT | SEQ ID NO: 721 |
| | | Probe | CTGCAACTGCCTCCTGCTCAAAGTCA | SEQ ID NO: 722 |
| | | Reverse Primer | CGGTCACGGAGCCAATCT | SEQ ID NO: 723 |
| EP300 | NM_001429.1 | Forward Primer | AGCCCCAGCAACTACAGTCT | SEQ ID NO: 724 |
| | | Probe | CACTGACATCATGGCTGGCCTTG | SEQ ID NO: 725 |
| | | Reverse Primer | TGTTCAAAGGTTGACCATGC | SEQ ID NO: 726 |
| EPAS1 | NM_001430.3 | Forward Primer | AAGCCTTGGAGGGTTTCATTG | SEQ ID NO: 727 |
| | | Probe | TGTCGCCATCTTGGGTCACCACG | SEQ ID NO: 728 |
| | | Reverse Primer | TGCTGATGTTTTCTGACAGAAAGAT | SEQ ID NO: 729 |
| EpCAM | NM_002354.1 | Forward Primer | GGGCCCTCCAGAACAATGAT | SEQ ID NO: 730 |
| | | Probe | CCGCTCTCATCGCAGTCAGGATCAT | SEQ ID NO: 731 |
| | | Reverse Primer | TGCACTGCTTGGCCTTAAAGA | SEQ ID NO: 732 |
| EPHA2 | NM_004431.2 | Forward Primer | CGCCTGTTCACCAAGATTGAC | SEQ ID NO: 733 |
| | | Probe | TGCGCCCGATGAGATCACCG | SEQ ID NO: 734 |
| | | Reverse Primer | GTGGCGTGCCTCGAAGTC | SEQ ID NO: 735 |
| EPHB2 | NM_004442.4 | Forward Primer | CAACCAGGCAGCTCCATC | SEQ ID NO: 736 |
| | | Probe | CACCTGATGCATGATGGACACTGC | SEQ ID NO: 737 |
| | | Reverse Primer | GTAATGCTGTCCACGGTGC | SEQ ID NO: 738 |
| EPHB4 | NM_004444.3 | Forward Primer | TGAACGGGGTATCCTCCTTA | SEQ ID NO: 739 |
| | | Probe | CGTCCCATTTGAGCCTGTCAATGT | SEQ ID NO: 740 |
| | | Reverse Primer | AGGTACCTCTCGGTCAGTGG | SEQ ID NO: 741 |
| EphB6 | NM_004445.1 | Forward Primer | ACTGGTCCTCCATCGGCT | SEQ ID NO: 742 |
| | | Probe | CCTTGCACCTCAAACCAAAGCTCC | SEQ ID NO: 743 |
| | | Reverse Primer | CCAGTGTAGCATGAGTGCTGA | SEQ ID NO: 744 |
| EPM2A | NM_005670.2 | Forward Primer | ACTGTGGCACTTAGGGGAGA | SEQ ID NO: 745 |
| | | Probe | CTGCCTCTGCCCAAAGCAAATGTC | SEQ ID NO: 746 |
| | | Reverse Primer | AGTGGAAATGTGTCCTGGCT | SEQ ID NO: 747 |
| ErbB3 | NM_001982.1 | Forward Primer | CGGTTATGTCATGCCAGATACAC | SEQ ID NO: 748 |
| | | Probe | CCTCAAAGGTACTCCCTCCTCCCGG | SEQ ID NO: 749 |
| | | Reverse Primer | GAACTGAGACCCACTGAAGAAAGG | SEQ ID NO: 750 |
| ERCC1 | NM_001983.1 | Forward Primer | GTCCAGGTGGATGTGAAAGA | SEQ ID NO: 751 |
| | | Probe | CAGCAGGCCCTCAAGGAGCTG | SEQ ID NO: 752 |
| | | Reverse Primer | CGGCCAGGATACACATCTTA | SEQ ID NO: 753 |
| ERCC2 | NM_000400.2 | Forward Primer | TGGCCTTCTTCACCAGCTA | SEQ ID NO: 754 |
| | | Probe | AGGCCACGGTGCTCTCCATGTACT | SEQ ID NO: 755 |
| | | Reverse Primer | CAAGGATCCCCTGCTCATAC | SEQ ID NO: 756 |
| EREG | NM_001432.1 | Forward Primer | ATAACAAAGTGTAGCTCTGACATGAATG | SEQ ID NO: 757 |
| | | Probe | TTGTTTGCATGGACAGTGCATCTATCTGGT | SEQ ID NO: 758 |
| | | Reverse Primer | CACACCTGCAGTAGTTTTGACTCA | SEQ ID NO: 759 |
| ERK1 | Z11696.1 | Forward Primer | ACGGATCACAGTGGAGGAAG | SEQ ID NO: 760 |
| | | Probe | CGCTGGCTCACCCCTACCTG | SEQ ID NO: 761 |
| | | Reverse Primer | CTCATCCGTCGGGTCATAGT | SEQ ID NO: 762 |
| ERK2 | NM_002745.1 | Forward Primer | AGTTCTTGACCCCTGGTCCT | SEQ ID NO: 763 |
| | | Probe | TCTCCAGCCCGTCTTGGCTT | SEQ ID NO: 764 |
| | | Reverse Primer | AAACGGCTCAAAGGAGTCAA | SEQ ID NO: 765 |
| ESPL1 | NM_012291.1 | Forward Primer | ACCCCAGACCGGATCAG | SEQ ID NO: 766 |
| | | Probe | CTGGCCCTCATGTCCCCTTCACG | SEQ ID NO: 767 |
| | | Reverse Primer | TGTAGGGCAGACTTCCTCAAACA | SEQ ID NO: 768 |
| EstR1 | NM_000125.1 | Forward Primer | CGTGGTGCCCCTCTATGAC | SEQ ID NO: 769 |
| | | Probe | CTGGAGATGCTGGACGCCC | SEQ ID NO: 770 |
| | | Reverse Primer | GGCTAGTGGGCGCATGTAG | SEQ ID NO: 771 |
| ETV4 | NM_001986.1 | Forward Primer | TCCAGTGCCTATGACCCC | SEQ ID NO: 772 |
| | | Probe | CAGACAAATCGCCATCAAGTCCCC | SEQ ID NO: 773 |
| | | Reverse Primer | ACTGTCCAAGGGCACCAG | SEQ ID NO: 774 |

TABLE A-continued

| Gene | Accession | Reagent | Sequence | Sequence ID Number |
|---|---|---|---|---|
| F3 | NM_001993.2 | Forward Primer | GTGAAGGATGTGAAGCAGACGTA | SEQ ID NO: 775 |
| | | Probe | TGGCACGGGTCTTCTCCTACC | SEQ ID NO: 776 |
| | | Reverse Primer | AACCGGTGCTCTCCACATTC | SEQ ID NO: 777 |
| FABP4 | NM_001442.1 | Forward Primer | GCTTTGCCACCAGGAAAGT | SEQ ID NO: 778 |
| | | Probe | CTGGCATGGCCAAACCTAACATGA | SEQ ID NO: 779 |
| | | Reverse Primer | CATCCCCATTCACACTGATG | SEQ ID NO: 780 |
| FAP | NM_004460.2 | Forward Primer | CTGACCAGAACCACGGCT | SEQ ID NO: 781 |
| | | Probe | CGGCCTGTCCACGAACCACTTATA | SEQ ID NO: 782 |
| | | Reverse Primer | GGAAGTGGGTCATGTGGG | SEQ ID NO: 783 |
| fas | NM_000043.1 | Forward Primer | GGATTGCTCAACAACCATGCT | SEQ ID NO: 784 |
| | | Probe | TCTGGACCCTCCTACCTCTGGTTCTTACGT | SEQ ID NO: 785 |
| | | Reverse Primer | GGCATTAACACTTTTGGACGATAA | SEQ ID NO: 786 |
| fasl | NM_000639.1 | Forward Primer | GCACTTTGGGATTCTTTCCATTAT | SEQ ID NO: 787 |
| | | Probe | ACAACATTCTCGGTGCCTGTAACAAAGAA | SEQ ID NO: 788 |
| | | Reverse Primer | GCATGTAAGAAGACCCTCACTGAA | SEQ ID NO: 789 |
| FASN | NM_004104.4 | Forward Primer | GCCTCTTCCTGTTCGACG | SEQ ID NO: 790 |
| | | Probe | TCGCCCACCTACGTACTGGCCTAC | SEQ ID NO: 791 |
| | | Reverse Primer | GCTTTGCCCGGTAGCTCT | SEQ ID NO: 792 |
| FBXO5 | NM_012177.2 | Forward Primer | GGCTATTCCTCATTTTCTCTACAAAGTG | SEQ ID NO: 793 |
| | | Probe | CCTCCAGGAGGCTACCTTCTTCATGTTCAC | SEQ ID NO: 794 |
| | | Reverse Primer | GGATTGTAGACTGTCACCGAAATTC | SEQ ID NO: 795 |
| FBXW7 | NM_033632.1 | Forward Primer | CCCCAGTTTCAACGAGACTT | SEQ ID NO: 796 |
| | | Probe | TCATTGCTCCCTAAAGAGTTGGCACTC | SEQ ID NO: 797 |
| | | Reverse Primer | GTTCCAGGAATGAAAGCACA | SEQ ID NO: 798 |
| FDXR | NM_004110.2 | Forward Primer | GAGATGATTCAGTTACCGGGAG | SEQ ID NO: 799 |
| | | Probe | AATCCACAGGATCCAAAATGGGCC | SEQ ID NO: 800 |
| | | Reverse Primer | ATCTTGTCCTGGAGACCCAA | SEQ ID NO: 801 |
| FES | NM_002005.2 | Forward Primer | CTCTGCAGGCCTAGGTGC | SEQ ID NO: 802 |
| | | Probe | CTCCTCAGCGGCTCCAGCTCATAT | SEQ ID NO: 803 |
| | | Reverse Primer | CCAGGACTGTGAAGAGCTGTC | SEQ ID NO: 804 |
| FGF18 | NM_003862.1 | Forward Primer | CGGTAGTCAAGTCCGGATCAA | SEQ ID NO: 805 |
| | | Probe | CAAGGAGACGGAATTCTACCTGTGC | SEQ ID NO: 806 |
| | | Reverse Primer | GCTTGCCTTTGCGGTTCA | SEQ ID NO: 807 |
| FGF2 | NM_002006.2 | Forward Primer | AGATGCAGGAGAGAGGAGC | SEQ ID NO: 808 |
| | | Probe | CCTGCAGACTGCTTTTTGCCCAAT | SEQ ID NO: 809 |
| | | Reverse Primer | GTTTTGCAGCCTTACCCAAT | SEQ ID NO: 810 |
| FGFR1 | NM_023109.1 | Forward Primer | CACGGGACATTCACCACATC | SEQ ID NO: 811 |
| | | Probe | ATAAAAAGACAACCAACGGCCGACTGC | SEQ ID NO: 812 |
| | | Reverse Primer | GGGTGCCATCCACTTCACA | SEQ ID NO: 813 |
| FGFR2 isoform 1 | NM_000141.2 | Forward Primer | GAGGGACTGTTGGCATGCA | SEQ ID NO: 814 |
| | | Probe | TCCCAGAGACCAACGTTCAAGCAGTTG | SEQ ID NO: 815 |
| | | Reverse Primer | GAGTGAGAATTCGATCCAAGTCTTC | SEQ ID NO: 816 |
| FHIT | NM_002012.1 | Forward Primer | CCAGTGGAGCGCTTCCAT | SEQ ID NO: 817 |
| | | Probe | TCGGCCACTTCATCAGGACGCAG | SEQ ID NO: 818 |
| | | Reverse Primer | CTCTCTGGGTCGTCTGAAACAA | SEQ ID NO: 819 |
| FIGF | NM_004469.2 | Forward Primer | GGTTCCAGCTTTCTGTAGCTGT | SEQ ID NO: 820 |
| | | Probe | ATTGGTGGCCACACCACCTCCTTA | SEQ ID NO: 821 |
| | | Reverse Primer | GCCGCAGGTTCTAGTTGCT | SEQ ID NO: 822 |
| FLJ12455 | NM_022078.1 | Forward Primer | CCACCAGCATGAAGTTTCG | SEQ ID NO: 823 |
| | | Probe | ACCCCTCACAAAGGCCATGTCTGT | SEQ ID NO: 824 |
| | | Reverse Primer | GGCTGTCTGAAGCACAACTG | SEQ ID NO: 825 |
| FLJ20712 | AK000719.1 | Forward Primer | GCCACACAAACATGCTCCT | SEQ ID NO: 826 |
| | | Probe | ATGTCTTTCCCAGCAGCTCTGCCT | SEQ ID NO: 827 |
| | | Reverse Primer | GCCACAGGAAACTTCCGA | SEQ ID NO: 828 |
| FLT1 | NM_002019.1 | Forward Primer | GGCTCCCGAATCTATCTTTG | SEQ ID NO: 829 |
| | | Probe | CTACAGCACCAAGAGCGACGTGTG | SEQ ID NO: 830 |
| | | Reverse Primer | TCCCACAGCAATACTCCGTA | SEQ ID NO: 831 |

TABLE A-continued

| Gene | Accession | Reagent | Sequence | Sequence ID Number |
|---|---|---|---|---|
| FLT4 | NM_002020.1 | Forward Primer | ACCAAGAAGCTGAGGACCTG | SEQ ID NO: 832 |
| | | Probe | AGCCCGCTGACCATGGAAGATCT | SEQ ID NO: 833 |
| | | Reverse Primer | CCTGGAAGCTGTAGCAGACA | SEQ ID NO: 834 |
| FOS | NM_005252.2 | Forward Primer | CGAGCCCTTTGATGACTTCCT | SEQ ID NO: 835 |
| | | Probe | TCCCAGCATCATCCAGGCCCAG | SEQ ID NO: 836 |
| | | Reverse Primer | GGAGCGGGCTGTCTCAGA | SEQ ID NO: 837 |
| FOXO3A | NM_001455.1 | Forward Primer | TGAAGTCCAGGACGATGATG | SEQ ID NO: 838 |
| | | Probe | CTCTACAGCAGCTCAGCCAGCCTG | SEQ ID NO: 839 |
| | | Reverse Primer | ACGGCTTGCTTACTGAAGGT | SEQ ID NO: 840 |
| FPGS | NM_004957.3 | Forward Primer | CAGCCCTGCCAGTTTGAC | SEQ ID NO: 841 |
| | | Probe | ATGCCGTCTTCTGCCCTAACCTGA | SEQ ID NO: 842 |
| | | Reverse Primer | GTTGCCTGTGGATGACACC | SEQ ID NO: 843 |
| FRP1 | NM_003012.2 | Forward Primer | TTGGTACCTGTGGGTTAGCA | SEQ ID NO: 844 |
| | | Probe | TCCCCAGGGTAGAATTCAATCAGAGC | SEQ ID NO: 845 |
| | | Reverse Primer | CACATCCAAATGCAAACTGG | SEQ ID NO: 846 |
| FST | NM_006350.2 | Forward Primer | GTAAGTCGGATGAGCCTGTCTGT | SEQ ID NO: 847 |
| | | Probe | CCAGTGACAATGCCACTTATGCCAGC | SEQ ID NO: 848 |
| | | Reverse Primer | CAGCTTCCTTCATGGCACACT | SEQ ID NO: 849 |
| Furin | NM_002569.1 | Forward Primer | AAGTCCTCGATACGCACTATAGCA | SEQ ID NO: 850 |
| | | Probe | CCCGGATGGTCTCCACGTCAT | SEQ ID NO: 851 |
| | | Reverse Primer | CTGGCATGTGGCACATGAG | SEQ ID NO: 852 |
| FUS | NM_004960.1 | Forward Primer | GGATAATTCAGACAACAACACCATCT | SEQ ID NO: 853 |
| | | Probe | TCAATTGTAACATTCTCACCCAGGCCTTG | SEQ ID NO: 854 |
| | | Reverse Primer | TGAAGTAATCAGCCACAGACTCAAT | SEQ ID NO: 855 |
| FUT1 | NM_000148.1 | Forward Primer | CCGTGCTCATTGCTAACCA | SEQ ID NO: 856 |
| | | Probe | TCTGTCCCTGAACTCCCAGAACCA | SEQ ID NO: 857 |
| | | Reverse Primer | CTGCCCAAAGCCAGATGTA | SEQ ID NO: 858 |
| FUT3 | NM_000149.1 | Forward Primer | CAGTTCGGTCCAACAGAAA | SEQ ID NO: 859 |
| | | Probe | AGCAGGCAACCACCATGTCATTTG | SEQ ID NO: 860 |
| | | Reverse Primer | TGCGAATTATATCCCGATGA | SEQ ID NO: 861 |
| FUT6 | NM_000150.1 | Forward Primer | CGTGTGTCTCAAGACGATCC | SEQ ID NO: 862 |
| | | Probe | TGTGTACCCTAATGGGTCCCGCTT | SEQ ID NO: 863 |
| | | Reverse Primer | GGTCCCTGTGCTGTCTGG | SEQ ID NO: 864 |
| FXYD5 | NM_014164.4 | Forward Primer | AGAGCACCAAAGCAGCTCAT | SEQ ID NO: 865 |
| | | Probe | CACTGATGACACCACGACGCTCTC | SEQ ID NO: 866 |
| | | Reverse Primer | GTGCTTGGGGATGGTCTCT | SEQ ID NO: 867 |
| FYN | NM_002037.3 | Forward Primer | GAAGCGCAGATCATGAAGAA | SEQ ID NO: 868 |
| | | Probe | CTGAAGCACGACAAGCTGGTCCAG | SEQ ID NO: 869 |
| | | Reverse Primer | CTCCTCAGACACCACTGCAT | SEQ ID NO: 870 |
| FZD1 | NM_003505.1 | Forward Primer | GGTGCACCAGTTCTACCCTC | SEQ ID NO: 871 |
| | | Probe | ACTTGAGCTCAGCGGAACACTGCA | SEQ ID NO: 872 |
| | | Reverse Primer | GCGTACATGGAGCACAGGA | SEQ ID NO: 873 |
| FZD2 | NM_001466.2 | Forward Primer | TGGATCCTCACCTGGTCG | SEQ ID NO: 874 |
| | | Probe | TGCGCTTCCACCTTCTTCACTGTC | SEQ ID NO: 875 |
| | | Reverse Primer | GCGCTGCATGTCTACCAA | SEQ ID NO: 876 |
| FZD6 | NM_003506.2 | Forward Primer | AATGAGAGAGGTGAAAGCGG | SEQ ID NO: 877 |
| | | Probe | CGGAGCTAGCACCCCCAGGTTAAG | SEQ ID NO: 878 |
| | | Reverse Primer | AGGTTCACCACAGTCCTGTTC | SEQ ID NO: 879 |
| G-Catenin | NM_002230.1 | Forward Primer | TCAGCAGCAAGGGCATCAT | SEQ ID NO: 880 |
| | | Probe | CGCCCGCAGGCCTCATCCT | SEQ ID NO: 881 |
| | | Reverse Primer | GGTGGTTTTCTTGAGCGTGTACT | SEQ ID NO: 882 |
| G1P2 | NM_005101.1 | Forward Primer | CAACGAATTCCAGGTGTCC | SEQ ID NO: 883 |
| | | Probe | CTGAGCAGCTCCATGTCGGTGTC | SEQ ID NO: 884 |
| | | Reverse Primer | GATCTGCGCCTTCAGCTC | SEQ ID NO: 885 |
| GADD45 | NM_001924.2 | Forward Primer | GTGCTGGTGACGAATCCA | SEQ ID NO: 886 |
| | | Probe | TTCATCTCAATGGAAGGATCCTGCC | SEQ ID NO: 887 |
| | | Reverse Primer | CCCGGCAAAAACAAATAAGT | SEQ ID NO: 888 |

TABLE A-continued

| Gene | Accession | Reagent | Sequence | Sequence ID Number |
|---|---|---|---|---|
| GADD45B | NM_015675.1 | Forward Primer<br>Probe<br>Reverse Primer | ACCCTCGACAAGACCACACT<br>AACTTCAGCCCCAGCTCCCAAGTC<br>TGGGAGTTCATGGGTACAGA | SEQ ID NO: 889<br>SEQ ID NO: 890<br>SEQ ID NO: 891 |
| GADD45G | NM_006705.2 | Forward Primer<br>Probe<br>Reverse Primer | CGCGCTGCAGATCCATTT<br>CGCTGATCCAGGCTTTCTGCTGC<br>CGCACTATGTCGATGTCGTTCT | SEQ ID NO: 892<br>SEQ ID NO: 893<br>SEQ ID NO: 894 |
| GAGE4 | NM_001474.1 | Forward Primer<br>Probe<br>Reverse Primer | GGAACAGGGTCACCCACAGA<br>TCAGGACCATCTTCACACTCACACCCA<br>GATTTGGCGGGTCCATCTC | SEQ ID NO: 895<br>SEQ ID NO: 896<br>SEQ ID NO: 897 |
| GBP1 | NM_002053.1 | Forward Primer<br>Probe<br>Reverse Primer | TTGGGAAATATTTGGGCATT<br>TTGGGACATTGTAGACTTGGCCAGAC<br>AGAAGCTAGGGTGGTTGTCC | SEQ ID NO: 898<br>SEQ ID NO: 899<br>SEQ ID NO: 900 |
| GBP2 | NM_004120.2 | Forward Primer<br>Probe<br>Reverse Primer | GCATGGGAACCATCAACCA<br>CCATGGACCAACTTCACTATGTGACAGAGC<br>TGAGGAGTTTGCCTTGATTCG | SEQ ID NO: 901<br>SEQ ID NO: 902<br>SEQ ID NO: 903 |
| GCLC | NM_001498.1 | Forward Primer<br>Probe<br>Reverse Primer | CTGTTGCAGGAAGGCATTGA<br>CATCTCCTGGCCCAGCATGTT<br>GTCAGTGGGTCTCTAATAAAGAGATGAG | SEQ ID NO: 904<br>SEQ ID NO: 905<br>SEQ ID NO: 906 |
| GCLM | NM_002061.1 | Forward Primer<br>Probe<br>Reverse Primer | TGTAGAATCAAACTCTTCATCATCAACTAG<br>TGCAGTTGACATGGCCTGTTCAGTCC<br>CACAGAATCCAGCTGTGCAACT | SEQ ID NO: 907<br>SEQ ID NO: 908<br>SEQ ID NO: 909 |
| GCNT1 | NM_001490.3 | Forward Primer<br>Probe<br>Reverse Primer | TGGTGCTTGGAGCATAGAAG<br>TGCCCTTCACAAAGGAAATCCCTG<br>GCAACGTCCTCAGCATTTC | SEQ ID NO: 910<br>SEQ ID NO: 911<br>SEQ ID NO: 912 |
| GDF15 | NM_004864.1 | Forward Primer<br>Probe<br>Reverse Primer | CGCTCCAGACCTATGATGACT<br>TGTTAGCCAAAGACTGCCACTGCA<br>ACAGTGGAAGGACCAGGACT | SEQ ID NO: 913<br>SEQ ID NO: 914<br>SEQ ID NO: 915 |
| GIT1 | NM_014030.2 | Forward Primer<br>Probe<br>Reverse Primer | GTGTATGACGAGGTGGATCG<br>AGCCAGCCACACTGCATCATTTTC<br>ACCAGAGTGCTGTGGTTTTG | SEQ ID NO: 916<br>SEQ ID NO: 917<br>SEQ ID NO: 918 |
| GJA1 | NM_000165.2 | Forward Primer<br>Probe<br>Reverse Primer | GTTCACTGGGGGTGTATGG<br>ATCCCCTCCCTCTCCACCCATCTA<br>AAATACCAACATGCACCTCTCTT | SEQ ID NO: 919<br>SEQ ID NO: 920<br>SEQ ID NO: 921 |
| GJB2 | NM_004004.3 | Forward Primer<br>Probe<br>Reverse Primer | TGTCATGTACGACGGCTTCT<br>AGGCGTTGCACTTCACCAGCC<br>AGTCCACAGTGTTGGGACAA | SEQ ID NO: 922<br>SEQ ID NO: 923<br>SEQ ID NO: 924 |
| GPX1 | NM_000581.2 | Forward Primer<br>Probe<br>Reverse Primer | GCTTATGACCGACCCCAA<br>CTCATCACCTGGTCTCCGGTGTGT<br>AAAGTTCCAGGCAACATCGT | SEQ ID NO: 925<br>SEQ ID NO: 926<br>SEQ ID NO: 927 |
| GPX2 | NM_002083.1 | Forward Primer<br>Probe<br>Reverse Primer | CACACAGATCTCCTACTCCATCCA<br>CATGCTGCATCCTAAGGCTCCTCAGG<br>GGTCCAGCAGTGTCTCCTGAA | SEQ ID NO: 928<br>SEQ ID NO: 929<br>SEQ ID NO: 930 |
| Grb10 | NM_005311.2 | Forward Primer<br>Probe<br>Reverse Primer | CTTCGCCTTTGCTGATTGC<br>CTCCAAACGCCTGCCTGACGACTG<br>CCATAACGCACATGCTCCAA | SEQ ID NO: 931<br>SEQ ID NO: 932<br>SEQ ID NO: 933 |
| GRB14 | NM_004490.1 | Forward Primer<br>Probe<br>Reverse Primer | TCCCACTGAAGCCCTTTCAG<br>CCTCCAAGCGAGTCCTTCTTCAACCG<br>AGTGCCCAGGCGTAAACATC | SEQ ID NO: 934<br>SEQ ID NO: 935<br>SEQ ID NO: 936 |
| GRB2 | NM_002086.2 | Forward Primer<br>Probe<br>Reverse Primer | GTCCATCAGTGCATGACGTT<br>AGGCCACGTATAGTCCTAGCTGACGC<br>AGCCCACTTGGTTTCTTGTT | SEQ ID NO: 937<br>SEQ ID NO: 938<br>SEQ ID NO: 939 |
| GRB7 | NM_005310.1 | Forward Primer<br>Probe<br>Reverse Primer | CCATCTGCATCCATCTTGTT<br>CTCCCCACCCTTGAGAAGTGCCT<br>GGCCACCAGGGTATTATCTG | SEQ ID NO: 940<br>SEQ ID NO: 941<br>SEQ ID NO: 942 |
| GRIK1 | NM_000830.2 | Forward Primer<br>Probe<br>Reverse Primer | GTTGGGTGCATCTCTCGG<br>AATTCATGCCGAGATACAGCCGCT<br>CGTGCTCCATCTTCCTAGCTT | SEQ ID NO: 943<br>SEQ ID NO: 944<br>SEQ ID NO: 945 |

TABLE A-continued

| Gene | Accession | Reagent | Sequence | Sequence ID Number |
|---|---|---|---|---|
| GRO1 | NM_001511.1 | Forward Primer | CGAAAAGATGCTGAACAGTGACA | SEQ ID NO: 946 |
| | | Probe | CTTCCTCCTCCCTTCTGGTCAGTTGGAT | SEQ ID NO: 947 |
| | | Reverse Primer | TCAGGAACAGCCACCAGTGA | SEQ ID NO: 948 |
| GRP | NM_002091.1 | Forward Primer | CTGGGTCTCATAGAAGCAAAGGA | SEQ ID NO: 949 |
| | | Probe | AGAAACCACCAGCCACCTCAACCCA | SEQ ID NO: 950 |
| | | Reverse Primer | CCACGAAGGCTGCTGATTG | SEQ ID NO: 951 |
| GRPR | NM_005314.1 | Forward Primer | ATGCTGCTGGCCATTCCA | SEQ ID NO: 952 |
| | | Probe | CCGTGTTTTCTGACCTCCATCCCTTCC | SEQ ID NO: 953 |
| | | Reverse Primer | AGGTCTGGTTGGTGCTTTCCT | SEQ ID NO: 954 |
| GSK3B | NM_002093.2 | Forward Primer | GACAAGGACGGCAGCAAG | SEQ ID NO: 955 |
| | | Probe | CCAGGAGTTGCCACCACTGTTGTC | SEQ ID NO: 956 |
| | | Reverse Primer | TTGTGGCCTGTCTGGACC | SEQ ID NO: 957 |
| GSTA3 | NM_000847.3 | Forward Primer | TCTCCAACTTCCCTCTGCTG | SEQ ID NO: 958 |
| | | Probe | AGGCCCTGAAAACCAGAATCAGCA | SEQ ID NO: 959 |
| | | Reverse Primer | ACTTCTTCACCGTGGGCA | SEQ ID NO: 960 |
| GSTM1 | NM_000561.1 | Forward Primer | AAGCTATGAGGAAAAGAAGTACACGAT | SEQ ID NO: 961 |
| | | Probe | TCAGCCACTGGCTTCTGTCATAATCAGGAG | SEQ ID NO: 962 |
| | | Reverse Primer | GGCCCAGCTTGAATTTTTCA | SEQ ID NO: 963 |
| GSTM3 | NM_000849.3 | Forward Primer | CAATGCCATCTTGCGCTACAT | SEQ ID NO: 964 |
| | | Probe | CTCGCAAGCACAACATGTGTGGTGAGA | SEQ ID NO: 965 |
| | | Reverse Primer | GTCCACTCGAATCTTTTCTTCTTCA | SEQ ID NO: 966 |
| GSTp | NM_000852.2 | Forward Primer | GAGACCCTGCTGTCCCAGAA | SEQ ID NO: 967 |
| | | Probe | TCCCACAATGAAGGTCTTGCCTCCCT | SEQ ID NO: 968 |
| | | Reverse Primer | GGTTGTAGTCAGCGAAGGAGATC | SEQ ID NO: 969 |
| GSTT1 | NM_000853.1 | Forward Primer | CACCATCCCCACCCTGTCT | SEQ ID NO: 970 |
| | | Probe | CACAGCCGCCTGAAAGCCACAAT | SEQ ID NO: 971 |
| | | Reverse Primer | GGCCTCAGTGTGCATCATTCT | SEQ ID NO: 972 |
| H2AFZ | NM_002106.2 | Forward Primer | CCGGAAAGGCCAAGACAA | SEQ ID NO: 973 |
| | | Probe | CCCGCTCGCAGAGAGCCGG | SEQ ID NO: 974 |
| | | Reverse Primer | AATACGGCCCACTGGGAACT | SEQ ID NO: 975 |
| HB-EGF | NM_001945.1 | Forward Primer | GACTCCTTCGTCCCCAGTTG | SEQ ID NO: 976 |
| | | Probe | TTGGGCCTCCCATAATTGCTTTGCC | SEQ ID NO: 977 |
| | | Reverse Primer | TGGCACTTGAAGGCTCTGGTA | SEQ ID NO: 978 |
| hCRA a | U78556.1 | Forward Primer | TGACACCCTTACCTTCCTGAGAA | SEQ ID NO: 979 |
| | | Probe | TCTGCTTTCCGCGCTCCCAGG | SEQ ID NO: 980 |
| | | Reverse Primer | AAAAACACGAGTCAAAAATAGAAGTCACT | SEQ ID NO: 981 |
| HDAC1 | NM_004964.2 | Forward Primer | CAAGTACCACAGCGATGACTACATTAA | SEQ ID NO: 982 |
| | | Probe | TTCTTGCGCTCCATCCGTCCAGA | SEQ ID NO: 983 |
| | | Reverse Primer | GCTTGCTGTACTCCGACATGTT | SEQ ID NO: 984 |
| HDAC2 | NM_001527.1 | Forward Primer | GGTGGCTACACAATCCGTAA | SEQ ID NO: 985 |
| | | Probe | TGCAGTCTCTATATGTCCAACATCGAGC | SEQ ID NO: 986 |
| | | Reverse Primer | TGGGAATCTCACAATCAAGG | SEQ ID NO: 987 |
| HDGF | NM_004494.1 | Forward Primer | TCCTAGGCATTCTGGACCTC | SEQ ID NO: 988 |
| | | Probe | CATTCCTACCCCTGATCCCAACCC | SEQ ID NO: 989 |
| | | Reverse Primer | GCTGTTGATGCTCCATCCTT | SEQ ID NO: 990 |
| hENT1 | NM_004955.1 | Forward Primer | AGCCGTGACTGTTGAGGTC | SEQ ID NO: 991 |
| | | Probe | AAGTCCAGCATCGCAGGCAGC | SEQ ID NO: 992 |
| | | Reverse Primer | AAGTAACGTTCCCAGGTGCT | SEQ ID NO: 993 |
| Hepsin | NM_002151.1 | Forward Primer | AGGCTGCTGGAGGTCATCTC | SEQ ID NO: 994 |
| | | Probe | CCAGAGGCCGTTTCTTGGCCG | SEQ ID NO: 995 |
| | | Reverse Primer | CTTCCTGCGGCCACAGTCT | SEQ ID NO: 996 |
| HER2 | NM_004448.1 | Forward Primer | CGGTGTGAGAAGTGCAGCAA | SEQ ID NO: 997 |
| | | Probe | CCAGACCATAGCACACTCGGGCAC | SEQ ID NO: 998 |
| | | Reverse Primer | CCTCTCGCAAGTGCTCCAT | SEQ ID NO: 999 |
| Herstatin | AF177761.2 | Forward Primer | CACCCTGTCCTATCCTTCCT | SEQ ID NO: 1000 |
| | | Probe | CCCTCTTGGGACCTAGTCTCTGCCT | SEQ ID NO: 1001 |
| | | Reverse Primer | GGCCAGGGGTAGAGAGTAGA | SEQ ID NO: 1002 |

TABLE A-continued

| Gene | Accession | Reagent | Sequence | Sequence ID Number |
|---|---|---|---|---|
| HES6 | NM_018645.3 | Forward Primer | TTAGGGACCCTGCAGCTCT | SEQ ID NO: 1003 |
| | | Probe | TAGCTCCCTCCCTCCACCCACTC | SEQ ID NO: 1004 |
| | | Reverse Primer | CTACAAAATTCTTCCTCCTGCC | SEQ ID NO: 1005 |
| HGF | M29145.1 | Forward Primer | CCGAAATCCAGATGATGATG | SEQ ID NO: 1006 |
| | | Probe | CTCATGGACCCTGGTGCTACACG | SEQ ID NO: 1007 |
| | | Reverse Primer | CCCAAGGAATGAGTGGATTT | SEQ ID NO: 1008 |
| HIF1A | NM_001530.1 | Forward Primer | TGAACATAAAGTCTGCAACATGGA | SEQ ID NO: 1009 |
| | | Probe | TTGCACTGCACAGGCCACATTCAC | SEQ ID NO: 1010 |
| | | Reverse Primer | TGAGGTTGGTTACTGTTGGTATCATATA | SEQ ID NO: 1011 |
| HK1 | NM_000188.1 | Forward Primer | TACGCACAGAGGCAAGCA | SEQ ID NO: 1012 |
| | | Probe | TAAGAGTCCGGGATCCCCAGCCTA | SEQ ID NO: 1013 |
| | | Reverse Primer | GAGAGAAGTGCTGGAGAGGC | SEQ ID NO: 1014 |
| HLA-DPB1 | NM_002121.4 | Forward Primer | TCCATGATGGTTCTGCAGGTT | SEQ ID NO: 1015 |
| | | Probe | CCCCGGACAGTGGCTCTGACG | SEQ ID NO: 1016 |
| | | Reverse Primer | TGAGCAGCACCATCAGTAACG | SEQ ID NO: 1017 |
| HLA-DRA | NM_019111.3 | Forward Primer | GACGATTTGCCAGCTTTGAG | SEQ ID NO: 1018 |
| | | Probe | TCAAGGTGCATTGGCCAACATAGC | SEQ ID NO: 1019 |
| | | Reverse Primer | TCCAGGTTGGCTTTGTCC | SEQ ID NO: 1020 |
| HLA-DRB1 | NM_002124.1 | Forward Primer | GCTTTCTCAGGACCTGGTTG | SEQ ID NO: 1021 |
| | | Probe | CATTTTCTGCAGTTGCCGAACCAG | SEQ ID NO: 1022 |
| | | Reverse Primer | AGGAAGCCACAAGGGAGG | SEQ ID NO: 1023 |
| HLA-G | NM_002127.2 | Forward Primer | CCTGCGCGGCTACTACAAC | SEQ ID NO: 1024 |
| | | Probe | CGAGGCCAGTTCTCACACCCTCCAG | SEQ ID NO: 1025 |
| | | Reverse Primer | CAGGTCGCAGCCAATCATC | SEQ ID NO: 1026 |
| HMGB1 | NM_002128.3 | Forward Primer | TGGCCTGTCCATTGGTGAT | SEQ ID NO: 1027 |
| | | Probe | TTCCACATCTCTCCCAGTTTCTTCGCAA | SEQ ID NO: 1028 |
| | | Reverse Primer | GCTTGTCATCTGCAGCAGTGTT | SEQ ID NO: 1029 |
| hMLH | NM_000249.2 | Forward Primer | CTACTTCCAGCAACCCCAGA | SEQ ID NO: 1030 |
| | | Probe | TCCACATCAGAATCTTCCCG | SEQ ID NO: 1031 |
| | | Reverse Primer | CTTTCGGGAATCATCTTCCA | SEQ ID NO: 1032 |
| HNRPAB | NM_004499.2 | Forward Primer | CAAGGGAGCGACCAACTGA | SEQ ID NO: 1033 |
| | | Probe | CTCCATATCCAAACAAAGCATGTGTGCG | SEQ ID NO: 1034 |
| | | Reverse Primer | GTTTGCCAAGTTAAATTTGGTACATAAT | SEQ ID NO: 1035 |
| HNRPD | NM_031370.2 | Forward Primer | GCCAGTAAGAACGAGGAGGA | SEQ ID NO: 1036 |
| | | Probe | AAGGCCATTCAAACTCCTCCCCAC | SEQ ID NO: 1037 |
| | | Reverse Primer | CGTCGCTGCTTCAGAGTGT | SEQ ID NO: 1038 |
| HoxA1 | NM_005522.3 | Forward Primer | AGTGACAGATGGACAATGCAAGA | SEQ ID NO: 1039 |
| | | Probe | TGAACTCCTTCCTGGAATACCCCA | SEQ ID NO: 1040 |
| | | Reverse Primer | CCGAGTCGCCACTGCTAAGT | SEQ ID NO: 1041 |
| HoxA5 | NM_019102.2 | Forward Primer | TCCCTTGTGTTCCTTCTGTGAA | SEQ ID NO: 1042 |
| | | Probe | AGCCCTGTTCTCGTTGCCCTAATTCATC | SEQ ID NO: 1043 |
| | | Reverse Primer | GGCAATAAACAGGCTCATGATTAA | SEQ ID NO: 1044 |
| HOXB13 | NM_006361.2 | Forward Primer | CGTGCCTTATGGTTACTTTGG | SEQ ID NO: 1045 |
| | | Probe | ACACTCGGCAGGAGTAGTACCCGC | SEQ ID NO: 1046 |
| | | Reverse Primer | CACAGGGTTTCAGCGAGC | SEQ ID NO: 1047 |
| HOXB7 | NM_004502.2 | Forward Primer | CAGCCTCAAGTTCGGTTTTC | SEQ ID NO: 1048 |
| | | Probe | ACCGGAGCCTTCCCAGAACAAACT | SEQ ID NO: 1049 |
| | | Reverse Primer | GTTGGAAGCAAACGCACA | SEQ ID NO: 1050 |
| HRAS | NM_005343.2 | Forward Primer | GGACGAATACGACCCCACT | SEQ ID NO: 1051 |
| | | Probe | ACCACCTGCTTCCGGTAGGAATCC | SEQ ID NO: 1052 |
| | | Reverse Primer | GCACGTCTCCCCATCAAT | SEQ ID NO: 1053 |
| HSBP1 | NM_001537.1 | Forward Primer | GGAGATGGCCGAGACTGAC | SEQ ID NO: 1054 |
| | | Probe | CAAGACCGTGCAGGACCTCACCT | SEQ ID NO: 1055 |
| | | Reverse Primer | CTGCAGGAGTGTCTGCACC | SEQ ID NO: 1056 |
| HSD17B1 | NM_000413.1 | Forward Primer | CTGGACCGCACGGACATC | SEQ ID NO: 1057 |
| | | Probe | ACCGCTTCTACCAATACCTCGCCCA | SEQ ID NO: 1058 |
| | | Reverse Primer | CGCCTCGCGAAAGACTTG | SEQ ID NO: 1059 |

TABLE A-continued

| Gene | Accession | Reagent | Sequence | Sequence ID Number |
|---|---|---|---|---|
| HSD17B2 | NM_002153.1 | Forward Primer | GCTTTCCAAGTGGGGAATTA | SEQ ID NO: 1060 |
| | | Probe | AGTTGCTTCCATCCAACCTGGAGG | SEQ ID NO: 1061 |
| | | Reverse Primer | TGCCTGCGATATTTGTTAGG | SEQ ID NO: 1062 |
| HSPA1A | NM_005345.4 | Forward Primer | CTGCTGCGACAGTCCACTA | SEQ ID NO: 1063 |
| | | Probe | AGAGTGACTCCCGTTGTCCCAAGG | SEQ ID NO: 1064 |
| | | Reverse Primer | CAGGTTCGCTCTGGGAAG | SEQ ID NO: 1065 |
| HSPA1B | NM_005346.3 | Forward Primer | GGTCCGCTTCGTCTTTCGA | SEQ ID NO: 1066 |
| | | Probe | TGACTCCCGCGGTCCCAAGG | SEQ ID NO: 1067 |
| | | Reverse Primer | GCACAGGTTCGCTCTGGAA | SEQ ID NO: 1068 |
| HSPA4 | NM_002154.3 | Forward Primer | TTCAGTGTGTCCAGTGCATC | SEQ ID NO: 1069 |
| | | Probe | CATTTTCCTCAGACTTGTGAACCTCCACT | SEQ ID NO: 1070 |
| | | Reverse Primer | ATCTGTTTCCATTGGCTCCT | SEQ ID NO: 1071 |
| HSPA5 | NM_005347.2 | Forward Primer | GGCTAGTAGAACTGGATCCCAACA | SEQ ID NO: 1072 |
| | | Probe | TAATTAGACCTAGGCCTCAGCTGCACTGCC | SEQ ID NO: 1073 |
| | | Reverse Primer | GGTCTGCCCAAATGCTTTTC | SEQ ID NO: 1074 |
| HSPA8 | NM_006597.3 | Forward Primer | CCTCCCTCTGGTGGTGCTT | SEQ ID NO: 1075 |
| | | Probe | CTCAGGGCCCACCATTGAAGAGGTTG | SEQ ID NO: 1076 |
| | | Reverse Primer | GCTACATCTACACTTGGTTGGCTTAA | SEQ ID NO: 1077 |
| HSPB1 | NM_001540.2 | Forward Primer | CCGACTGGAGGAGCATAAA | SEQ ID NO: 1078 |
| | | Probe | CGCACTTTTCTGAGCAGACGTCCA | SEQ ID NO: 1079 |
| | | Reverse Primer | ATGCTGGCTGACTCTGCTC | SEQ ID NO: 1080 |
| HSPCA | NM_005348.2 | Forward Primer | CAAAAGGCAGAGGCTGATAA | SEQ ID NO: 1081 |
| | | Probe | TGACCAGATCCTTCACAGACTTGTCGT | SEQ ID NO: 1082 |
| | | Reverse Primer | AGCGCAGTTTCATAAAGCAA | SEQ ID NO: 1083 |
| HSPE1 | NM_002157.1 | Forward Primer | GCAAGCAACAGTAGTCGCTG | SEQ ID NO: 1084 |
| | | Probe | TCTCCACCCTTTCCTTTAGAACCCG | SEQ ID NO: 1085 |
| | | Reverse Primer | CCAACTTTCACGCTAACTGGT | SEQ ID NO: 1086 |
| HSPG2 | NM_005529.2 | Forward Primer | GAGTACGTGTGCCGAGTGTT | SEQ ID NO: 1087 |
| | | Probe | CAGCTCCGTGCCTCTAGAGGCCT | SEQ ID NO: 1088 |
| | | Reverse Primer | CTCAATGGTGACCAGGACA | SEQ ID NO: 1089 |
| ICAM1 | NM_000201.1 | Forward Primer | GCAGACAGTGACCATCTACAGCTT | SEQ ID NO: 1090 |
| | | Probe | CCGGCGCCCAACGTGATTCT | SEQ ID NO: 1091 |
| | | Reverse Primer | CTTCTGAGACCTCTGGCTTCGT | SEQ ID NO: 1092 |
| ICAM2 | NM_000873.2 | Forward Primer | GGTCATCCTGACACTGCAAC | SEQ ID NO: 1093 |
| | | Probe | TTGCCCACAGCCACCAAAGTG | SEQ ID NO: 1094 |
| | | Reverse Primer | TGCACTCAATGGTGAAGGAC | SEQ ID NO: 1095 |
| ID1 | NM_002165.1 | Forward Primer | AGAACCGCAAGGTGAGCAA | SEQ ID NO: 1096 |
| | | Probe | TGGAGATTCTCCAGCACGTCATCGAC | SEQ ID NO: 1097 |
| | | Reverse Primer | TCCAACTGAAGGTCCCTGATG | SEQ ID NO: 1098 |
| ID2 | NM_002166.1 | Forward Primer | AACGACTGCTACTCCAAGCTCAA | SEQ ID NO: 1099 |
| | | Probe | TGCCCAGCATCCCCAGAACAA | SEQ ID NO: 1100 |
| | | Reverse Primer | GGATTTCCATCTTGCTCACCTT | SEQ ID NO: 1101 |
| ID3 | NM_002167.2 | Forward Primer | CTTCACCAAATCCCTTCCTG | SEQ ID NO: 1102 |
| | | Probe | TCACAGTCCTTCGCTCCTGAGCAC | SEQ ID NO: 1103 |
| | | Reverse Primer | CTCTGGCTCTTCAGGCTACA | SEQ ID NO: 1104 |
| ID4 | NM_001546.2 | Forward Primer | TGGCCTGGCTCTTAATTTG | SEQ ID NO: 1105 |
| | | Probe | CTTTTGTTTTGCCCAGTATAGACTCGGAAG | SEQ ID NO: 1106 |
| | | Reverse Primer | TGCAATCATGCAAGACCAC | SEQ ID NO: 1107 |
| IFIT1 | NM_001548.1 | Forward Primer | TGACAACCAAGCAAATGTGA | SEQ ID NO: 1108 |
| | | Probe | AAGTTGCCCCAGGTCACCAGACTC | SEQ ID NO: 1109 |
| | | Reverse Primer | CAGTCTGCCCATGTGGTAAT | SEQ ID NO: 1110 |
| IGF1 | NM_000618.1 | Forward Primer | TCCGGAGCTGTGATCTAAGGA | SEQ ID NO: 1111 |
| | | Probe | TGTATTGCGCACCCCTCAAGCCTG | SEQ ID NO: 1112 |
| | | Reverse Primer | CGGACAGAGCGAGCTGACTT | SEQ ID NO: 1113 |
| IGF1R | NM_000875.2 | Forward Primer | GCATGGTAGCCGAAGATTTCA | SEQ ID NO: 1114 |
| | | Probe | CGCGTCATACCAAAATCTCCGATTTTGA | SEQ ID NO: 1115 |
| | | Reverse Primer | TTTCCGGTAATAGTCTGTCTCATAGATATC | SEQ ID NO: 1116 |

TABLE A-continued

| Gene | Accession | Reagent | Sequence | Sequence ID Number |
|---|---|---|---|---|
| IGF2 | NM_000612.2 | Forward Primer | CCGTGCTTCCGGACAACTT | SEQ ID NO: 1117 |
| | | Probe | TACCCCGTGGGCAAGTTCTTCCAA | SEQ ID NO: 1118 |
| | | Reverse Primer | TGGACTGCTTCCAGGTGTCA | SEQ ID NO: 1119 |
| IGFBP2 | NM_000597.1 | Forward Primer | GTGGACAGCACCATGAACA | SEQ ID NO: 1120 |
| | | Probe | CTTCCGGCCAGCACTGCCTC | SEQ ID NO: 1121 |
| | | Reverse Primer | CCTTCATACCCGACTTGAGG | SEQ ID NO: 1122 |
| IGFBP3 | NM_000598.1 | Forward Primer | ACGCACCGGGTGTCTGA | SEQ ID NO: 1123 |
| | | Probe | CCCAAGTTCCACCCCCTCCATTCA | SEQ ID NO: 1124 |
| | | Reverse Primer | TGCCCTTTCTTGATGATGATTATC | SEQ ID NO: 1125 |
| IGFBP5 | NM_000599.1 | Forward Primer | TGGACAAGTACGGGATGAAGCT | SEQ ID NO: 1126 |
| | | Probe | CCCGTCAACGTACTCCATGCCTGG | SEQ ID NO: 1127 |
| | | Reverse Primer | CGAAGGTGTGGCACTGAAAGT | SEQ ID NO: 1128 |
| IGFBP6 | NM_002178.1 | Forward Primer | TGAACCGCAGAGACCAACAG | SEQ ID NO: 1129 |
| | | Probe | ATCCAGGCACCTCTACCACGCCCTC | SEQ ID NO: 1130 |
| | | Reverse Primer | GTCTTGGACACCCGCAGAAT | SEQ ID NO: 1131 |
| IGFBP7 | NM_001553 | Forward Primer | GGGTCACTATGGAGTTCAAAGGA | SEQ ID NO: 1132 |
| | | Probe | CCCGGTCACCAGGCAGGAGTTCT | SEQ ID NO: 1133 |
| | | Reverse Primer | GGGTCTGAATGGCCAGGTT | SEQ ID NO: 1134 |
| IHH | NM_002181.1 | Forward Primer | AAGGACGAGGAGAACACAGG | SEQ ID NO: 1135 |
| | | Probe | ATGACCCAGCGCTGCAAGGAC | SEQ ID NO: 1136 |
| | | Reverse Primer | AGATAGCCAGCGAGTTCAGG | SEQ ID NO: 1137 |
| IL-8 | NM_000584.2 | Forward Primer | AAGGAACCATCTCACTGTGTGTAAAC | SEQ ID NO: 1138 |
| | | Probe | TGACTTCCAAGCTGGCCGTGGC | SEQ ID NO: 1139 |
| | | Reverse Primer | ATCAGGAAGGCTGCCAAGAG | SEQ ID NO: 1140 |
| IL10 | NM_000572.1 | Forward Primer | GGCGCTGTCATCGATTTCTT | SEQ ID NO: 1141 |
| | | Probe | CTGCTCCACGGCCTTGCTCTTG | SEQ ID NO: 1142 |
| | | Reverse Primer | TGGAGCTTATTAAAGGCATTCTTCA | SEQ ID NO: 1143 |
| IL1B | NM_000576.2 | Forward Primer | AGCTGAGGAAGATGCTGGTT | SEQ ID NO: 1144 |
| | | Probe | TGCCCACAGACCTTCCAGGAGAAT | SEQ ID NO: 1145 |
| | | Reverse Primer | GGAAAGAAGGTGCTCAGGTC | SEQ ID NO: 1146 |
| IL6 | NM_000600.1 | Forward Primer | CCTGAACCTTCCAAAGATGG | SEQ ID NO: 1147 |
| | | Probe | CCAGATTGGAAGCATCCATCTTTTTCA | SEQ ID NO: 1148 |
| | | Reverse Primer | ACCAGGCAAGTCTCCTCATT | SEQ ID NO: 1149 |
| IL6ST | NM_002184.2 | Forward Primer | GGCCTAATGTTCCAGATCCT | SEQ ID NO: 1150 |
| | | Probe | CATATTGCCCAGTGGTCACCTCACA | SEQ ID NO: 1151 |
| | | Reverse Primer | AAAATTGTGCCTTGGAGGAG | SEQ ID NO: 1152 |
| ILT-2 | NM_006669.1 | Forward Primer | AGCCATCACTCTCAGTGCAG | SEQ ID NO: 1153 |
| | | Probe | CAGGTCCTATCGTGGCCCCTGA | SEQ ID NO: 1154 |
| | | Reverse Primer | ACTGCAGAGTCAGGGTCTCC | SEQ ID NO: 1155 |
| IMP-1 | NM_006546.2 | Forward Primer | GAAAGTGTTTGCGGAGCAC | SEQ ID NO: 1156 |
| | | Probe | CTCCTACAGCGGCCAGTTCTTGGT | SEQ ID NO: 1157 |
| | | Reverse Primer | GAAGGCGTAGCCGGATTT | SEQ ID NO: 1158 |
| IMP2 | NM_006548.3 | Forward Primer | CAATCTGATCCCAGGGTTGAA | SEQ ID NO: 1159 |
| | | Probe | CTCAGCGCACTTGGCATCTTTTCAACA | SEQ ID NO: 1160 |
| | | Reverse Primer | GGCCCTGCTGGTGGAGATA | SEQ ID NO: 1161 |
| ING1L | NM_001564.1 | Forward Primer | TGTTTCCAAGATCCTGCTGA | SEQ ID NO: 1162 |
| | | Probe | CCATCTTTGCTTTATCTGAGGCTCGTTC | SEQ ID NO: 1163 |
| | | Reverse Primer | TCTTTCTGGTTGGCTGGAAT | SEQ ID NO: 1164 |
| ING5 | NM_032329.4 | Forward Primer | CCTACAGCAAGTGCAAGGAA | SEQ ID NO: 1165 |
| | | Probe | CCAGCTGCACTTTGTCGTCACTGT | SEQ ID NO: 1166 |
| | | Reverse Primer | CATCTCGTAGGTCTGCATGG | SEQ ID NO: 1167 |
| INHA | NM_002191.2 | Forward Primer | CCTCCCAGTTTCATCTTCCACTA | SEQ ID NO: 1168 |
| | | Probe | ATGTGCAGCCCACAACCACCATGA | SEQ ID NO: 1169 |
| | | Reverse Primer | AGGGACTGGAAGGGACAGGTT | SEQ ID NO: 1170 |
| INHBA | NM_002192.1 | Forward Primer | GTGCCCGAGCCATATAGCA | SEQ ID NO: 1171 |
| | | Probe | ACGTCCGGGTCCTCACTGTCCTTCC | SEQ ID NO: 1172 |
| | | Reverse Primer | CGGTAGTGGTTGATGACTGTTGA | SEQ ID NO: 1173 |

TABLE A-continued

| Gene | Accession | Reagent | Sequence | Sequence ID Number |
|---|---|---|---|---|
| INHBB | NM_002193.1 | Forward Primer | AGCCTCCAGGATACCAGCAA | SEQ ID NO: 1174 |
| | | Probe | AGCTAAGCTGCCATTTGTCACCG | SEQ ID NO: 1175 |
| | | Reverse Primer | TCTCCGACTGACAGGCATTTG | SEQ ID NO: 1176 |
| IRS1 | NM_005544.1 | Forward Primer | CCACAGCTCACCTTCTGTCA | SEQ ID NO: 1177 |
| | | Probe | TCCATCCCAGCTCCAGCCAG | SEQ ID NO: 1178 |
| | | Reverse Primer | CCTCAGTGCCAGTCTCTTCC | SEQ ID NO: 1179 |
| ITGA3 | NM_002204.1 | Forward Primer | CCATGATCCTCACTCTGCTG | SEQ ID NO: 1180 |
| | | Probe | CACTCCAGACCTCGCTTAGCATGG | SEQ ID NO: 1181 |
| | | Reverse Primer | GAAGCTTTGTAGCCGGTGAT | SEQ ID NO: 1182 |
| ITGA4 | NM_000885.2 | Forward Primer | CAACGCTTCAGTGATCAATCC | SEQ ID NO: 1183 |
| | | Probe | CGATCCTGCATCTGTAAATCGCCC | SEQ ID NO: 1184 |
| | | Reverse Primer | GTCTGGCCGGGATTCTTT | SEQ ID NO: 1185 |
| ITGA5 | NM_002205.1 | Forward Primer | AGGCCAGCCCTACATTATCA | SEQ ID NO: 1186 |
| | | Probe | TCTGAGCCTTGTCCTATCCGGC | SEQ ID NO: 1187 |
| | | Reverse Primer | GTCTTCTCCACAGTCCAGCA | SEQ ID NO: 1188 |
| ITGA6 | NM_000210.1 | Forward Primer | CAGTGACAAACAGCCCTTCC | SEQ ID NO: 1189 |
| | | Probe | TCGCCATCTTTTGTGGGATTCCTT | SEQ ID NO: 1190 |
| | | Reverse Primer | GTTTAGCCTCATGGGCGTC | SEQ ID NO: 1191 |
| ITGA7 | NM_002206.1 | Forward Primer | GATATGATTGGTCGCTGCTTTG | SEQ ID NO: 1192 |
| | | Probe | CAGCCAGGACCTGGCCATCCG | SEQ ID NO: 1193 |
| | | Reverse Primer | AGAACTTCCATTCCCCACCAT | SEQ ID NO: 1194 |
| ITGAV | NM_002210.2 | Forward Primer | ACTCGGACTGCACAAGCTATT | SEQ ID NO: 1195 |
| | | Probe | CCGACAGCCACAGAATAACCCAAA | SEQ ID NO: 1196 |
| | | Reverse Primer | TGCCATCACCATTGAAATCT | SEQ ID NO: 1197 |
| ITGB1 | NM_002211.2 | Forward Primer | TCAGAATTGGATTTGGCTCA | SEQ ID NO: 1198 |
| | | Probe | TGCTAATGTAAGGCATCACAGTCTTTTCCA | SEQ ID NO: 1199 |
| | | Reverse Primer | CCTGAGCTTAGCTGGTGTTG | SEQ ID NO: 1200 |
| ITGB3 | NM_000212.1 | Forward Primer | ACCGGGAGCCCTACATGAC | SEQ ID NO: 1201 |
| | | Probe | AAATACCTGCAACCGTTACTGCCGTGAC | SEQ ID NO: 1202 |
| | | Reverse Primer | CCTTAAGCTCTTTCACTGACTCAATCT | SEQ ID NO: 1203 |
| ITGB4 | NM_000213.2 | Forward Primer | CAAGGTGCCCTCAGTGGA | SEQ ID NO: 1204 |
| | | Probe | CACCAACCTGTACCCGTATTGCGA | SEQ ID NO: 1205 |
| | | Reverse Primer | GCGCACACCTTCATCTCAT | SEQ ID NO: 1206 |
| ITGB5 | NM_002213.3 | Forward Primer | TCGTGAAAGATGACCAGGAG | SEQ ID NO: 1207 |
| | | Probe | TGCTATGTTTCTACAAAACCGCCAAGG | SEQ ID NO: 1208 |
| | | Reverse Primer | GGTGAACATCATGACGCAGT | SEQ ID NO: 1209 |
| K-ras | NM_033360.2 | Forward Primer | GTCAAAATGGGGAGGGACTA | SEQ ID NO: 1210 |
| | | Probe | TGTATCTTGTTGAGCTATCCAAACTGCCC | SEQ ID NO: 1211 |
| | | Reverse Primer | CAGGACCACCACAGAGTGAG | SEQ ID NO: 1212 |
| KCNH2 iso a/b | NM_000238.2 | Forward Primer | GAGCGCAAAGTGGAAATCG | SEQ ID NO: 1213 |
| | | Probe | TAGGAAGCAGCTCCCATCTTTCCGGTA | SEQ ID NO: 1214 |
| | | Reverse Primer | TCTTCACGGGCACCACATC | SEQ ID NO: 1215 |
| KCNH2 iso a/c | NM_172057.1 | Forward Primer | TCCTGCTGCTGGTCATCTAC | SEQ ID NO: 1216 |
| | | Probe | TGTCTTCACACCCTACTCGGCTGC | SEQ ID NO: 1217 |
| | | Reverse Primer | CCTTCTTCCGTCTCCTTCAG | SEQ ID NO: 1218 |
| KCNK4 | NM_016611.2 | Forward Primer | CCTATCAGCCGCTGGTGT | SEQ ID NO: 1219 |
| | | Probe | ATCCTGCTCGGCCTGGCTTACTTC | SEQ ID NO: 1220 |
| | | Reverse Primer | TGGTGGTGAGCACTGAGG | SEQ ID NO: 1221 |
| KDR | NM_002253.1 | Forward Primer | GAGGACGAAGGCCTCTACAC | SEQ ID NO: 1222 |
| | | Probe | CAGGCATGCAGTGTTCTTGGCTGT | SEQ ID NO: 1223 |
| | | Reverse Primer | AAAAATGCCTCCACTTTTGC | SEQ ID NO: 1224 |
| Ki-67 | NM_002417.1 | Forward Primer | CGGACTTTGGGTGCGACTT | SEQ ID NO: 1225 |
| | | Probe | CCACTTGTCGAACCACCGCTCGT | SEQ ID NO: 1226 |
| | | Reverse Primer | TTACAACTCTTCCACTGGGACGAT | SEQ ID NO: 1227 |
| KIAA0125 | NM_014792.2 | Forward Primer | GTGTCCTGGTCCATGTGGT | SEQ ID NO: 1228 |
| | | Probe | CACGTGTCTCCACCTCCAAGGAGA | SEQ ID NO: 1229 |
| | | Reverse Primer | GGGAGGTGCACACTGAGG | SEQ ID NO: 1230 |

TABLE A-continued

| Gene | Accession | Reagent | Sequence | Sequence ID Number |
|---|---|---|---|---|
| KIF22 | NM_007317.1 | Forward Primer | CTAAGGCACTTGCTGGAAGG | SEQ ID NO: 1231 |
| | | Probe | TCCATAGGCAAGCACACTGGCATT | SEQ ID NO: 1232 |
| | | Reverse Primer | TCTTCCCAGCTCCTGTGG | SEQ ID NO: 1233 |
| KIF2C | NM_006845.2 | Forward Primer | AATTCCTGCTCCAAAAGAAAGTCTT | SEQ ID NO: 1234 |
| | | Probe | AAGCCGCTCCACTCGCATGTCC | SEQ ID NO: 1235 |
| | | Reverse Primer | CGTGATGCGAAGCTCTGAGA | SEQ ID NO: 1236 |
| KIFC1 | XM_371813.1 | Forward Primer | CCACAGGGTTGAAGAACCAG | SEQ ID NO: 1237 |
| | | Probe | AGCCAGTTCCTGCTGTTCCTGTCC | SEQ ID NO: 1238 |
| | | Reverse Primer | CACCTGATGTGCCAGACTTC | SEQ ID NO: 1239 |
| Kitlng | NM_000899.1 | Forward Primer | GTCCCCGGGATGGATGTT | SEQ ID NO: 1240 |
| | | Probe | CATCTCGCTTATCCAACAATGACTTGGCA | SEQ ID NO: 1241 |
| | | Reverse Primer | GATCAGTCAAGCTGTCTGACAATTG | SEQ ID NO: 1242 |
| KLF5 | NM_001730.3 | Forward Primer | GTGCAACCGCAGCTTCTC | SEQ ID NO: 1243 |
| | | Probe | CTCTGACCACCTGGCCCTGCATAT | SEQ ID NO: 1244 |
| | | Reverse Primer | CGGGCAGTGCTCAGTTCT | SEQ ID NO: 1245 |
| KLF6 | NM_001300.4 | Forward Primer | CACGAGACCGGCTACTTCTC | SEQ ID NO: 1246 |
| | | Probe | AGTACTCCTCCAGAGACGGCAGCG | SEQ ID NO: 1247 |
| | | Reverse Primer | GCTCTAGGCAGGTCTGTTGC | SEQ ID NO: 1248 |
| KLK10 | NM_002776.1 | Forward Primer | GCCCAGAGGCTCCATCGT | SEQ ID NO: 1249 |
| | | Probe | CCTCTTCCTCCCCAGTCGGCTGA | SEQ ID NO: 1250 |
| | | Reverse Primer | CAGAGGTTTGAACAGTCAGACA | SEQ ID NO: 1251 |
| KLK6 | NM_002774.2 | Forward Primer | GACGTGAGGGTCCTGATTCT | SEQ ID NO: 1252 |
| | | Probe | TTACCCCAGCTCCATCCTTGCATC | SEQ ID NO: 1253 |
| | | Reverse Primer | TCCTCACTCATCACGTCCTC | SEQ ID NO: 1254 |
| KLRK1 | NM_007360.1 | Forward Primer | TGAGAGCCAGGCTTCTTGTA | SEQ ID NO: 1255 |
| | | Probe | TGTCTCAAAATGCCAGCCTTCTGAA | SEQ ID NO: 1256 |
| | | Reverse Primer | ATCCTGGTCCTCTTTGCTGT | SEQ ID NO: 1257 |
| KNTC2 | NM_006101.1 | Forward Primer | ATGTGCCAGTGAGCTTGAGT | SEQ ID NO: 1258 |
| | | Probe | CCTTGGAGAAACACAAGCACCTGC | SEQ ID NO: 1259 |
| | | Reverse Primer | TGAGCCCCTGGTTAACAGTA | SEQ ID NO: 1260 |
| KRAS2 | NM_004985.3 | Forward Primer | GAGACCAAGGTTGCAAGGC | SEQ ID NO: 1261 |
| | | Probe | AAGCTCAAAGGTTCACACAGGGCC | SEQ ID NO: 1262 |
| | | Reverse Primer | CAGTCCATGCTGTGAAACTCTC | SEQ ID NO: 1263 |
| KRT19 | NM_002276.1 | Forward Primer | TGAGCGGCAGAATCAGGAGTA | SEQ ID NO: 1264 |
| | | Probe | CTCATGGACATCAAGTCGCGGCTG | SEQ ID NO: 1265 |
| | | Reverse Primer | TGCGGTAGGTGGCAATCTC | SEQ ID NO: 1266 |
| KRT8 | NM_002273.1 | Forward Primer | GGATGAAGCTTACATGAACAAGGTAGA | SEQ ID NO: 1267 |
| | | Probe | CGTCGGTCAGCCCTTCCAGGC | SEQ ID NO: 1268 |
| | | Reverse Primer | CATATAGCTGCCTGAGGAAGTTGAT | SEQ ID NO: 1269 |
| LAMA3 | NM_000227.2 | Forward Primer | CAGATGAGGCACATGGAGAC | SEQ ID NO: 1270 |
| | | Probe | CTGATTCCTCAGGTCCTTGGCCTG | SEQ ID NO: 1271 |
| | | Reverse Primer | TTGAAATGGCAGAACGGTAG | SEQ ID NO: 1272 |
| LAMB3 | NM_000228.1 | Forward Primer | ACTGACCAAGCCTGAGACCT | SEQ ID NO: 1273 |
| | | Probe | CCACTCGCCATACTGGGTGCAGT | SEQ ID NO: 1274 |
| | | Reverse Primer | GTCACACTTGCAGCATTTCA | SEQ ID NO: 1275 |
| LAMC2 | NM_005562.1 | Forward Primer | ACTCAAGCGGAAATTGAAGCA | SEQ ID NO: 1276 |
| | | Probe | AGGTCTTATCAGCACAGTCTCCGCCTCC | SEQ ID NO: 1277 |
| | | Reverse Primer | ACTCCCTGAAGCCGAGACACT | SEQ ID NO: 1278 |
| LAT | NM_014387.2 | Forward Primer | GTGAACGTTCCGGAGAGC | SEQ ID NO: 1279 |
| | | Probe | ATCCAGAGACGCTTCTGCGCTCTC | SEQ ID NO: 1280 |
| | | Reverse Primer | ACATTCACATACTCCCGGCT | SEQ ID NO: 1281 |
| LCN2 | NM_005564.2 | Forward Primer | CGCTGGGCAACATTAAGAG | SEQ ID NO: 1282 |
| | | Probe | TCACCACTCGGACGAGGTAACTCG | SEQ ID NO: 1283 |
| | | Reverse Primer | AGCATGCTGGTTGTAGTTGGT | SEQ ID NO: 1284 |
| LDLRAP1 | NM_015627.1 | Forward Primer | CAGTGCCTCTCGCCTGTC | SEQ ID NO: 1285 |
| | | Probe | ACTGGGACAAGCCTGACAGCAGC | SEQ ID NO: 1286 |
| | | Reverse Primer | TGAAGAGGTCATCCTGCTCTG | SEQ ID NO: 1287 |

TABLE A-continued

| Gene | Accession | Reagent | Sequence | Sequence ID Number |
|---|---|---|---|---|
| LEF | NM_016269.2 | Forward Primer | GATGACGGAAAGCATCCAG | SEQ ID NO: 1288 |
| | | Probe | TGGAGGCCTCTACAACAAGGGACC | SEQ ID NO: 1289 |
| | | Reverse Primer | CCCGGAATAACTCGAGTAGGA | SEQ ID NO: 1290 |
| LGALS3 | NM_002306.1 | Forward Primer | AGCGGAAAATGGCAGACAAT | SEQ ID NO: 1291 |
| | | Probe | ACCCAGATAACGCATCATGGAGCGA | SEQ ID NO: 1292 |
| | | Reverse Primer | CTTGAGGGTTTGGGTTTCCA | SEQ ID NO: 1293 |
| LGMN | NM_001008530.1 | Forward Primer | TTGGTGCCGTTCCTATAGATG | SEQ ID NO: 1294 |
| | | Probe | CAGTGCTTGCCTCCATCTTCAGGA | SEQ ID NO: 1295 |
| | | Reverse Primer | GAACCTGCCACGATCACC | SEQ ID NO: 1296 |
| LILRB3 | NM_006864.1 | Forward Primer | CACCTGGTCTGGGAAGATACC | SEQ ID NO: 1297 |
| | | Probe | ACCGAGACCCCAATCAAAACCTCC | SEQ ID NO: 1298 |
| | | Reverse Primer | AAGAGCAGCAGGACGAAGG | SEQ ID NO: 1299 |
| LMNB1 | NM_005573.1 | Forward Primer | TGCAAACGCTGGTGTCACA | SEQ ID NO: 1300 |
| | | Probe | CAGCCCCCCAACTGACCTCATC | SEQ ID NO: 1301 |
| | | Reverse Primer | CCCCACGAGTTCTGGTTCTTC | SEQ ID NO: 1302 |
| LMYC | NM_012421.1 | Forward Primer | CCCATCCAGAACACTGATTG | SEQ ID NO: 1303 |
| | | Probe | TGACCTCCATCCCTTTCACTTGAATG | SEQ ID NO: 1304 |
| | | Reverse Primer | CTGCTTTCTATGCACCCTTTC | SEQ ID NO: 1305 |
| LOX | NM_002317.3 | Forward Primer | CCAATGGGAGAACAACGG | SEQ ID NO: 1306 |
| | | Probe | CAGGCTCAGCAAGCTGAACACCTG | SEQ ID NO: 1307 |
| | | Reverse Primer | CGCTGAGGCTGGTACTGTG | SEQ ID NO: 1308 |
| LOXL2 | NM_002318.1 | Forward Primer | TCAGCGGGCTCTTAAACAA | SEQ ID NO: 1309 |
| | | Probe | CAGCTGTCCCCGCAGTAAAGAAGC | SEQ ID NO: 1310 |
| | | Reverse Primer | AAGACAGGAGTTGACCACGC | SEQ ID NO: 1311 |
| LRP5 | NM_002335.1 | Forward Primer | CGACTATGACCCACTGGACA | SEQ ID NO: 1312 |
| | | Probe | CGCCCATCCACCCAGTAGATGAAC | SEQ ID NO: 1313 |
| | | Reverse Primer | CTTGGCTCGCTTGATGTTC | SEQ ID NO: 1314 |
| LRP6 | NM_002336.1 | Forward Primer | GGATGTAGCCATCTCTGCCT | SEQ ID NO: 1315 |
| | | Probe | ATAGACCTCAGGGCCTTCGCTGTG | SEQ ID NO: 1316 |
| | | Reverse Primer | AGTTCAAAGCCAATAGGGCA | SEQ ID NO: 1317 |
| LY6D | NM_003695.2 | Forward Primer | AATGCTGATGACTTGGAGCAG | SEQ ID NO: 1318 |
| | | Probe | CACAGACCCCACAGAGGATGAAGC | SEQ ID NO: 1319 |
| | | Reverse Primer | CTGCATCCTCTGTGGGGT | SEQ ID NO: 1320 |
| MAD | NM_002357.1 | Forward Primer | TGGTTCTGATTAGGTAACGTATTGGA | SEQ ID NO: 1321 |
| | | Probe | CTGCCCACAACTCCCTTGCACGTAA | SEQ ID NO: 1322 |
| | | Reverse Primer | GGTCAAGGTGGGACACTGAAG | SEQ ID NO: 1323 |
| MAD1L1 | NM_003550.1 | Forward Primer | AGAAGCTGTCCCTGCAAGAG | SEQ ID NO: 1324 |
| | | Probe | CATGTTCTTCACAATCGCTGCATCC | SEQ ID NO: 1325 |
| | | Reverse Primer | AGCCGTACCAGCTCAGACTT | SEQ ID NO: 1326 |
| MAD2L1 | NM_002358.2 | Forward Primer | CCGGGAGCAGGGAATCAC | SEQ ID NO: 1327 |
| | | Probe | CGGCCACGATTTCGGCGCT | SEQ ID NO: 1328 |
| | | Reverse Primer | ATGCTGTTGATGCCGAATGA | SEQ ID NO: 1329 |
| MADH2 | NM_005901.2 | Forward Primer | GCTGCCTTTGGTAAGAACATGTC | SEQ ID NO: 1330 |
| | | Probe | TCCATCTTGCCATTCACGCCGC | SEQ ID NO: 1331 |
| | | Reverse Primer | ATCCCAGCAGTCTCTTCACAACT | SEQ ID NO: 1332 |
| MADH4 | NM_005359.3 | Forward Primer | GGACATTACTGGCCTGTTCACA | SEQ ID NO: 1333 |
| | | Probe | TGCATTCCAGCCTCCCATTTCCA | SEQ ID NO: 1334 |
| | | Reverse Primer | ACCAATACTCAGGAGCAGGATGA | SEQ ID NO: 1335 |
| MADH7 | NM_005904.1 | Forward Primer | TCCATCAAGGCTTTCGACTA | SEQ ID NO: 1336 |
| | | Probe | CTGCAGGCTGTACGCCTTCTCG | SEQ ID NO: 1337 |
| | | Reverse Primer | CTGCTGCATAAACTCGTGGT | SEQ ID NO: 1338 |
| MAP2 | NM_031846.1 | Forward Primer | CGGACCACCAGGTCAGAG | SEQ ID NO: 1339 |
| | | Probe | CCACTCTTCCCTGCTCTGCGAATT | SEQ ID NO: 1340 |
| | | Reverse Primer | CAGGGGTAGTGGGTGTTGAG | SEQ ID NO: 1341 |
| MAP2K1 | NM_002755.2 | Forward Primer | GCCTTTCTTACCCAGAAGCAGAA | SEQ ID NO: 1342 |
| | | Probe | TCTCAAAGTCGTCATCCTTCAGTTCTCCCA | SEQ ID NO: 1343 |
| | | Reverse Primer | CAGCCCCCAGCTCACTGAT | SEQ ID NO: 1344 |

TABLE A-continued

| Gene | Accession | Reagent | Sequence | Sequence ID Number |
|---|---|---|---|---|
| MAP3K1 | XM_042066.8 | Forward Primer<br>Probe<br>Reverse Primer | GGTTGGCATCAAAAGGAACT<br>AATTGTCCCTGAAACTCTCCTGCACC<br>TGCCATAAATGCAATTGTCC | SEQ ID NO: 1345<br>SEQ ID NO: 1346<br>SEQ ID NO: 1347 |
| MAPK14 | NM_139012.1 | Forward Primer<br>Probe<br>Reverse Primer | TGAGTGGAAAAGCCTGACCTATG<br>TGAAGTCATCAGCTTTGTGCCACCACC<br>GGACTCCATCTCTTCTTGGTCAA | SEQ ID NO: 1348<br>SEQ ID NO: 1349<br>SEQ ID NO: 1350 |
| Maspin | NM_002639.1 | Forward Primer<br>Probe<br>Reverse Primer | CAGATGGCCACTTTGAGAACATT<br>AGCTGACAACAGTGTGAACGACCAGACC<br>GGCAGCATTAACCACAAGGATT | SEQ ID NO: 1351<br>SEQ ID NO: 1352<br>SEQ ID NO: 1353 |
| MAX | NM_002382.3 | Forward Primer<br>Probe<br>Reverse Primer | CAAACGGGCTCATCATAATGC<br>TGATGTGGTCCCTACGTTTTCGTTCCA<br>TCCCGCAAACTGTGAAAGCT | SEQ ID NO: 1354<br>SEQ ID NO: 1355<br>SEQ ID NO: 1356 |
| MCM2 | NM_004526.1 | Forward Primer<br>Probe<br>Reverse Primer | GACTTTTGCCCGCTACCTTTC<br>ACAGCTCATTGTTGTCACGCCGGA<br>GCCACTAACTGCTTCAGTATGAAGAG | SEQ ID NO: 1357<br>SEQ ID NO: 1358<br>SEQ ID NO: 1359 |
| MCM3 | NM_002388.2 | Forward Primer<br>Probe<br>Reverse Primer | GGAGAACAATCCCCTTGAGA<br>TGGCCTTTCTGTCTACAAGGATCACCA<br>ATCTCCTGGATGGTGATGGT | SEQ ID NO: 1360<br>SEQ ID NO: 1361<br>SEQ ID NO: 1362 |
| MCM6 | NM_005915.2 | Forward Primer<br>Probe<br>Reverse Primer | TGATGGTCCTATGTGTCACATTCA<br>CAGGTTTCATACCAACACAGGCTTCAGCAC<br>TGGGACAGGAAACACACCAA | SEQ ID NO: 1363<br>SEQ ID NO: 1364<br>SEQ ID NO: 1365 |
| MCP1 | NM_002982.1 | Forward Primer<br>Probe<br>Reverse Primer | CGCTCAGCCAGATGCAATC<br>TGCCCCAGTCACCTGCTGTTA<br>GCACTGAGATCTTCCTATTGGTGAA | SEQ ID NO: 1366<br>SEQ ID NO: 1367<br>SEQ ID NO: 1368 |
| MDK | NM_002391.2 | Forward Primer<br>Probe<br>Reverse Primer | GGAGCCGACTGCAAGTACA<br>ATCACACGCACCCCAGTTCTCAAA<br>GACTTTGGTGCCTGTGCC | SEQ ID NO: 1369<br>SEQ ID NO: 1370<br>SEQ ID NO: 1371 |
| MDM2 | NM_002392.1 | Forward Primer<br>Probe<br>Reverse Primer | CTACAGGGACGCCATCGAA<br>CTTACACCAGCATCAAGATCCGG<br>ATCCAACCAATCACCTGAATGTT | SEQ ID NO: 1372<br>SEQ ID NO: 1373<br>SEQ ID NO: 1374 |
| MGAT5 | NM_002410.2 | Forward Primer<br>Probe<br>Reverse Primer | GGAGTCGAAGGTGGACAATC<br>AATGGCACCGGAACAAACTCAACC<br>TGGGAACAGCTGTAGTGGAGT | SEQ ID NO: 1375<br>SEQ ID NO: 1376<br>SEQ ID NO: 1377 |
| MGMT | NM_002412.1 | Forward Primer<br>Probe<br>Reverse Primer | GTGAAATGAAACGCACCACA<br>CAGCCCTTTGGGAAGCTGG<br>GACCCTGCTCACAACCAGAC | SEQ ID NO: 1378<br>SEQ ID NO: 1379<br>SEQ ID NO: 1380 |
| mGST1 | NM_020300.2 | Forward Primer<br>Probe<br>Reverse Primer | ACGGATCTACCACACCATTGC<br>TTTGACACCCCTTCCCCAGCCA<br>TCCATATCCAACAAAAAAACTCAAAG | SEQ ID NO: 1381<br>SEQ ID NO: 1382<br>SEQ ID NO: 1383 |
| MMP1 | NM_002421.2 | Forward Primer<br>Probe<br>Reverse Primer | GGGAGATCATCGGGACAACTC<br>AGCAAGATTTCCTCCAGGTCCATCAAAAGG<br>GGGCCTGGTTGAAAAGCAT | SEQ ID NO: 1384<br>SEQ ID NO: 1385<br>SEQ ID NO: 1386 |
| MMP12 | NM_002426.1 | Forward Primer<br>Probe<br>Reverse Primer | CCAACGCTTGCCAAATCCT<br>AACCAGCTCTCTGTGACCCCAATT<br>ACGGTAGTGACAGCATCAAAACTC | SEQ ID NO: 1387<br>SEQ ID NO: 1388<br>SEQ ID NO: 1389 |
| MMP2 | NM_004530.1 | Forward Primer<br>Probe<br>Reverse Primer | CCATGATGGAGAGGCAGACA<br>CTGGGAGCATGGCGATGGATACCC<br>GGAGTCCGTCCTTACCGTCAA | SEQ ID NO: 1390<br>SEQ ID NO: 1391<br>SEQ ID NO: 1392 |
| MMP7 | NM_002423.2 | Forward Primer<br>Probe<br>Reverse Primer | GGATGGTAGCAGTCTAGGGATTAACT<br>CCTGTATGCTGCAACTCATGAACTTGGC<br>GGAATGTCCCATACCCAAAGAA | SEQ ID NO: 1393<br>SEQ ID NO: 1394<br>SEQ ID NO: 1395 |
| MMP9 | NM_004994.1 | Forward Primer<br>Probe<br>Reverse Primer | GAGAACCAATCTCACCGACA<br>ACAGGTATTCCTCTGCCAGCTGCC<br>CACCCGAGTGTAACCATAGC | SEQ ID NO: 1396<br>SEQ ID NO: 1397<br>SEQ ID NO: 1398 |
| MRP1 | NM_004996.2 | Forward Primer<br>Probe<br>Reverse Primer | TCATGGTGCCCGTCAATG<br>ACCTGATACGTCTTGGTCTTCATCGCCAT<br>CGATTGTCTTTGCTCTTCATGTG | SEQ ID NO: 1399<br>SEQ ID NO: 1400<br>SEQ ID NO: 1401 |

TABLE A-continued

| Gene | Accession | Reagent | Sequence | Sequence ID Number |
|---|---|---|---|---|
| MRP2 | NM_000392.1 | Forward Primer | AGGGGATGACTTGGACACAT | SEQ ID NO: 1402 |
|  |  | Probe | CTGCCATTCGACATGACTGCAATTT | SEQ ID NO: 1403 |
|  |  | Reverse Primer | AAAACTGCATGGCTTTGTCA | SEQ ID NO: 1404 |
| MRP3 | NM_003786.2 | Forward Primer | TCATCCTGGCGATCTACTTCCT | SEQ ID NO: 1405 |
|  |  | Probe | TCTGTCCTGGCTGGAGTCGCTTTCAT | SEQ ID NO: 1406 |
|  |  | Reverse Primer | CCGTTGAGTGGAATCAGCAA | SEQ ID NO: 1407 |
| MRP4 | NM_005845.1 | Forward Primer | AGCGCCTGGAATCTACAACT | SEQ ID NO: 1408 |
|  |  | Probe | CGGAGTCCAGTGTTTTCCCACTTG | SEQ ID NO: 1409 |
|  |  | Reverse Primer | AGAGCCCCTGGAGAGAAGAT | SEQ ID NO: 1410 |
| MRPL40 | NM_003776.2 | Forward Primer | ACTTGCAGGCTGCTATCCTT | SEQ ID NO: 1411 |
|  |  | Probe | TTCCTACTCTCAGGGGCAGCATGTT | SEQ ID NO: 1412 |
|  |  | Reverse Primer | AGCAGACTTGAACCCTGGTC | SEQ ID NO: 1413 |
| MSH2 | NM_000251.1 | Forward Primer | GATGCAGAATTGAGGCAGAC | SEQ ID NO: 1414 |
|  |  | Probe | CAAGAAGATTTACTTCGTCGATTCCCAGA | SEQ ID NO: 1415 |
|  |  | Reverse Primer | TCTTGGCAAGTCGGTTAAGA | SEQ ID NO: 1416 |
| MSH3 | NM_002439.1 | Forward Primer | TGATTACCATCATGGCTCAGA | SEQ ID NO: 1417 |
|  |  | Probe | TCCCAATTGTCGCTTCTTCTGCAG | SEQ ID NO: 1418 |
|  |  | Reverse Primer | CTTGTGAAAATGCCATCCAC | SEQ ID NO: 1419 |
| MSH6 | NM_000179.1 | Forward Primer | TCTATTGGGGGATTGGTAGG | SEQ ID NO: 1420 |
|  |  | Probe | CCGTTACCAGCTGGAAATTCCTGAGA | SEQ ID NO: 1421 |
|  |  | Reverse Primer | CAAATTGCGAGTGGTGAAAT | SEQ ID NO: 1422 |
| MT3 | NM_005954.1 | Forward Primer | GTGTGAGAAGTGTGCCAAGG | SEQ ID NO: 1423 |
|  |  | Probe | CTCTCCGCCTTTGCACACACAGT | SEQ ID NO: 1424 |
|  |  | Reverse Primer | CTGCACTTCTCTGCTTCTGC | SEQ ID NO: 1425 |
| MTA1 | NM_004689.2 | Forward Primer | CCGCCCTCACCTGAAGAGA | SEQ ID NO: 1426 |
|  |  | Probe | CCCAGTGTCCGCCAAGGAGCG | SEQ ID NO: 1427 |
|  |  | Reverse Primer | GGAATAAGTTAGCCGCGCTTCT | SEQ ID NO: 1428 |
| MUC1 | NM_002456.1 | Forward Primer | GGCCAGGATCTGTGGTGGTA | SEQ ID NO: 1429 |
|  |  | Probe | CTCTGGCCTTCCGAGAAGGTACC | SEQ ID NO: 1430 |
|  |  | Reverse Primer | CTCCACGTCGTGGACATTGA | SEQ ID NO: 1431 |
| MUC2 | NM_002457.1 | Forward Primer | CTATGAGCCATGTGGGAACC | SEQ ID NO: 1432 |
|  |  | Probe | AGCTTCGAGACCTGCAGGACCATC | SEQ ID NO: 1433 |
|  |  | Reverse Primer | ATGTTGGAGTGGATGCCG | SEQ ID NO: 1434 |
| MUC5B | XM_039877.11 | Forward Primer | TGCCCTTGCACTGTCCTAA | SEQ ID NO: 1435 |
|  |  | Probe | TCAGCCATCCTGCACACCTACACC | SEQ ID NO: 1436 |
|  |  | Reverse Primer | CAGCCACACTCATCCACG | SEQ ID NO: 1437 |
| MUTYH | NM_012222.1 | Forward Primer | GTACGACCAAGAGAAACGGG | SEQ ID NO: 1438 |
|  |  | Probe | TCTGCCCGTCTTCTCCATGGTAGG | SEQ ID NO: 1439 |
|  |  | Reverse Primer | CCTGTCCAGGTCCATCTCA | SEQ ID NO: 1440 |
| MVP | NM_017458.1 | Forward Primer | ACGAGAACGAGGGCATCTATGT | SEQ ID NO: 1441 |
|  |  | Probe | CGCACCTTTCCGGTCTTGACATCCT | SEQ ID NO: 1442 |
|  |  | Reverse Primer | GCATGTAGGTGCTTCCAATCAC | SEQ ID NO: 1443 |
| MX1 | NM_002462.2 | Forward Primer | GAAGGAATGGGAATCAGTCATGA | SEQ ID NO: 1444 |
|  |  | Probe | TCACCCTGGAGATCAGCTCCCGA | SEQ ID NO: 1445 |
|  |  | Reverse Primer | GTCTATTAGAGTCAGATCCGGGACAT | SEQ ID NO: 1446 |
| MXD4 | NM_006454.2 | Forward Primer | AGAAACTGGAGGAGCAGGAC | SEQ ID NO: 1447 |
|  |  | Probe | TGCAGCTGCTCCTTGATGCTCAGT | SEQ ID NO: 1448 |
|  |  | Reverse Primer | CTTCAGGAAACGATGCTCCT | SEQ ID NO: 1449 |
| MYBL2 | NM_002466.1 | Forward Primer | GCCGAGATCGCCAAGATG | SEQ ID NO: 1450 |
|  |  | Probe | CAGCATTGTCTGTCCTCCCTGGCA | SEQ ID NO: 1451 |
|  |  | Reverse Primer | CTTTTGATGGTAGAGTTCCAGTGATTC | SEQ ID NO: 1452 |
| MYH11 | NM_002474.1 | Forward Primer | CGGTACTTCTCAGGGCTAATATATACG | SEQ ID NO: 1453 |
|  |  | Probe | CTCTTCTGCGTGGTGGTCAACCCCTA | SEQ ID NO: 1454 |
|  |  | Reverse Primer | CCGAGTAGATGGGCAGGTGTT | SEQ ID NO: 1455 |
| MYLK | NM_053025.1 | Forward Primer | TGACGGAGCGTGAGTGCAT | SEQ ID NO: 1456 |
|  |  | Probe | CCCTCCGAGATCTGCCGCATGTACT | SEQ ID NO: 1457 |
|  |  | Reverse Primer | ATGCCCTGCTTGTGGATGTAC | SEQ ID NO: 1458 |

TABLE A-continued

| Gene | Accession | Reagent | Sequence | Sequence ID Number |
|---|---|---|---|---|
| NAT2 | NM_000015.1 | Forward Primer | TAACTGACATTCTTGAGCACCAGAT | SEQ ID NO: 1459 |
| | | Probe | CGGGCTGTTCCCTTTGAGAACCTTAACA | SEQ ID NO: 1460 |
| | | Reverse Primer | ATGGCTTGCCCACAATGC | SEQ ID NO: 1461 |
| NAV2 | NM_182964.3 | Forward Primer | CTCTCCCAGCACAGCTTGA | SEQ ID NO: 1462 |
| | | Probe | CCTCACTGAGTCAACCAGCCTGGA | SEQ ID NO: 1463 |
| | | Reverse Primer | CACCAGTGTCATCCAGCAAC | SEQ ID NO: 1464 |
| NCAM1 | NM_000615.1 | Forward Primer | TAGTTCCCAGCTGACCATCA | SEQ ID NO: 1465 |
| | | Probe | CTCAGCCTCGTCGTTCTTATCCACC | SEQ ID NO: 1466 |
| | | Reverse Primer | CAGCCTTGTTCTCAGCAATG | SEQ ID NO: 1467 |
| NDE1 | NM_017668.1 | Forward Primer | CTACTGCGGAAAGTCGGG | SEQ ID NO: 1468 |
| | | Probe | CTGGAGTCCAAACTCGCTTCCTGC | SEQ ID NO: 1469 |
| | | Reverse Primer | GGACTGATCGTACACGAGGTT | SEQ ID NO: 1470 |
| NDRG1 | NM_006096.2 | Forward Primer | AGGGCAACATTCCACAGC | SEQ ID NO: 1471 |
| | | Probe | CTGCAAGGACACTCATCACAGCCA | SEQ ID NO: 1472 |
| | | Reverse Primer | CAGTGCTCCTACTCCGGC | SEQ ID NO: 1473 |
| NDUFS3 | NM_004551.1 | Forward Primer | TATCCATCCTGATGGCGTC | SEQ ID NO: 1474 |
| | | Probe | CCCAGTGCTGACTTTCCTCAGGGA | SEQ ID NO: 1475 |
| | | Reverse Primer | TTGAACTGTGCATTGGTGTG | SEQ ID NO: 1476 |
| NEDD8 | NM_006156.1 | Forward Primer | TGCTGGCTACTGGGTGTTAGT | SEQ ID NO: 1477 |
| | | Probe | TGCAGTCCTGTGTGCTTCCCTCTC | SEQ ID NO: 1478 |
| | | Reverse Primer | GACAACCAGGGACACAGTCA | SEQ ID NO: 1479 |
| NEK2 | NM_002497.1 | Forward Primer | GTGAGGCAGCGCGACTCT | SEQ ID NO: 1480 |
| | | Probe | TGCCTTCCCGGGCTGAGGACT | SEQ ID NO: 1481 |
| | | Reverse Primer | TGCCAATGGTGTACAACACTTCA | SEQ ID NO: 1482 |
| NF2 | NM_000268.2 | Forward Primer | ACTCCAGAGCTGACCTCCAC | SEQ ID NO: 1483 |
| | | Probe | CTACAATGACTTCCCAGGCTGGGC | SEQ ID NO: 1484 |
| | | Reverse Primer | TCAGGGCTTCAGTGTCTCAC | SEQ ID NO: 1485 |
| NFKBp50 | NM_003998.1 | Forward Primer | CAGACCAAGGAGATGGACCT | SEQ ID NO: 1486 |
| | | Probe | AAGCTGTAAACATGAGCCGCACCA | SEQ ID NO: 1487 |
| | | Reverse Primer | AGCTGCCAGTGCTATCCG | SEQ ID NO: 1488 |
| NFKBp65 | NM_021975.1 | Forward Primer | CTGCCGGGATGGCTTCTAT | SEQ ID NO: 1489 |
| | | Probe | CTGAGCTCTGCCCGGACCGCT | SEQ ID NO: 1490 |
| | | Reverse Primer | CCAGGTTCTGGAAACTGTGGAT | SEQ ID NO: 1491 |
| NISCH | NM_007184.1 | Forward Primer | CCAAGGAATCATGTTCGTTCAG | SEQ ID NO: 1492 |
| | | Probe | TGGCCAGCAGCCTCTCGTCCAC | SEQ ID NO: 1493 |
| | | Reverse Primer | TGGTGCTCGGGAGTCAGACT | SEQ ID NO: 1494 |
| Nkd-1 | NM_033119.3 | Forward Primer | GAGAGAGTGAGCGAACCCTG | SEQ ID NO: 1495 |
| | | Probe | CCAGGCTCCAAGAAGCAGCTGAAG | SEQ ID NO: 1496 |
| | | Reverse Primer | CGTCGCACTGGAGCTCTT | SEQ ID NO: 1497 |
| NMB | NM_021077.1 | Forward Primer | GGCTGCTGGTACAAATACTGC | SEQ ID NO: 1498 |
| | | Probe | TGTCTGCCCCTATTATTGGTGTCATTTCT | SEQ ID NO: 1499 |
| | | Reverse Primer | CAATCTAAGCCACGCTGTTG | SEQ ID NO: 1500 |
| NMBR | NM_002511.1 | Forward Primer | TGATCCATCTCTAGGCCACA | SEQ ID NO: 1501 |
| | | Probe | TTGTCACCTTAGTTGCCCGGGTTC | SEQ ID NO: 1502 |
| | | Reverse Primer | GAGCAAATGGGTTGACACAA | SEQ ID NO: 1503 |
| NME1 | NM_000269.1 | Forward Primer | CCAACCCTGCAGACTCCAA | SEQ ID NO: 1504 |
| | | Probe | CCTGGGACCATCCGTGGAGACTTCT | SEQ ID NO: 1505 |
| | | Reverse Primer | ATGTATAATGTTCCTGCCAACTTGTATG | SEQ ID NO: 1506 |
| NOS3 | NM_000603.2 | Forward Primer | ATCTCCGCCTCGCTCATG | SEQ ID NO: 1507 |
| | | Probe | TTCACTCGCTTCGCCATCACCG | SEQ ID NO: 1508 |
| | | Reverse Primer | TCGGAGCCATACAGGATTGTC | SEQ ID NO: 1509 |
| NOTCH1 | NM_017617.2 | Forward Primer | CGGGTCCACCAGTTTGAATG | SEQ ID NO: 1510 |
| | | Probe | CCGCTCTGCAGCCGGGACA | SEQ ID NO: 1511 |
| | | Reverse Primer | GTTGTATTGGTTCGGCACCAT | SEQ ID NO: 1512 |
| NOTCH2 | NM_024408.2 | Forward Primer | CACTTCCCTGCTGGGATTAT | SEQ ID NO: 1513 |
| | | Probe | CCGTGTTGCACAGCTCATCACACT | SEQ ID NO: 1514 |
| | | Reverse Primer | AGTTGTCAAACAGGCACTCG | SEQ ID NO: 1515 |

TABLE A-continued

| Gene | Accession | Reagent | Sequence | Sequence ID Number |
|---|---|---|---|---|
| NPM1 | NM_002520.2 | Forward Primer | AATGTTGTCCAGGTTCTATTGC | SEQ ID NO: 1516 |
| | | Probe | AACAGGCATTTTGGACAACACATTCTTG | SEQ ID NO: 1517 |
| | | Reverse Primer | CAAGCAAAGGGTGGAGTTC | SEQ ID NO: 1518 |
| NR4A1 | NM_002135.2 | Forward Primer | CACAGCTTGCTTGTCGATGTC | SEQ ID NO: 1519 |
| | | Probe | CCTTCGCCTGCCTCTCTGCCC | SEQ ID NO: 1520 |
| | | Reverse Primer | ATGCCGGTCGGTGATGAG | SEQ ID NO: 1521 |
| NRG1 | NM_013957.1 | Forward Primer | CGAGACTCTCCTCATAGTGAAAGGTAT | SEQ ID NO: 1522 |
| | | Probe | ATGACCACCCCGGCTCGTATGTCA | SEQ ID NO: 1523 |
| | | Reverse Primer | CTTGGCGTGTGGAAATCTACAG | SEQ ID NO: 1524 |
| NRP1 | NM_003873.1 | Forward Primer | CAGCTCTCTCCACGCGATTC | SEQ ID NO: 1525 |
| | | Probe | CAGGATCTACCCCGAGAGAGCCACTCAT | SEQ ID NO: 1526 |
| | | Reverse Primer | CCCAGCAGCTCCATTCTGA | SEQ ID NO: 1527 |
| NRP2 | NM_003872.1 | Forward Primer | CTACAGCCTAAACGGCAAGG | SEQ ID NO: 1528 |
| | | Probe | AGGACCCCAGGACCCAGCAG | SEQ ID NO: 1529 |
| | | Reverse Primer | GTTCCCTTCGAACAGCTTTG | SEQ ID NO: 1530 |
| NTN1 | NM_004822.1 | Forward Primer | AGAAGGACTATGCCGTCCAG | SEQ ID NO: 1531 |
| | | Probe | ATCCACATCCTGAAGGCGGACAAG | SEQ ID NO: 1532 |
| | | Reverse Primer | CCGTGAACTTCCACCAGTC | SEQ ID NO: 1533 |
| NUFIP1 | NM_012345.1 | Forward Primer | GCTTCCACATCGTGGTATTG | SEQ ID NO: 1534 |
| | | Probe | CTTCTGATAGGTTTCCTCGGCATCAGA | SEQ ID NO: 1535 |
| | | Reverse Primer | AACTGCAGGGTTGAAGGACT | SEQ ID NO: 1536 |
| ODC1 | NM_002539.1 | Forward Primer | AGAGATCACCGGCGTAATCAA | SEQ ID NO: 1537 |
| | | Probe | CCAGCGTTGGACAAATACTTTCCGTCA | SEQ ID NO: 1538 |
| | | Reverse Primer | CGGGCTCAGCTATGATTCTCA | SEQ ID NO: 1539 |
| OPN, osteopontin | NM_000582.1 | Forward Primer | CAACCGAAGTTTTCACTCCAGTT | SEQ ID NO: 1540 |
| | | Probe | TCCCCACAGTAGACACATATGATGGCCG | SEQ ID NO: 1541 |
| | | Reverse Primer | CCTCAGTCCATAAACCACACTATCA | SEQ ID NO: 1542 |
| ORC1L | NM_004153.2 | Forward Primer | TCCTTGACCATACCGGAGG | SEQ ID NO: 1543 |
| | | Probe | TGCATGTACATCTCCGGTGTCCCT | SEQ ID NO: 1544 |
| | | Reverse Primer | CAGTGGCAGTCTTCCCTGTC | SEQ ID NO: 1545 |
| OSM | NM_020530.3 | Forward Primer | GTTTCTGAAGGGGAGGTCAC | SEQ ID NO: 1546 |
| | | Probe | CTGAGCTGGCCTCCTATGCCTCAT | SEQ ID NO: 1547 |
| | | Reverse Primer | AGGTGTCTGGTTTGGGACA | SEQ ID NO: 1548 |
| OSMR | NM_003999.1 | Forward Primer | GCTCATCATGGTCATGTGCT | SEQ ID NO: 1549 |
| | | Probe | CAGGTCTCCTTGATCCACTGACTTTTCA | SEQ ID NO: 1550 |
| | | Reverse Primer | TGTAAGGGTCAGGGATGTCA | SEQ ID NO: 1551 |
| P14ARF | S78535.1 | Forward Primer | CCCTCGTGCTGATGCTACT | SEQ ID NO: 1552 |
| | | Probe | CTGCCCTAGACGCTGGCTCCTC | SEQ ID NO: 1553 |
| | | Reverse Primer | CATCATGACCTGGTCTTCTAGG | SEQ ID NO: 1554 |
| p16-INK4 | L27211.1 | Forward Primer | GCGGAAGGTCCCTCAGACA | SEQ ID NO: 1555 |
| | | Probe | CTCAGAGCCTCTCTGGTTCTTTCAATCGG | SEQ ID NO: 1556 |
| | | Reverse Primer | TGATGATCTAAGTTTCCCGAGGTT | SEQ ID NO: 1557 |
| p21 | NM_000389.1 | Forward Primer | TGGAGACTCTCAGGGTCGAAA | SEQ ID NO: 1558 |
| | | Probe | CGGCGGCAGACCAGCATGAC | SEQ ID NO: 1559 |
| | | Reverse Primer | GGCGTTTGGAGTGGTAGAAATC | SEQ ID NO: 1560 |
| p27 | NM_004064.1 | Forward Primer | CGGTGGACCACGAAGAGTTAA | SEQ ID NO: 1561 |
| | | Probe | CCCGGGACTTGAGAAGCACTGCA | SEQ ID NO: 1562 |
| | | Reverse Primer | GGCTCGCCTCTTCCATGTC | SEQ ID NO: 1563 |
| P53 | NM_000546.2 | Forward Primer | CTTTGAACCCTTGCTTGCAA | SEQ ID NO: 1564 |
| | | Probe | AAGTCCTGGGTGCTTCTGACGCACA | SEQ ID NO: 1565 |
| | | Reverse Primer | CCCGGGACAAAGCAAATG | SEQ ID NO: 1566 |
| p53R2 | AB036063.1 | Forward Primer | CCCAGCTAGTGTTCCTCAGA | SEQ ID NO: 1567 |
| | | Probe | TCGGCCAGCTTTTTCCAATCTTTG | SEQ ID NO: 1568 |
| | | Reverse Primer | CCGTAAGCCCTTCCTCTATG | SEQ ID NO: 1569 |
| PADI4 | NM_012387.1 | Forward Primer | AGCAGTGGCTTGCTTTCTTC | SEQ ID NO: 1570 |
| | | Probe | CCTGTGATGTCCCAGTTTCCCACTC | SEQ ID NO: 1571 |
| | | Reverse Primer | TGCTAGGACCATGTTGGGAT | SEQ ID NO: 1572 |

TABLE A-continued

| Gene | Accession | Reagent | Sequence | Sequence ID Number |
|---|---|---|---|---|
| PAI1 | NM_000602.1 | Forward Primer | CCGCAACGTGGTTTTCTCA | SEQ ID NO: 1573 |
| | | Probe | CTCGGTGTTGGCCATGCTCCAG | SEQ ID NO: 1574 |
| | | Reverse Primer | TGCTGGGTTTCTCCTCCTGTT | SEQ ID NO: 1575 |
| Pak1 | NM_002576.3 | Forward Primer | GAGCTGTGGGTTGTTATGGA | SEQ ID NO: 1576 |
| | | Probe | ACATCTGTCAAGGAGCCTCCAGCC | SEQ ID NO: 1577 |
| | | Reverse Primer | CCATGCAAGTTTCTGTCACC | SEQ ID NO: 1578 |
| PARC | NM_015089.1 | Forward Primer | GGAGCTGACCTGCTTCCTAC | SEQ ID NO: 1579 |
| | | Probe | TCCTTATGCATCGAGGCCAGGC | SEQ ID NO: 1580 |
| | | Reverse Primer | AGCAGAGCACCACAGCATAG | SEQ ID NO: 1581 |
| PCAF | NM_003884.3 | Forward Primer | AGGTGGCTGTGTTACTGCAA | SEQ ID NO: 1582 |
| | | Probe | TGCCACAGTTCTGCGACAGTCTACC | SEQ ID NO: 1583 |
| | | Reverse Primer | CACCTGTGTGGTTTCGTACC | SEQ ID NO: 1584 |
| PCNA | NM_002592.1 | Forward Primer | GAAGGTGTTGGAGGCACTCAAG | SEQ ID NO: 1585 |
| | | Probe | ATCCCAGCAGGCCTCGTTGATGAG | SEQ ID NO: 1586 |
| | | Reverse Primer | GGTTTACACCGCTGGAGCTAA | SEQ ID NO: 1587 |
| PDGFA | NM_002607.2 | Forward Primer | TTGTTGGTGTGCCCTGGTG | SEQ ID NO: 1588 |
| | | Probe | TGGTGGCGGTCACTCCCTCTGC | SEQ ID NO: 1589 |
| | | Reverse Primer | TGGGTTCTGTCCAAACACTGG | SEQ ID NO: 1590 |
| PDGFB | NM_002608.1 | Forward Primer | ACTGAAGGAGACCCTTGGAG | SEQ ID NO: 1591 |
| | | Probe | TCTCCTGCCGATGCCCCTAGG | SEQ ID NO: 1592 |
| | | Reverse Primer | TAAATAACCCTGCCCACACA | SEQ ID NO: 1593 |
| PDGFC | NM_016205.1 | Forward Primer | AGTTACTAAAAAATACCACGAGGTCCTT | SEQ ID NO: 1594 |
| | | Probe | CCCTGACACCGGTCTTTGGTCTCAACT | SEQ ID NO: 1595 |
| | | Reverse Primer | GTCGGTGAGTGATTTGTGCAA | SEQ ID NO: 1596 |
| PDGFD | NM_025208.2 | Forward Primer | TATCGAGGCAGGTCATACCA | SEQ ID NO: 1597 |
| | | Probe | TCCAGGTCAACTTTTGACTTCCGGT | SEQ ID NO: 1598 |
| | | Reverse Primer | TAACGCTTGGCATCATCATT | SEQ ID NO: 1599 |
| PDGFRa | NM_006206.2 | Forward Primer | GGGAGTTTCCAAGAGATGGA | SEQ ID NO: 1600 |
| | | Probe | CCCAAGACCCGACCAAGCACTAG | SEQ ID NO: 1601 |
| | | Reverse Primer | CTTCAACCACCTTCCCAAAC | SEQ ID NO: 1602 |
| PDGFRb | NM_002609.2 | Forward Primer | CCAGCTCTCCTTCCAGCTAC | SEQ ID NO: 1603 |
| | | Probe | ATCAATGTCCCTGTCCGAGTGCTG | SEQ ID NO: 1604 |
| | | Reverse Primer | GGGTGGCTCTCACTTAGCTC | SEQ ID NO: 1605 |
| PFN1 | NM_005022.2 | Forward Primer | GGAAAACGTTCGTCAACATC | SEQ ID NO: 1606 |
| | | Probe | CAACCAGGACACCCACCTCAGCT | SEQ ID NO: 1607 |
| | | Reverse Primer | AAAACTTGACCGGTCTTTGC | SEQ ID NO: 1608 |
| PFN2 | NM_053024.1 | Forward Primer | TCTATACGTCGATGGTGACTGC | SEQ ID NO: 1609 |
| | | Probe | CTCCCCACCTTGACTCTTTGTCCG | SEQ ID NO: 1610 |
| | | Reverse Primer | GCCGACAGCCACATTGTAT | SEQ ID NO: 1611 |
| PGK1 | NM_000291.1 | Forward Primer | AGAGCCAGTTGCTGTAGAACTCAA | SEQ ID NO: 1612 |
| | | Probe | TCTCTGCTGGGCAAGGATGTTCTGTTC | SEQ ID NO: 1613 |
| | | Reverse Primer | CTGGGCCTACACAGTCCTTCA | SEQ ID NO: 1614 |
| PI3K | NM_002646.2 | Forward Primer | TGCTACCTGGACAGCCCG | SEQ ID NO: 1615 |
| | | Probe | TCCTCCTGAAACGAGCTGTGTCTGACTT | SEQ ID NO: 1616 |
| | | Reverse Primer | AGGCCGTCCTTCAGTAACCA | SEQ ID NO: 1617 |
| PI3KC2A | NM_002645.1 | Forward Primer | ATACCAATCACCGCACAAACC | SEQ ID NO: 1618 |
| | | Probe | TGCGCTGTGACTGGACTTAACAAATAGCCT | SEQ ID NO: 1619 |
| | | Reverse Primer | CACACTAGCATTTTCTCCGCATA | SEQ ID NO: 1620 |
| PIK3CA | NM_006218.1 | Forward Primer | GTGATTGAAGAGCATGCCAA | SEQ ID NO: 1621 |
| | | Probe | TCCTGCTTCTCGGGATACAGACCA | SEQ ID NO: 1622 |
| | | Reverse Primer | GTCCTGCGTGGGAATAGC | SEQ ID NO: 1623 |
| PIM1 | NM_002648.2 | Forward Primer | CTGCTCAAGGACACCGTCTA | SEQ ID NO: 1624 |
| | | Probe | TACACTCGGGTCCCATCGAAGTCC | SEQ ID NO: 1625 |
| | | Reverse Primer | GGATCCACTCTGGAGGGC | SEQ ID NO: 1626 |
| Pin1 | NM_006221.1 | Forward Primer | GATCAACGGCTACATCCAGA | SEQ ID NO: 1627 |
| | | Probe | TCAAAGTCCTCCTCTCCCGACTTGA | SEQ ID NO: 1628 |
| | | Reverse Primer | TGAACTGTGAGGCCAGAGAC | SEQ ID NO: 1629 |

TABLE A-continued

| Gene | Accession | Reagent | Sequence | Sequence ID Number |
|---|---|---|---|---|
| PKD1 | NM_000296.2 | Forward Primer | CAGCACCAGCGATTACGAC | SEQ ID NO: 1630 |
| | | Probe | AGCCATTGTGAGGACTCTCCCAGC | SEQ ID NO: 1631 |
| | | Reverse Primer | CTGAATAGGCCCACGTCC | SEQ ID NO: 1632 |
| PKR2 | NM_002654.3 | Forward Primer | CCGCCTGGACATTGATTCAC | SEQ ID NO: 1633 |
| | | Probe | ACCCATCACAGCCCGGAACACTG | SEQ ID NO: 1634 |
| | | Reverse Primer | CTGGGCCAATGGTACAGATGA | SEQ ID NO: 1635 |
| PLA2G2A | NM_000300.2 | Forward Primer | GCATCCCTCACCCATCCTA | SEQ ID NO: 1636 |
| | | Probe | AGGCCAGGCAGGAGCCCTTCTATA | SEQ ID NO: 1637 |
| | | Reverse Primer | GCTGGAAATCTGCTGGATGT | SEQ ID NO: 1638 |
| PLAUR | NM_002659.1 | Forward Primer | CCCATGGATGCTCCTCTGAA | SEQ ID NO: 1639 |
| | | Probe | CATTGACTGCCGAGGCCCCATG | SEQ ID NO: 1640 |
| | | Reverse Primer | CCGGTGGCTACCAGACATTG | SEQ ID NO: 1641 |
| PLK | NM_005030.2 | Forward Primer | AATGAATACAGTATTCCCAAGCACAT | SEQ ID NO: 1642 |
| | | Probe | AACCCCGTGGCCGCCTCC | SEQ ID NO: 1643 |
| | | Reverse Primer | TGTCTGAAGCATCTTCTGGATGA | SEQ ID NO: 1644 |
| PLK3 | NM_004073.2 | Forward Primer | TGAAGGAGACGTACCGCTG | SEQ ID NO: 1645 |
| | | Probe | CAAGCAGGTTCACTACACGCTGCC | SEQ ID NO: 1646 |
| | | Reverse Primer | CAGGCAGTGAGAGGCTGG | SEQ ID NO: 1647 |
| PLOD2 | NM_000935.2 | Forward Primer | CAGGGAGGTGGTTGCAAAT | SEQ ID NO: 1648 |
| | | Probe | TCCAGCCTTTTCGTGGTGACTCAA | SEQ ID NO: 1649 |
| | | Reverse Primer | TCTCCCAGGATGCATGAAG | SEQ ID NO: 1650 |
| PMS1 | NM_000534.2 | Forward Primer | CTTACGGTTTTCGTGGAGAAG | SEQ ID NO: 1651 |
| | | Probe | CCTCAGCTATACAACAAATTGACCCCAAG | SEQ ID NO: 1652 |
| | | Reverse Primer | AGCAGCCGTTCTTGTTGTAA | SEQ ID NO: 1653 |
| PMS2 | NM_000535.2 | Forward Primer | GATGTGGACTGCCATTCAAA | SEQ ID NO: 1654 |
| | | Probe | TCGAAATTTACATCCGGTATCTTCCTGG | SEQ ID NO: 1655 |
| | | Reverse Primer | TGCGAGATTAGTTGGCTGAG | SEQ ID NO: 1656 |
| PPARG | NM_005037.3 | Forward Primer | TGACTTTATGGAGCCCAAGTT | SEQ ID NO: 1657 |
| | | Probe | TTCCAGTGCATTGAACTTCACAGCA | SEQ ID NO: 1658 |
| | | Reverse Primer | GCCAAGTCGCTGTCATCTAA | SEQ ID NO: 1659 |
| PPID | NM_005038.1 | Forward Primer | TCCTCATTTGGATGGGAAAC | SEQ ID NO: 1660 |
| | | Probe | TTCCTTTAATTACTTGGCCAAACACCACA | SEQ ID NO: 1661 |
| | | Reverse Primer | CCAATATCCTTGCCACTCCTA | SEQ ID NO: 1662 |
| PPM1D | NM_003620.1 | Forward Primer | GCCATCCGCAAAGGCTTT | SEQ ID NO: 1663 |
| | | Probe | TCGCTTGTCACCTTGCCATGTGG | SEQ ID NO: 1664 |
| | | Reverse Primer | GGCCATTCCGCCAGTTTC | SEQ ID NO: 1665 |
| PPP2R4 | NM_178001.1 | Forward Primer | GGCTCAGAGCATAAGGCTTC | SEQ ID NO: 1666 |
| | | Probe | TTGGTCACTTCTCCCAACTTGGGC | SEQ ID NO: 1667 |
| | | Reverse Primer | ACGGGAACTCAGAAAACTGG | SEQ ID NO: 1668 |
| PR | NM_000926.2 | Forward Primer | GCATCAGGCTGTCATTATGG | SEQ ID NO: 1669 |
| | | Probe | TGTCCTTACCTGTGGGAGCTGTAAGGTC | SEQ ID NO: 1670 |
| | | Reverse Primer | AGTAGTTGTGCTGCCCTTCC | SEQ ID NO: 1671 |
| PRDX2 | NM_005809.4 | Forward Primer | GGTGTCCTTCGCCAGATCAC | SEQ ID NO: 1672 |
| | | Probe | TTAATGATTTGCCTGTGGGACGCTCC | SEQ ID NO: 1673 |
| | | Reverse Primer | CAGCCGCAGAGCCTCATC | SEQ ID NO: 1674 |
| PRDX3 | NM_006793.2 | Forward Primer | TGACCCCAATGGAGTCATCA | SEQ ID NO: 1675 |
| | | Probe | CATTTGAGCGTCAACGATCTCCCAGTG | SEQ ID NO: 1676 |
| | | Reverse Primer | CCAAGCGGAGGGTTTCTTC | SEQ ID NO: 1677 |
| PRDX4 | NM_006406.1 | Forward Primer | TTACCCATTTGGCCTGGATTAA | SEQ ID NO: 1678 |
| | | Probe | CCAAGTCCTCCTTGTCTTCGAGGGGT | SEQ ID NO: 1679 |
| | | Reverse Primer | CTGAAAGAAGTGGAATCCTTATTGG | SEQ ID NO: 1680 |
| PRDX6 | NM_004905.2 | Forward Primer | CTGTGAGCCAGAGGATGTCA | SEQ ID NO: 1681 |
| | | Probe | CTGCCAATTGTGTTTTCCTGCAGC | SEQ ID NO: 1682 |
| | | Reverse Primer | TGTGATGACACCAGGATGTG | SEQ ID NO: 1683 |
| PRKCA | NM_002737.1 | Forward Primer | CAAGCAATGCGTCATCAATGT | SEQ ID NO: 1684 |
| | | Probe | CAGCCTCTGCGGAATGGATCACACT | SEQ ID NO: 1685 |
| | | Reverse Primer | GTAAATCCGCCCCCTCTTCT | SEQ ID NO: 1686 |

TABLE A-continued

| Gene | Accession | Reagent | Sequence | Sequence ID Number |
|---|---|---|---|---|
| PRKCB1 | NM_002738.5 | Forward Primer | GACCCAGCTCCACTCCTG | SEQ ID NO: 1687 |
| | | Probe | CCAGACCATGGACCGCCTGTACTT | SEQ ID NO: 1688 |
| | | Reverse Primer | CCCATTCACGTACTCCATCA | SEQ ID NO: 1689 |
| PRKCD | NM_006254.1 | Forward Primer | CTGACACTTGCCGCAGAGAA | SEQ ID NO: 1690 |
| | | Probe | CCCTTTCTCACCCACCTCATCTGCAC | SEQ ID NO: 1691 |
| | | Reverse Primer | AGGTGGTCCTTGGTCTGGAA | SEQ ID NO: 1692 |
| PRKR | NM_002759.1 | Forward Primer | GCGATACATGAGCCCAGAACA | SEQ ID NO: 1693 |
| | | Probe | AGGTCCACTTCCTTTCCATAGTCTTGCGA | SEQ ID NO: 1694 |
| | | Reverse Primer | TCAGCAAGAATTAGCCCCAAAG | SEQ ID NO: 1695 |
| pS2 | NM_003225.1 | Forward Primer | GCCCTCCCAGTGTGCAAAT | SEQ ID NO: 1696 |
| | | Probe | TGCTGTTTCGACGACACCGTTCG | SEQ ID NO: 1697 |
| | | Reverse Primer | CGTCGATGGTATTAGGATAGAAGCA | SEQ ID NO: 1698 |
| PTCH | NM_000264.2 | Forward Primer | CCACGACAAAGCCGACTAC | SEQ ID NO: 1699 |
| | | Probe | CCTGAAACAAGGCTGAGAATCCCG | SEQ ID NO: 1700 |
| | | Reverse Primer | TACTCGATGGGCTCTGCTG | SEQ ID NO: 1701 |
| PTEN | NM_000314.1 | Forward Primer | TGGCTAAGTGAAGATGACAATCATG | SEQ ID NO: 1702 |
| | | Probe | CCTTTCCAGCTTTACAGTGAATTGCTGCA | SEQ ID NO: 1703 |
| | | Reverse Primer | TGCACATATCATTACACCAGTTCGT | SEQ ID NO: 1704 |
| PTGER3 | NM_000957.2 | Forward Primer | TAACTGGGGCAACCTTTTCT | SEQ ID NO: 1705 |
| | | Probe | CCTTTGCCTTCCTGGGGCTCTT | SEQ ID NO: 1706 |
| | | Reverse Primer | TTGCAGGAAAAGGTGACTGT | SEQ ID NO: 1707 |
| PTHLH | NM_002820.1 | Forward Primer | AGTGACTGGGAGTGGGCTAGAA | SEQ ID NO: 1708 |
| | | Probe | TGACACCTCCACAACGTCGCTGGA | SEQ ID NO: 1709 |
| | | Reverse Primer | AAGCCTGTTACCGTGAATCGA | SEQ ID NO: 1710 |
| PTHR1 | NM_000316.1 | Forward Primer | CGAGGTACAAGCTGAGATCAAGAA | SEQ ID NO: 1711 |
| | | Probe | CCAGTGCCAGTGTCCAGCGGCT | SEQ ID NO: 1712 |
| | | Reverse Primer | GCGTGCCTTTCGCTTGAA | SEQ ID NO: 1713 |
| PTK2 | NM_005607.3 | Forward Primer | GACCGGTCGAATGATAAGGT | SEQ ID NO: 1714 |
| | | Probe | ACCAGGCCCGTCACATTCTCGTAC | SEQ ID NO: 1715 |
| | | Reverse Primer | CTGGACATCTCGATGACAGC | SEQ ID NO: 1716 |
| PTK2B | NM_004103.3 | Forward Primer | CAAGCCCAGCCGACCTAAG | SEQ ID NO: 1717 |
| | | Probe | CTCCGCAAACCAACCTCCTGGCT | SEQ ID NO: 1718 |
| | | Reverse Primer | GAACCTGGAACTGCAGCTTTG | SEQ ID NO: 1719 |
| PTP4A3 | NM_007079.2 | Forward Primer | CCTGTTCTCGGCACCTTAAA | SEQ ID NO: 1720 |
| | | Probe | ACCTGACTGCCCCGGGGTCTAATA | SEQ ID NO: 1721 |
| | | Reverse Primer | TATTGCCTTCGGGTGTCC | SEQ ID NO: 1722 |
| PTP4A3 v2 | NM_032611.1 | Forward Primer | AATATTTGTGCGGGGTATGG | SEQ ID NO: 1723 |
| | | Probe | CCAAGAGAAACGAGATTTAAAAACCCACC | SEQ ID NO: 1724 |
| | | Reverse Primer | AACGAGATCCCTGTGCTTGT | SEQ ID NO: 1725 |
| PTPD1 | NM_007039.2 | Forward Primer | CGCTTGCCTAACTCATACTTTCC | SEQ ID NO: 1726 |
| | | Probe | TCCACGCAGCGTGGCACTG | SEQ ID NO: 1727 |
| | | Reverse Primer | CCATTCAGACTGCGCCACTT | SEQ ID NO: 1728 |
| PTPN1 | NM_002827.2 | Forward Primer | AATGAGGAAGTTTCGGATGG | SEQ ID NO: 1729 |
| | | Probe | CTGATCCAGACAGCCGACCAGCT | SEQ ID NO: 1730 |
| | | Reverse Primer | CTTCGATCACAGCCAGGTAG | SEQ ID NO: 1731 |
| PTPRF | NM_002840.2 | Forward Primer | TGTTTTAGCTGAGGGACGTG | SEQ ID NO: 1732 |
| | | Probe | CCGACGTCCCAAACCTAGCTAGG | SEQ ID NO: 1733 |
| | | Reverse Primer | TACCAACCCTGGAATGTTGA | SEQ ID NO: 1734 |
| PTPRJ | NM_002843.2 | Forward Primer | AACTTCCGGTACCTCGTTCGT | SEQ ID NO: 1735 |
| | | Probe | ACTACATGAAGCAGAGTCCTCCCGAATCG | SEQ ID NO: 1736 |
| | | Reverse Primer | AGCACTGCAATGCACCAGAA | SEQ ID NO: 1737 |
| PTPRO | NM_030667.1 | Forward Primer | CATGGCCTGATCATGGTGT | SEQ ID NO: 1738 |
| | | Probe | CCCACAGCAAATGCTGCAGAAAGT | SEQ ID NO: 1739 |
| | | Reverse Primer | CCATGTGTACAAACTGCAGGA | SEQ ID NO: 1740 |
| PTTG1 | NM_004219.2 | Forward Primer | GGCTACTCTGATCTATGTTGATAAGGAA | SEQ ID NO: 1741 |
| | | Probe | CACACGGGTGCCTGGTTCTCCA | SEQ ID NO: 1742 |
| | | Reverse Primer | GCTTCAGCCCATCCTTAGCA | SEQ ID NO: 1743 |

TABLE A-continued

| Gene | Accession | Reagent | Sequence | Sequence ID Number |
|---|---|---|---|---|
| RAB32 | NM_006834.2 | Forward Primer | CCTGCAGCTGTGGGACAT | SEQ ID NO: 1744 |
|  |  | Probe | CGATTTGGCAACATGACCCGAGTA | SEQ ID NO: 1745 |
|  |  | Reverse Primer | AGCACCAACAGCTTCCTTG | SEQ ID NO: 1746 |
| RAB6C | NM_032144.1 | Forward Primer | GCGACAGCTCCTCTAGTTCCA | SEQ ID NO: 1747 |
|  |  | Probe | TTCCCGAAGTCTCCGCCCG | SEQ ID NO: 1748 |
|  |  | Reverse Primer | GGAACACCAGCTTGAATTTCCT | SEQ ID NO: 1749 |
| RAC1 | NM_006908.3 | Forward Primer | TGTTGTAAATGTCTCAGCCCC | SEQ ID NO: 1750 |
|  |  | Probe | CGTTCTTGGTCCTGTCCCTTGGA | SEQ ID NO: 1751 |
|  |  | Reverse Primer | TTGAGCAAAGCGTACAAAGG | SEQ ID NO: 1752 |
| RAD51C | NM_058216.1 | Forward Primer | GAACTTCTTGAGCAGGAGCATACC | SEQ ID NO: 1753 |
|  |  | Probe | AGGGCTTCATAATCACCTTCTGTTC | SEQ ID NO: 1754 |
|  |  | Reverse Primer | TCCACCCCCAAGAATATCATCTAGT | SEQ ID NO: 1755 |
| RAD54L | NM_003579.2 | Forward Primer | AGCTAGCCTCAGTGACACACATG | SEQ ID NO: 1756 |
|  |  | Probe | ACACAACGTCGGCAGTGCAACCTG | SEQ ID NO: 1757 |
|  |  | Reverse Primer | CCGGATCTGACGGCTGTT | SEQ ID NO: 1758 |
| RAF1 | NM_002880.1 | Forward Primer | CGTCGTATGCGAGAGTCTGT | SEQ ID NO: 1759 |
|  |  | Probe | TCCAGGATGCCTGTTAGTTCTCAGCA | SEQ ID NO: 1760 |
|  |  | Reverse Primer | TGAAGGCGTGAGGTGTAGAA | SEQ ID NO: 1761 |
| RALBP1 | NM_006788.2 | Forward Primer | GGTGTCAGATATAAATGTGCAAATGC | SEQ ID NO: 1762 |
|  |  | Probe | TGCTGTCCTGTCGGTCTCAGTACGTTCA | SEQ ID NO: 1763 |
|  |  | Reverse Primer | TTCGATATTGCCAGCAGCTATAAA | SEQ ID NO: 1764 |
| RANBP2 | NM_006267.3 | Forward Primer | TCCTTCAGCTTTCACACTGG | SEQ ID NO: 1765 |
|  |  | Probe | TCCAGAAGAGTCATGCAACTTCATTTCTG | SEQ ID NO: 1766 |
|  |  | Reverse Primer | AAATCCTGTTCCCACCTGAC | SEQ ID NO: 1767 |
| ranBP7 | NM_006391.1 | Forward Primer | AACATGATTATCCAAGCCGC | SEQ ID NO: 1768 |
|  |  | Probe | AAGCCAATTTTGTCCACAATGGCA | SEQ ID NO: 1769 |
|  |  | Reverse Primer | GCCAACAAGCACTGTTATCG | SEQ ID NO: 1770 |
| RANBP9 | NM_005493.2 | Forward Primer | CAAGTCAGTTGAGACGCCAGTT | SEQ ID NO: 1771 |
|  |  | Probe | TTCTATGGCGGCCTGACTTCCTCCA | SEQ ID NO: 1772 |
|  |  | Reverse Primer | TGCAGCTCTCGTCCAAAGTG | SEQ ID NO: 1773 |
| RAP1GDS1 | NM_021159.3 | Forward Primer | TGTGGATGCTGGATTGATTT | SEQ ID NO: 1774 |
|  |  | Probe | CCACTGGTGCAGCTGCTAAATAGCA | SEQ ID NO: 1775 |
|  |  | Reverse Primer | AAGCAGCACTTCCTGGTCTT | SEQ ID NO: 1776 |
| RARA | NM_000964.1 | Forward Primer | AGTCTGTGAGAAACGACCGAAAC | SEQ ID NO: 1777 |
|  |  | Probe | TCGGGCTTGGGCACCTCCTTCTT | SEQ ID NO: 1778 |
|  |  | Reverse Primer | CGGCGTCAGCGTGTAGCT | SEQ ID NO: 1779 |
| RARB | NM_016152.2 | Forward Primer | TGCCTGGACATCCTGATTCT | SEQ ID NO: 1780 |
|  |  | Probe | TGCACCAGGTATACCCCAGAACAAGA | SEQ ID NO: 1781 |
|  |  | Reverse Primer | AAGGCCGTCTGAGAAAGTCA | SEQ ID NO: 1782 |
| RASSF1 | NM_007182.3 | Forward Primer | AGTGGGAGACACCTGACCTT | SEQ ID NO: 1783 |
|  |  | Probe | TTGATCTTCTGCTCAATCTCAGCTTGAGA | SEQ ID NO: 1784 |
|  |  | Reverse Primer | TGATCTGGGCATTGTACTCC | SEQ ID NO: 1785 |
| RBM5 | NM_005778.1 | Forward Primer | CGAGAGGGAGAGCAAGACCAT | SEQ ID NO: 1786 |
|  |  | Probe | CTGCGCGGCCTTCCCATCA | SEQ ID NO: 1787 |
|  |  | Reverse Primer | TCTCGAATATCGCTCTCTGTGATG | SEQ ID NO: 1788 |
| RBX1 | NM_014248.2 | Forward Primer | GGAACCACATTATGGATCTTTGC | SEQ ID NO: 1789 |
|  |  | Probe | TAGAATGTCAAGCTAACCAGGCGTCCGC | SEQ ID NO: 1790 |
|  |  | Reverse Primer | CATGCGACAGTACACTCTTCTGAA | SEQ ID NO: 1791 |
| RCC1 | NM_001269.2 | Forward Primer | GGGCTGGGTGAGAATGTG | SEQ ID NO: 1792 |
|  |  | Probe | ATACCAGGGCCGGCTTCTTCCTCT | SEQ ID NO: 1793 |
|  |  | Reverse Primer | CACAACATCCTCCGGAATG | SEQ ID NO: 1794 |
| REG4 | NM_032044.2 | Forward Primer | TGCTAACTCCTGCACAGCC | SEQ ID NO: 1795 |
|  |  | Probe | TCCTCTTCCTTTCTGCTAGCCTGGC | SEQ ID NO: 1796 |
|  |  | Reverse Primer | TGCTAGGTTTCCCCTCTGAA | SEQ ID NO: 1797 |
| RFC | NM_003056.1 | Forward Primer | TCAAGACCATCATCACTTTCATTGT | SEQ ID NO: 1798 |
|  |  | Probe | CCTCCCGGTCCGCAAGCAGTT | SEQ ID NO: 1799 |
|  |  | Reverse Primer | GGATCAGGAAGTACACGGAGTATAACT | SEQ ID NO: 1800 |

TABLE A-continued

| Gene | Accession | Reagent | Sequence | Sequence ID Number |
|---|---|---|---|---|
| RhoB | NM_004040.2 | Forward Primer | AAGCATGAACAGGACTTGACC | SEQ ID NO: 1801 |
| | | Probe | CTTTCCAACCCCTGGGGAAGACAT | SEQ ID NO: 1802 |
| | | Reverse Primer | CCTCCCCAAGTCAGTTGC | SEQ ID NO: 1803 |
| rhoC | NM_175744.1 | Forward Primer | CCCGTTCGGTCTGAGGAA | SEQ ID NO: 1804 |
| | | Probe | TCCGGTTCGCCATGTCCCG | SEQ ID NO: 1805 |
| | | Reverse Primer | GAGCACTCAAGGTAGCCAAAGG | SEQ ID NO: 1806 |
| RIZ1 | NM_012231.1 | Forward Primer | CCAGACGAGCGATTAGAAGC | SEQ ID NO: 1807 |
| | | Probe | TGTGAGGTGAATGATTTGGGGGA | SEQ ID NO: 1808 |
| | | Reverse Primer | TCCTCCTCTTCCTCCTCCTC | SEQ ID NO: 1809 |
| RNF11 | NM_014372.3 | Forward Primer | ACCCTGGAAGAGATGGATCA | SEQ ID NO: 1810 |
| | | Probe | CCATCATACAGATCACACACTCCCGG | SEQ ID NO: 1811 |
| | | Reverse Primer | ATTGGGTCCCCATAAACAAA | SEQ ID NO: 1812 |
| ROCK1 | NM_005406.1 | Forward Primer | TGTGCACATAGGAATGAGCTTC | SEQ ID NO: 1813 |
| | | Probe | TCACTCTCTTTGCTGGCCAACTGC | SEQ ID NO: 1814 |
| | | Reverse Primer | GTTTAGCACGCAATTGCTCA | SEQ ID NO: 1815 |
| ROCK2 | NM_004850.3 | Forward Primer | GATCCGAGACCCTCGCTC | SEQ ID NO: 1816 |
| | | Probe | CCCATCAACGTGGAGAGCTTGCT | SEQ ID NO: 1817 |
| | | Reverse Primer | AGGACCAAGGAATTTAAGCCA | SEQ ID NO: 1818 |
| RPLPO | NM_001002.2 | Forward Primer | CCATTCTATCATCAACGGGTACAA | SEQ ID NO: 1819 |
| | | Probe | TCTCCACAGACAAGGCCAGGACTCG | SEQ ID NO: 1820 |
| | | Reverse Primer | TCAGCAAGTGGGAAGGTGTAATC | SEQ ID NO: 1821 |
| RPS13 | NM_001017.2 | Forward Primer | CAGTCGGCTTTACCCTATCG | SEQ ID NO: 1822 |
| | | Probe | CAACTTCAACCAAGTGGGGACGCT | SEQ ID NO: 1823 |
| | | Reverse Primer | TCTGCTCCTTCACGTCGTC | SEQ ID NO: 1824 |
| RRM1 | NM_001033.1 | Forward Primer | GGGCTACTGGCAGCTACATT | SEQ ID NO: 1825 |
| | | Probe | CATTGGAATTGCCATTAGTCCCAGC | SEQ ID NO: 1826 |
| | | Reverse Primer | CTCTCAGCATCGGTACAAGG | SEQ ID NO: 1827 |
| RRM2 | NM_001034.1 | Forward Primer | CAGCGGGATTAAACAGTCCT | SEQ ID NO: 1828 |
| | | Probe | CCAGCACAGCCAGTTAAAAGATGCA | SEQ ID NO: 1829 |
| | | Reverse Primer | ATCTGCGTTGAAGCAGTGAG | SEQ ID NO: 1830 |
| RTN4 | NM_007008.1 | Forward Primer | GACTGGAGTGGTGTTTGGTG | SEQ ID NO: 1831 |
| | | Probe | CCAGCCTATTCCTGCTGCTTTCATTG | SEQ ID NO: 1832 |
| | | Reverse Primer | CTGTTACGCTCACAATGCTG | SEQ ID NO: 1833 |
| RUNX1 | NM_001754.2 | Forward Primer | AACAGAGACATTGCCAACCA | SEQ ID NO: 1834 |
| | | Probe | TTGGATCTGCTTGCTGTCCAAACC | SEQ ID NO: 1835 |
| | | Reverse Primer | GTGATTTGCCCAGGAAGTTT | SEQ ID NO: 1836 |
| RXRA | NM_002957.3 | Forward Primer | GCTCTGTTGTGTCCTGTTGC | SEQ ID NO: 1837 |
| | | Probe | TCAGTCACAGGAAGGCCAGAGCC | SEQ ID NO: 1838 |
| | | Reverse Primer | GTACGGAGAAGCCACTTCACA | SEQ ID NO: 1839 |
| S100A1 | NM_006271.1 | Forward Primer | TGGACAAGGTGATGAAGGAG | SEQ ID NO: 1840 |
| | | Probe | CCTCCCCGTCTCCATTCTCGTCTA | SEQ ID NO: 1841 |
| | | Reverse Primer | AGCACCACATACTCCTGGAA | SEQ ID NO: 1842 |
| S100A2 | NM_005978.2 | Forward Primer | TGGCTGTGCTGGTCACTACCT | SEQ ID NO: 1843 |
| | | Probe | CACAAGTACTCCTGCCAAGAGGGCGAC | SEQ ID NO: 1844 |
| | | Reverse Primer | TCCCCCTTACTCAGCTTGAACT | SEQ ID NO: 1845 |
| S100A4 | NM_002961.2 | Forward Primer | GACTGCTGTCATGGCGTG | SEQ ID NO: 1846 |
| | | Probe | ATCACATCCAGGGCCTTCTCCAGA | SEQ ID NO: 1847 |
| | | Reverse Primer | CGAGTACTTGTGGAAGGTGGAC | SEQ ID NO: 1848 |
| S100A8 | NM_002964.3 | Forward Primer | ACTCCCTGATAAAGGGGAATTT | SEQ ID NO: 1849 |
| | | Probe | CATGCCGTCTACAGGGATGACCTG | SEQ ID NO: 1850 |
| | | Reverse Primer | TGAGGACACTCGGTCTCTAGC | SEQ ID NO: 1851 |
| S100A9 | NM_002965.2 | Forward Primer | CTTTGGGACAGAGTGCAAGA | SEQ ID NO: 1852 |
| | | Probe | CGATGACTTGCAAAATGTCGCAGC | SEQ ID NO: 1853 |
| | | Reverse Primer | TGGTCTCTATGTTGCGTTCC | SEQ ID NO: 1854 |
| S100P | NM_005980.2 | Forward Primer | AGACAAGGATGCCGTGGATAA | SEQ ID NO: 1855 |
| | | Probe | TTGCTCAAGGACCTGGACGCCAA | SEQ ID NO: 1856 |
| | | Reverse Primer | GAAGTCCACCTGGGCATCTC | SEQ ID NO: 1857 |

TABLE A-continued

| Gene | Accession | Reagent | Sequence | Sequence ID Number |
|---|---|---|---|---|
| SAT | NM_002970.1 | Forward Primer | CCTTTTACCACTGCCTGGTT | SEQ ID NO: 1858 |
| | | Probe | TCCAGTGCTCTTTCGGCACTTCTG | SEQ ID NO: 1859 |
| | | Reverse Primer | ACAATGCTGTGTCCTTCCG | SEQ ID NO: 1860 |
| SBA2 | NM_018639.3 | Forward Primer | GGACTCAACGATGGGCAG | SEQ ID NO: 1861 |
| | | Probe | CCCTGTCTGCACCTCCCAGATCTT | SEQ ID NO: 1862 |
| | | Reverse Primer | CGGAAAGATTCAAAAGCAGG | SEQ ID NO: 1863 |
| SDC1 | NM_002997.1 | Forward Primer | GAAATTGACGAGGGGTGTCT | SEQ ID NO: 1864 |
| | | Probe | CTCTGAGCGCCTCCATCCAAGG | SEQ ID NO: 1865 |
| | | Reverse Primer | AGGAGCTAACGGAGAACCTG | SEQ ID NO: 1866 |
| SEMA3B | NM_004636.1 | Forward Primer | GCTCCAGGATGTGTTTCTGTTG | SEQ ID NO: 1867 |
| | | Probe | TCGCGGGACCACCGGACC | SEQ ID NO: 1868 |
| | | Reverse Primer | ACGTGGAGAAGACGGCATAGA | SEQ ID NO: 1869 |
| SEMA3F | NM_004186.1 | Forward Primer | CGCGAGCCCCTCATTATACA | SEQ ID NO: 1870 |
| | | Probe | CTCCCCACAGCGCATCGAGGAA | SEQ ID NO: 1871 |
| | | Reverse Primer | CACTCGCCGTTGACATCCT | SEQ ID NO: 1872 |
| SEMA4B | NM_020210.1 | Forward Primer | TTCCAGCCCAACACAGTGAA | SEQ ID NO: 1873 |
| | | Probe | ACTTTGGCCTGCCCGCTCCTCT | SEQ ID NO: 1874 |
| | | Reverse Primer | GAGTCGGGTCGCCAGGTT | SEQ ID NO: 1875 |
| SFRP2 | NM_003013.2 | Forward Primer | CAAGCTGAACGGTGTGTCC | SEQ ID NO: 1876 |
| | | Probe | CAGCACCGATTTCTTCAGGTCCCT | SEQ ID NO: 1877 |
| | | Reverse Primer | TGCAAGCTGTCTTTGAGCC | SEQ ID NO: 1878 |
| SFRP4 | NM_003014.2 | Forward Primer | TACAGGATGAGGCTGGGC | SEQ ID NO: 1879 |
| | | Probe | CCTGGGACAGCCTATGTAAGGCCA | SEQ ID NO: 1880 |
| | | Reverse Primer | GTTGTTAGGGCAAGGGGC | SEQ ID NO: 1881 |
| SGCB | NM_000232.1 | Forward Primer | CAGTGGAGACCAGTTGGGTAGTG | SEQ ID NO: 1882 |
| | | Probe | CACACATGCAGAGCTTGTAGCGTACCCA | SEQ ID NO: 1883 |
| | | Reverse Primer | CCTTGAAGAGCGTCCCATCA | SEQ ID NO: 1884 |
| SHC1 | NM_003029.3 | Forward Primer | CCAACACCTTCTTGGCTTCT | SEQ ID NO: 1885 |
| | | Probe | CCTGTGTTCTTGCTGAGCACCCTC | SEQ ID NO: 1886 |
| | | Reverse Primer | CTGTTATCCCAACCCAAACC | SEQ ID NO: 1887 |
| SHH | NM_000193.2 | Forward Primer | GTCCAAGGCACATATCCACTG | SEQ ID NO: 1888 |
| | | Probe | CACCGAGTTCTCTGCTTTCACCGA | SEQ ID NO: 1889 |
| | | Reverse Primer | GAAGCAGCCTCCCGATTT | SEQ ID NO: 1890 |
| SI | NM_001041.1 | Forward Primer | AACGGACTCCCTCAATTTGT | SEQ ID NO: 1891 |
| | | Probe | TGTCCATGGTCATGCAAATCTTGC | SEQ ID NO: 1892 |
| | | Reverse Primer | GAAATTGCAGGGTCCAAGAT | SEQ ID NO: 1893 |
| Siah-1 | NM_003031.2 | Forward Primer | TTGGCATTGGAACTACATTCA | SEQ ID NO: 1894 |
| | | Probe | TCCGCGGTATCCTCGGATTAGTTC | SEQ ID NO: 1895 |
| | | Reverse Primer | GGTATGGAGAAGGGGGTCC | SEQ ID NO: 1896 |
| SIAT4A | NM_003033.2 | Forward Primer | AACCACAGTTGGAGGAGGAC | SEQ ID NO: 1897 |
| | | Probe | CAGAGACAGTTTCCCTCCCCGCT | SEQ ID NO: 1898 |
| | | Reverse Primer | CGAAGGAAGGGTGTTGGTAT | SEQ ID NO: 1899 |
| SIAT7B | NM_006456.1 | Forward Primer | TCCAGCCCAAATCCTCCT | SEQ ID NO: 1900 |
| | | Probe | TGGCACATCCTACCCCAGATGCTA | SEQ ID NO: 1901 |
| | | Reverse Primer | GGTGTCCTGGAGTCCTTGAA | SEQ ID NO: 1902 |
| SIM2 | NM_005069.2 | Forward Primer | GATGGTAGGAAGGGATGTGC | SEQ ID NO: 1903 |
| | | Probe | CGCCTCTCCACGCACTCAGCTAT | SEQ ID NO: 1904 |
| | | Reverse Primer | CACAAGGAGCTGTGAATGAGG | SEQ ID NO: 1905 |
| SIN3A | NM_015477.1 | Forward Primer | CCAGAGTCATGCTCATCCAG | SEQ ID NO: 1906 |
| | | Probe | CTGTCCCTGCACTGGTGCAACTG | SEQ ID NO: 1907 |
| | | Reverse Primer | CCACCTTCAGCCTCTGAAAT | SEQ ID NO: 1908 |
| SIR2 | NM_012238.3 | Forward Primer | AGCTGGGGTGTCTGTTTCAT | SEQ ID NO: 1909 |
| | | Probe | CCTGACTTCAGGTCAAGGGATGG | SEQ ID NO: 1910 |
| | | Reverse Primer | ACAGCAAGGCGAGCATAAAT | SEQ ID NO: 1911 |
| SKP1A | NM_006930.2 | Forward Primer | CCATTGCCTTTGCTTTGTTCAT | SEQ ID NO: 1912 |
| | | Probe | TCCCATGGTTTTTATTCTGCCCTGCTG | SEQ ID NO: 1913 |
| | | Reverse Primer | TTCCGGATTTCCTTTCTTTGC | SEQ ID NO: 1914 |

TABLE A-continued

| Gene | Accession | Reagent | Sequence | Sequence ID Number |
|---|---|---|---|---|
| SKP2 | NM_005983.2 | Forward Primer | AGTTGCAGAATCTAAGCCTGGAA | SEQ ID NO: 1915 |
| | | Probe | CCTGCGGCTTTCGGATCCCA | SEQ ID NO: 1916 |
| | | Reverse Primer | TGAGTTTTTTGCGAGAGTATTGACA | SEQ ID NO: 1917 |
| SLC25A3 | NM_213611.1 | Forward Primer | TCTGCCAGTGCTGAATTCTT | SEQ ID NO: 1918 |
| | | Probe | TGCTGACATTGCCCTGGCTCCTAT | SEQ ID NO: 1919 |
| | | Reverse Primer | TTCGAACCTTAGCAGCTTCC | SEQ ID NO: 1920 |
| SLC2A1 | NM_006516.1 | Forward Primer | GCCTGAGTCTCCTGTGCC | SEQ ID NO: 1921 |
| | | Probe | ACATCCCAGGCTTCACCCTGAATG | SEQ ID NO: 1922 |
| | | Reverse Primer | AGTCTCCACCCTCAGGCAT | SEQ ID NO: 1923 |
| SLC31A1 | NM_001859.2 | Forward Primer | CCGTTCGAAGAGTCGTGAG | SEQ ID NO: 1924 |
| | | Probe | TCTCCGAATCTTAACCCGTCACCC | SEQ ID NO: 1925 |
| | | Reverse Primer | AGTCCAGCCACTAGCACCTC | SEQ ID NO: 1926 |
| SLC5A8 | NM_145913.2 | Forward Primer | CCTGCTTTCAACCACATTGA | SEQ ID NO: 1927 |
| | | Probe | TCCCATTGCTCTTGCCACTCTGAT | SEQ ID NO: 1928 |
| | | Reverse Primer | AGAGCAGCTTCACAAACGAG | SEQ ID NO: 1929 |
| SLC7A5 | NM_003486.4 | Forward Primer | GCGCAGAGGCCAGTTAAA | SEQ ID NO: 1930 |
| | | Probe | AGATCACCTCCTCGAACCCACTCC | SEQ ID NO: 1931 |
| | | Reverse Primer | AGCTGAGCTGTGGGTTGC | SEQ ID NO: 1932 |
| SLPI | NM_003064.2 | Forward Primer | ATGGCCAATGTTTGATGCT | SEQ ID NO: 1933 |
| | | Probe | TGGCCATCCATCTCACAGAAATTGG | SEQ ID NO: 1934 |
| | | Reverse Primer | ACACTTCAAGTCACGCTTGC | SEQ ID NO: 1935 |
| SMARCA3 | NM_003071.2 | Forward Primer | AGGGACTGTCCTGGCACAT | SEQ ID NO: 1936 |
| | | Probe | AGCAAAAGACCCAGGACATCTGCA | SEQ ID NO: 1937 |
| | | Reverse Primer | CAACAAATTTGCCGCAGTC | SEQ ID NO: 1938 |
| SNAI1 | NM_005985.2 | Forward Primer | CCCAATCGGAAGCCTAACTA | SEQ ID NO: 1939 |
| | | Probe | TCTGGATTAGAGTCCTGCAGCTCGC | SEQ ID NO: 1940 |
| | | Reverse Primer | GTAGGGCTGCTGGAAGGTAA | SEQ ID NO: 1941 |
| SNAI2 | NM_003068.3 | Forward Primer | GGCTGGCCAAACATAAGCA | SEQ ID NO: 1942 |
| | | Probe | CTGCACTGCGATGCCCAGTCTAGAAAATC | SEQ ID NO: 1943 |
| | | Reverse Primer | TCCTTGTCACAGTATTTACAGCTGAA | SEQ ID NO: 1944 |
| SNRPF | NM_003095.1 | Forward Primer | GGCTGGTCGGCAGAGAGTAG | SEQ ID NO: 1945 |
| | | Probe | AAACTCATGTAAACCACGGCCGAATGTTG | SEQ ID NO: 1946 |
| | | Reverse Primer | TGAGGAAAGGTTTGGGATTGA | SEQ ID NO: 1947 |
| SOD1 | NM_000454.3 | Forward Primer | TGAAGAGAGGCATGTTGGAG | SEQ ID NO: 1948 |
| | | Probe | TTTGTCAGCAGTCACATTGCCCAA | SEQ ID NO: 1949 |
| | | Reverse Primer | AATAGACACATCGGCCACAC | SEQ ID NO: 1950 |
| SOD2 | NM_000636.1 | Forward Primer | GCTTGTCCAAATCAGGATCCA | SEQ ID NO: 1951 |
| | | Probe | AACAACAGGCCTTATTCCACTGCTGGG | SEQ ID NO: 1952 |
| | | Reverse Primer | AGCGTGCTCCCACACATCA | SEQ ID NO: 1953 |
| SOS1 | NM_005633.2 | Forward Primer | TCTGCACCAAATTCTCCAAG | SEQ ID NO: 1954 |
| | | Probe | AACACCGTTAACACCTCCGCCTG | SEQ ID NO: 1955 |
| | | Reverse Primer | GTGGTACTGGAAGCACCAGA | SEQ ID NO: 1956 |
| SOX17 | NM_022454.2 | Forward Primer | TCGTGTGCAAGCCTGAGA | SEQ ID NO: 1957 |
| | | Probe | CTCCCCTACCAGGGGCATGACTC | SEQ ID NO: 1958 |
| | | Reverse Primer | CTGTCGGGGAGATTCACAC | SEQ ID NO: 1959 |
| SPARC | NM_003118.1 | Forward Primer | TCTTCCCTGTACACTGGCAGTTC | SEQ ID NO: 1960 |
| | | Probe | TGGACCAGCACCCCATTGACGG | SEQ ID NO: 1961 |
| | | Reverse Primer | AGCTCGGTGTGGGAGAGGTA | SEQ ID NO: 1962 |
| SPINT2 | NM_021102.1 | Forward Primer | AGGAATGCAGCGGATTCCT | SEQ ID NO: 1963 |
| | | Probe | CCCAAGTGCTCCCAGAAGGCAGG | SEQ ID NO: 1964 |
| | | Reverse Primer | TCGCTGGAGTGGTCTTCAGA | SEQ ID NO: 1965 |
| SPRY1 | AK026960.1 | Forward Primer | CAGACCAGTCCCTGGTCATAGG | SEQ ID NO: 1966 |
| | | Probe | CTGGGTCCGGATTGCCCTTTCAG | SEQ ID NO: 1967 |
| | | Reverse Primer | CCTTCAAGTCATCCACAATCAGTT | SEQ ID NO: 1968 |
| SPRY2 | NM_005842.1 | Forward Primer | TGTGGCAAGTGCAAATGTAA | SEQ ID NO: 1969 |
| | | Probe | CAGAGGCCTTGGGTAGGTGCACTC | SEQ ID NO: 1970 |
| | | Reverse Primer | GTCGCAGATCCAGTCTGATG | SEQ ID NO: 1971 |

TABLE A-continued

| Gene | Accession | Reagent | Sequence | Sequence ID Number |
|---|---|---|---|---|
| SR-A1 | NM_021228.1 | Forward Primer | AGATGGAAGAAGCCAACCTG | SEQ ID NO: 1972 |
| | | Probe | CTGGATCAGCTCCTGGGCCTTC | SEQ ID NO: 1973 |
| | | Reverse Primer | CTGTGGCTGAGGATCTGGT | SEQ ID NO: 1974 |
| ST14 | NM_021978.2 | Forward Primer | TGACTGCACATGGAACATTG | SEQ ID NO: 1975 |
| | | Probe | AGGTGCCCAACAACCAGCATGT | SEQ ID NO: 1976 |
| | | Reverse Primer | AAGAATTTGAAGCGCACCTT | SEQ ID NO: 1977 |
| STAT1 | NM_007315.1 | Forward Primer | GGGCTCAGCTTTCAGAAGTG | SEQ ID NO: 1978 |
| | | Probe | TGGCAGTTTTCTTCTGTCACCAAAA | SEQ ID NO: 1979 |
| | | Reverse Primer | ACATGTTCAGCTGGTCCACA | SEQ ID NO: 1980 |
| STAT3 | NM_003150.1 | Forward Primer | TCACATGCCACTTTGGTGTT | SEQ ID NO: 1981 |
| | | Probe | TCCTGGGAGAGATTGACCAGCA | SEQ ID NO: 1982 |
| | | Reverse Primer | CTTGCAGGAAGCGGCTATAC | SEQ ID NO: 1983 |
| STAT5A | NM_003152.1 | Forward Primer | GAGGCGCTCAACATGAAATTC | SEQ ID NO: 1984 |
| | | Probe | CGGTTGCTCTGCACTTCGGCCT | SEQ ID NO: 1985 |
| | | Reverse Primer | GCCAGGAACACGAGGTTCTC | SEQ ID NO: 1986 |
| STAT5B | NM_012448.1 | Forward Primer | CCAGTGGTGGTGATCGTTCA | SEQ ID NO: 1987 |
| | | Probe | CAGCCAGGACAACAATGCGACGG | SEQ ID NO: 1988 |
| | | Reverse Primer | GCAAAAGCATTGTCCCAGAGA | SEQ ID NO: 1989 |
| STC1 | NM_003155.1 | Forward Primer | CTCCGAGGTGAGGAGGACT | SEQ ID NO: 1990 |
| | | Probe | CACATCAAACGCACATCCCATGAG | SEQ ID NO: 1991 |
| | | Reverse Primer | ACCTCTCCCTGGTTATGCAC | SEQ ID NO: 1992 |
| STK11 | NM_000455.3 | Forward Primer | GGACTCGGAGACGCTGTG | SEQ ID NO: 1993 |
| | | Probe | TTCTTGAGGATCTTGACGGCCCTC | SEQ ID NO: 1994 |
| | | Reverse Primer | GGGATCCTTCGCAACTTCTT | SEQ ID NO: 1995 |
| STK15 | NM_003600.1 | Forward Primer | CATCTTCCAGGAGGACCACT | SEQ ID NO: 1996 |
| | | Probe | CTCTGTGGCACCCTGGACTACCTG | SEQ ID NO: 1997 |
| | | Reverse Primer | TCCGACCTTCAATCATTTCA | SEQ ID NO: 1998 |
| STMN1 | NM_005563.2 | Forward Primer | AATACCCAACGCACAAATGA | SEQ ID NO: 1999 |
| | | Probe | CACGTTCTCTGCCCCGTTTCTTG | SEQ ID NO: 2000 |
| | | Reverse Primer | GGAGACAATGCAAACCACAC | SEQ ID NO: 2001 |
| STMY3 | NM_005940.2 | Forward Primer | CCTGGAGGCTGCAACATACC | SEQ ID NO: 2002 |
| | | Probe | ATCCTCCTGAAGCCCTTTTCGCAGC | SEQ ID NO: 2003 |
| | | Reverse Primer | TACAATGGCTTTGGAGGATAGCA | SEQ ID NO: 2004 |
| STS | NM_000351.2 | Forward Primer | GAAGATCCCTTTCCTCCTACTGTTC | SEQ ID NO: 2005 |
| | | Probe | CTTCGTGGCTCTCGGCTTCCCA | SEQ ID NO: 2006 |
| | | Reverse Primer | GGATGATGTTCGGCCTTGAT | SEQ ID NO: 2007 |
| SURV | NM_001168.1 | Forward Primer | TGTTTTGATTCCCGGGCTTA | SEQ ID NO: 2008 |
| | | Probe | TGCCTTCTTCCTCCCTCACTTCTCACCT | SEQ ID NO: 2009 |
| | | Reverse Primer | CAAAGCTGTCAGCTCTAGCAAAAG | SEQ ID NO: 2010 |
| TAGLN | NM_003186.2 | Forward Primer | GATGGAGCAGGTGGCTCAGT | SEQ ID NO: 2011 |
| | | Probe | CCCAGAGTCCTCAGCCGCCTTCAG | SEQ ID NO: 2012 |
| | | Reverse Primer | AGTCTGGAACATGTCAGTCTTGATG | SEQ ID NO: 2013 |
| TBP | NM_003194.1 | Forward Primer | GCCCGAAACGCCGAATATA | SEQ ID NO: 2014 |
| | | Probe | TACCGCAGCAAACCGCTTGGG | SEQ ID NO: 2015 |
| | | Reverse Primer | CGTGGCTCTCTTATCCTCATGAT | SEQ ID NO: 2016 |
| TCF-1 | NM_000545.3 | Forward Primer | GAGGTCCTGAGCACTGCC | SEQ ID NO: 2017 |
| | | Probe | CTGGGTTCACAGGCTCCTTTGTCC | SEQ ID NO: 2018 |
| | | Reverse Primer | GATGTGGGACCATGCTTGT | SEQ ID NO: 2019 |
| TCF-7 | NM_003202.2 | Forward Primer | GCAGCTGCAGTCAACAGTTC | SEQ ID NO: 2020 |
| | | Probe | AAGTCATGGCCCAAATCCAGTGTG | SEQ ID NO: 2021 |
| | | Reverse Primer | CTGTGAATGGGAGGGGT | SEQ ID NO: 2022 |
| TCF7L1 | NM_031283.1 | Forward Primer | CCGGGACACTTTCCAGAAG | SEQ ID NO: 2023 |
| | | Probe | TCTCACTTCGGCGAAATAGTCCCG | SEQ ID NO: 2024 |
| | | Reverse Primer | AGAACGCGCTGTCCTGAG | SEQ ID NO: 2025 |

TABLE A-continued

| Gene | Accession | Reagent | Sequence | Sequence ID Number |
|---|---|---|---|---|
| TCF7L2 | NM_030756.1 | Forward Primer | CCAATCACGACAGGAGGATT | SEQ ID NO: 2026 |
| | | Probe | AGACACCCCTACCCCACAGCTCTG | SEQ ID NO: 2027 |
| | | Reverse Primer | TGGACACGGAAGCATTGAC | SEQ ID NO: 2028 |
| TCFL4 | NM_170607.2 | Forward Primer | CTGACTGCTCTGCTTAAAGGTGAA | SEQ ID NO: 2029 |
| | | Probe | TAGCAGGAACAACAACAAAAGCCAACCAA | SEQ ID NO: 2030 |
| | | Reverse Primer | ATGTCTTGCACTGGCTACCTTGT | SEQ ID NO: 2031 |
| TEK | NM_000459.1 | Forward Primer | ACTTCGGTGCTACTTAACAACTTACATC | SEQ ID NO: 2032 |
| | | Probe | AGCTCGGACCACGTACTGCTCCCTG | SEQ ID NO: 2033 |
| | | Reverse Primer | CCTGGGCCTTGGTGTTGAC | SEQ ID NO: 2034 |
| TERC | U86046.1 | Forward Primer | AAGAGGAACGGAGCGAGTC | SEQ ID NO: 2035 |
| | | Probe | CACGTCCCACAGCTCAGGGAATC | SEQ ID NO: 2036 |
| | | Reverse Primer | ATGTGTGAGCCGAGTCCTG | SEQ ID NO: 2037 |
| TERT | NM_003219.1 | Forward Primer | GACATGGAGAACAAGCTGTTTGC | SEQ ID NO: 2038 |
| | | Probe | ACCAAACGCAGGAGCAGCCCG | SEQ ID NO: 2039 |
| | | Reverse Primer | GAGGTGTCACCAACAAGAAATCAT | SEQ ID NO: 2040 |
| TFF3 | NM_003226.1 | Forward Primer | AGGCACTGTTCATCTCAGTTTTTCT | SEQ ID NO: 2041 |
| | | Probe | CAGAAAGCTTGCCGGGAGCAAAGG | SEQ ID NO: 2042 |
| | | Reverse Primer | CATCAGGCTCCAGATATGAACTTTC | SEQ ID NO: 2043 |
| TGFA | NM_003236.1 | Forward Primer | GGTGTGCCACAGACCTTCCT | SEQ ID NO: 2044 |
| | | Probe | TTGGCCTGTAATCACCTGTGCAGCCTT | SEQ ID NO: 2045 |
| | | Reverse Primer | ACGGAGTTCTTGACAGAGTTTTGA | SEQ ID NO: 2046 |
| TGFB2 | NM_003238.1 | Forward Primer | ACCAGTCCCCCAGAAGACTA | SEQ ID NO: 2047 |
| | | Probe | TCCTGAGCCCGAGGAAGTCCC | SEQ ID NO: 2048 |
| | | Reverse Primer | CCTGGTGCTGTTGTAGATGG | SEQ ID NO: 2049 |
| TGFB3 | NM_003239.1 | Forward Primer | GGATCGAGCTCTTCCAGATCCT | SEQ ID NO: 2050 |
| | | Probe | CGGCCAGATGAGCACATTGCC | SEQ ID NO: 2051 |
| | | Reverse Primer | GCCACCGATATAGCGCTGTT | SEQ ID NO: 2052 |
| TGFBI | NM_000358.1 | Forward Primer | GCTACGAGTGCTGTCCTGG | SEQ ID NO: 2053 |
| | | Probe | CCTTCTCCCCAGGGACCTTTTCAT | SEQ ID NO: 2054 |
| | | Reverse Primer | AGTGGTAGGGCTGCTGGAC | SEQ ID NO: 2055 |
| TGFBR1 | NM_004612.1 | Forward Primer | GTCATCACCTGGCCTTGG | SEQ ID NO: 2056 |
| | | Probe | AGCAATGACAGCTGCCAGTTCCAC | SEQ ID NO: 2057 |
| | | Reverse Primer | GCAGACGAAGCACACTGGT | SEQ ID NO: 2058 |
| TGFBR2 | NM_003242.2 | Forward Primer | AACACCAATGGGTTCCATCT | SEQ ID NO: 2059 |
| | | Probe | TTCTGGGCTCCTGATTGCTCAAGC | SEQ ID NO: 2060 |
| | | Reverse Primer | CCTCTTCATCAGGCCAAACT | SEQ ID NO: 2061 |
| THBS1 | NM_003246.1 | Forward Primer | CATCCGCAAAGTGACTGAAGAG | SEQ ID NO: 2062 |
| | | Probe | CCAATGAGCTGAGGCGGCCTCC | SEQ ID NO: 2063 |
| | | Reverse Primer | GTACTGAACTCCGTTGTGATAGCATAG | SEQ ID NO: 2064 |
| THY1 | NM_006288.2 | Forward Primer | GGACAAGACCCTCTCAGGCT | SEQ ID NO: 2065 |
| | | Probe | CAAGCTCCCAAGAGCTTCCAGAGC | SEQ ID NO: 2066 |
| | | Reverse Primer | TTGGAGGCTGTGGGTCAG | SEQ ID NO: 2067 |
| TIMP1 | NM_003254.1 | Forward Primer | TCCCTGCGGTCCCAGATAG | SEQ ID NO: 2068 |
| | | Probe | ATCCTGCCCGGAGTGGAACTGAAGC | SEQ ID NO: 2069 |
| | | Reverse Primer | GTGGGAACAGGGTGGACACT | SEQ ID NO: 2070 |
| TIMP2 | NM_003255.2 | Forward Primer | TCACCCTCTGTGACTTCATCGT | SEQ ID NO: 2071 |
| | | Probe | CCCTGGGACACCCTGAGCACCA | SEQ ID NO: 2072 |
| | | Reverse Primer | TGTGGTTCAGGCTCTTCTTCTG | SEQ ID NO: 2073 |
| TIMP3 | NM_000362.2 | Forward Primer | CTACCTGCCTTGCTTTGTGA | SEQ ID NO: 2074 |
| | | Probe | CCAAGAACGAGTGTCTCTGGACCG | SEQ ID NO: 2075 |
| | | Reverse Primer | ACCGAAATTGGAGAGCATGT | SEQ ID NO: 2076 |
| TJP1 | NM_003257.1 | Forward Primer | ACTTTGCTGGGACAAAGGTC | SEQ ID NO: 2077 |
| | | Probe | CTCGGGCCTGCCCACTTCTTC | SEQ ID NO: 2078 |
| | | Reverse Primer | CACATGGACTCCTCAGCATC | SEQ ID NO: 2079 |

TABLE A-continued

| Gene | Accession | Reagent | Sequence | Sequence ID Number |
|---|---|---|---|---|
| TK1 | NM_003258.1 | Forward Primer | GCCGGGAAGACCGTAATTGT | SEQ ID NO: 2080 |
| | | Probe | CAAATGGCTTCCTCTGGAAGGTCCCA | SEQ ID NO: 2081 |
| | | Reverse Primer | CAGCGGCACCAGGTTCAG | SEQ ID NO: 2082 |
| TLN1 | NM_006289.2 | Forward Primer | AAGCAGAAGGGAGAGCGTAAGA | SEQ ID NO: 2083 |
| | | Probe | CTTCCAGGCACACAAGAATTGTGGGC | SEQ ID NO: 2084 |
| | | Reverse Primer | CCTTGGCCTCAATCTCACTCA | SEQ ID NO: 2085 |
| TMEPAI | NM_020182.3 | Forward Primer | CAGAAGGATGCCTGTGGC | SEQ ID NO: 2086 |
| | | Probe | ATTCCGTTGCCTGACACTGTGCTC | SEQ ID NO: 2087 |
| | | Reverse Primer | GTAGACCTGCGGCTCTGG | SEQ ID NO: 2088 |
| TMSB10 | NM_021103.2 | Forward Primer | GAAATCGCCAGCTTCGATAA | SEQ ID NO: 2089 |
| | | Probe | CGTCTCCGTTTTCTTCAGCTTGGC | SEQ ID NO: 2090 |
| | | Reverse Primer | GTCGGCAGGGTGTTCTTTT | SEQ ID NO: 2091 |
| TMSB4X | NM_021109.2 | Forward Primer | CACATCAAAGAACTACTGACAACGAA | SEQ ID NO: 2092 |
| | | Probe | CCGCGCCTGCCTTTCCCA | SEQ ID NO: 2093 |
| | | Reverse Primer | CCTGCCAGCCAGATAGATAGACA | SEQ ID NO: 2094 |
| TNC | NM_002160.1 | Forward Primer | AGCTCGGAACCTCACCGT | SEQ ID NO: 2095 |
| | | Probe | CAGCCTTCGGGCTGTGGACATAC | SEQ ID NO: 2096 |
| | | Reverse Primer | GTAGCAGCCTTGAGGCCC | SEQ ID NO: 2097 |
| TNF | NM_000594.1 | Forward Primer | GGAGAAGGGTGACCGACTCA | SEQ ID NO: 2098 |
| | | Probe | CGCTGAGATCAATCGGCCCGACTA | SEQ ID NO: 2099 |
| | | Reverse Primer | TGCCCAGACTCGGCAAAG | SEQ ID NO: 2100 |
| TNFRSF5 | NM_001250.3 | Forward Primer | TCTCACCTCGCTATGGTTCGT | SEQ ID NO: 2101 |
| | | Probe | TGCCTCTGCAGTGCGTCCTCTGG | SEQ ID NO: 2102 |
| | | Reverse Primer | GATGGACAGCGGTCAGCAA | SEQ ID NO: 2103 |
| TNFRSF6B | NM_003823.2 | Forward Primer | CCTCAGCACCAGGGTACCA | SEQ ID NO: 2104 |
| | | Probe | TGACGGCACGCTCACACTCCTCAG | SEQ ID NO: 2105 |
| | | Reverse Primer | TGTCCTGGAAAGCCACAAAGT | SEQ ID NO: 2106 |
| TNFSF4 | NM_003326.2 | Forward Primer | CTTCATCTTCCCTCTACCCAGA | SEQ ID NO: 2107 |
| | | Probe | CAGGGGTTGGACCCTTTCCATCTT | SEQ ID NO: 2108 |
| | | Reverse Primer | GCTGCATTTCCCACATTCTC | SEQ ID NO: 2109 |
| TOP2A | NM_001067.1 | Forward Primer | AATCCAAGGGGGAGAGTGAT | SEQ ID NO: 2110 |
| | | Probe | CATATGGACTTTGACTCAGCTGTGGC | SEQ ID NO: 2111 |
| | | Reverse Primer | GTACAGATTTTGCCCGAGGA | SEQ ID NO: 2112 |
| TOP2B | NM_001068.1 | Forward Primer | TGTGGACATCTTCCCCTCAGA | SEQ ID NO: 2113 |
| | | Probe | TTCCCTACTGAGCCACCTTCTCTG | SEQ ID NO: 2114 |
| | | Reverse Primer | CTAGCCCGACCGGTTCGT | SEQ ID NO: 2115 |
| TP | NM_001953.2 | Forward Primer | CTATATGCAGCCAGAGATGTGACA | SEQ ID NO: 2116 |
| | | Probe | ACAGCCTGCCACTCATCACAGCC | SEQ ID NO: 2117 |
| | | Reverse Primer | CCACGAGTTTCTTACTGAGAATGG | SEQ ID NO: 2118 |
| TP53BP1 | NM_005657.1 | Forward Primer | TGCTGTTGCTGAGTCTGTTG | SEQ ID NO: 2119 |
| | | Probe | CCAGTCCCCAGAAGACCATGTCTG | SEQ ID NO: 2120 |
| | | Reverse Primer | CTTGCCTGGCTTCACAGATA | SEQ ID NO: 2121 |
| TP53BP2 | NM_005426.1 | Forward Primer | GGGCCAAATATTCAGAAGC | SEQ ID NO: 2122 |
| | | Probe | CCACCATAGCGGCCATGGAG | SEQ ID NO: 2123 |
| | | Reverse Primer | GGATGGGTATGATGGGACAG | SEQ ID NO: 2124 |
| TP53I3 | NM_004881.2 | Forward Primer | GCGGACTTAATGCAGAGACA | SEQ ID NO: 2125 |
| | | Probe | CAGTATGACCCACCTCCAGGAGCC | SEQ ID NO: 2126 |
| | | Reverse Primer | TCAAGTCCCAAAATGTTGCT | SEQ ID NO: 2127 |
| TRAG3 | NM_004909.1 | Forward Primer | GACGCTGGTCTGGTGAAGATG | SEQ ID NO: 2128 |
| | | Probe | CCAGGAAACCACGAGCCTCCAGC | SEQ ID NO: 2129 |
| | | Reverse Primer | TGGGTGGTTGTTGGACAATG | SEQ ID NO: 2130 |
| TRAIL | NM_003810.1 | Forward Primer | CTTCACAGTGCTCCTGCAGTCT | SEQ ID NO: 2131 |
| | | Probe | AAGTACACGTAAGTTACAGCCACACA | SEQ ID NO: 2132 |
| | | Reverse Primer | CATCTGCTTCAGCTCGTTGGT | SEQ ID NO: 2133 |

TABLE A-continued

| Gene | Accession | Reagent | Sequence | Sequence ID Number |
|---|---|---|---|---|
| TS | NM_001071.1 | Forward Primer<br>Probe<br>Reverse Primer | GCCTCGGTGTGCCTTTCA<br>CATCGCCAGCTACGCCCTGCTC<br>CGTGATGTGCGCAATCATG | SEQ ID NO: 2134<br>SEQ ID NO: 2135<br>SEQ ID NO: 2136 |
| TST | NM_003312.4 | Forward Primer<br>Probe<br>Reverse Primer | GGAGCCGGATGCAGTAGGA<br>ACCACGGATATGGCCCGAGTCCA<br>AAGTCCATGAAAGGCATGTTGA | SEQ ID NO: 2137<br>SEQ ID NO: 2138<br>SEQ ID NO: 2139 |
| TUBA1 | NM_006000.1 | Forward Primer<br>Probe<br>Reverse Primer | TGTCACCCCGACTCAACGT<br>AGACGCACCGCCCGGACTCAC<br>ACGTGGACTGAGATGCATTCAC | SEQ ID NO: 2140<br>SEQ ID NO: 2141<br>SEQ ID NO: 2142 |
| TUBB | NM_001069.1 | Forward Primer<br>Probe<br>Reverse Primer | CGAGGACGAGGCTTAAAAAC<br>TCTCAGATCAATCGTGCATCCTTAGTGAA<br>ACCATGCTTGAGGACAACAG | SEQ ID NO: 2143<br>SEQ ID NO: 2144<br>SEQ ID NO: 2145 |
| TUFM | NM_003321.3 | Forward Primer<br>Probe<br>Reverse Primer | GTATCACCATCAATGCGGC<br>CATGTGGAGTATAGCACTGCCGCC<br>CAGTCTGTGTGGGCGTAGTG | SEQ ID NO: 2146<br>SEQ ID NO: 2147<br>SEQ ID NO: 2148 |
| TULP3 | NM_003324.2 | Forward Primer<br>Probe<br>Reverse Primer | TGTGTATAGTCCTGCCCCTCAA<br>CCGGATTATCCGACATCTTACTGTGA<br>CCCGATCCATTCCCCTTTTA | SEQ ID NO: 2149<br>SEQ ID NO: 2150<br>SEQ ID NO: 2151 |
| tusc4 | NM_006545.4 | Forward Primer<br>Probe<br>Reverse Primer | GGAGGAGCTAAATGCCTCAG<br>ACTCATCAATGGGCAGAGTGCACC<br>CCTTCAAGTGGATGGTGTTG | SEQ ID NO: 2152<br>SEQ ID NO: 2153<br>SEQ ID NO: 2154 |
| UBB | NM_018955.1 | Forward Primer<br>Probe<br>Reverse Primer | GAGTCGACCCTGCACCTG<br>AATTAACAGCCACCCCTCAGGCG<br>GCGAATGCCATGACTGAA | SEQ ID NO: 2155<br>SEQ ID NO: 2156<br>SEQ ID NO: 2157 |
| UBC | NM_021009.2 | Forward Primer<br>Probe<br>Reverse Primer | ACGCACCCTGTCTGACTACA<br>CATCCAGAAAGAGTCCACCCTGCA<br>ACCTCTAAGACGGAGCACCA | SEQ ID NO: 2158<br>SEQ ID NO: 2159<br>SEQ ID NO: 2160 |
| UBE2C | NM_007019.2 | Forward Primer<br>Probe<br>Reverse Primer | TGTCTGGCGATAAAGGGATT<br>TCTGCCTTCCCTGAATCAGACAACC<br>ATGGTCCCTACCCATTTGAA | SEQ ID NO: 2161<br>SEQ ID NO: 2162<br>SEQ ID NO: 2163 |
| UBE2M | NM_003969.1 | Forward Primer<br>Probe<br>Reverse Primer | CTCCATAATTTATGGCCTGCAGTA<br>TCTTCTTGGAGCCCAACCCCGAG<br>TGCGGCCTCCTTGTTCAG | SEQ ID NO: 2164<br>SEQ ID NO: 2165<br>SEQ ID NO: 2166 |
| UBL1 | NM_003352.3 | Forward Primer<br>Probe<br>Reverse Primer | GTGAAGCCACCGTCATCATG<br>CTGACCAGGAGGCAAAACCTTCAACTGA<br>CCTTCCTTCTTATCCCCCAAGT | SEQ ID NO: 2167<br>SEQ ID NO: 2168<br>SEQ ID NO: 2169 |
| UCP2 | NM_003355.2 | Forward Primer<br>Probe<br>Reverse Primer | ACCATGCTCCAGAAGGAGG<br>CCCCGAGCCTTCTACAAAGGGTTC<br>AACCCAAGCGGAGAAAGG | SEQ ID NO: 2170<br>SEQ ID NO: 2171<br>SEQ ID NO: 2172 |
| UGT1A1 | NM_000463.2 | Forward Primer<br>Probe<br>Reverse Primer | CCATGCAGCCTGGAATTTG<br>CTACCCAGTGCCCCAACCCATTCTC<br>GAGAGGCCTGGGCACGTA | SEQ ID NO: 2173<br>SEQ ID NO: 2174<br>SEQ ID NO: 2175 |
| UMPS | NM_000373.1 | Forward Primer<br>Probe<br>Reverse Primer | TGCGGAAATGAGCTCCAC<br>CCCTGGCCACTGGGGACTACACTA<br>CCTCAGCCATTCTAACCGC | SEQ ID NO: 2176<br>SEQ ID NO: 2177<br>SEQ ID NO: 2178 |
| UNC5A | XM_030300.7 | Forward Primer<br>Probe<br>Reverse Primer | GACAGCTGATCCAGGAGCC<br>CGGGTCCTGCACTTCAAGGACAGT<br>ATGGATAGGCGCAGGTTG | SEQ ID NO: 2179<br>SEQ ID NO: 2180<br>SEQ ID NO: 2181 |
| UNC5B | NM_170744.2 | Forward Primer<br>Probe<br>Reverse Primer | AGAACGGAGGCCGTGACT<br>CGGGACGCTGCTCGACTCTAAGAA<br>CATGCACAGCCCATCTGT | SEQ ID NO: 2182<br>SEQ ID NO: 2183<br>SEQ ID NO: 2184 |
| UNC5C | NM_003728.2 | Forward Primer<br>Probe<br>Reverse Primer | CTGAACACAGTGGAGCTGGT<br>ACCTGCCGCACACAGAGTTTGC<br>CTGGAAGATCTGCCCTTCTC | SEQ ID NO: 2185<br>SEQ ID NO: 2186<br>SEQ ID NO: 2187 |

TABLE A-continued

| Gene | Accession | Reagent | Sequence | Sequence ID Number |
|---|---|---|---|---|
| upa | NM_002658.1 | Forward Primer | GTGGATGTGCCCTGAAGGA | SEQ ID NO: 2188 |
| | | Probe | AAGCCAGGCGTCTACACGAGAGTCTCAC | SEQ ID NO: 2189 |
| | | Reverse Primer | CTGCGGATCCAGGGTAAGAA | SEQ ID NO: 2190 |
| UPP1 | NM_003364.2 | Forward Primer | ACGGGTCCTGCCTCAGTT | SEQ ID NO: 2191 |
| | | Probe | TCAGCTTTCTCTGCATTGGCTCCC | SEQ ID NO: 2192 |
| | | Reverse Primer | CGGGGCAATCATTGTGAC | SEQ ID NO: 2193 |
| VCAM1 | NM_001078.2 | Forward Primer | TGGCTTCAGGAGCTGAATACC | SEQ ID NO: 2194 |
| | | Probe | CAGGCACACACAGGTGGGACACAAT | SEQ ID NO: 2195 |
| | | Reverse Primer | TGCTGTCGTGATGAGAAAATAGTG | SEQ ID NO: 2196 |
| VCL | NM_003373.2 | Forward Primer | GATACCACAACTCCCATCAAGCT | SEQ ID NO: 2197 |
| | | Probe | AGTGGCAGCCACGGCGCC | SEQ ID NO: 2198 |
| | | Reverse Primer | TCCCTGTTAGGCGCATCAG | SEQ ID NO: 2199 |
| VCP | NM_007126.2 | Forward Primer | GGCTTTGGCAGCTTCAGAT | SEQ ID NO: 2200 |
| | | Probe | AGCTCCACCCTGGTTCCCTGAAG | SEQ ID NO: 2201 |
| | | Reverse Primer | CTCCACTGCCCTGACTGG | SEQ ID NO: 2202 |
| VDAC1 | NM_003374.1 | Forward Primer | GCTGCGACATGGATTTCGA | SEQ ID NO: 2203 |
| | | Probe | TTGCTGGGCCTTCCATCCGG | SEQ ID NO: 2204 |
| | | Reverse Primer | CCAGCCCTCGTAACCTAGCA | SEQ ID NO: 2205 |
| VDAC2 | NM_003375.2 | Forward Primer | ACCCACGGACAGACTTGC | SEQ ID NO: 2206 |
| | | Probe | CGCGTCCAATGTGTATTCCTCCAT | SEQ ID NO: 2207 |
| | | Reverse Primer | AGCTTTGCCAAGGTCAGC | SEQ ID NO: 2208 |
| VDR | NM_000376.1 | Forward Primer | GCCCTGGATTTCAGAAAGAG | SEQ ID NO: 2209 |
| | | Probe | CAAGTCTGGATCTGGGACCCTTCC | SEQ ID NO: 2210 |
| | | Reverse Primer | AGTTACAAGCCAGGGAAGGA | SEQ ID NO: 2211 |
| VEGF | NM_003376.3 | Forward Primer | CTGCTGTCTTGGGTGCATTG | SEQ ID NO: 2212 |
| | | Probe | TTGCCTTGCTGCTCTACCTCCACCA | SEQ ID NO: 2213 |
| | | Reverse Primer | GCAGCCTGGGACCACTTG | SEQ ID NO: 2214 |
| VEGF_altsplice1 | AF486837.1 | Forward Primer | TGTGAATGCAGACCAAAGAAAGA | SEQ ID NO: 2215 |
| | | Probe | AGAGCAAGACAAGAAAATCCCTGTGGGC | SEQ ID NO: 2216 |
| | | Reverse Primer | GCTTTCTCCGCTCTGAGCAA | SEQ ID NO: 2217 |
| VEGF_altsplice2 | AF214570.1 | Forward Primer | AGCTTCCTACAGCACAACAAAT | SEQ ID NO: 2218 |
| | | Probe | TGTCTTGCTCTATCTTTCTTGGTCTGCA | SEQ ID NO: 2219 |
| | | Reverse Primer | CTCGGCTTGTCACATTTTTC | SEQ ID NO: 2220 |
| VEGFB | NM_003377.2 | Forward Primer | TGACGATGGCCTGGAGTGT | SEQ ID NO: 2221 |
| | | Probe | CTGGGCAGCACCAAGTCCGGA | SEQ ID NO: 2222 |
| | | Reverse Primer | GGTACCGGATCATGAGGATCTG | SEQ ID NO: 2223 |
| VEGFC | NM_005429.2 | Forward Primer | CCTCAGCAAGACGTTATTTGAAATT | SEQ ID NO: 2224 |
| | | Probe | CCTCTCTCTCAAGGCCCCAAACCAGT | SEQ ID NO: 2225 |
| | | Reverse Primer | AAGTGTGATTGGCAAACTGATTG | SEQ ID NO: 2226 |
| VIM | NM_003380.1 | Forward Primer | TGCCCTTAAAGGAACCAATGA | SEQ ID NO: 2227 |
| | | Probe | ATTTCACGCATCTGGCGTTCCA | SEQ ID NO: 2228 |
| | | Reverse Primer | GCTTCAACGGCAAAGTTCTCTT | SEQ ID NO: 2229 |
| WIF | NM_007191.2 | Forward Primer | TACAAGCTGAGTGCCCAGG | SEQ ID NO: 2230 |
| | | Probe | TACAAAAGCCTCCATTTCGGCACC | SEQ ID NO: 2231 |
| | | Reverse Primer | CACTCGCAGATGCGTCTTT | SEQ ID NO: 2232 |
| WISP1 | NM_003882.2 | Forward Primer | AGAGGCATCCATGAACTTCACA | SEQ ID NO: 2233 |
| | | Probe | CGGGCTGCATCAGCACACGC | SEQ ID NO: 2234 |
| | | Reverse Primer | CAAACTCCACAGTACTTGGGTTGA | SEQ ID NO: 2235 |
| Wnt-3a | NM_033131.2 | Forward Primer | ACAAAGCTACCAGGGAGTCG | SEQ ID NO: 2236 |
| | | Probe | TTTGTCCACGCCATTGCCTCAG | SEQ ID NO: 2237 |
| | | Reverse Primer | TGAGCGTGTCACTGCAAAG | SEQ ID NO: 2238 |
| Wnt-5a | NM_003392.2 | Forward Primer | GTATCAGGACCACATGCAGTACATC | SEQ ID NO: 2239 |
| | | Probe | TTGATGCCTGTCTTCGCGCCTTCT | SEQ ID NO: 2240 |
| | | Reverse Primer | TGTCGGAATTGATACTGGCATT | SEQ ID NO: 2241 |

TABLE A-continued

| Gene | Accession | Reagent | Sequence | Sequence ID Number |
|---|---|---|---|---|
| Wnt-5b | NM_032642.2 | Forward Primer | TGTCTTCAGGGTCTTGTCCA | SEQ ID NO: 2242 |
| | | Probe | TTCCGTAAGAGGCCTGGTGCTCTC | SEQ ID NO: 2243 |
| | | Reverse Primer | GTGCACGTGGATGAAAGAGT | SEQ ID NO: 2244 |
| WNT2 | NM_003391.1 | Forward Primer | CGGTGGAATCTGGCTCTG | SEQ ID NO: 2245 |
| | | Probe | CTCCCTCTGCTCTTGACCTGGCTC | SEQ ID NO: 2246 |
| | | Reverse Primer | CCATGAAGAGTTGACCTCGG | SEQ ID NO: 2247 |
| WWOX | NM_016373.1 | Forward Primer | ATCGCAGCTGGTGGGTGTA | SEQ ID NO: 2248 |
| | | Probe | CTGCTGTTTACCTTGGCGAGGCCTTT | SEQ ID NO: 2249 |
| | | Reverse Primer | AGCTCCCTGTTGCATGGACTT | SEQ ID NO: 2250 |
| XPA | NM_000380.2 | Forward Primer | GGGTAGAGGGAAAAGGGTTC | SEQ ID NO: 2251 |
| | | Probe | CAAAGGCTGAACTGGATTCTTAACCAAGA | SEQ ID NO: 2252 |
| | | Reverse Primer | TGCACCACCATTGCTATTATT | SEQ ID NO: 2253 |
| XPC | NM_004628.2 | Forward Primer | GATACATCGTCTGCGAGGAA | SEQ ID NO: 2254 |
| | | Probe | TTCAAAGACGTGCTCCTGACTGCC | SEQ ID NO: 2255 |
| | | Reverse Primer | CTTTCAATGACTGCCTGCTC | SEQ ID NO: 2256 |
| XRCC1 | NM_006297.1 | Forward Primer | GGAGATGAAGCCCCCAAG | SEQ ID NO: 2257 |
| | | Probe | AGAAGCAACCCCAGACCAAAACCA | SEQ ID NO: 2258 |
| | | Reverse Primer | GTCCAGCTGCCTGAGTGG | SEQ ID NO: 2259 |
| YB-1 | NM_004559.1 | Forward Primer | AGACTGTGGAGTTTGATGTTGTTGA | SEQ ID NO: 2260 |
| | | Probe | TTGCTGCCTCCGCACCCTTTTCT | SEQ ID NO: 2261 |
| | | Reverse Primer | GGAACACCACCAGGACCTGTAA | SEQ ID NO: 2262 |
| YWHAH | NM_003405.2 | Forward Primer | CATGGCCTCCGCTATGAA | SEQ ID NO: 2263 |
| | | Probe | AGGTTCATTCAGCTCTGTCACCGC | SEQ ID NO: 2264 |
| | | Reverse Primer | GGAGATTTCGATCTTCATTGGA | SEQ ID NO: 2265 |
| zbtb7 | NM_015898.2 | Forward Primer | CTGCGTTCACACCCCAGT | SEQ ID NO: 2266 |
| | | Probe | TCTCTCCAGAACAGCTCGCCCTGT | SEQ ID NO: 2267 |
| | | Reverse Primer | CTCAGCCACGACAGATGGT | SEQ ID NO: 2268 |
| ZG16 | NM_152338.1 | Forward Primer | TGCTGAGCCTCCTCTCCTT | SEQ ID NO: 2269 |
| | | Probe | TACTCCTCATCACAGTGCCCCTGC | SEQ ID NO: 2270 |
| | | Reverse Primer | GGATGGGGGTTAGTGATAAGG | SEQ ID NO: 2271 |

TABLE B

| Gene | Locus Link | Sequence | Sequence ID Number |
|---|---|---|---|
| A-Catenin | NM_001903.1 | CGTTCCGATCCTCTATACTGCATCCCAGGCATGCCTACAGCACCCTGATGTCGCAGCCTATAAGGCCAACAGGGACCT | SEQ ID NO: 2272 |
| ABCB1 | NM_000927.2 | AAACACCACTGGAGCATTGACTACCAGGCTCGCCAATGATGCTTCAAGTTAAAGGGGCTATAGGTTCCAGGCTTG | SEQ ID NO: 2273 |
| ABCC5 | NM_005688.1 | TGCAGACTGTACCATGCTGACCATTGCCATCGCCTGCACACGGTTCTAGGCTCCGATAGGATTATGGTGCTGGCC | SEQ ID NO: 2274 |
| ABCC6 | NM_001171.2 | GGATGAACCTGCTGCAGGAGGCTATCTCGGCAGAGGCTATCTGGGCAGCCCTGAGACGGTGCAGCTC | SEQ ID NO: 2275 |
| ACP1 | NM_004300.2 | GCTACCAAGTCCGTGCTGTTTGTGTCTGGGTAACATTGTCGATAGCATTGCAGAAGCAGTTTTC | SEQ ID NO: 2276 |
| ADAM10 | NM_001110.1 | CCCATCAACTTGTGCCAGTACAGGGTCTGTGCAGTGGAGTAGGCACTTCAGTGGTCGAACCATCACC | SEQ ID NO: 2277 |
| ADAM17 | NM_003183.3 | GAAGTGCCAGGAGGCGATTAATGCTACTTGCAAAGGCGTGTTCCTACTGCACAGGTATAGCAGTGAGTGCCCG | SEQ ID NO: 2278 |
| ADAMTS12 | NM_030955.2 | GGAGAAGGGTGGAGTGCAGACCCCAGATGGATTCTGACTGTGCGGCCATCCAGAGACCTGACCCTG | SEQ ID NO: 2279 |
| ADPRT | NM_001618.2 | TTGACAACCTGCTGGACATCGAGGTGGCCTACAGTCTGCTCAGGGGAGGGTCTGATGATAGCAGCAAGGATCCCAT | SEQ ID NO: 2280 |
| AGXT | NM_000030.1 | CTTTTCCCTCCAGTGCCACCTCCTGGAAACAGTCCACTTGGGCGCAAAACCCAGTGCCTCCAAAT | SEQ ID NO: 2281 |
| AKAP12 | NM_005100.2 | TAGAGAGCCCCTGACAATCCTGAGGCTTCATCAGAGACCATTTAACATTTCCTCTTTCCAAGACCAACC | SEQ ID NO: 2282 |
| AKT1 | NM_005163.1 | CGCTTCTATGGCGCTGAGATTGTGTCAGCCCTGGACTACCTGCCACTTCGGAGAAGAACGTGGTGTACCGGGA | SEQ ID NO: 2283 |
| AKT2 | NM_001626.2 | TCCTGCCACCCTTCAAACCTCCAGTCACGTCCGAGTCGACACAAGGTACTTCGATGATGAATTTACCGCC | SEQ ID NO: 2284 |
| AKT3 | NM_005465.1 | TTGTCTCTGCCTTGGACTATCTACATTCCGAAAGATTGTGTACCGGCTCTGATCTCAAGTGTGGAAGAATCTAATGCTGG | SEQ ID NO: 2285 |
| AL137428 | AL137428.1 | CAAGAGAGGCTCTACCCTGGGACTGGGAGAATTTCCAAGGCCACCTTTGAGGATCGCAGAGCTCATTT | SEQ ID NO: 2286 |
| ALCAM | NM_001627.1 | GAGGAATATGGAATCCAAGGGGGCCAGTTCCTGCCGTTCCTGCCGTCCTGCTTCTGCCTCTTGATCTCCGCCAC | SEQ ID NO: 2287 |
| ALDH1A1 | NM_000689.1 | GAAGGAGATAAGGAGGATGTTGACAAGGCAGTGAAGGCCGCAAGACAGGCTTTTCAGATTGGATCTCCGTGGCG | SEQ ID NO: 2288 |
| ALDOA | NM_000034.2 | GCCTGTACGTGCCAGCTCCCCGACTGCCAGAGCCTCAACTGTCTCTGCTTCGAGATCAAGTCCGATGA | SEQ ID NO: 2289 |
| AMFR | NM_001144.2 | GATGGTTCAGCTCTGCAAGGATCGATTTGAATATCTTTCTTCCGCCCACCACGCCGATGAGCAGCCACGGTCGA | SEQ ID NO: 2290 |
| ANGPT2 | NM_001147.1 | CCGTGAAAGCTGCTCTGTAAAAGCTGACACAGCCCTCCCCAAGTGAGCAGGAGCAGCTGTTCTTCCCACTGCAA | SEQ ID NO: 2291 |
| ANTXR1 | NM_032208.1 | CTCCAGGTGTACCTCCAACCCTAGCCTTCTCCCAAGCTGCCTACAACAGAGTCCCAGCCTTCTC | SEQ ID NO: 2292 |

TABLE B-continued

| Gene | Locus Link | Sequence | Sequence ID Number |
|---|---|---|---|
| ANXA1 | NM_000700.1 | GCCCCTATCCTACCTTCAATCCATCCTCGATGTCCGCTTGCATAAGGCCATAATGTTAAAGG | SEQ ID NO: 2293 |
| ANXA2 | NM_004039.1 | CAAGACACTAAGGGCGACTACCAGAAAGCGCTGCTGACCTGTGTGGAGATGACTGAAGCCCGACACG | SEQ ID NO: 2294 |
| ANXA5 | NM_001154.2 | GCTCAAGCCTGGAAAGATGACGTGGTGGGGACACTTCAGGTACTACCAGCCTGGATGTTGTGGTTCT | SEQ ID NO: 2295 |
| AP-1 (JUN official) | NM_002228.2 | GACTGCAAAGATGGAAACGACCTTCTATGACGATGCCTCCACGGGAGCCAATGTTCAGAAACAAATCGAGTGGGT | SEQ ID NO: 2296 |
| APC | NM_000038.1 | GGACACAGGAATGTTTCTCCATACAGGTTCACGGGAGCCAATGTTCAGAAACAAATCGAGTGGGT | SEQ ID NO: 2297 |
| APEX-1 | NM_001641.2 | GATGAAGCCTTTCGCAAGTTCCTGAGGGCCTGGCTTCCCGAAAGCCCCTTGTCGTGTGAGACCT | SEQ ID NO: 2298 |
| APG-1 | NM_014278.2 | ACCCCGGCCTGTATATCATTGGGATCAAGAACTCGAGACTTGGAAATGCAGCAAAGAGCCAGATAG | SEQ ID NO: 2299 |
| APN (ANPEP official) | NM_001150.1 | CCACCTTGGACCAAAGTAAAGCGTGGAATGTCGTACCGCCTCCCCACACGCTGAAACCCGATTCCTACCAGGTGACGCTGAGA | SEQ ID NO: 2300 |
| APOC1 | NM_001645.3 | GGAAACACACTGGAGGACAAGGCTCGGGAACTCATCAGCCGCATCAAACAGAGTGAACTTTCTGCCAAGATGCG | SEQ ID NO: 2301 |
| AREG | NM_001657.1 | TGTGAGTGAAATGCCTTCTAGTAGTGAACCGTCCTCGGGAGCCGACTATGACTACTCAGAGAGTATGATAACGAACCACAA | SEQ ID NO: 2302 |
| ARG | NM_005158.2 | CGCAGTGCAGCTGAGTATCTGCTCAGCAGTCTAATCAATGGCAGCTTCCTGTGCGAGAAAGTGAGAGTAGCCCTGGGCA | SEQ ID NO: 2303 |
| ARHF | NM_019034.2 | ACTGGCCCACTTAGTCCTCCAAGCTCCCAACCTGCTCTCCCTGTGCCTTCTACCAGCCTGTGGAGTTCAG | SEQ ID NO: 2304 |
| ATOH1 | NM_005172.1 | GCAGCCACCTGCAACTTTGCAGGCGAGAGAGCATCCCGTCTACCCGCCTGAGCTGTCCCTCCTGGA | SEQ ID NO: 2305 |
| ATP5A1 | NM_004046.3 | GATGCTGCCACTGCTACAGCATGGTTGCGTGCTGCTCTAACTGAGTTGCTGAAGCAAGGACA | SEQ ID NO: 2306 |
| ATP5E | NM_006886.2 | CCGCTTTCGCTACAGCATGGTGGCCTACTGGAGACAGGCTGGACTCAGCTACATCCGATACTCCCA | SEQ ID NO: 2307 |
| AURKB | NM_004217.1 | AGCTGCAGAAGAGCTGCACATTTGACGACATCATGGACAGCAACAGCCACGATCATGAGGAGTTGGCAGATGC | SEQ ID NO: 2308 |
| Axin 2 | NM_004655.2 | GGCTATGTCTTTGCACCAGCCAGCGCCAACGACGACAGTGAGATATCCAGTGATGCGCTGACGGAT | SEQ ID NO: 2309 |
| axin1 | NM_003502.2 | CCGTGTGACAGCATCGTTGTGGCGTACTACTTCTGCGGGAACCATCCCCCTACCGCCACCCTGGTGAG | SEQ ID NO: 2310 |
| B-Catenin | NM_001904.1 | GGCTCTTGTGCGTACTGTCCTTCGGGCGTGGTGACAGGGAAGACATCACTGAGCCTGCCATCTGTGCTCTTCGTCATCTGA | SEQ ID NO: 2311 |
| BAD | NM_032989.1 | GGGTCAGGTGCCTCGAGATCGGGCTTGGGCCCAGAGACATGTTCCAGATCCCAGAGTTTGAGCCGAGTGAGCAG | SEQ ID NO: 2312 |
| BAG1 | NM_004323.2 | CGTTGTCAGCACTTGGAATACAAGATGGTTGCCGGTCATGTTAATTGGAAAAAGAACAGTCCAGGAAGAGAGTTGAAC | SEQ ID NO: 2313 |

TABLE B-continued

| Gene | Locus Link | Sequence | Sequence ID Number |
|---|---|---|---|
| BAG2 | NM_004282.2 | CTAGGGGCAAAAAGCATGACTGCTTTTTCCTGTCTGGCATGGAATCACGCAGTCACCTTGGGCATTTAG | SEQ ID NO: 2314 |
| BAG3 | NM_004281.2 | GAAAGTAAGCCAGGCCCAGTTGGACCAGAACTCCCTCCTGGACACATTCCAATTCAAGTGATCCGCAAAGAGGT | SEQ ID NO: 2315 |
| Bak | NM_001188.1 | CCATTCCCACCATTCTACCTGAGGCCAGGACGTCTGGGGTGTGGGATTGTGGGTCTATGTTCCC | SEQ ID NO: 2316 |
| Bax | NM_004324.1 | CCGCCCGTGGACACAGAGACTCCCCCCGAGAGGTCTTTTTCCGAGTGGCAGCTGACATGTTTTCTGACGGCAA | SEQ ID NO: 2317 |
| BBC3 | NM_014417.1 | CCTGGGAGGGTCCTGTACAATCTCATCATGGGACTCCTGCCCTTACCCAGGGGCCACAGAGCCCCCGAGATGGAGCCCAATTAG | SEQ ID NO: 2318 |
| BCAS1 | NM_003657.1 | CCCCGAGACAACGAGATAAGTGCTGTTGCCGATGCCAACGGAAACGAAAGAATCTTGGGAAGAGGCCAAACCCGAG | SEQ ID NO: 2319 |
| Bcl2 | NM_000633.1 | CAGATGGACCTAGTACCCACTGAGATTTCCACGCCCAAGGACAGCCATGGGAAAAATGCCCTTAAATCATAGG | SEQ ID NO: 2320 |
| BCL2L10 | NM_020396.2 | GCTGGGATGGCTTTTGTCACTTCTTCAGGACCCCCTTTCCACTGGCTTTTTGGAGAAACAGCTGGTCCAGGC | SEQ ID NO: 2321 |
| BCL2L11 | NM_138621.1 | AATTACCAAGCAGCCGAAGACCCACGAATGGTTATCTTACGACTGTTACATTGTCCGCCTG | SEQ ID NO: 2322 |
| BCL2L12 | NM_138639.1 | AACCCACCCCTGTCTTGGAGCTCTCAAACTGAGGCTGCCACCCCTTCCCGTCAGCTGAG | SEQ ID NO: 2323 |
| Bclx | NM_001191.1 | CTTTTGTGGAACTCTATGGAACAATGCAGCAGCCAGGAGCCCAGGAACGCTTCAACCGCTG | SEQ ID NO: 2324 |
| BCRP | NM_004827.1 | TGTACTGGCGAAGAATATTTGGTAAAGCAGGGCATCATCGATCTCTCACCCTGGGGCTTGTGTGAAGAATCACGTGGC | SEQ ID NO: 2325 |
| BFGF | NM_007083.1 | CCAGGAAGAATGCTTAAGATGTGAGTGGATGGATCTCAATGACCTGGCGAAGACTGAAAATACAACTCCCATCACCA | SEQ ID NO: 2326 |
| BGN | NM_001711.3 | GAGCTCCGCAAGGATGACTTCAAGGGTCTTCAGCCACCTCCAGCCCCTCGTCCTGTGAACAACAAG | SEQ ID NO: 2327 |
| BID | NM_001196.2 | GGGACTGTGAGGTCAACAACGTTCCAGCCTTCAGGGATGAGTGCATCACAAACCTACTGGTGTTTGGCTTCC | SEQ ID NO: 2328 |
| BIK | NM_001197.3 | ATTCCTATGGCTCTGCAATTGTCAACTGTGCCTGGCCTGTGCCCAGGAAGAGCCATTCACTCCTGCC | SEQ ID NO: 2329 |
| BIN1 | NM_004305.1 | CCTGCAAAGGGAACAAGAGCCCTTCCCCTCCAGAATGGCTCCCCGCCACCCCGAGATCGAGTCAACCACG | SEQ ID NO: 2330 |
| BLMH | NM_000386.2 | GGTTGCTGCCTCCATCAAAGATGGAGGCTGTGTGTTTGGCTGTGATGTTGGAAAACACTTCAATAGCAAGCTGG | SEQ ID NO: 2331 |
| BMP2 | NM_001200.1 | ATGTGGACGCTCTTTCAATGACGTGTCCCCGCTGCTCTTAGACGGACTGCGGTCTCCTAAAGGTCGACCATGGT | SEQ ID NO: 2332 |
| BMP4 | NM_001202.2 | GGGCTAGCCATTGAGGTGACTCACCTTCACCATCAGACTCGGACCCACCAGGGCCAGCATGTCAGGATTAGC | SEQ ID NO: 2333 |
| BMP7 | NM_001719.1 | TCGTGGAACATGACAAGGAATTCTTCCACCCAAACGCTACCACCGCTGAGAGTTCCGTTTGATCTTTCCA | SEQ ID NO: 2334 |

TABLE B-continued

| Gene | Locus Link | Sequence | Sequence ID Number |
|---|---|---|---|
| BMPR1A | NM_004329.2 | TTGGTTCAGCGAACTATTGCCAAACAGATTGCCAAGTGTCCGGCAAGTTGGTAAAGGCCGATATGGAGA | SEQ ID NO: 2335 |
| BRAF | NM_004333.1 | CCTTCCGACCAGCAGATGAAGATCATCGAAATCAATTTGGGCAACGAGACCGATCCTCAGCTCCAATGTGCATATAAA | SEQ ID NO: 2336 |
| BRCA1 | NM_007295.1 | TCAGGGGCTAGAAATCTGTTGCTATGGGCCCTTCACCAACATGCCCACAGATCAACTGGAATGG | SEQ ID NO: 2337 |
| BRCA2 | NM_000059.1 | AGTTCGTGCTTTGCAAGATGGTGCAGAGCTTTATGGAGCAGTGAAGAATCAGCAGACCCAGCTTACCTT | SEQ ID NO: 2338 |
| BRK | NM_005975.1 | GTGCAGGAAAAGTTCACAAATGGAGTGTCTGCGTCCAATACACGCGTGTCTTCTCCTTACTCCATCGTGTGC | SEQ ID NO: 2339 |
| BTF3 | NM_001207.2 | CAGTGATCCACTTTAACAACCCTAAAGTTCAGGCATCTCTGCCAGCGAACATTTCACCATTACAGGCCATGCT | SEQ ID NO: 2340 |
| BTRC | NM_033637.2 | GTTGGGACACAGTTGGTCTGCAGTCGGCCCAGGACGGTCTACTCAGCACAACTGACTGCTTCA | SEQ ID NO: 2341 |
| BUB1 | NM_004336.1 | CCGAGGTTAATCCAGCACGTATGGGGCCAAGTGTAGGCTCCCAGCAGGAACTGAGAGCGCCATGTCTT | SEQ ID NO: 2342 |
| BUB1B | NM_001211.3 | TCAACAGAGGCTGAACCACTAGAAAGACTACAGTCCCGACAATTCCAAGCTCGAGTGTCTCGGCAAACTCTGTTG | SEQ ID NO: 2343 |
| BUB3 | NM_004725.1 | CTGAAGCAGATGGTTCATCATTTCCTGGGCTGTGTTAAACAAAGCGAGGTTAAGGTTAGACTCAACTGCTTCTGATGGCAAGCTTCAC | SEQ ID NO: 2344 |
| c-abl | NM_005157.2 | CCATCTCGCTGAGATACGAAGGGAGGGTGTACCATTACAGGATCAACACTGCTTCTGCGCTGTAAAGATGCTCAAGCCGAGGTCT | SEQ ID NO: 2345 |
| c-kit | NM_000222.1 | GAGGCAACTGCTTATGCTTAATTAAGTCAGATGCGGCCATGATGCGCCATGACTGTCGCTGTAAAGATGCTCAAGCCGAGTGCC | SEQ ID NO: 2346 |
| c-myb (MYB official) | NM_005375.1 | AACTCAGAACTTGGAAAATGCCCTTCTTTAACTTCACCAGACCACCAGAGCGGTACTGCTCAATGCAGAGAACCCG | SEQ ID NO: 2347 |
| c-Src | NM_005417.3 | TGAGGAGTGGTATTTTGGCAAGATCACCAGACGGAGTCAGAGCGTTACTGCTCAATGCAGAGAACCCGAGAG | SEQ ID NO: 2348 |
| C20 orf1 | NM_012112.2 | TCAGCTGTGAGCTGCCGATACCGCCCGGCAATGGGACCTGCTCTTAACCTCAAACCTAGGACCGT | SEQ ID NO: 2349 |
| C20ORF126 | NM_030815.2 | CCCAGCACTGCTCGTTACTGTCTGCCATCCATGGCTGTGAGGTCCCAGTATGAACTGCCGTGAAGTCAA | SEQ ID NO: 2350 |
| C8orf4 | NM_020130.2 | CTACGAGTCAGCCATCCATCCATGGCTACCACTTCGACACAGCCTCTCGTAAGAAGACCGTGGGCA | SEQ ID NO: 2351 |
| CA9 | NM_001216.1 | ATCCTAGCCCTGGTTTTGGCCTCCTTTTGCTGTCACCAGCGTCGCGTTCCTTGTGCAGATGAAGGCAG | SEQ ID NO: 2352 |
| Cad17 | NM_004063.2 | GAAGGCCAAGAACCGAGTCAAATTATATTCCAGTTTAAGGCAACATCCTCCTGCTGTGACTTTTGAACTAACTGGGGA | SEQ ID NO: 2353 |
| CALD1 | NM_004342.4 | CACTAAGGTTTGAGACAGTTCCAGAAAGAACCAAGCTCAAGACGCAGAGCTCAGTTGTAGAGGGCTAATTCGC | SEQ ID NO: 2354 |
| CAPG | NM_001747.1 | GATTGTCACTGATGGGAGGAGCCTGAGATGAATCCAGTGCTCTGGGCCCCAAGCCTGCTCTGAAGG | SEQ ID NO: 2355 |
| CAPN1 | NM_005186.2 | CAAGAAGCTGTACGAGCTCATCATCACCCGCTACTCGGAGCCGGTCGACTTTGACAATTTCGTTTGCTGC | SEQ ID NO: 2356 |
| CASP8 | NM_033357.1 | CCTCGGGGATACTGTCTGATCATCATCAACAATCACAATTTTGCAAAGCACGGAGAAAGTGCCCAAACTTC | SEQ ID NO: 2357 |

TABLE B-continued

| Gene | Locus Link | Sequence | Sequence ID Number |
|---|---|---|---|
| CASP9 | NM_001229.2 | TGAATGCCGTGGATTGCACGTGGCCTCTTGAGCAGTGGCTGTCCAGGGCTAGTGACTTGTGTCCCATGATCCCTGT | SEQ ID NO: 2358 |
| CAT | NM_001752.1 | ATCCATTCGATCTCACCAAGGTTTGCCTCCACAAGGACTACCCCTCTCATCCCAGTTGGTAAACTGTCTTAAACCGGA | SEQ ID NO: 2359 |
| CAV1 | NM_001753.3 | GTGGCTCAACATTGTGTTCCATTCAGCTGATCAGTGGGCCTCAAGGAGGGGCTGTAAAATGGAGGCCATTG | SEQ ID NO: 2360 |
| CBL | NM_005188.1 | TCATTCACAAACTGGCAGTTATATCTTCCGCTGAGCTGTACTCGTCTGGGTCAGTGGGCTATTGGGTATG | SEQ ID NO: 2361 |
| CCL20 | NM_004591.1 | CCATGTGCTGTACCAAGAGTTTGCTCCTCCTGGCTCTGCTCAGTGCTGCTACTCCACCTCTGCGCGC | SEQ ID NO: 2362 |
| CCL3 | NM_002983.1 | AGCAGACAGTGCTCAGTCCTTTCTTGGCTCTCCTGACACTCCGAGCCCACATTCCGTTCCTCAGAATCATGCAG | SEQ ID NO: 2363 |
| CCNA2 | NM_001237.2 | CCATACCTCAAGTATTTGCCATCAGTTATTGCTGGAGCTGCCTTTCATTAGCACTTCTACACAGTCACGGGACAAAGCT | SEQ ID NO: 2364 |
| CCNB1 | NM_031966.1 | TTTCAGTTGTTTGCAGGAGACCATGTACATGACTGTCTCCATTATTGATCGGTTCATGCAGAATAATTGTGCCCAAGAAGATG | SEQ ID NO: 2365 |
| CCNB2 | NM_004701.2 | AGGCTTCTGCAGGAGAGACTCTGCACATGTGCGTTGGCATTATGGATCGATTTTTACAGGTTCAGCCAGTTTCCC | SEQ ID NO: 2366 |
| CCND1 | NM_001758.1 | GCATGTTCGTGGCCTCTAAGATGAAGGAGACCATCCCCCTGACGGCCGAGAAGCTGTGCATCTACACCG | SEQ ID NO: 2367 |
| CCND3 | NM_001760.2 | CCTCTGTGCTACAGATTATACCTTTGCCATGTACCCGCCCATCCATGATCGGCCACGGCAGCATTGGGGCTGCAGTG | SEQ ID NO: 2368 |
| CCNE1 | NM_001238.1 | AAAGAAGATGATGACCGGGTTTACCCAAACTCAACGTGCCAAGCCTCGGATTATTGCACCATCCAAGAGGCTC | SEQ ID NO: 2369 |
| CCNE2 | NM_057749.1 | ATGCTGTGGCTCCTTCCTAACTGGGGCTTTCTTGACATGTAGGTTGCTTGGTAATAACCTTTTTGTATATCACAATTTGGGT | SEQ ID NO: 2370 |
| CCNE2 variant 1 | NM_057749var1 | GGTCACCAAGAAACATCAGTGATATGAAATTAGGAATTGTGGCCACCTGTATTATCTGGGGGATCAGTCCTTGCATTATCATTGAA | SEQ ID NO: 2371 |
| CCR7 | NM_001838.2 | GGATGACATGCCACTCAGCTCTTGGCTCCACTGGGATGGGAGGAGGACAAGGAAATGTCAGG | SEQ ID NO: 2372 |
| CD105 | NM_000118.1 | GCAGGTGTCAGCAAGTATGATCAGCAATGAGCGCGGTGGTCAATATCCGTCGAGCTCATCACCACCAGCGGAAAAA | SEQ ID NO: 2373 |
| CD134 (TNFRSF4 official) | NM_003327.1 | GCCCAGTGCGGAGAACAGGTCCAGCTTGATTCTGCGTCTGCACTTAAGCTGTTCTCCAGTGCGTGTGATT | SEQ ID NO: 2374 |
| CD18 | NM_000211.1 | CGTCAGGACCCCACCATGTCTGCCCATCACCGGGCCGAGACATGGCTTGGCCACAGCTCTTGAGGATGTCACCAATTAACC | SEQ ID NO: 2375 |
| CD24 | NM_013230.1 | TCCAACTAATGCCACCACCAAGGCGGCTGGTGGTGCCCAGTCAGTCTGCCGCCAGTCAGCAGCCAGTCTCTTCGTGGTCTCACTCTCTC | SEQ ID NO: 2376 |
| CD28 | NM_006139.1 | TGTGAAAGGAAACACCTTTGTCTGCACTCCCCTATTTCCCGGACCTTCTAAGCCCTTTGGGTGCT | SEQ ID NO: 2377 |
| CD31 | NM_000442.1 | TGTATTTCAAGACCTCTGTGCACTTATTATGAACCTGCCCTGCCTCCCAAGAACACAGCAATTCCTCAGGCTAA | SEQ ID NO: 2378 |

TABLE B-continued

| Gene | Locus Link | Sequence | Sequence ID Number |
|---|---|---|---|
| CD34 | NM_001773.1 | CCACTGCACACACCTCAGAGGCTGTTCTTGGGCCCTACACCTTGAGGAGGGCAGGTAAACTCCTG | SEQ ID NO: 2379 |
| CD3z | NM_000734.1 | AGATGAAGTGGAAGGCGCCTTTTCACCGCGCCATCCTGCAGGCACAGTTGCCGATTACAGAGGCA | SEQ ID NO: 2380 |
| CD44E | X55150 | ATCACCGACACAGACACAGAATCCCTGCTACCAATATGGACTCCAGTCATAGTACAACGCTTCAGCTACTGCAAATCCAAACACAGGT | SEQ ID NO: 2381 |
| CD44s | M59040.1 | GACGAAGACAGTCCCTGGATCACCGACAGCACAGAGAATCCCTGCTACCAGAGACCAAGACACATTCCACCCCAGT | SEQ ID NO: 2382 |
| CD44v3 | AJ251595v3 | CACACAAAACAGAACCAGGACTGGACCAGTGGACCAAGCCATTCAAATCCGAAGTGCTACTTCAG | SEQ ID NO: 2383 |
| CD44v6 | AJ251595v6 | CTCATACCAGCCATCCAATGCAAGGAAGGACAACACCAAGCCCAGAGGACAGTTCCTGGACTGATTTCTTCAACCCAA | SEQ ID NO: 2384 |
| CD68 | NM_001251.1 | TGGTTCCCAGCCCTGTGTCCACCTCCAAGCCCCAGATTCAGATTCGAGTTCATGTACACAACCCAGGGTGGAGGAG | SEQ ID NO: 2385 |
| CD80 | NM_005191.2 | TTCAGTTGCTTTGCAGGAAGTGTCTAGAGGAATATGTGGGCACAGAAGTAGCTCTGGTGACCTTGATCAA | SEQ ID NO: 2386 |
| CD82 | NM_022231.2 | GTGCAGGCTCAGGTGAAGTGCTGCGGCTGGGTCAGCTTCTACAACTGGACACACGCTGAGCTCATGAATCGCCCTGAGGTC | SEQ ID NO: 2387 |
| CD8A | NM_171827.1 | AGGGTGAGGTGCTTGAGTCTCCAACGGCAAGGAACAAGTACTTCTTGATACCTGGGATACTGTGCCC | SEQ ID NO: 2388 |
| CD9 | NM_001769.1 | GGGCGTGGACACAGTTTATCTCAGAAGACATCTGCCCCAAGAAGACGTACTCGAAACCTTCACCGTG | SEQ ID NO: 2389 |
| CDC2 | NM_001786.2 | GAGAGCGACGCGGTTGTTGTAGCTGCCGCGGAATAATAAGCCGGATCTACCATAC | SEQ ID NO: 2390 |
| CDC20 | NM_001255.1 | TGGATTGGAGTTCTGGACTACGCCTCTTCTGTCCCTGTTAGACTGTGCACTGGTGTACCTGTGGAGTGCAAGC | SEQ ID NO: 2391 |
| cdc25A | NM_001789.1 | TCTTGCTGGCTACGCCTTCTTCTGTCCCTGTTAGACGTTCTCCATATCAGAACTGTGCCACAATGCAG | SEQ ID NO: 2392 |
| CDC25B | NM_021874.1 | AAACGAGCAGTTTGCCATCAGACGCTTCCAGTCTATGCCGTCAGAGAGCTGTCTGGGCCACAGCCCCGTGCTTCGGAACATCACCAAC | SEQ ID NO: 2393 |
| CDC25C | NM_001790.2 | GGTGAGCAGAAGTGGCCTATATCGCTCTCCCCGTCGATGCCAGAGAACTTGAACAGGCCAAGACTGAAG | SEQ ID NO: 2394 |
| CDC4 | NM_018315.2 | GCAGTCCGCTGTGTTCAATATGATGCAGGAAGGGTTGTTAGTGGAGCAATATGATTTTATGGTAAAGGTGTGGGATCC | SEQ ID NO: 2395 |
| CDC42 | NM_001791.2 | TCCAGAGACTGCTGAAAAGTGGCCCGTGACCTGAAGTGTCAAGTATGTGGAGTGTTCTGCACTTACACA | SEQ ID NO: 2396 |
| CDC42BPA | NM_003607.2 | GAGCTGAAAGACGCACACTGTCAGAGGAAACTTGGCCATGCAGGAGAATTCATGAGACATCAATGAGCGGC | SEQ ID NO: 2397 |
| CDC6 | NM_001254.2 | GCAACACTCCCCATTTACCTCCCTTGTTCTCCACCAAAGCAAGAAAGAATGGTCCCCTCA | SEQ ID NO: 2398 |
| CDCA7 v2 | NM_145810.1 | AAGACCGTGGATGGCTACATGAATGAAGATGAAGAAGATGACCTGCCCAGAAGACCTCGCTCCAGATCATCCGTGACCCT | SEQ ID NO: 2399 |
| CDH1 | NM_004360.2 | TGAGTGTCCCCCGGTATCTTCCCCGCCTGCCAATCCGATGAAATTTATTGATGAAAATCTGAAAGCGGCTG | SEQ ID NO: 2400 |
| CDH11 | NM_001797.2 | GTCGGCAGAAGCAGGACTTGTACCTTCGCCATGATGATCAGCGATGCCGATCCCGCCCATGAGTAG | SEQ ID NO: 2401 |

TABLE B-continued

| Gene | Locus Link | Sequence | Sequence ID Number |
|---|---|---|---|
| CDH3 | NM_001793.3 | ACCCATGTACCGTCCTCGGCCAGCCAACCCAGATGAAATCGGCCAACTTTATAATTGAGAACCTGAAGGCGG | SEQ ID NO: 2402 |
| CDK2 | NM_001798.2 | AATGCTGCACTACGACCCTAACAAGCGGATTTCGGCCAAGGCAGCCCTGGCTTCACCCTTTCTTCCAGGATGTGACCAA | SEQ ID NO: 2403 |
| CDX1 | NM_001804.1 | AGCAACACCAGCCTCCTGGCCACCTCCTCCAATGCTTGAAAGAGGAGTTTCTGCCATAGCCC | SEQ ID NO: 2404 |
| Cdx2 | NM_001265.2 | GGGCAGGCAAGGTTTACACTGCGGAAGCCAAAGGCAGTAAGATAGAAAAGCTGGACTGACCAAAGAC | SEQ ID NO: 2405 |
| CEACAM1 | NM_001712.2 | ACTTGCCTGTTCAGAGCACTCATTCCTTCCCACCCCAGTCCTGTCCTATCACTCTAATTCGGATTTGCCA | SEQ ID NO: 2406 |
| CEACAM6 | NM_002483.2 | CACAGCCTCACTTCTACCTTCTGGAACCTGCTGCCAAGCTCACTATTGAATCACGCCATTCAA | SEQ ID NO: 2407 |
| CEBPB | NM_005194.2 | GCAACCCACGTGTAACTGTCAGCCGGGCCCTGAGTAATGCTTAAAGATGTTCCTACGGGCTTGT | SEQ ID NO: 2408 |
| CEGP1 | NM_020974.1 | TGACAATCAGCACACCTGCATTCACCGCTCGGAAGAGGGCCTGAGCTGCATGAATAAGGATCACGGCTGTAGTCACA | SEQ ID NO: 2409 |
| CENPA | NM_001809.2 | TAAATTCACTCGTGGTGTGGACTTCAATTGGCAAGCCCAGGCCCTATTGGCCCTACAAGAGGC | SEQ ID NO: 2410 |
| CENPE | NM_001813.1 | GGATGCTGGTGACCTCTTCTTCCCTCCACGTTGCAACAGGAATTAAAGCTAAAAGAAAACGAAGAGTTACTTGGTGCCTTGGC | SEQ ID NO: 2411 |
| CENPF | NM_016343.2 | CTCCCGTCAACAGCGTTCTTCTTCCAAACACTGGACCGAGTGCATCCAGATGAAGGCCAGACTCACCC | SEQ ID NO: 2412 |
| CES2 | NM_003869.4 | ACTTTGCGAGAAATGGGAACCCAATGGCGAGGGGTCTGCCACACTGGCCGCTGTTCGACCAGGAGGAGCAATACCTG | SEQ ID NO: 2413 |
| CGA (CHGA official) | NM_001275.2 | CTGAAGGAGCTTCCAAGACCTGCTTCTCCAAGGCGCCAAGGAGAGGGCCACATCAGCAGAAGAAACACAGCGTTTG | SEQ ID NO: 2414 |
| CGB | NM_000737.2 | CCACCATAGGCAGAGGCAGGCCTTCCTACACCCCTACTCCCTGTGCCTCCAGCCTCGACTAGTCCCTAGCACTCGACGACT | SEQ ID NO: 2415 |
| CHAF1B | NM_005441.1 | GAGGCCAGTGTGGAAACAGTGTGGAGCTGATGAGTCTGCTGCCCTGGTGTTGCTGTGTGCTGGCCTCGGA | SEQ ID NO: 2416 |
| CHD2 | NM_001271.1 | CTCTGTGTGCGAGGCTGTCAGCCACACTAGGTATCAGGGATCCAGATGGTACCAGCCCACAGTCTTACC | SEQ ID NO: 2417 |
| CHFR | NM_018223.1 | AAGGAAGTGGTCCCTGTGGCAAGTGATGAAGTCTCCAGCTTTGCTCAGCTCTCCCAGACAGAAAGACTGCGTC | SEQ ID NO: 2418 |
| Chk1 | NM_001274.1 | GATAAATTGGTACAAGGGATCAGCTTTTCCCAGCCCACACATGTCCTGATCATATGCTTTTGAATAGTCAGTTACTTGGCACCC | SEQ ID NO: 2419 |
| Chk2 | NM_007194.1 | ATGTGGAACCCCCACCTACTTGGCGCCTGAAGTTCTTGTTTCTGTTGGGACTGCTGGGTATAACCGTGCTGTGGACTG | SEQ ID NO: 2420 |
| CIAP1 | NM_001166.2 | TGCCTGCTGGGAAGCTCAGTAACTGGGAACCCAAAGATGATGCTATGTCAGAACACCGAGGCCATTTTCC | SEQ ID NO: 2421 |
| cIAP2 | NM_001165.2 | GGATATTTCCTGGCTCTTATTCAAACTCCCATCAAATCCTGTAAACTCCAGAGCCAAATCAAGATTTTTCTGCCTTGATGAGAAG | SEQ ID NO: 2422 |
| CKS1B | NM_001826.1 | GGTCCCTAAACCCATCTGATGTCTGAATCGATGGAGAATCTTGGCGTTCAGCAGAGTCAGGATGGTCCATTA | SEQ ID NO: 2423 |

TABLE B-continued

| Gene | Locus Link | Sequence | Sequence ID Number |
|---|---|---|---|
| CKS2 | NM_001827.1 | GGCTGGACGTGGTTTTGTCTGCTGCGCCCGCTCTTCGCGCTCTCGTTCATTTTCTGCAGCG | SEQ ID NO: 2424 |
| Claudin 4 | NM_001305.2 | GGCTGCTTTGCTGCAACTGTCCACCCCGCACAGACAAGCCTTACTCCGCCAAGTATTCTGCTGCCGCTCTG | SEQ ID NO: 2425 |
| CLDN1 | NM_021101.3 | TCTGGGAGGTGCCCTACTTTGCTGTTCCTGTCCCGAAAAACAACCTCTTACCCAAGGCCCTATCCA | SEQ ID NO: 2426 |
| CLDN7 | NM_001307.3 | GGTCTGCCCTAGTCATCCTGGGAGGTGCACTGTCTTCCTGTTCCTGCTCCTGGGAATGAGAGCAAGGCTGGGTAC | SEQ ID NO: 2427 |
| CLIC1 | NM_001288.3 | CGGTACTTGAGCAATGCCTACGCCCGGGAAGAATTCGCTTCCACCTGTCCAGATGATGAGAGATCGA | SEQ ID NO: 2428 |
| CLTC | NM_004859.1 | ACCGTATGGACAGCCACAGCCTGGCTTTGGGTACAGCATGTGAGATGAAGCGCTGATCCTGTAGTCA | SEQ ID NO: 2429 |
| CLU | NM_001831.1 | CCCCAGGATACCTACCACTGCCCTTCAGCCTGCCCACCGGAGGCCTCACTTCTTCTTTCCCAAGTCCCGCA | SEQ ID NO: 2430 |
| cMet | NM_000245.1 | GACATTTCCAGTCCTGCAGTCAATGCCTCTGCCCCCACCCTTTGTTCAGTGTGGCTGGCTGCCACGACAAATGTGCGATCGGAG | SEQ ID NO: 2431 |
| cMYC | NM_002467.1 | TCCCTCCACTCGGAAGGACTATCCTGCTGCCAAGAGGGTCAAGTTGGACAGTGCCTGAGACGATCAGCAGACAACCG | SEQ ID NO: 2432 |
| CNN | NM_001299.2 | TCCACCCTCCTGGCTTTGGCCAGCATGGCCGAAGACCGAAAGGAAACAAGGTGAACGTGGGAGTGA | SEQ ID NO: 2433 |
| COL1A1 | NM_000088.2 | GTGGCCATCGAGCTTCCTGCCGCCTGATGTCCAAGGACAGAAGACACGTCTGGCTAGGAGAACTATCAATGCTGGCAGCCAGTG | SEQ ID NO: 2434 |
| COL1A2 | NM_000089.2 | CAGCCAAGAACTGGTATAGAGGACTTCAAGAGACTCCAGAAGCGCTATTCTCACAGGTTGCAGCTCTTCATCAGCACTTGTAATGGGGAG | SEQ ID NO: 2435 |
| COPS3 | NM_003653.2 | ATGCCCAGTGTTCCTGACTTGCAAGCACTCTATGGTGACATCTACGGCTGATCTGTGAGCTGTATCCTGCCCTTCGTAGAAAAGCCTCGGC | SEQ ID NO: 2436 |
| COX2 | NM_000963.1 | TCTGCAGAGTTGGAAGCACTTCACCATTTCCGACGACATCTACGGCTCAACATTTTTTGTAGCCACAGGCTTCCACGGAC | SEQ ID NO: 2437 |
| COX3 | MITO_COX3 | TCGAGTCTCCCTTCACCATTTCCGACGACGTACGGCTTCCACAAATCGAAAGGAGAGGAGCATCTTGGCATCCTTTCACGTC | SEQ ID NO: 2438 |
| CP | NM_000096.1 | CGTGAGTACACAGATGCCTCCTTCACAAATCGAAAGGAGAGGAGCATCTTGGCATCCTGG | SEQ ID NO: 2439 |
| CRBP | NM_002899.2 | TGGTCTGCAAGCAAGTATTCAAGAAGTGCAGTGAGGCCCAAGCAGACAACCTTGTCCCAACCAATCAGC | SEQ ID NO: 2440 |
| CREBBP | NM_004380.1 | TGGGAAGCAGCTGTGTACCATTCCTCCGCGATGCTGCCTACTACAGCTATCAGAATAGGTATCATTTCTGTGAGAAGTGTTTC | SEQ ID NO: 2441 |
| CRIP2 | NM_001312.1 | GTGCTACGCCACCCTGTTCGGACCCAAAGGCGTGAACATCGGGGCGCCGAGGCTCCTACATCTACGAGAAGCCCCTG | SEQ ID NO: 2442 |
| cripto (TDGF1 official) | NM_003212.1 | GGGTCTGTGCCCATGACACCTGGCTGCCCAAGAAGTGTTCCCTGTGTAAATGCTGGCACGGTCA | SEQ ID NO: 2443 |
| CRK(a) | NM_016823.2 | CTCCCTAACCTGCAGAATGGGCCCATATATGCCAGGGTTATCCAGAAGCGAGTCCCCAATGCCTACGACAAGACA | SEQ ID NO: 2444 |

TABLE B-continued

| Gene | Locus Link | Sequence | Sequence ID Number |
|---|---|---|---|
| CRMP1 | NM_001313.1 | AAGGTTTTTGGATTGCAAGGGTTTCCAGGGCATGTATGACGGTCCTGTGTACCAGCTACACCC | SEQ ID NO: 2445 |
| CRYAB | NM_001885.1 | GATGTGATTGAGGTGCATGGAAAACATGAAGAGCGCCAGGATGAACATGGTTTCATCTCCAGGGAGTTC | SEQ ID NO: 2446 |
| CSEL1 | NM_001316.2 | TTACGCAGCTCATGCTCTTGAACGGCTCTTTACTATGCGAGGGCCTAACAATGCCACTCTCTTTACAGCTGC | SEQ ID NO: 2447 |
| CSF1 | NM_000757.3 | TGCAGCGGCTGATTGCAGATGAGACCTCGTGCCAAATTACATTGAGTTTGTAGACCAGAACAGTTG | SEQ ID NO: 2448 |
| CSK (SRC) | NM_004383.1 | CCTGAACATGAAGGAGCTGAAGCTGCTGCAGACCATCGGGAAGGGGAGTTCGGAGACGTGATG | SEQ ID NO: 2449 |
| CTAG1B | NM_001327.1 | GCTCTCCATCAGCTCCTGTCTCCGGGTGACAGTGCTTCTGCAGGCTGACAGCCAGTGATGATCACGCAGTGCTTTCTGCCCGTGTT | SEQ ID NO: 2450 |
| CTGF | NM_001901.1 | GAGTTCAAGTGCCCTGACGGCCAGGTCATGAAGAAGACATGATGTTCATCAAGACCCTGTGCCTGCCATTACAACT | SEQ ID NO: 2451 |
| CTHRC1 | NM_138455.2 | GCTCACTTCGGCTAAAATGCAGAAATGCATGTCTCAGCGTTGGTATTTCACATTCAATGAGCTGA | SEQ ID NO: 2452 |
| CTLA4 | NM_005214.2 | CACTGAGGTTCCGGGTGACAGTGCTTCTCGGCAGGCTGACAGCCAGTGAAGTCTGTGGCAACCTAC | SEQ ID NO: 2453 |
| CTNNBIP1 | NM_020248.2 | GTTTTCCAGGTCGGAGAATCGGAAGAACCGAGGCAGTAGCTGCAAAGCCCTTGGAACACCCTGGATGCT | SEQ ID NO: 2454 |
| CTSB | NM_001908.1 | GGGCCAGAGATCTACAAAAAACGGCCCCCGTGGAGGAGCTTTCTCTGTGTATTCGGACTTCCTGC | SEQ ID NO: 2455 |
| CTSD | NM_001909.1 | GTACATGATCCCCCTGTGTGAGAAGGTGTCCACCCTGCCCGCGGATCACACTCGAGAGCTGGGAGGCAAAGGCTACAAGCTGTCCC | SEQ ID NO: 2456 |
| CTSH | NM_004390.1 | GCAAGTTCCAACCTGGAGAAGGCCATCGCTTGTCAAGGATGTAGCCAACATCACAATCTATGACGAGGAAGCGATG | SEQ ID NO: 2457 |
| CTSL | NM_001912.1 | GGGAGGCTTATCTCACTGAGTGAGCAGAGAATCTGGTAGACTGCTCTCGGGCCTCAAGGCAATCAGGGCTGCAATGTATGG | SEQ ID NO: 2458 |
| CTSL2 | NM_001333.2 | TGTCTCACTGAGCGAGCAGAATCTGGTGGACTGTTCGCGTCCTGCTTTGTGGCTGCTCTTGATAAGGCTTGTGTGC | SEQ ID NO: 2459 |
| CUL1 | NM_003592.2 | ATGCCCTGGTAATGTCTGCATTCAACAATGACGCTGGTTTGTGACCTATGCTGCAGAACTCGCCTCCATCTGGATATGG | SEQ ID NO: 2460 |
| CUL4A | NM_003589.1 | AAGCATCTTCCTGTTCTTGGACCGACCACCTACTTCTGAAAAGCCAATGTTGCCAGAGCCAACGTCAAGCATCTCAAAGATT | SEQ ID NO: 2461 |
| CXCL12 | NM_000609.3 | GAGCTACAGATGCCCATGCCGATTCTTCGAAAAGCCAATGTTGCCAGAGCCAACGTCAAGCATCTCAAA | SEQ ID NO: 2462 |
| CXCR4 | NM_003467.1 | TGACCGCTTCTACCCCAATGACTTGTGGGTGGTTGTGTTCCAGTTTCAGCACACATGGTTGGCCTTATCCT | SEQ ID NO: 2463 |
| CYBA | NM_000101.1 | GGTGCCTACTCCATTGTGGCGGCGTGTTTGTGTGCCGTCTGGAGTACCCCGGGGAAGAGGAAGAAGGGCTCCAC | SEQ ID NO: 2464 |
| CYP1B1 | NM_000104.2 | CCAGCTTTGTGCCTGTCACTATTCCTCATGCCAACACTCTCTGTCTTGGCTACCACATTCCC | SEQ ID NO: 2465 |
| CYP2C8 | NM_000770.2 | CCGTGTTCAAGAGGAAGCTCACTGCCCTTGTGACGGAGAGTTGAGAAAAACCAAGGCTTCACCCTGTGATCCCACT | SEQ ID NO: 2466 |

TABLE B-continued

| Gene | Locus Link | Sequence | Sequence ID Number |
|---|---|---|---|
| CYP3A4 | NM_017460.3 | AGAACAAGGACAACATAGATCCTTACATATACACACCCTTTGGAAGTGGACCCAGAAACTGCATTGGCATGAGGTTTGC | SEQ ID NO: 2467 |
| CYR61 | NM_001554.3 | TGCTCATTCTTGAGGAGCATTAAGGTATTTCGAAACTGCCAAGGGTGCTGTGTGCAGGACACTAATGCAGCCAC | SEQ ID NO: 2468 |
| DAPK1 | NM_004938.1 | CGCTGACATCATGAATGTTCCTCGACCGGCTGGAGGCGAGTTTGGATATGACAAAGACACATCGTTGCTGAAAGAGA | SEQ ID NO: 2469 |
| DCC | NM_005215.1 | AAATGTCCTCCTCGACTGCTCCGCGGAGTCCGACCGAGGAGTTCCAGTGATCAAGTCAAGTGGAAGAAAGATGGCATTCA | SEQ ID NO: 2470 |
| DCC_exons18-23 | X76132_18-23 | GGTCACCGTTGGTGTCATCACAGTGCTGGTAGTGTCATCGTGGCTGTGATTTGCACCCGACGCTC | SEQ ID NO: 2471 |
| DCC_exons6-7 | X76132_6-7 | ATGGAGATGTGGTCATTCCTAGTGATTATTTTCAGATAGTGGGAGGAAGCAACTTACGGATACTTGGGGTGGTG | SEQ ID NO: 2472 |
| DCK | NM_000788.1 | GCCGCCACAAGACTAAGGAATGGCCACCCCGCCCAAGAGAACTGCCCGTCTTTCTCAGCCAGCTCTGAGGGGACCCGCATCAAGAGAAATCTCCATCGAAGGGAACATCG | SEQ ID NO: 2473 |
| DDB1 | NM_001923.2 | TGCGGATCATCCGGAATGGAATTGGAATCCACGAGCATGCCAGCATTGACTTACCAGGCATCAAAGGA | SEQ ID NO: 2474 |
| DET1 | NM_017996.2 | CTTGTGGAGATCACCCAATCAGGTTCTATGCCCGGGACTCGGGCTGCTCAAGTTTGAGATTCCAGGCGGG | SEQ ID NO: 2475 |
| DHFR | NM_000791.2 | TTGCTATAACTAAGTGCTTCTCCAAGACCCCAACTGAGTCGAGTGCTACAGTGAGTGAGTTGCCATTCCAC | SEQ ID NO: 2476 |
| DHPS | NM_013407.1 | GGGAACGGGATCAATAGAATCGAAAACCTGCTGTGTGCCCAATGAGAATTACTGCAAGTTTGAGGACTGGCTGATGC | SEQ ID NO: 2477 |
| DIABLO | NM_019887.1 | CACAATGGCGGCTCTGAAGAGTTGGCTGTCGCGCAGCGTAACTTCATTCTTCAGGTACAGAGACAGTGTTTGTGT | SEQ ID NO: 2478 |
| DIAPH1 | NM_005219.2 | CAAGCAGTCAAGGAGGAGAACCAGAAGCGCGCGGGAGAACAGAAGAAGAAAAGATGAGGCGAGCAAAACT | SEQ ID NO: 2479 |
| DICER1 | NM_177438.1 | TCCAATTCCAGCATCACTGTGGAGAAAAGCTGTTTGTCTCCCCAGCATACTTTATCGCCTTCACTGCC | SEQ ID NO: 2480 |
| DKK1 | NM_012242.1 | TGACAACTACCAGCCGAGGAGATGAGCCTTGTGCCACTGAGAGTGCGGCACTGACTGAGTACTGCGCTAGTCCC | SEQ ID NO: 2481 |
| DLC1 | NM_006094.3 | GATTCAGACGAGGATGAGCCTTGTGCCATCAGTGCCAGATCAGTGGCAAATGACTTTCCAAAGGACAGCAAGAGGTG | SEQ ID NO: 2482 |
| DPYD | NM_000110.2 | AGGACCGCAAGGAGGGTTTGTCACTGGTTACACTGCCAGATCTGGACATGTAGGCACTGCCATGGCCTCCCATGTGCTCAGTAAGGACTTCGGCGGGACATC | SEQ ID NO: 2483 |
| DR4 | NM_003844.1 | TGCACAGAGGGTGTGGGTTACACCAATGCTTCCAACAATTGTTTGTTGCTTGTACTCCCATGTACAGCTTGTAAATCAGATGAAGA | SEQ ID NO: 2484 |
| DR5 | NM_003842.2 | CTCTGAGACAGTGCTTCGATGATGACTTTGCAGACTTTGCCCTTTGACTCCTCGGGAGCCGCTCATGAGGAAGTTGGGCCTCATGG | SEQ ID NO: 2485 |
| DRG1 | NM_004147.3 | CCTGGATCTCCCAGGTATCATTGAAGGTGCCAAGGATGGGAAAGGTAGAGGTCGTCAAGTCATTGCA | SEQ ID NO: 2486 |
| DSP | NM_004415.1 | TGGCACTACTGCATGATTGACATAGAGAAGATCAGGGCCATGACAATCGCCAAGCTGAAAACAATGCGGCAGG | SEQ ID NO: 2487 |

TABLE B-continued

| Gene | Locus Link | Sequence | Sequence ID Number |
|---|---|---|---|
| DTYMK | NM_012145.1 | AAATCGCTGGGAACAAGTGCCGTTAATTAAGGAAAAGTTGAGCCAGGGCGTGACCCTCGTCGTGGACAGATACGCATT | SEQ ID NO: 2488 |
| DUSP1 | NM_004417.2 | AGACATCAGCTCCTGTTCAACGAGGCCATTGACTTCATAGACTTCCAAGACATCTGAGGAAGGGTGTTTGTC | SEQ ID NO: 2489 |
| DUSP2 | NM_004418.2 | TATCCCTGTGGAGGACAAACCAGATGTGGAGATCAGTGCCTGGTTCCAAGAGGCCATAGGCTTCATTGACTGGGTG | SEQ ID NO: 2490 |
| DUT | NM_001948.2 | ACACATGGAGTGCTTCTGGAACTATCAGCCCACTTGACCACCAGTTTGTGGAAGCACAGCAAGAG | SEQ ID NO: 2491 |
| DYRK1B | NM_004714.1 | AGCATGACACGGAGATGAAGTACTATATAGTACACCTGAAGCGGCACTTCATGTTCCGGACCACCTGTGCCTGGTATT | SEQ ID NO: 2492 |
| E2F1 | NM_005225.1 | ACTCCCTCTACCCTTGAGCAAGGACGGGGTCCCTGAGCTGTTCTTTCTGCCCCATACTGAAGGAACTGAGGCCTG | SEQ ID NO: 2493 |
| EDN1 endothelin | NM_001955.1 | TGCCACCTGGACATCATTGGGTCAACACTCCCGAGCACGTTGTCTCCGTATGGACTTGGAAGCCCTAGGTCCA | SEQ ID NO: 2494 |
| EFNA1 | NM_004428.2 | TACATCTCCAAACCCATCCACCAGACCGCTGCTGCTTGAAGAGCCGCTGCTCCACTGGAAGTGTCTGAGGATGAAGGTGTTCGTCTGCTG | SEQ ID NO: 2495 |
| EFNA3 | NM_004952.3 | ACTACATCTCCACGCCCATCCACACCTGCAACCCCAAGTTCCTGAGAGTCCTGAGGCTTGGTGATCTATCC | SEQ ID NO: 2496 |
| EFNB1 | NM_004429.3 | GGAGCCCGTATCCTGCAGAGCTCCCTGAAGGCCCTACTACGAGAAGGTCAGCGGGGACT | SEQ ID NO: 2497 |
| EFNB2 | NM_004093.2 | TGACATTTATCATCCCGAAGGAGATGAGTTCGAGTTTCTGGAGAAAGCATCAAAACTGCCGAGGAATCTCAAC | SEQ ID NO: 2498 |
| EFP | NM_005082.2 | TTGAACAGAGCCTGACCAAGAGGGATGAGTTCCAGCAGCTGCCCAAAAGTGTGATCCAAGCTGTCCCAATACA | SEQ ID NO: 2499 |
| EGFR | NM_005228.1 | TGTCGATGGACTTCCAGAACCACCTGGGCAGCAGCTGCCCAAAAGTGTCATTGTACGCTCATGTTGAT | SEQ ID NO: 2500 |
| EGLN1 | NM_022051.1 | TCAATGCCGGACGAAAGCCATGGTTGCTTGTTATCCGGCAATGGAACGGGTTATGTACGTCATGTTGATAATCCAAA | SEQ ID NO: 2501 |
| EGLN3 | NM_022073.2 | GCTGGTCCTCTACTGCGGAGCCGGCTGGCAAATACTCAAGGAGAGGTCTAAGGCAATGGTGG | SEQ ID NO: 2502 |
| EGR1 | NM_001964.2 | GTCCCCGCTGCAGATCTCTGACCCGTTCGACCCCTCGCCCACCATGGACAACTACCCTAAGCTGGAG | SEQ ID NO: 2503 |
| EGR3 | NM_004430.2 | CCATGTGGATGAATGAGGTGTCTCCTTTCCATACCCAGTCTCACCTTCTCCCCACCCTCACCTCTTCTCAGGCA | SEQ ID NO: 2504 |
| EI24 | NM_004879.2 | AAAGTGGTGAATGCCATTTGTTTCAGGATATAGCTGACCTGGCATTTGAGGTATCAGGAGGAAGCCTCAC | SEQ ID NO: 2505 |
| EIF4E | NM_001968.1 | GATCTAAGATGGCGACTGTCGAACCAGAAACCACCCTACTCCTAATCCCCGACTACAGAAGAGGAGAAAACGAATCTAA | SEQ ID NO: 2506 |
| EIF4EL3 | NM_004846.1 | AAGCCCGGGTTGAATGCCATGACCTCTCCCTCTCGATGGCACCATCATTGAAGCTGGCGTCA | SEQ ID NO: 2507 |

TABLE B-continued

| Gene | Locus Link | Sequence | Sequence ID Number |
|---|---|---|---|
| ELAVL1 | NM_001419.2 | GACAGGAGGCCTCTATCCTGTCCCTCCACCCTCCACCTCAATCCCTCCATCTTCCCAGACCTACCTCAC | SEQ ID NO: 2508 |
| EMP1 | NM_001423.1 | GCTAGTACTTTGATGCTCCCTTGATGGGGTCTCCCTGCAGAGAGCCTCCCTGCAGCCACCAGACTTGGCCTTCCAGCTGTTC | SEQ ID NO: 2509 |
| EMR3 | NM_032571.2 | TGGCCTACCTCTTCACCATCATCAACAGCCTTCCAAGGCTTCTTCATCTTCTTGGTCTACTGCCTCCTCA | SEQ ID NO: 2510 |
| EMS1 | NM_005231.2 | GGCAGTGTCACTGAGTCCTTGAAATCTCCCCGCCGGGTCTCTGGATTGGGACGCACAGTGCA | SEQ ID NO: 2511 |
| ENO1 | NM_001428.2 | CAAGGCCGTGAACGAGAAGTCCTGCAACTGCTCCTGCTCAAAGTCAACCAGATTGGCTCCGTGACCG | SEQ ID NO: 2512 |
| EP300 | NM_001429.1 | AGCCCCAGCAACTACAGTCTGGGATGCCAAGCCAGCAGCCATGATGTCAGTGCCCAGCATGTCAACCTTTGAACA | SEQ ID NO: 2513 |
| EPAS1 | NM_001430.3 | AAGCCTTGGAGGGTTTCATTGCCGTGGTGACCGAAGATGGCGACATGATCTTTCTGTCAGAAAAACATCAGCA | SEQ ID NO: 2514 |
| EpCAM | NM_002354.1 | GGGCCCTCCAGAACAATGATGGGCTTTATGATCCTGACTGCCGATGAGAGCGGGCTCTTTAAGGCCAAGCAGTGCA | SEQ ID NO: 2515 |
| EPHA2 | NM_004431.2 | CGCCTGTTCACCAAGATTGACACCATTGCGCCCGATGAGATCACCGTCAGCAGCAGCGACTTCGAGGCCACGCCAC | SEQ ID NO: 2516 |
| EPHB2 | NM_004442.4 | CAACCAGGCAGCTCCATCGGCAGTGTCCATCATGATCAGTTGAGCCGCACTGAGACAGCATTAC | SEQ ID NO: 2517 |
| EPHB4 | NM_004444.3 | TGAACGGGTATCCTCCTTAGCCACGGGCCCGTTCAATGTCACCACTGACCGAGAGGTACCT | SEQ ID NO: 2518 |
| EphB6 | NM_004445.1 | ACTGGTCCTCCCATCGGCTCCCCAGGAGCTTTGGTTTGCTTTGGGCAGAGGCAGCTAGCCAGGACACATTTCCACT | SEQ ID NO: 2519 |
| EPM2A | NM_005670.2 | ACTGTGCACTTAGGGGAGATGACATTTGCCCTTCTCTCTCCCGGGAAGGTACTCCTCTCCCGGGAAGGCACCCTTTCTTCAGTGG | SEQ ID NO: 2520 |
| ErbB3 | NM_001982.1 | CGGTTATGTCATGCCAGATACACACCTCAAAGGTACTCCTCTCCCGGGAAGGCACCCTTTCTTCAGTGGGTCTCAGTTC | SEQ ID NO: 2521 |
| ERCC1 | NM_001983.1 | GTCCAGGTGATGTGAAAGATCCCAGCAGGCCCTCAAGGAGCTGCCTAAGATGTGTATCTGGCCG | SEQ ID NO: 2522 |
| ERCC2 | NM_000400.2 | TGGCCTTCTTCACCAGTACCAGGTCATGAGGAGCACCGTGCCTCCTGGTATGAGCAGGGGATCTTG | SEQ ID NO: 2523 |
| EREG | NM_001432.1 | ATAACAAAGTTAGCTCTGACATGAATGGCTATTGTTTGCATGGACAGTGCATCTATCTGTGGACATGAGTCAAAACTACTGCAGGTGTG | SEQ ID NO: 2524 |
| ERK1 | Z11696.1 | ACGGATCACAGTGGAGGAAGCGCTGGCTCACCCTGGAGCAGTAGTCATGAGACCGACGATGAG | SEQ ID NO: 2525 |
| ERK2 | NM_002745.1 | AGTTCTTGACCCCTGTCTCTCCAGCCGTCTTGGCTTATCCACTTTGACTCCTTTGAGCCGTTT | SEQ ID NO: 2526 |
| ESPL1 | NM_012291.1 | ACCCCAGACCGGATCAGGCAAGCTGCCCTCATGTCCCCTTCACGGTGTTTGAGGAAGTCTGCCCTACA | SEQ ID NO: 2527 |
| EstR1 | NM_000125.1 | CGTGGTGCCCCTCTATGACCTGCTGCTGGAGATGCTGGACGCCCACCGCCTACATGCGCCCACTAGCC | SEQ ID NO: 2528 |
| ETV4 | NM_001986.1 | TCCAGTGCCTATGACCCCCCCAGACAAATCGCCATCAAGTCCCCTGGTGCCCTTGGACAGT | SEQ ID NO: 2529 |

TABLE B-continued

| Gene | Locus Link | Sequence | Sequence ID Number |
|---|---|---|---|
| F3 | NM_001993.2 | GTGAAGGATGTGAAGCAGACGACGTACTTGGCACGGGTCTTCTCTACCGGCAGGGAATGTGAGAGCACCGGTT | SEQ ID NO: 2530 |
| FABP4 | NM_001442.1 | GCTTTGCCACCAGGAAAGTGGCTGGCATGGCCAAACCTAACATGATCATCAGTGTGAATGGGGATG | SEQ ID NO: 2531 |
| FAP | NM_004460.2 | CTGACCAGAACCACGGCTTATCCGGCTGTCCACGAACCACTTATACACCCACCACTTCC | SEQ ID NO: 2532 |
| fas | NM_000043.1 | GGATTGCTCAACAACCATGCTGGGCATCTGACCTCTGTTCTTACAGGCACCGAGAATGTTGATTCAGTGAGGGTCTTCTTACATGC | SEQ ID NO: 2533 |
| fasI | NM_000639.1 | GCACTTTGGGATTCTTTCCATTATGATTCTTTGTTACAGCCACCCAGAGCTACACCCAGAGACTACCGGGCAAAGC | SEQ ID NO: 2534 |
| FASN | NM_004104.4 | GCCTCTTCCTGTTCGACGGCTCGCCCACCTACGTAGCCCTCAGTGAACATGGACCCTCCTGGAGGAGAATTTCGGTGACAGTCTACAATCC | SEQ ID NO: 2535 |
| FBXO5 | NM_012177.2 | GGCTATTCCTCATTTTCTACAAAGTGGCCTCAGTGACATGAACATGAAGAAGTAGCCTTCCGGAGGAGAATTTCGGTGACAGTCTACAATCC | SEQ ID NO: 2536 |
| FBXW7 | NM_033632.1 | CCCCAGTTCAACGAGACTTCATTCATTGCTCCCGCCCATTTGGATCCTGTGGATTTCTGGCACTCTATGTGCTTTCATTCCTGGAAC | SEQ ID NO: 2537 |
| FDXR | NM_004110.2 | GAGATGATTCAGTTACCGGAGCCCGCCTCCTCCAGCGGCTCAGTCCTCGTGGATCCTCATATGCTCACAGCTCTTCACAGTCCTGG | SEQ ID NO: 2538 |
| FES | NM_002005.2 | CTCTGCAGGCCTAGGTGCAGTTCCTCCAGCAAGGACAAGGAGACGGAATTCTACCTGCATGAACCGCAAAGGCAAGC | SEQ ID NO: 2539 |
| FGF18 | NM_003862.1 | CGGTAGTCAAGTCCGGATCAAGGCAAGGAAGCCTTGCAAACCTGCAGAGCTGCTTTTTGCCCAATATAGATTGGGTAAGGCTGC | SEQ ID NO: 2540 |
| FGF2 | NM_002006.2 | AGATGCAGGAGAGAGGAAGCTTGCAAACCTGCAGAGCTGCTTTTTGCCCAATATAGATTGGGTAAGGCTGCAAAAC | SEQ ID NO: 2541 |
| FGFR1 | NM_023109.1 | CACGGGACATTCACCACTGACTACTATAAAAGACAACAACGGCCGACTGCCTGTGAAGTGGATGGCACCC | SEQ ID NO: 2542 |
| FGFR2 isoform 1 | NM_000141.2 | GAGGGACTGTTGGCATGCAGTGACCTGTTGGCCCTCCAGAGACCAAAGTTCAAGCAGTTGGTAGAAGACTTGGATGCGAATTCTCACTC | SEQ ID NO: 2543 |
| FHIT | NM_002012.1 | CCAGTGAGCGCCTTCCATGATGCCTCTGCCTCTGATGAAGTGGCCGATTTGTTTCAGACGACCCAGAGAG | SEQ ID NO: 2544 |
| FIGF | NM_004469.2 | GGTTCCAGCTTTCTGTAGCTGTGGACAGACATGGCCTTTGTGAAGCCACACACCTCCTTACAAAGCAACTAGAACCTGCGGC | SEQ ID NO: 2545 |
| FLJ12455 | NM_022078.1 | CCACCACGACCATGAAGTTTCGGACAGACATGGCCTCTGCCAGTTGTGAGGGGTTCCAGTTGTGCTTCAGACAGCC | SEQ ID NO: 2546 |
| FLJ20712 | AK000719.1 | GCCACACAAACATGCTCCTGCTCCTGCCGAGGCAGAGCTGCTGGGAAAGACATTTCGGAAGTTTCCTGTGGC | SEQ ID NO: 2547 |
| FLT1 | NM_002019.1 | GGCTCCCGAATCTATCTTTGACAAAATCTACGACCACCAAGAGCGACGTGTGTCTTACGGAGTATTGCTGTGGGA | SEQ ID NO: 2548 |
| FLT4 | NM_002020.1 | ACCAAGAAGCTGAGGACCTGTGGCTGCAGCCCCGCTGACCATGGAAGATCTGTCTGCTACAGCTTCCAGG | SEQ ID NO: 2549 |
| FOS | NM_005252.2 | CGAGCCCTTTGATGACTTCTTGTTCCCAGCATCATCCAGGCCCAGTTGGCTCTGAGACAGCCCCGCTCC | SEQ ID NO: 2550 |
| FOXO3A | NM_001455.1 | TGAAGTCCAGGACGATGATGCCTCTGCCCATGCTCTTCACAGCAGCTCAGCCAGCCTGTCACGTGTCACCTTCAGTAAGCAAGCCGT | SEQ ID NO: 2551 |
| FPGS | NM_004957.3 | CAGCCCTGCCAGTTTGACTATGCCCGTCTTCTGCCCTAACCTGACAGAGGTGTCATCCACAGGCAAC | SEQ ID NO: 2552 |

TABLE B-continued

| Gene | Locus Link | Sequence | Sequence ID Number |
|---|---|---|---|
| FRP1 | NM_003012.2 | TTGGTACCTGTGGGTTAGCATCAAGTTCTCCCAGGTAGAATTCAATCAGAGCTTGCATTTGGAT GTG | SEQ ID NO: 2553 |
| FST | NM_006350.2 | GTAAGTCGGATGAGCCTGTCTGTGCCAGTGACAATGCCACTTATGCCAGCGAGTGTGCCATGAAGGAAGCTG | SEQ ID NO: 2554 |
| Furin | NM_002569.1 | AAGTCCTCGATACGCACTATAGCACCAGACACTGGAGACCATCCGGGCAGCGTCTGCGCCCCTGCCACGCCTCATGTGCCACATGCCAG | SEQ ID NO: 2555 |
| FUS | NM_004960.1 | GGATAATTCAGACAACAACACCATCTTTGTGCAAGGCCTGGTGAGAATGTTACAATTGAGTCTGTGGCTGA TTACTTCA | SEQ ID NO: 2556 |
| FUT1 | NM_000148.1 | CCGTGCTCATTGCTACTAACCACTACTGTCTGTCCCCAGAACTCCCAGAACCACTACATCTCGGCTTTGGGCAG | SEQ ID NO: 2557 |
| FUT3 | NM_000149.1 | CAGTTCCGGTCCAACAGAGAAAGCAGGCAACCACCATGTCATTTGAAAACAGTTTCATCGGGATATAATTCGCA | SEQ ID NO: 2558 |
| FUT6 | NM_000150.1 | CGTGTGTCTCAAGACGATCCACTGTGTACCCTAATGGTCCCGCTTCCCAGACAGCACAGGGACC | SEQ ID NO: 2559 |
| FXYD5 | NM_014164.4 | AGAGCACCACAAAGCAGCTCATCCCACCACTGATGACGACCAAGCTGGTCTATGCAGTGTCTGAGGAG | SEQ ID NO: 2560 |
| FYN | NM_002037.3 | GAAGCCAGATCATGAAGAAGCTGAAGCACCGACAAGTCGCAGTGTTCCCGTGAGCTCAAGTTCTTCCTGTCTCCATGTA | SEQ ID NO: 2561 |
| FZD1 | NM_003505.1 | GGTGCACCAGTTCTACCCTCTAGTGAAAGTGCAGTGTTCCCGTGAGCTCAAGTTCTTCCTGTCTCCATGTA CGC | SEQ ID NO: 2562 |
| FZD2 | NM_001466.2 | TGGATCCTCCACCTGGTTCGGTGCTGCTGTCGCCTTCCACCTTCTTCACTGTGTCACCACGTACTTGGTAGACAT GCAGCGC | SEQ ID NO: 2563 |
| FZD6 | NM_003506.2 | AATGAGAGAGGTGAAAGCGACGGACTAGCACCCCAGGTTAAGAGAACAGGACTGTGGTGAACCT | SEQ ID NO: 2564 |
| G-Catenin | NM_002230.1 | TCAGCAGCAAGGGCATCATGGAGGAGGAGAGCAGCCTGCGGGCGCCAGTACACGCTCAAGAGAAAACCACC | SEQ ID NO: 2565 |
| G1P2 | NM_005101.1 | CAACGAATTCCAGGTGTCCCTGAGCGTCCATGTCGGTGTCAGAGCTGAAGGCGCAGATC | SEQ ID NO: 2566 |
| GADD45 | NM_001924.2 | GTGCTGTGACAGAATCCACATTCATCTCAATGGAAGGATCCTGCCTTAAGTCAACTTATTTGTTTTGCCGGG | SEQ ID NO: 2567 |
| GADD45B | NM_015675.1 | ACCCTCGACAAGACACACATTTGGGACTTGGGAGCTGGTGCTCTGTACCCATGAACTCCCA | SEQ ID NO: 2568 |
| GADD45G | NM_006705.2 | CGCGCTGCAGATCCATTTTACGCTGATCAGGCTTTCTGCTGCGAGAACGACATGACATAGTGCG | SEQ ID NO: 2569 |
| GAGE4 | NM_001474.1 | GGAACAGGGTCACCCAGACTGGGTGTGAGTGTGAAGATGGTCCTGATGGGCAGGAGATGGACCCGCC AAATC | SEQ ID NO: 2570 |
| GBP1 | NM_002053.1 | TTTGGAAATATTTGGGCATTGGTCTCGGCCAAGTCTACAATGTCCAATATCAAGGACAACCACCCTAGCTTCT | SEQ ID NO: 2571 |
| GBP2 | NM_004120.2 | GCATGGGAACCATCAACCAGCCCATGGACCAACTTCACTATGTGACAGAGCTGAATCAAGGCAAACTCCTCA | SEQ ID NO: 2572 |
| GCLC | NM_001498.1 | CTGTTGCAGGAAGGCATTGATCATCCTCGGCCCAGCATGTTGCTCATCTTTATTAGAGACCCACTGAC | SEQ ID NO: 2573 |
| GCLM | NM_002061.1 | TGTAGAGATCAAACTCTTCATCATCAACTAGAAGTGCAGTTGACATGGCCTGTTCAGTCTTGGAGTTGCACAGCTGGATTCTGTG | SEQ ID NO: 2574 |

TABLE B-continued

| Gene | Locus Link | Sequence | Sequence ID Number |
|---|---|---|---|
| GCNT1 | NM_001490.3 | TGGTGCTTGGAGCATAGAAGACTGCCCTTCACAAAGGAAATCCCTGATTATTGTTGAAATGCTGAGGACGTTGC | SEQ ID NO: 2575 |
| GDF15 | NM_004864.1 | CGCTCCAGACCCTATGATGACTTGTTAGCCAAAGACTGCCACTGCATATGAGCAGTCCTGGTCCTTCCACTGT | SEQ ID NO: 2576 |
| GIT1 | NM_014030.2 | GTGTATGACGAGGTGGATCGAAGAGAAAATGATGCAGTGTGGCTACCCAAAACCACAGCACTCTGGT | SEQ ID NO: 2577 |
| GJA1 | NM_000165.2 | GTTCACTGGGGTGTATGGGTAGATGGTGAGAGGGAGGTGAAGTGAGAGGTGCATGTTGGTATTT | SEQ ID NO: 2578 |
| GJB2 | NM_004004.3 | TGTCATGTACGACGGCTTCTCCATGCAGCGACTGGTGAAGTGCAACGCCTGGCCTTGTCCCAACACTGTGGACT | SEQ ID NO: 2579 |
| GPX1 | NM_000581.2 | GCTTATGACCGACCCCAAGCTCATCACCTGGTCTCCGGTGTCGCAACGATGTTGCCTGGAACTTT | SEQ ID NO: 2580 |
| GPX2 | NM_002083.1 | CACACAGATCTCCTACTCCATCCAGTCCTGAGGAGCCTTAGGATGCAGCAGCCCTTCAGGAGACACTGCTGGACC | SEQ ID NO: 2581 |
| Grb10 | NM_005311.2 | CTTCGCCTTTGCTGATTGCCTCTCCAAACGCCTGCCTGACGACTGCCTTGGAGCATGTGCTTATGG | SEQ ID NO: 2582 |
| GRB14 | NM_004490.1 | TCCCACTGAAGCCCTTTCAGTTGCGTTGAAGAGACTCGCTTGGAGGAAAAAGGATGTTTACGCCTGGGCACT | SEQ ID NO: 2583 |
| GRB2 | NM_002086.2 | GTCCATCAGTGCCATGACGTTTAAGGCCACGTATAGTCCTAGCTGACGCCAATAATAAAAACAAGAAACCAAGTGGGCT | SEQ ID NO: 2584 |
| GRB7 | NM_005310.1 | CCATCTGCATCCATCTTGTTTGGGCTCCCCCTTTGAGAAGTGCCTCAGATAATACCCTGGTGCC | SEQ ID NO: 2585 |
| GRIK1 | NM_000830.2 | GTTGGGTGCATCTCTCCGGGCTTCCCGGCAGCGCCATGAATTAAGAGCTAGGAAGATGGAGCACG | SEQ ID NO: 2586 |
| GRO1 | NM_001511.1 | CGAAAAGATGCTGAACAGTGACAAATCCAACTGACCAGAAGGAGGAGGAAGCTCACTGGTGGCTGTTCCTGA | SEQ ID NO: 2587 |
| GRP | NM_002091.1 | CTGGGTCTCATAGAAGCAAAGGAGAACAGAAACCACACCTCAACCCAAGGCCTTGGGCAATCAGCAGCCTTCGTGG | SEQ ID NO: 2588 |
| GRPR | NM_005314.1 | ATGCTGCTGGCCATTCCAGAGGCCGTGTGTTTTCTGACCTCCATCCCTTGACCTGAGGAAAGCACCAACCAGACCT | SEQ ID NO: 2589 |
| GSK3B | NM_002093.2 | GACAAGGACGGCAGAAGGTGACACACAGTGTGGCAACTCCTGGGCACCAGGGTCCAGACAGGCCACAA | SEQ ID NO: 2590 |
| GSTA3 | NM_000847.3 | TCTCCAACTTCCCCTGCTGAAGACTACACCCTGAAAACCAGAATCAGCAACCTGCCCACCGTGAAGAAGT | SEQ ID NO: 2591 |
| GSTM1 | NM_000561.1 | AAGCTATGAGAAAAGACATACACAGGGACGCTCTGATTATGACAGAAGCCAGTGCTGCTGAATGAAAAATTCAAGCTGGGCC | SEQ ID NO: 2592 |
| GSTM3 | NM_000849.3 | CAATGCCATCTTGCGCTACATCGCTCGCAAGCACAACAACATGTGTGGTGAGACTGAAGAAGAAGAAAGATTCGAGTGGAC | SEQ ID NO: 2593 |
| GSTp | NM_000852.2 | GAGACCCTGCTGTCCCAGAACCAGGGAGGCAAGACCTTCATTGTGGGAGACCAGATCTCCTTCGCTGACTACAACC | SEQ ID NO: 2594 |

TABLE B-continued

| Gene | Locus Link | Sequence | Sequence ID Number |
|---|---|---|---|
| GSTT1 | NM_000853.1 | CACCATCCCCACCCTGTCTTCCACAGCCGCCTGAAAGCCACAATGAGAATGATGCACACTGAGGCC | SEQ ID NO: 2595 |
| H2AFZ | NM_002106.2 | CCGGAAAGGCCAAGACAAAGGCGGTTTCCCGCTCGAGAGATCGGCTTGCAGTCAGTGGGCCGTATT | SEQ ID NO: 2596 |
| HB-EGF | NM_001945.1 | GACTCCTTCGTCCCCAGTTGCCGTCTAGGATTGGGCCTCCCATAAATTGCTTTGCCAAGAGCCTTCAAGTGCCA | SEQ ID NO: 2597 |
| hCRA_a | U78556.1 | TGACACCCTTACCTTCCTGAGAAATACCCCCTGGGAGCGCGGAAAGCACAGGTCGACTTTTTGACTCGTGTTTTT | SEQ ID NO: 2598 |
| HDAC1 | NM_004964.2 | CAAGTACCACAGCGATGACTACATTAAATTCTTGCGCTCCATCCGTCCAGATAACATGTCGGAGTACAGCAAGC | SEQ ID NO: 2599 |
| HDAC2 | NM_001527.1 | GGTGGCTACACAATCCGTAATGTTGCTCAGATGTTGGACATATGAGACTGCAGTTGCCCTTGATTGTGAGATTCCCA | SEQ ID NO: 2600 |
| HDGF | NM_004494.1 | TCCTAGGCATTCTGACCTCTGGGTTGGGATCAGGGGTAGGAGTGAAGATGGAGCATCAACAGC | SEQ ID NO: 2601 |
| hENT1 | NM_004955.1 | AGCCGTGACGTTGAGGTCAAGTCCAGCATCGCAGGGCAGCAGCACCTGGGAACGTTACTT | SEQ ID NO: 2602 |
| Hepsin | NM_002151.1 | AGGCTGCTGAGGTCATCTCCGTGTGTGATTGCCCCAGAGGCCGTTTCTTGGCCGCCATCTGCCAAGACTGTGGCCGCAGGAAG | SEQ ID NO: 2603 |
| HER2 | NM_004448.1 | CGGTGTGAGAAGTGCAGCAAGCCCTGTGCCAGCCTCTTGGGACCCCAGTGTCGTATGGTCTGGGCATGGAGCACTTGCGAGAGG | SEQ ID NO: 2604 |
| Herstatin | AF177761.2 | CACCCTGTCCTATCCTTCCCTCAGACCCTCTTGGGACCCAGTCTCTGCCTTCTCTACTCTCTACCCCTGGCC | SEQ ID NO: 2605 |
| HES6 | NM_018645.3 | TTAGGGACCCTGCAGCTTCTGAGTGGTGGAGGGGAGCTACGGGCAGGAGAAGAATTTTGTAG | SEQ ID NO: 2606 |
| HGF | M29145.1 | CCGAAATACCAGATGATGATCTCATGGACCCTGGTGCTACACGGGAAATCCACTCATTCCTTGGG | SEQ ID NO: 2607 |
| HIF1A | NM_001530.1 | TGAACATAAAGTCTGCAACATGGAAGGTATTGCACTGCACAGGCCACATTCACGTATATGATACAACAGTAACCAACCTCA | SEQ ID NO: 2608 |
| HK1 | NM_000188.1 | TACGCACAGAGGCAAGCAGCAGTCAGCTTAAGAGTGCCGGGATCCCAGCCTACTGCCTCTCCCAGCACTTCTCTC | SEQ ID NO: 2609 |
| HLA-DPB1 | NM_002121.4 | TCCATGATGGTTCTGCAGGTTTCTGCGGGACCAGTGGCTCGACGGCGTTACTGATGGTCTGCTCA | SEQ ID NO: 2610 |
| HLA-DRA | NM_019111.3 | GACGATTTGCCAGCTTTGAGGCTCAAGGTGCATTGGCCACATAGCTGTGACAAAGCCAACCTGA | SEQ ID NO: 2611 |
| HLA-DRB1 | NM_002124.1 | GCTTTCTCAGGACCTGTGTTGCTACTGGTTCGCAACTGCAGAAAATGTCCTCCCCTTGTGGCTTCCT | SEQ ID NO: 2612 |
| HLA-G | NM_002127.2 | CCTGCGCGGCTACTACAACAGAGCGAGGCCAGTTCTCACACCCTCCAGTTGGATGATTGGCTGCGACCTG | SEQ ID NO: 2613 |
| HMGB1 | NM_002128.3 | TGGCCTGTCCATTGGTGATGTTGCGAAGAAACTGGGAGAAGATGTGGAGAAATAACACTGCTGAGATGACAAGC | SEQ ID NO: 2614 |
| hMLH | NM_000249.2 | CTACTTCCAGCAACCCAGAAGAGACATCGGGAAGATTCTGATGTGGAAATGGTGGAAATGATTCCCGAAAG | SEQ ID NO: 2615 |
| HNRPAB | NM_004499.2 | CAAGGGAGCGACCAACTGCATCGCACACATGCTTGTTTGGATATGGAGTGAACAATTATGTACCAAATTTAACTTGGCAAAC | SEQ ID NO: 2616 |
| HNRPD | NM_031370.2 | GCCAGTAAGAACGAGGAGGATGAAGGCCATTCAAACTCCTCCCCACGACACTCTGAAGCAGCACG | SEQ ID NO: 2617 |
| HoxA1 | NM_005522.3 | AGTGACAGATGACAATGACAAGAATGAACTCCTTCCTGGAATACCCCATACTTAGCAGTGGCGACTCGG | SEQ ID NO: 2618 |

TABLE B-continued

| Gene | Locus Link | Sequence | Sequence ID Number |
|---|---|---|---|
| HoxA5 | NM_019102.2 | TCCCTTGTGTTCCTTCTGTGAAGAAGCCCTGTTCTCGTTGCCCTAATTCATCTTTAATCATGAGCCTGTTTATTGCC | SEQ ID NO: 2619 |
| HOXB13 | NM_006361.2 | CGTGCCTTATGTTACTTGGAGGCGGTACTCCTGCCGGTGTCCCGAGCTGCTGAAACCCTGTG | SEQ ID NO: 2620 |
| HOXB7 | NM_004502.2 | CAGCCTCAAGTTCGGTTTTCCTACCGGAGCCTTCCAGAACAAACTTCTGTGCTTTGCTTCCAAC | SEQ ID NO: 2621 |
| HRAS | NM_005343.2 | GGACGAATACGACCCACTATAGAGGATTCCTACCGAAGCAGGTGTCATTGATGGGAGACGTGC | SEQ ID NO: 2622 |
| HSBP1 | NM_001537.1 | GGAGATGGCCGAGACTGACCCCAAGACCGTGCAGGACCTCACCTGGTGCAGACACTCCTGCAG | SEQ ID NO: 2623 |
| HSD17B1 | NM_000413.1 | CTGGACCGCACGGACATCCACCTTCCACCGCTTCTACCAATAACCTGCCCACAAGCAAGCAAGTCTTTCGCGAGGCG | SEQ ID NO: 2624 |
| HSD17B2 | NM_002153.1 | GCTTTCCAAGTGGGGAATTAAAGTTGCTTCCATCCAACCTGGAGGCTTCTAACAATATCGCAGGCA | SEQ ID NO: 2625 |
| HSPA1A | NM_005345.4 | CTGCTGCGACAGTTCCACTACCTTTTTCGAGAGTGACTCCCCGTGTCCCAAGGCTCTCCAGAGCGAACCTG | SEQ ID NO: 2626 |
| HSPA1B | NM_005346.3 | GGTCCCGCTTCGTCTTTCGAGAGTGACTCCCCGCGGTCGAGGTTCACAAGTCTGAGGAAATGAGGAGCCAATGAACAGAT | SEQ ID NO: 2627 |
| HSPA4 | NM_002154.3 | TTCAGTGTGTCCAGTGCATCTTTAGTGGAGGTTCACAAGTCTGAGGAAATGAGGAGCCAATGAACAGAT | SEQ ID NO: 2628 |
| HSPA5 | NM_005347.2 | GGCTAGTAGAACTGGATCCCAACACACCAAAACTTCTTAATTAGAACCTAGGCCTCAGCTGCACTGCCCGAAAAGCATTGGGCAGACC | SEQ ID NO: 2629 |
| HSPA8 | NM_006597.3 | CCTCCCCTCTGGTGGTGCTTCCTCAGGGCCCACCATTGAAGAGGTTGATTAAGCCAACCAAGTGTAGATGTAGC | SEQ ID NO: 2630 |
| HSPB1 | NM_001540.2 | CCGACTGGAGAGCATAAAAGCGCAGCCGAGCCCAGCGCCCCGCACTTTTCTGAGCAGAAGACGTCCAGAGCAGAGTCAGCCAGCAT | SEQ ID NO: 2631 |
| HSPCA | NM_005348.2 | CAAAAGGCAGAGGCTGATAAGAACGACAAGTCTGTGAAGGATCTGGTCATCTTGCTTTATGAAACTGCGCT | SEQ ID NO: 2632 |
| HSPE1 | NM_002157.1 | GCAAGCAACAGTAGTCGCTGTTGGATCGGGTTCTAAAGGAAGGAAGGTGGAGAGATTCAACCAGTTAGCGTGAAAGTTGG | SEQ ID NO: 2633 |
| HSPG2 | NM_005529.2 | GAGTACGTGTGCCGAGTGTTGGGCAGCTCCCGTGCCTCCTAGAGGCCTTCTCTGTCCTGTCACCATTGAG | SEQ ID NO: 2634 |
| ICAM1 | NM_000201.1 | GCAGACAGTGACCATCTACAGCTTTCCGGCCCCAACGTGATTCTGAAGAAGCCAGAGGTCTCAGAAG | SEQ ID NO: 2635 |
| ICAM2 | NM_000873.2 | GGTCATCCTGACACTGCAAACCCACTTTGGTGCTGTGGGCAAGTCCTTCACCATTGAGTGCA | SEQ ID NO: 2636 |
| ID1 | NM_002165.1 | AGAACCGCAAGGTGAGCAAGTGGAGATTCCCAGCACGTCATCGACTACATCAGGGACCTTCAGTTGGA | SEQ ID NO: 2637 |
| ID2 | NM_002166.1 | AACGACTGCTACTCCAAGCTCAAGGAGCTGGTGCCCAGCATCCCCCAGAACAAGAAGGTGAGCAAGATGGAAATCC | SEQ ID NO: 2638 |
| ID3 | NM_002167.2 | CTTCACCAAATCCCTTCCTGGAGACTAAACCTGGTGCTCAGGAGCCGAAGGACTGTGAACTTGTAGCCTGAAGAGCCAGAG | SEQ ID NO: 2639 |
| ID4 | NM_001546.2 | TGGCCTGGCTCTTAATTTGCTTTTGTTTTGCCCAGTATAGACTCGGAAGTAAGAGTTATAGCTAGTGGTCTTGCATGATTGCA | SEQ ID NO: 2640 |

TABLE B-continued

| Gene | Locus Link | Sequence | Sequence ID Number |
|---|---|---|---|
| IFIT1 | NM_001548.1 | TGACAACCAAGCAAATGTGAGGAGTCTGGTGACCTGGGCAACTTTGCCTGGATGTATTACCACATGGGCAGACTG | SEQ ID NO: 2641 |
| IGF1 | NM_000618.1 | TCCGGAGCTGTGATCTAAGGAGGCTGGAGATGTATTGCGACCACCCCTCAAGCCTGCCAAGTCAGCTCGCTCTGTCCG | SEQ ID NO: 2642 |
| IGF1R | NM_000875.2 | GCATGGTAGCCGAAGATTCACAGTCAAAATCGGAGATTTTGGTATGACGGAGATATCTATGAGACAGACTATTACCGGAAA | SEQ ID NO: 2643 |
| IGF2 | NM_000612.2 | CCGTGCTTCCGACAACTTCCCCAGATACCCCGTGGGCAAGTTCTTCCAATATGACACCTGGAAGCAGTCCA | SEQ ID NO: 2644 |
| IGFBP2 | NM_000597.1 | GTGGACAGCACCATGAACATGTTGGGCGGGGAGGCAGTGCTGGCCTGGGCCGGGAAGCCCCTCAAGTCGGGTATGAAGG | SEQ ID NO: 2645 |
| IGFBP3 | NM_000598.1 | ACGCACCGGGTGTCTGATCCCAAGTTCCACCCCCTCCATTCAAAGATAATCATCATCAAGAAAGGGCA | SEQ ID NO: 2646 |
| IGFBP5 | NM_000599.1 | TGGACAAGTACGGGATGAAGCTGCCAGGCATGGAAGCTGTTCAGTGCCACACCTTCG | SEQ ID NO: 2647 |
| IGFBP6 | NM_002178.1 | TGAACCGCAGAGACCAACAGGAATCCAGGGCACCTCTACCACGCCCTCCCAGCCCAATTCTGCGGGTGTCCAAGAC | SEQ ID NO: 2648 |
| IGFBP7 | NM_001553 | GGGTCACTATGGAGTTCAAAGGACACAGAACTCCTGCCTGGTGACCGGACAACCTGGCCATTCAGACCC | SEQ ID NO: 2649 |
| IHH | NM_002181.1 | AAGGACGAGGAGAACAACAGGCGCCGACCGGCCCTCATGATGACCGCTGCAAGGACCGCGCCTGAACTCGCTGGCTATCT | SEQ ID NO: 2650 |
| IL-8 | NM_000584.2 | AAGGAACCATCTCACTGTGTGTAAACATGACTTCCAAGCTGGCCGTGGCTCTCTTGGCAGCCTTCCTGAT | SEQ ID NO: 2651 |
| IL10 | NM_000572.1 | GGCGCTGTCATCGATTTCTTCCCTGTGAAAAACAAGAGCAAGGCCGTGGAGCAGGTGAAGATGCCTTTAATAAGCTCCA | SEQ ID NO: 2652 |
| IL1B | NM_000576.2 | AGCTGAGGAAGATGCTGGTTCCCTGCCCACAGACCTTCCAGGAGAATGACCTGAGCACCTTCTTTTCC | SEQ ID NO: 2653 |
| IL6 | NM_000600.1 | CCTGAACCTTCCAAAGATGGCTGAAAAAGATGGATGCTTCCAATCTGGATTCAATGAGGAGACTTGCCTGGT | SEQ ID NO: 2654 |
| IL6ST | NM_002184.2 | GGCCTAATGTTCCAGATCCTTCAAAGAGTCATATTGCCCAGTGGTCACCTCACACTTCCTCCAAGGCACAATTTT | SEQ ID NO: 2655 |
| ILT-2 | NM_006669.1 | AGCCATCACTCTCAGTCAGCCCTATCGTGGCCCCTCGAGGAGACCCTGACTCTGCAGT | SEQ ID NO: 2656 |
| IMP-1 | NM_006546.2 | GAAAGTGTTTGCGAGCACAAGAATCTCCTACAGCGCGCAGTTCTTCTGTCAAATCCGGCTACGCCTTC | SEQ ID NO: 2657 |
| IMP2 | NM_006548.3 | CAATCTGATCCCAGGGTTGAACCTCAGCGCACTTGGCGCATCTGCCGTGCTATCTCCACCAGCAGGGCC | SEQ ID NO: 2658 |
| ING1L | NM_001564.1 | TGTTTCCAAGATCCTGCTGAAAGTGAACGAGCCTCAGATAAAGCAACAAGACAAGCAAGATGGATTCCAGCAGACCTACGAAAGA | SEQ ID NO: 2659 |
| ING5 | NM_032329.4 | CCTACAGCAAGTGCAAGGAATACAGTGACGACAAAGTGCAGTGGCCATGCAGACCTACGAGATG | SEQ ID NO: 2660 |
| INHA | NM_002191.2 | CCTCCCAGTTTCATCTTCCACTACTGTCATGTGGTGGGCTGCAGATCCCACCAAAACCTGTCCCTTCCAGTCCCT | SEQ ID NO: 2661 |
| INHBA | NM_002192.1 | GTGCCCGAGCCATATAGCAGGCACGTCCGGGTCCTCACTGTCCTTCCACTCAACAGTCATCAACCACTACCG | SEQ ID NO: 2662 |

TABLE B-continued

| Gene | Locus Link | Sequence | Sequence ID Number |
|---|---|---|---|
| INHBB | NM_002193.1 | AGCCTCCAGGATACCAGCGATGCGGTGACAAATGCCAGCTTAGCTACAAATGCCTGTCAGTCGGAGA | SEQ ID NO: 2663 |
| IRS1 | NM_005544.1 | CCACAGCTCACCTTCTGTCAGTGTCCATCCCAGCTCCCAGCCAGCTCCCAGAGAGAGACTGGCACTGAGG | SEQ ID NO: 2664 |
| ITGA3 | NM_002204.1 | CCATGATCCTCACTCTGCTGGACTATACACTCCAGACCTCGCTTAGCATGGTAAATCACCGGCTACAAAGCTTC | SEQ ID NO: 2665 |
| ITGA4 | NM_000885.2 | CAACGCTTCAGTGATCAATCCGGGCGATTTACAGATGCAGGATCGGAAAGAATCCCGGCCAGAC | SEQ ID NO: 2666 |
| ITGA5 | NM_002205.1 | AGGCCAGCCCTACATTATCAGAGAGCAAGACCGGATAGAGGACAAGGCTCAGATCTTGCTGACTGTGGAGAAGAC | SEQ ID NO: 2667 |
| ITGA6 | NM_000210.1 | CAGTGACAAACAGCCCTTCCAACCCAAGGAATCCCACAAAAGATGCGATGACGCCCATGAGGCTAAAC | SEQ ID NO: 2668 |
| ITGA7 | NM_002206.1 | GATATGATTGGTCGCTGCTTTGTGCTCCAGCCAGGACCTGGCCATCCGGGATGAGTTGGATGTGGGGAATGGAAGTTCT | SEQ ID NO: 2669 |
| ITGAV | NM_002210.2 | ACTCGGACTGCACAAGCTATTTTGATGACAGCTATTTGGGTTATTCTGTGGCTGTCGGAGATTTCAATGGTGATGGCA | SEQ ID NO: 2670 |
| ITGB1 | NM_002211.2 | TCAGAATTGGCTCATTTGTGAAAAGACTGTGATGCCTTACATTAGCACACACCAGCTAAGCTCAGG | SEQ ID NO: 2671 |
| ITGB3 | NM_002212.1 | ACCGGGAGCCCTACAGTGCCCTCAATGACCGAAAATACCTGCCAACCGTTACTGCCCGTTACTGTGACGAGATTGAGTCAGTGAAAGAGCTTAAGG | SEQ ID NO: 2672 |
| ITGB4 | NM_000213.2 | CAAGGTGCCCTCAGTGGAGCTCACCAACCCTGTACCCGTATTGCGACTATGAGATGAAGGTGCGC | SEQ ID NO: 2673 |
| ITGB5 | NM_002213.3 | TCGTGAAAGATGACCAGGAGGAGGCGTGTGCTATGTTTGCACAAAACGCCAAGGACTGCTCATGATGTTCACC | SEQ ID NO: 2674 |
| K-ras | NM_033360.2 | GTCAAAATGGGGAGGGACTAGGGCAGTTTGGATAGCTCAACAAGATACAATCTCACTCTGTGGTGGTCCTG | SEQ ID NO: 2675 |
| KCNH2 iso a/b | NM_000238.2 | GAGGCAAAGTGGAAATCGCCTTCTACCGGAAATGGATGGGAGCTGCTTCCTATGTCTGGTGGTGTGCCCGTGAAGA | SEQ ID NO: 2676 |
| KCNH2 iso a/c | NM_172057.1 | TCCTGCTGCTGGTCATCTACACGCGTGTCTTCTTCACACGCTGCTTCCTGCTGCTGAAGGAGACGGAAGAAGG | SEQ ID NO: 2677 |
| KCNK4 | NM_016611.2 | CCTATCAGCCACGGCCCTGGTGGTTCTGGATCCTGCCAGGCATCAGTGTCAGTGTTCTTGGCTGTGCAAAGTGGAGGCATTTTT | SEQ ID NO: 2678 |
| KDR | NM_002253.1 | GAGGACGAAGGCCTCTACACCTGCGCCCAGGCATGGTGTCTCCACCTGAAGGAGAGGCTCCTCAGTGTGCACCTCCC | SEQ ID NO: 2679 |
| Ki-67 | NM_002417.1 | CGGACTTTGGGTGCCATGTGGTCGACTTGACGAAGTGGCCTTGACAAGTGGCCGGATCGTCCCAGTGGAAGAGTTGTAA | SEQ ID NO: 2680 |
| KIAA0125 | NM_014792.2 | GTGTCCTGGTCCATGTGGTGAAGGCAGAATGCCAGTGTCTCCACCTGCCTGCTGTTGCCTCCACAGGAGCCCACGTGCACCTCC | SEQ ID NO: 2681 |
| KIF22 | NM_007317.1 | CTAAGCACTTGGTGGAAGGCAGAATGCTTGCTGCCTGTCCTATGACCCACAGAGCTGGGAAGA | SEQ ID NO: 2682 |
| KIF2C | NM_006845.2 | AATTCCTGCTCCAAAAGAAAGTCTTCGAAGCCGCCATGTCCACTCGCATGTCCACTGTCTCAGAGCTTCCATCACG | SEQ ID NO: 2683 |
| KIFC1 | XM_371813.1 | CCACACAGGGTTGAAGACCAGAAGCCAGTTCCTGCTGTTCCTGTCCAGAAGTCTGGCACATCAGGTG | SEQ ID NO: 2684 |

TABLE B-continued

| Gene | Locus Link | Sequence | Sequence ID Number |
|---|---|---|---|
| Kitlng | NM_000899.1 | GTCCCCGGGATGGATGTTTGCCAAGTCATTGTTGGATAAGCGAGATGGTAGTACAATTGTCAGACAGCTTGACTGATC | SEQ ID NO: 2685 |
| KLF5 | NM_001730.3 | GTGCAACCGCAGCTTCTGCGCCTCTGACCACCTGGCCCTGCATATGAAGAGCACCAGAACTGAGCACTGCCCG | SEQ ID NO: 2686 |
| KLF6 | NM_001300.4 | CACGAGACCGGCTACTTCTCGGCGCTCCGTCTCTGAGGAGTACTGGCAACAGACCTGCCTAGAGC | SEQ ID NO: 2687 |
| KLK10 | NM_002776.1 | GCCCAGAGGCTCCATCCGTCCATCCTCTTCCTCCCCCAGTCGGCTGAACTCTCCCCTTGTCTGCACTGTTCAAACCTCTG | SEQ ID NO: 2688 |
| KLK6 | NM_002774.2 | GACGTGAGGGTCCTGATTCTCCCTGGTTTTACCCAGCTCCATCCCTGCATCACTGGGAGGACGTGATGAGTGAGGA | SEQ ID NO: 2689 |
| KLRK1 | NM_007360.1 | TGAGAGCCAGGCTTCTTGTATGTCTCAAAATGCCAGCCTTCTGAAAGTATACAGCAAAGAGGACCAGGAT | SEQ ID NO: 2690 |
| KNTC2 | NM_006101.1 | ATGTGCCAGTGAGCTTGAGTCTCTTGGAGAAACACAAGACACCTGCTAGAAAGTACTGTTAACCAGGGGCTCA | SEQ ID NO: 2691 |
| KRAS2 | NM_004985.3 | GAGACACCAAGGTTGCAAGGCCCTGTGTGAAGGCCTTTCATAGAGAGTTTCACAGACATGGACTG | SEQ ID NO: 2692 |
| KRT19 | NM_002276.1 | TGAGCGGCAGAATCAGGAGTACCAGCGGCTCATGATGGAGCGCCATCAAGTCGCGGCTGAAGCAGGAGATTGCCACTACCGCA | SEQ ID NO: 2693 |
| KRT8 | NM_002273.1 | GGATGAAGCTTACATGAACAAGGTAGAGCTCGAGTCTCGCCTGGAAGGGCTGACCGACGATCAACTTCCTCAGGCAGTATATG | SEQ ID NO: 2694 |
| LAMA3 | NM_000227.2 | CAGATGAGGCGACATGGAGACCTCCAGGCCAAGGACCTCGAGGAATCAGTTGCTCAACTACCGTTCTGCCATTTCAA | SEQ ID NO: 2695 |
| LAMB3 | NM_000228.1 | ACTGACCAAGCCTGAGACCTACTGCGACCCAGTATGGCGAGTTGGCAGATGAAATGTGCAAGTGTGAC | SEQ ID NO: 2696 |
| LAMC2 | NM_005562.1 | ACTCAAGCGGAAATTGAAGCAGAGTCTTATCAGCAGACAGTCTCCGCCTCCTGGATTCAGTGTCTCGGCTTCAGGGAGT | SEQ ID NO: 2697 |
| LAT | NM_014387.2 | GTGAACGTTCCGGAGAGCGGGGAGAGTACCCTGGATTAACGAGTCTCTGGATGGCAGCCGGGAGTATGTGAATGT | SEQ ID NO: 2698 |
| LCN2 | NM_005564.2 | CGCTGGGCAACATTAAGAGTTACCCTGGATTAACGAGTCGTTCCGAGTGGTGAGCACAACTACAACCAGCATGCT | SEQ ID NO: 2699 |
| LDLRAP1 | NM_015627.1 | CAGTGCTCTCGCCTGCGATGGGACAAGCCTGACAGCAGCGGCACAGAGCAGGATGACCTCTTCA | SEQ ID NO: 2700 |
| LEF | NM_016269.2 | GATGACGAAAGCATCCAGATGGAGGCCTCTACAACAAGGAGACCCCTTCCTGAGTTATTCCGGG | SEQ ID NO: 2701 |
| LGALS3 | NM_002306.1 | AGCGGAAAAATGGCAGACAATTTTTCGCTCAGCAGCCCCAACTGATGCGTTATCTGGGTCTGGAAACCCAAACCCTCAAG | SEQ ID NO: 2702 |
| LGMN | NM_001008530.1 | TTGGTGCCGTTCCTATAGATCCTGGAGTTTTGATTGGGGTCTGGCCTTCGTCGTCTGCAGGTTC | SEQ ID NO: 2703 |
| LILRB3 | NM_006864.1 | CACCTGGTCTGGGAAGATACCTGGAGGTTCTGTCCGTCCATCGTCGACCTCATCCGGAAGACCAGACTCGTGGGG | SEQ ID NO: 2704 |
| LMNB1 | NM_005573.1 | TGCAAACGCTGGTGTCACAGACACTGCTGTCATTCAAGTGAAGTAGAGGTCAGAAGGGTCATAGAAAGCAG | SEQ ID NO: 2705 |
| LMYC | NM_012421.1 | CCCATCCAGAACACGGGCCAGGTGTTCAGCTTGCTGAGCCTGGGCTCACAGTACCAGCCTCAGCG | SEQ ID NO: 2706 |
| LOX | NM_002317.3 | CCAATGGGAGAACAACGGGCCAGGTGTTCAGCTTGCTGAGCCTGGGCTCACAGTACCAGCCTCAGCG | SEQ ID NO: 2707 |

TABLE B-continued

| Gene | Locus Link | Sequence | Sequence ID Number |
|---|---|---|---|
| LOXL2 | NM_002318.1 | TCAGCCGGCTCTTAAACAGCTGTCCCCGCAGTAAAGAAGCCTGCGTGTCAACTCCTGTCTT | SEQ ID NO: 2708 |
| LRP5 | NM_002335.1 | CGACTATGACCCACTGACAAGTTCATCTACTGGGTGGATGGGCGCCAGAACATCAAGCGAGCCAAG | SEQ ID NO: 2709 |
| LRP6 | NM_002336.1 | GGATGTAGCCATCTCTGCCTCTATAGACCTCAGGGCCTTCGTCTGCTTGCCCTATTGGCTTTGAACT | SEQ ID NO: 2710 |
| LY6D | NM_003695.2 | AATGCTGATGACTTGGAGCAGGCCCCACAGACCCCTGCCACAACTCCCTTGCACGTAAACTTCAGTGTCCCACCTTGA | SEQ ID NO: 2711 |
| MAD | NM_002357.1 | TGGTTCTGATTAGGTAACGTATTGGACCTGCCAGAGCGATTGTGAAGAACATGAAGTCTGAGCTGTACGGCTCC | SEQ ID NO: 2712 |
| MAD1L1 | NM_003550.1 | AGAAGCTGTCCCTGCAAGAGAGCAGGATGCAGCGATTGTGAAGAACATGAAGTCTGAGCTGTACGGCT | SEQ ID NO: 2713 |
| MAD2L1 | NM_002358.2 | CCCGGGAGCAGGGAATCACCCTGCGCGGGAGCCCGAAATCGTGGCCCAGTTCTTCTTCATTCGGCATCAACAGCAT | SEQ ID NO: 2714 |
| MADH2 | NM_005901.2 | GCTGCCTTTGGTAAGGAACATGTCGTCCATTCTGCCATTCACGCCCCAGTTGTGAAGAGACTGCTGGGAT | SEQ ID NO: 2715 |
| MADH4 | NM_005359.3 | GGACATTACTGGCCTGTTCCACAATGAGCTTGCATTCCAGCCTCCATTTCCAATCATCCTGCTCCTGAGTATTGGT | SEQ ID NO: 2716 |
| MADH7 | NM_005904.1 | TCCATCAAGGCTTTCGACTACACGAGAGAGGCGTACAGCCTGCGAGCGCCAATGACCAGTTATGCAGCAG | SEQ ID NO: 2717 |
| MAP2 | NM_031846.1 | CGGACCACCAGTCAGAGCCAATTCCAGAAGCAGAAGGTGGGAGAACTGAAGAGAGTGGTACCTCAACACCCACTACCCTG | SEQ ID NO: 2718 |
| MAP2K1 | NM_002755.2 | GCCTTTCTTACCCAGAAGCAGAAGGTTGGGAGAACAGTGAAGATGACCTTTGAGAAGATCAGTGAGCTGGGGCTG | SEQ ID NO: 2719 |
| MAP3K1 | XM_042066.8 | GGTTGGCATCAAAAGGAACTGTGCAGGAGAACTGTGTGCAGGAGAGTTTCAGGGACACAATTACTGGGACAATTCATTTATGGCA | SEQ ID NO: 2720 |
| MAPK14 | XM_139012.1 | TGAGTGAAAAGCCTGACCTATGATGAAGCATATTTAGCTGACAACAGTGACGTGTGAACAGTGACCAAGAAGAGATGGAGTCC | SEQ ID NO: 2721 |
| Maspin | NM_002639.1 | CAGATGCCACTTTGAGAACATATTTAGCTGACAACAGTGACCAATCTTGTGTTAATGCTGCC | SEQ ID NO: 2722 |
| MAX | NM_002382.3 | CAAACCGGCTCATCATAATGACTGAACGAAAACGTAGGGACCCACATCAAGAACAGCTTTCACAGTTTGCGGGA | SEQ ID NO: 2723 |
| MCM2 | NM_004526.1 | GACTTTTGCCCCCTACCTTTGAGACAGAATATGGCCTTTCTGTCTACAAGGATCACCAGACCATCACCATCCAGGGC | SEQ ID NO: 2724 |
| MCM3 | NM_002388.2 | GGAGAACAATCCCCTTGAGACAGAATATGGCCTTTCTGTCTACAAGGATCACCAGACCATCACCATCCAGGAGAT | SEQ ID NO: 2725 |
| MCM6 | NM_005915.2 | TGATGGTCCTATGTGTCACATTCATCACACAGGTTCATACCAACACAGGCTTCCTTGGTGTGTTCCTGTCCCA | SEQ ID NO: 2726 |
| MCP1 | NM_002982.1 | CGCTCAGCCAGATGCAATCAATGCCCCAGTCACCTGCTGTTATAACTTCACCAATAGGAAGATCTCAGTGC | SEQ ID NO: 2727 |
| MDK | NM_002391.2 | GGAGCCGACTGCAAGTACAAGTTTGAACTTGGGGGTGCGTGATGGGGCACAGGCACCAAAGTC | SEQ ID NO: 2728 |
| MDM2 | NM_002392.1 | CTACAGGGACGCCATCGAATCCGGATCTTGATGCTGTAAGTGTAGCATTGAACATTCAGGTGATTGATTGGAT | SEQ ID NO: 2729 |

TABLE B-continued

| Gene | Locus Link | Sequence | Sequence ID Number |
|---|---|---|---|
| MGAT5 | NM_002410.2 | GGAGTCGAAGGTGGACAATCTTGTTGTCAATGGCACCGGAACAAACTCAACCAACTCCACTACAGCTGTTCCCA | SEQ ID NO: 2730 |
| MGMT | NM_002412.1 | GTGAAATGAAACGCACCACACTGGACAGCCCTTGGGAAGCTGTCTGGTTGTGAGCAGGGTC | SEQ ID NO: 2731 |
| mGST1 | NM_020300.2 | ACGGATCTACCACACACCATTGCATATTTGACACCCCCTTCCCCAGCCAAATAGAGCTTTGAGTTTTTTGTTGGATATGGA | SEQ ID NO: 2732 |
| MMP1 | NM_002421.2 | GGGAGATCATCGGGACAACTCTCCTTTTGATGGACCTGGAGGAAATCTTGCTCATGCTTTTCAACCAGGCCC | SEQ ID NO: 2733 |
| MMP12 | NM_002426.1 | CCAACGCTTGCCAAATCCTGACAATTCAGAACCAGCTCTTCTGTGACCCCAATTTGAGTTTTGATGCTGTCACTACCGT | SEQ ID NO: 2734 |
| MMP2 | NM_004530.1 | CCATGATGGAGGCAGACATCATGATCAACTTTGGCCGCTGGGAGCATGGCGATGGATACCCCTTTGACGGTAAGGACGACTCC | SEQ ID NO: 2735 |
| MMP7 | NM_002423.2 | GGATGGTAGCAGTCTAGGGATTAACTTCCTGTATGCTGCACAACTCATGAACTTGGCCATTCTTTGGGTATGGGACATTCC | SEQ ID NO: 2736 |
| MMP9 | NM_004994.1 | GAGAACCAATCTCACCGACAGGACAGCTGGCAGGAATACTGTACCGCTATGGTTACACTCGGGTG | SEQ ID NO: 2737 |
| MRP1 | NM_004996.2 | TCATGGTGCCCGTCAATGCTGTGATGGCGAAGACCAAGACGTATCAGTGGCCACATGAAGAGCAAAGACAATCG | SEQ ID NO: 2738 |
| MRP2 | NM_000392.1 | AGGGGATGACTTGGACACACATCGCCATTCGACATGACTGCAATTTTGACAAAGCCATGCAGTTTT | SEQ ID NO: 2739 |
| MRP3 | NM_003786.2 | TCATCCTGGCGATCTACTTCCTCTGGCAGAACCTAGTCCCCTCGTCCTGCTTTCATGGTCCTTGCTTGATTCCACTCAACGG | SEQ ID NO: 2740 |
| MRP4 | NM_005845.1 | AGCGCCTGGAATCTACAACTGGAGTCCAGTTGTTTCCCACTGTCATCTTCTCTCCAGGGCTCT | SEQ ID NO: 2741 |
| MRPL40 | NM_003776.2 | ACTTGCAGGCTGCTATCCTTAACATGCTGCCCCTGAGAGTAGGAATGACCAGGGTTCAAGTCTGCT | SEQ ID NO: 2742 |
| MSH2 | NM_000251.1 | GATGCAGAATTGAGGCAGACTTTACAAGAAGATTTACTTCGTCGATTCCCGATTCTTAACCGACTTGCCAAGA | SEQ ID NO: 2743 |
| MSH3 | NM_002439.1 | TGATTACCACATGGCTCAGATTGGCTTCCTATGTTCCAGCTGGAAATTCCTGAGAATTTCACCACTCGCAATTTG | SEQ ID NO: 2744 |
| MSH6 | NM_000179.1 | TCTATTGGGGATTGTGTAGGAACCGTTACCAGCTGTGTGTGTGCAAAGGCGAGAGGCAGCTGAGGCAGAAGACAGAGAGTG | SEQ ID NO: 2745 |
| MT3 | NM_005954.1 | GTGTGAGAAGTGTGCCAAGGACTGTGTGTGCAAAGGCGAGAGGCAGCTGAGGCAGCAAAGCAGAGAGAGTGCAG | SEQ ID NO: 2746 |
| MTA1 | NM_004689.2 | CCGCCCTCACCTGAAGAGAAACGCGCTCCTGGCCGGACACTGGGGGAGGAGGAGGAAGAAGCGCGGCTAACTTATTCC | SEQ ID NO: 2747 |
| MUC1 | NM_002456.1 | GGCCAGGATCTGTGGTGGTACAATTGACTCTGGCCTTCCGAGAAGTACCATCAATGTCCACGACGTGGAG | SEQ ID NO: 2748 |
| MUC2 | NM_002457.1 | CTATGAGCCATGTGGGAACCGAGCTTCGAGACCTGCGAGGACCTGCAGGACCATCAACGGCATCCACTCCAACAT | SEQ ID NO: 2749 |
| MUC5B | XM_039877.11 | TGCCCTTGCACTGTCCTAACGGTCTCAGCCATCCTGCCACACCCACGTGATGAGTGTGGCTG | SEQ ID NO: 2750 |
| MUTYH | NM_012222.1 | GTACGACCAAGAGAAACGGGACCTACCATGGAAGAAGACGGGCAGAAGATGAGAGATGACCTGGACAGG | SEQ ID NO: 2751 |

TABLE B-continued

| Gene | Locus Link | Sequence | Sequence ID Number |
|---|---|---|---|
| MVP | NM_017458.1 | ACGAGAACGAGGGCATCTATGTCCAGAGATGTCAAGACCGGAAAGGTGCGCGCTGATTGAAGCACCTACATGC | SEQ ID NO: 2752 |
| MX1 | NM_002462.2 | GAAGGAATGGGAATCAGTCATGAGCTAATCACCCTGAGAGATCAGCTCCCGAGATGTCCGATCTGACTCTAATAGAC | SEQ ID NO: 2753 |
| MXD4 | NM_006454.2 | AGAAACTGGAGGAGCAGGACGCGCCGGCACTGCAGCTCAAGGACAGCTGCAGCAGGAGCATCGTTTCCTGAAG | SEQ ID NO: 2754 |
| MYBL2 | NM_002466.1 | GCCGAGATCGCCAAGAGATGTTGCCAGGGAGGACAGACAATGCTGTGAAGAATCACTGAACTCTACCATCAAAAG | SEQ ID NO: 2755 |
| MYH11 | NM_002474.1 | CGGTACTTCTCAGGGCTAATATACGTACTCTGGCCTCTTCTGCCTGGTGGTCAACCCCTATAAACACCTGCCCATCTACTCGG | SEQ ID NO: 2756 |
| MYLK | NM_053025.1 | TGACGGAGCGTGAGTGCATCAAGTACATGCGCGCAGATCTCCGAGGGGAGTGGAGTACATCCACAAGCAGGGCAT | SEQ ID NO: 2757 |
| NAT2 | NM_000015.1 | TAACTGACATTCTTTGAGCACCAGATCCGGGCTGTGTCCCTTTGAGACCCTTAACATGCATTGTGGGCAAGCCAT | SEQ ID NO: 2758 |
| NAV2 | NM_182964.3 | CTCTCCCAGACACAGCTTGAACCTCACTGAGTCAACCAGCCTGGACATGTTGCTGACACTGGTG | SEQ ID NO: 2759 |
| NCAM1 | NM_000615.1 | TAGTTCCAGCTGACCATCAAAAAGTGGATAAGAACGACGAGGCTGAGTACATCTGCATTGCTGAGAACAAGGCTG | SEQ ID NO: 2760 |
| NDE1 | NM_017668.1 | CTACTGCGGAAAGTCGGGGCACTGCTGGAGTCTCAAACTCGCTTCCTGCCCAAACCTCGTGTACGATCAGTCC | SEQ ID NO: 2761 |
| NDRG1 | NM_006096.2 | AGGGGCAACATTCCACACGTGCCCTGGCTGTGATGAGTGTCCTTGCAGGGGCCGGAGTAGGAGCACTG | SEQ ID NO: 2762 |
| NDUFS3 | NM_004551.1 | TATCCATCCTGATGGCGTCATCCCAGTGCTGCTCAGTTCCTCAGGGATGCTGACTCTTCGTGTGCTCTTATGACTGTCCTGGTGTCCCTGGTGTC | SEQ ID NO: 2763 |
| NEDD8 | NM_006156.1 | TGCTGGCTACTGGGTGTTAGTTGCAGTCCTGTGTGCTTCCCTCTCTTATGACTGTGTCCCTGGTGTC | SEQ ID NO: 2764 |
| NEK2 | NM_002497.1 | GTGAGGCAGCCGACTCTGGGCGACTCGGCCCATGCCTCGCCGGCCATCTGGGACTCGGGAAGTCATGAGGACTATGAAGTGTGTACACCATTGGCA | SEQ ID NO: 2765 |
| NF2 | NM_000268.2 | ACTCCAGAGCTGACCTCCACCGACCCAGCCTGGTGCGGCTCATGTTTAGGGAGTCATTGTAGGGACACTGAAGCCCTGA | SEQ ID NO: 2766 |
| NFKBp50 | NM_003998.1 | CAGACCAAGGAGATGACCCTCAGCGTGGTGCCGCTCATGTTTACAGCTTTTCTTCCGGATAGCACTGGCAGCT | SEQ ID NO: 2767 |
| NFKBp65 | NM_021975.1 | CTGCCGGGATGGCTTCTATGAGGCTGAGCTGTCGCCCCGACCCCTGCCCCTGAGTCCATCCACAGTTTCCAGAACCTGG | SEQ ID NO: 2768 |
| NISCH | NM_007184.1 | CCAAGGAATCATGTTCGTTCAGGAGAGCCCTGGCCAGGCCCAGCGCCTCTCGTCCTCCACTGACAGTCTGACTCCCGAGCACCA | SEQ ID NO: 2769 |
| Nkd-1 | NM_033119.3 | GAGAGAGTGAGCGAACCCTGCCAGGCTCCAAGAAGCAGCTGAAGTTTGAAGAGCTCCAGTGCGACG | SEQ ID NO: 2770 |
| NMB | NM_021077.1 | GGCTGCTGCTACAAATACTGAGAAATGACACCAATAATAGGGGCAGACACAACAGCGTGGCTTAGATTG | SEQ ID NO: 2771 |
| NMBR | NM_002511.1 | TGATCCATCTCTAGGCCACATGATTGTCCACCTTAGTTGCCCGGGTTCTCAGTTTGCCAATTCTTGTGTCAACCCATTTGCTC | SEQ ID NO: 2772 |
| NME1 | NM_000269.1 | CCAACCCTGCGAGACTCCAAGCCTGGACCATCCGTGGAGACTTCCGTCATACAAGTTGGCAGGAACATTATACAT | SEQ ID NO: 2773 |

TABLE B-continued

| Gene | Locus Link | Sequence | Sequence ID Number |
|---|---|---|---|
| NOS3 | NM_000603.2 | ATCTCCGCCTCGCTCATGGGCACGGTGATGGCGAAGGCGAGTGAAGGCGACAATCCTGTATGGCTCCGA | SEQ ID NO: 2774 |
| NOTCH1 | NM_017617.2 | CGGGTCCACCAGTTTGAATGGTCAATGCGAGTGGCTGTGTCCCGGCTGCAGAGCGGCATGGTGCCGAACCAATACAAC | SEQ ID NO: 2775 |
| NOTCH2 | NM_024408.2 | CACTTCCCTGCTGGGATTATATCAACAACCAGTGTGATGAGCTGTGCAAACGGTCGAGTGCCTGTTTGACAACT | SEQ ID NO: 2776 |
| NPM1 | NM_002520.2 | AATGTTGTCCAGGTTCTATTGCCAAGAATGTTGTCCAAAATGCCTGTTTAGTTTTTAAAGATGGAACTCCACCCTTTGCTTG | SEQ ID NO: 2777 |
| NR4A1 | NM_002135.2 | CACAGCTTGCTTGTCGATGTCCCTGCCTTCCGCCTTCTGCCCTTGCTCCTCATCACCGACCGGCAT | SEQ ID NO: 2778 |
| NRG1 | NM_013957.1 | CGAGACTCTCCTCATAGTGAAAGGTATGTCAGCCATGAAGTAGTCACACCCCGGCTCGTATGTCACCTGTAGATTTCCACACGCCAAG | SEQ ID NO: 2779 |
| NRP1 | NM_003873.1 | CAGCTCTCTCCACGCCATTCATCAGGATCTACCCCGAGAGACCACCCAGGACCCCAGCAGCCAAAGCTGTTCGAAGGGAAC | SEQ ID NO: 2780 |
| NRP2 | NM_003872.1 | CTACAGCCTAAACGGCAAGGACTGGGAATACATTCAGGACCTGAAGGCGGACAAGGCGGGGGACTGGTGGAAGTTCACGG | SEQ ID NO: 2781 |
| NTN1 | NM_004822.1 | AGAAGGACTATGCCGTCCAGATCCACATCCTGAAGGTCCGATGGATGTTCCTCGGCATCAGAGTCCTTCAACCCTGCA | SEQ ID NO: 2782 |
| NUFIP1 | NM_012345.1 | GCTTCCACATCCGTGTATTGGAGACAGTCTTCTGATAGGTTTCTGATAGGTTTCTCACACCAGTGAGTCAAACCCGCAGTT | SEQ ID NO: 2783 |
| ODC1 | NM_002539.1 | AGAGATCACCGGCGTAATCAACCCAGCGTTGGACAAATACTTTCCGTCAGACTCTGAGTGAGAATCATAGCTGAGCCCG | SEQ ID NO: 2784 |
| OPN, osteopontin | NM_000582.1 | CAACCGAAGTTTCACTCAGTGTCTCCCACAGTAGACACATATGATGGCCAGAGTGATGTGTGTTTATGGACTGAGG | SEQ ID NO: 2785 |
| ORC1L | NM_004153.2 | TCCTTGACCATACCGGAGGGTGCATGTACATCTCCGGTGTCCCTGGGACAGGGAAGACTGCCACTG | SEQ ID NO: 2786 |
| OSM | NM_020530.3 | GTTTCTGAAGGGGAGTCACAGGTCCTCAGCCTGAGCTCGGCCTCATCATGTCCCAAACCAGACACCT | SEQ ID NO: 2787 |
| OSMR | NM_003999.1 | GCTCATCATGTCTACTTGAAAAGTCAGTGGATCAAGGAGACCTGTTATCCTGACATCCCTGACCCTTACA | SEQ ID NO: 2788 |
| P14ARF | S78535.1 | CCCTCGTGCTGATGCTACTGAGGAGCCAGCGTCTAGGGCAGCAGCCGCTTCCTAGAAGACCAGGTCATGATG | SEQ ID NO: 2789 |
| p16-INK4 | L27211.1 | GCGGAAGGTCCCCTCAGATCAGACATCCCCGATTGAAAAGAACCAGAGAGGCTCTGAGAAACCTCGGGAAACTTAGATCATCA | SEQ ID NO: 2790 |
| p21 | NM_000389.1 | TGGAGACTCTCAGGGTCGAAAACGGCGGCAGACCAGCATGACACAGATTTCTACCACTCCAAACGCC | SEQ ID NO: 2791 |
| p27 | NM_004064.1 | CGGTGGACCACGAAGAGTTAACCCGGGACTTGGAGAAGCACTGCAGAGACATGGAAGAGGCGAGCC | SEQ ID NO: 2792 |
| P53 | NM_000546.2 | CTTTGAACCCTTGCTTGCAATAGGTGTGCGTCAAGAGTGCAGGAGCACCCAGGACTTCCATTTGCTTTGTCCGGG | SEQ ID NO: 2793 |
| p53R2 | AB036063.1 | CCCAGCTAGTTCCTCAGAACAAAGATTGGAAAAAGCTGGCCGAGAACCATTATACATAGAGGAAGGCTTACGG | SEQ ID NO: 2794 |

TABLE B-continued

| Gene | Locus Link | Sequence | Sequence ID Number |
|---|---|---|---|
| PADI4 | NM_012387.1 | AGCAGTGGCTTGCTTTCTTCCTGTGATGTCCCACTTGCCCAGTTCCCACTCTGAAGATCCCAACATGGTCCTAGCA | SEQ ID NO: 2795 |
| PAI1 | NM_000602.1 | CCGCAACGTGGTTTTTCTCACCCTATGGAATACTGGGGTGCCTCGGTGTTGGCCATGCTCCAGTCTGACAACAGGAGGAGAAACCCAGCA | SEQ ID NO: 2796 |
| Pak1 | NM_002576.3 | GAGCTGTGGGTTGTTATGGAATACTGGCTGCTGAGGCTCCTTGACAGATGTGTGACAGAAACTTGCATGG | SEQ ID NO: 2797 |
| PARC | NM_015089.1 | GGAGCTGACCTGCTTCCTACATCGCCTGGCCTCGGCCTCGATGCATAAGGACTACCTCGGTACGAAACCACAGGTG | SEQ ID NO: 2798 |
| PCAF | NM_003884.3 | AGGTGCTGTGTTACTGCAACGTGCCACAGTTCTGCAGACAGTTCTGGGATACAGGCCTGCTGGGATATTAGCTCCAGCGGTGTAAACC | SEQ ID NO: 2799 |
| PCNA | NM_002592.1 | GAAGGTGTTGGAGGCACTCAAGGACCTCATCAACAGGCCTGCTGGGATATTAGCTCCAGCGGTGTAAACC | SEQ ID NO: 2800 |
| PDGFA | NM_002607.2 | TTGTTGTGTGCCCTGGTGCCGTGGTGCGGTCACTCCCTCGCTGCCAGTGTTTGACAGAACCCA | SEQ ID NO: 2801 |
| PDGFB | NM_002608.1 | ACTGAAGGAGACCCCTTGGAGCCTAGGGGCATCGGGCCAGGAGAGTGTGTGGGCAGGGTTATTTA | SEQ ID NO: 2802 |
| PDGFC | NM_016205.1 | AGTTACTAAAAATACCACGAGGTCCTTCAGTTGAGACCAAAGACCGGTCTCAGGGGATTGCACAAATCACTCACCGAC | SEQ ID NO: 2803 |
| PDGFD | NM_025208.2 | TATCGAGGCAGGTCATACCATGACCGGAAGTCAAAAGTTGACCTGGATAGGCTCAATGATGATGCCAAGCGTTA | SEQ ID NO: 2804 |
| PDGFRa | NM_006206.2 | GGGAGTTTCAAGAGATGGACTAGTGCTTGGTCGGGGTCTTGGGGTCTTGGAGCGTTTGGGAAGGTGGTTGAAG | SEQ ID NO: 2805 |
| PDGFRb | NM_002609.2 | CCAGCTCTCCTTCCAGCTACAGATCAATGTCCCTGTCCGAGTGCTGAGCTAAGTGAGAGCCACCC | SEQ ID NO: 2806 |
| PFN1 | NM_005022.2 | GGAAAACGTTCTGTCAACATCACGCCAGCTGTCCCAGCTGAGGTGGTGTCCTGGTTGGCAAAGACCGGTCAAGTTTT | SEQ ID NO: 2807 |
| PFN2 | NM_053024.1 | TCTATACGTCGATGGTGACTGTAGAACTCAAATCTCTGCTGGGCAAGGATGTTCTGTTCTTGAAGGACTGTGTAGGCC | SEQ ID NO: 2808 |
| PGK1 | NM_000291.1 | AGAGCCAGTTGCTGTAGAACTCAAATCTCTGCTGGGCAAGGATGTTCTGTTCTTGAAGGACTGTGTAGGCCCAG | SEQ ID NO: 2809 |
| PI3K | NM_002646.2 | TGCTACCTGGACAGCCCGTTGGTGCGCTTCCTCTTCCTGAAACGAGCTGTCTGACTTGAGAGTGACTCACTACTTCTTCTGGTTACTGAAGGACGGCCT | SEQ ID NO: 2810 |
| PI3KC2A | NM_002645.1 | ATACCAATCACCCGCACAAACCCAGCTATTTGTTAAGTCCAGTCACGCAGCGCAAAGAACATATGCGAGAAAATGCTAGTGTG | SEQ ID NO: 2811 |
| PIK3CA | NM_006218.1 | GTGATTGAAGAGCATGCCAATTGGTCTGTATCCGAGAAGCAGGATTTAGCTATTCCACGCAGGAC | SEQ ID NO: 2812 |
| PIM1 | NM_002648.2 | CTGCTCAAGGACACCGTCTACACGGACTTCGATGGGACCCCGAGTGTTGGGAGAGGACTTTGAGTCTTCGGCCTCACAGTTCA | SEQ ID NO: 2813 |
| Pin1 | NM_006221.1 | GATCAACGGCTACATCCAGAAGATCAAGTCGGGAGAAGCTCCTCACAATGGCTCGGGGACGTGGGCCTATTCAG | SEQ ID NO: 2814 |
| PKD1 | NM_000296.2 | CAGCACCAGCGATTACGACGTTGGCTGGGAGAGTCCTCACACAGCCCGGAACACTGTACCATTGGCCCAG | SEQ ID NO: 2815 |
| PKR2 | NM_002654.3 | CCGCCTGGACATTGATTGATTCACCACCCATCACAGCCCGGAACACTGTACCATTGGCCCAG | SEQ ID NO: 2816 |
| PLA2G2A | NM_000300.2 | GCATCCCTCACCCATCCTAGAGGCCAGGCAGGAGCAGGAGCCCTTTATACCCCAGAATGAGACATCCAGCAGATTTCCAGC | SEQ ID NO: 2817 |

TABLE B-continued

| Gene | Locus Link | Sequence | Sequence ID Number |
|---|---|---|---|
| PLAUR | NM_002659.1 | CCCATGGATGCTCCCTGAAGAGACTTTCCTCATTGACTGCCGAGGCCCCTGATGAATCAATGTCTGGTAGCCACCGG | SEQ ID NO: 2818 |
| PLK | NM_005030.2 | AATGAATACAGTATTCCCAAGCACATCAAACCCGTGCCGCGCCTCCCCTCATCCAGAAGATGCTTCAGACA | SEQ ID NO: 2819 |
| PLK3 | NM_004073.2 | TGAAGGAGACTACCCGTGCATCAAGCAGGTTCACTACACGGTCCTGCCTGCCAGCCTCTCACTGCCTG | SEQ ID NO: 2820 |
| PLOD2 | NM_000935.2 | CAGGGAGGTGGTTGCAAATTTCTAAGTACAATTGCTCTATTGAGTCACCAGAAAGGCTGGAGCTTCATGCATCCTGGGAGA | SEQ ID NO: 2821 |
| PMS1 | NM_000534.2 | CTTACGGTTTTCGTGAGAAGCCTTGGGGTCAATTTGTTGTATAGCTGAGTTTTAATTACAACAAGAACGGCTGCT | SEQ ID NO: 2822 |
| PMS2 | NM_000535.2 | GATGTGGACTGCCATTCAAACCAGAAGATACCGGATGTAAATTTCGAGTTTTGCCTCAGCCAACTAATCTCGCA | SEQ ID NO: 2823 |
| PPARG | NM_005037.3 | TGACTTTATGGAGCCCAAGTTTGAGTTTGCTGTGAAGTTCAATGCACTGGAATTAGAGCAGCGACTTGGC | SEQ ID NO: 2824 |
| PPID | NM_005038.1 | TCCTCATTTGGATGGGAAACATGTGGTGTTTGGCCAAGTAATTAAAGGAATAGGAGTGGCAAGGATATTGG | SEQ ID NO: 2825 |
| PPM1D | NM_003620.1 | GCCATCCGCAAAGGCTTTCTCGCTTGGGGCCCAAGTTGGGAGAAGAACTGGCGGAATGGCC | SEQ ID NO: 2826 |
| PPP2R4 | NM_178001.1 | GGCTCAGAGACATAAGGCTTCAGGGCCCAAGTTGGGAGAAGTGACCAAAGTCTAGCCAGTTTTCTGAGTTCCCGT | SEQ ID NO: 2827 |
| PR | NM_000926.2 | GCATCAGGCTGTCATTATGGTGTCCTGTGGGAGCTGTAAGGTCTTCTTTAAGAGGGCAATGGAAGGGCAGCACAACTACT | SEQ ID NO: 2828 |
| PRDX2 | NM_005809.4 | GGTGTCCTTCCAGATCACTGTTAATGATTGCCTGTGGGACGCTCCTGTGATGAGGCTCTGCCGGCTG | SEQ ID NO: 2829 |
| PRDX3 | NM_006793.2 | TGACCCCAATGAGTCATCAGCATTGAGCGTCAACGATCTCCCAGTGGGCCGAAGCGTGAAGAAACCCTCCGCTTGG | SEQ ID NO: 2830 |
| PRDX4 | NM_006406.1 | TTACCCATTTGCCTGCCTGATTAATAACCCTCGAAGACAAGGAGACTTGGGCAATAAGGATTCCACTTCTTCAG | SEQ ID NO: 2831 |
| PRDX6 | NM_004905.2 | CTGTGAGCCAGAGGATGTCAGCTGCCAATTGTGTTTTCCTGCAGCAATTCCATAAACACATCCTGGTGTCATCACA | SEQ ID NO: 2832 |
| PRKCA | NM_002737.1 | CAAGCAATGCGTCATCAATGTCCCAGCCTCTGCGGAATGGATCACTGAAGAAGAGGGGGCGGATTTAC | SEQ ID NO: 2833 |
| PRKCB1 | NM_002738.5 | GACCCAGCTTCCACTCCTGCTTCCAGACCATGGACCGCCTGTACTTTGTGATGGAGTACGTGAATGGG | SEQ ID NO: 2834 |
| PRKCD | NM_006254.1 | CTGACACTTGCCGCAGAGAATCCCTTTCTCCACCTCATCTGCCACCTTCCAGACCAAGGACCACCT | SEQ ID NO: 2835 |
| PRKR | NM_002759.1 | GCGATACATGAGCCAGAGCCAGAAGATTTCTTCGCAAGACTATGGAAAGGAAGTGGACCTTCACGCTTTGGGCTAATTCTTGCTGA | SEQ ID NO: 2836 |
| pS2 | NM_003225.1 | GCCCTCCCAGTGTGCAAATAAGGGCGTTTGCAAATACCGTTCGTGTGGGTCCCCTGTGCTTCTATCCTAATACCATCGACG | SEQ ID NO: 2837 |
| PTCH | NM_000264.2 | CCAACGACAAAGCCGACTACATGCCTGAAAACAAGGCTGAGAATCCCGGCAGCAGAGCCCATCGAGTA | SEQ ID NO: 2838 |
| PTEN | NM_000314.1 | TGGCTAAGTGAAGATGACAATCATGTTGCAGCAATTCACTGTAAAGCTGGAAAGGGACGAACTGGTAATATGATGTGCA | SEQ ID NO: 2839 |

TABLE B-continued

| Gene | Locus Link | Sequence | Sequence ID Number |
|---|---|---|---|
| PTGER3 | NM_000957.2 | TAACTGGGCAACCTTTTCTTCGCCTTCCTCTGCCTTGCCTTCCTCTGGCGCTGACAGTCACCTTTTCCTGCAA | SEQ ID NO: 2840 |
| PTHLH | NM_002820.1 | AGTGACTGGGAGTGGGCTAGAAGGGACCACCTGTCTGACACCTCCACAACGTCGCTGGAGCTCGATTCACGGTAACAGGCTT | SEQ ID NO: 2841 |
| PTHR1 | NM_000316.1 | CGAGGTACAAGCTGAGATCAAGAATCTTGGAGCCCTGACACTGGCACTGGACTTCAAGCGAAAGGCACGC | SEQ ID NO: 2842 |
| PTK2 | NM_005607.3 | GACCGGTCGAATGATAAGGTGTACGAGAATGACGGGCCTGGTGAAAGCCTGTCATCGAGATGTCCAG | SEQ ID NO: 2843 |
| PTK2B | NM_004103.3 | CAAGCCCAGCCGACCTAAGTACAGACCCCCTCCGCAAACCAACCTCTGGCTCCAAAGCTGCAGTTCCAGGTTC | SEQ ID NO: 2844 |
| PTP4A3 | NM_007079.2 | AATATTTGTGCCGGGTATGGGGTGGGTTTTTAAATCTCGTTTCTTGGACAAGCACACAGGGATCTCGTT | SEQ ID NO: 2845 |
| PTP4A3 v2 | NM_032611.1 | CCTGTTCTCGGCACCTTAAATTATTAGACCCCGGGCAGTCAGGTGCTCCCGGACACCCGAAGGCAATA | SEQ ID NO: 2846 |
| PTPD1 | NM_007039.2 | CGCTTGCCTAACTCATCATACTTTCCCGTTGACACTTGATCTCCACCGAGCTGGCACTGGACGTAAGTGCGCAGTCTGAATGG | SEQ ID NO: 2847 |
| PTPN1 | NM_002827.2 | AATGAGAAGTTTCGGATGGGGTTCAGACAGCCGACCAGCTGCTCGCGCTTCTCTCCTACCTGGCTGTGATCGAAG | SEQ ID NO: 2848 |
| PTPRF | NM_002840.2 | TGTTTTAGCTGAGGGACGTGGTGCCGACGTCCCCAAACCTAGCTAGGCTAAGTCAAGATCAACATTCCAGGTTGGTA | SEQ ID NO: 2849 |
| PTPRJ | NM_002843.2 | AACTTCCGGTACCTCGTTCGTTGACTACATGAAGCAGAGTCCTCCCGAATCGCCGATTCTGTGCATTGCAGTGCT | SEQ ID NO: 2850 |
| PTPRO | NM_030667.1 | CATGGCCTGATCATGTGTGCCCACAGCAAATGCAGAAGTATCCTGCAGTTTGTACACATGG | SEQ ID NO: 2851 |
| PTTG1 | NM_004219.2 | GGCTACTTCGATCTATGTTGATAAGGAAAATGGAGAACCAGGCACCCGTGTGGTTGCTAAGGATGGGCTGAAGC | SEQ ID NO: 2852 |
| RAB32 | NM_006834.2 | CCTGCAGCTGTGGGACATCGCGGGGCAGGAGCGATTTGGCAACATGACCCCGAGTATACCAAGGAAGCTGTTGGTGCT | SEQ ID NO: 2853 |
| RAB6C | NM_032144.1 | GCGACAGCTCCTCTAGTTCCACCATGTCCGCGGGCAGGAGACTTCGGGGAATCCGCTGAGGAAATTCAAGCTGGTGTTCC | SEQ ID NO: 2854 |
| RAC1 | NM_006908.3 | TGTTGTAAATGTCTCAGCCCCCTCGTTCTTGTTCTCCTTGGAGACCTTTGTACGCTTTGCTCAA | SEQ ID NO: 2855 |
| RAD51C | NM_058216.1 | GAACTTCTTGAGCAGGAGCATACCCAGGGCTTCAGCACTTCGTTCAGCAATGATGATATTCTTGGGGGTGGA | SEQ ID NO: 2856 |
| RAD54L | NM_003579.2 | AGCTAGCCTCAGTGACACATGACAGGTTGCACTGCCGACGTTGTCAACAGCCGTCAGATCCGG | SEQ ID NO: 2857 |
| RAF1 | NM_002880.1 | CGTCGTATGCCGAGAGTCGTGTTTCCAGGATGCAAATGCCTTCTCTGCCGTCTGTGGTCTCCAGCACACAGATATTCTACACCTCACGCCTTCA | SEQ ID NO: 2858 |
| RALBP1 | NM_006788.2 | GGTGTCAGATATAAATGCAAATGCAGAAGTGCCTTCGTCGTCCGGTCTCAGTGCTCACTTTATAGCTGCTGGCAATATCGAA | SEQ ID NO: 2859 |
| RANBP2 | NM_006267.3 | TCCTTCAGCTTTCACACTGGGCTCAGAAATGAAGTTGCATGATGACTCTTCTGGAAGTCAGGTGGGAACAGGATTT | SEQ ID NO: 2860 |

TABLE B-continued

| Gene | Locus Link | Sequence | Sequence ID Number |
|---|---|---|---|
| ranBP7 | NM_006391.1 | AACATGATTATCCAAGCCGCTGGACTGCCATTGTGACAAAATTGGCTTTTATCTTCAGTCCGATAACAGTGCTTGTTGGC | SEQ ID NO: 2861 |
| RANBP9 | NM_005493.2 | CAAGTCAGTTGAGACGCCAGTTGTGTGGAGGAAGTCAGGCCCGCCATAGAAAAGAATGATCCACTTTGGACGAGAGCTGCA | SEQ ID NO: 2862 |
| RAP1GDS1 | NM_021159.3 | TGTGGATGCTGGATTGATTCACCACTGGTCGTCAGCTGCTAAATAGCAAAGACCAGGAAGTGCTGCTT | SEQ ID NO: 2863 |
| RARA | NM_000964.1 | AGTCTGTGAGAAACGACCGAAACAAGAAGAAGAGGAGGTGCCAAGCCCGAGTGCTCTGAGAGCTACACCGCTGACGCCG | SEQ ID NO: 2864 |
| RARB | NM_016152.2 | TGCCTGGACATCCTGATTCTTAGAATTTGCACCAGTATACCCCAGAACAAGACACCATGACTTTCTCAGACGGCCTT | SEQ ID NO: 2865 |
| RASSF1 | NM_007182.3 | AGTGGGAGACACCTGACCTTTCTCAAGCTGAGATTGAGCAGAAGATCAAGGAGTACAATGCCCAGATCA | SEQ ID NO: 2866 |
| RBM5 | NM_005778.1 | CGAGAGGGAGAGCAAGACCATGCTGCGCGGCCTTCCCATCACCTGTCCATCACAGAGAGCGATATTCAGA | SEQ ID NO: 2867 |
| RBX1 | NM_014248.2 | GGAACCACATTATGGATCTTTGCATAGAATGTCAAGCTACCAGGCGTCCGCTACTTCAGAGAGTGTACTGTCGCATG | SEQ ID NO: 2868 |
| RCC1 | NM_001269.2 | GGGCTGGGTGAGAATGTGATGGAGAGGAAGAAGCCGGTCCTGGTATCCATTCCGGAGGATGTGTG | SEQ ID NO: 2869 |
| REG4 | NM_032044.2 | TGCTAACTCCTGCACAGCCCGTCCTCCTTTCTGCTAGCCTGGCTCTAAATCTGCTCATTATTTCAGAGGGGAAACCTAGCA | SEQ ID NO: 2870 |
| RFC | NM_003056.1 | TCAAGACCATCATCACTTCACTTTGACCATCTTTCCAACCCCTGGGAAGACATTTGCAACTGACTTGGGGAGGTCCGCCGTCGGGGCGCGGGTATATACCTCCGTGTACTTCCTGATCC | SEQ ID NO: 2871 |
| RhoB | NM_004040.2 | AAGCATGAACAGGACTTGACCATCTTTCCAACCCCTGGGAAGACATTTGCAACTGACTTGGGGAGG | SEQ ID NO: 2872 |
| rhoC | NM_175744.1 | CCCGTTCGCTCTGAGGAAGGCCGGGAACATGGCGGATCGGATCGTGCCTTTGGCTACCTTGAGTGCTC | SEQ ID NO: 2873 |
| RIZ1 | NM_012231.1 | CCAGACCAGCGATTAGAAGCGGCAGCTTGTGAGGTGAATGATTTGGGGGAAGAGAGAGGAGGAAGAGGAGGA | SEQ ID NO: 2874 |
| RNF11 | NM_014372.3 | ACCCTGAAGAGATGGATCAGAAAAAAGATCCGGGAGTGTGTGATCTGATGACTTTGTTTATGGGGACCCAAT | SEQ ID NO: 2875 |
| ROCK1 | NM_005406.1 | TGTGCACATAGGAATGAGCTTCAGATGCAGTTGGCCAGCAGTGATATTGAGCAATTGCGTGCTAAAC | SEQ ID NO: 2876 |
| ROCK2 | NM_004850.3 | GATCCGAGAACCCTGCTCGCCCCATCAACGTGGAGAGCTTGCTGGATGGCTTAAATTCCTTGGTCCT | SEQ ID NO: 2877 |
| RPLP0 | NM_001002.2 | CCATTCTATCATCAACGGGTACAAACGAGTCCTGGCCTTGTCTGTGAGACGGATTACACCTTCCCACTTGCTGA | SEQ ID NO: 2878 |
| RPS13 | NM_001017.2 | CAGTCGGCTTTACCCTACTGCGCAGCGTCCCCACTTGGTTGAAGTTGAACATCTGACGACGTGAAGGAGCAGA | SEQ ID NO: 2879 |
| RRM1 | NM_001033.1 | GGGCTACTGGCAGCTACATTGCTGGGACTAATGCAATTCCAATGGCCTTGTACCGATGCTGAGAG | SEQ ID NO: 2880 |
| RRM2 | NM_001034.1 | CAGCGGGATTAAAACAGTCCTTTAACCAGCAGCAGCCAGTTAAAAGATGCAGCCTCACTGCTTCAACGCAGAT | SEQ ID NO: 2881 |

TABLE B-continued

| Gene | Locus Link | Sequence | Sequence ID Number |
|---|---|---|---|
| RTN4 | NM_007008.1 | GACTGGAGTGGTGTTTGGTGCCAGCCTATTCTGCTGCTTTCATTGACACAGTATTCAGCATTGTGAGCGTAACAG | SEQ ID NO: 2882 |
| RUNX1 | NM_001754.2 | AACAGAGACATTGCCAACCATATTGGATCTGCTTGCTGTCCAAACCAGCAAACTTCCTGGGCAAATCAC | SEQ ID NO: 2883 |
| RXRA | NM_002957.3 | GCTCTGTTGTGTCCTGTTGCCGGCTCTGGCCTTCCTGTGACTGACTGTGAAGTTGGCTTCCGTAC | SEQ ID NO: 2884 |
| S100A1 | NM_006271.1 | TGGACAAGGTGATGAAGGAGCTAGACAGAATGAGACAGGGAGGTGGACTTCCAGGAGTATGTGGTGCT | SEQ ID NO: 2885 |
| S100A2 | NM_005978.2 | TGGCTGCTGCTGGTCACTACCTTCCACAAGTACTCCTGCCAAGAGGGCGACAAGTTCAAGCTGAGTAAGGGGGA | SEQ ID NO: 2886 |
| S100A4 | NM_002961.2 | GACTGCTGTCATGGCCGTGCCCTCTGGAGAAGCCCTGGATGTGATGGTGTCCACCTTCCACAAGTACTCG | SEQ ID NO: 2887 |
| S100A8 | NM_002964.3 | ACTCCCTGATAAAGGGGAATTTCCATGCCGTCTACAAGGGGATGACTGAAGAAATTGCTAGAGACCGAGTGTCCTCA | SEQ ID NO: 2888 |
| S100A9 | NM_002965.2 | CTTTGGGACAGAGTGCAAGACGATGACTGCAAAATGTCGCAGCTGGAACGCCAACAATAGAGACCA | SEQ ID NO: 2889 |
| S100P | NM_005980.2 | AGACAAGGATGCCGTGGATAAATTGCTCAAGACCTGGACGCCTGGAATGGAGAGTGCCCAGGTGGACTTC | SEQ ID NO: 2890 |
| SAT | NM_002970.1 | CCTTTTACCACTGCCTGTTGCAGAAGTGCCAAAGAGCACTGGACTCCGGAAGGACACAGCATTGT | SEQ ID NO: 2891 |
| SBA2 | NM_018639.3 | GGACTCAACGATGGGCAGATCAAGATCTGGGACAGGTGTCAGACAGGGCGCCTCTGAGCGCCTGAGCTCTCAAGGCCAGGTTCTCCGTTACG | SEQ ID NO: 2892 |
| SDC1 | NM_002997.1 | GAAATTGACAGAGGGTGTCTTGGGCAGAGCTGGCTCTGAGGCGCCTCCATCCAAGGCCAGGTTCTCCGTTAGCTCCT | SEQ ID NO: 2893 |
| SEMA3B | NM_004636.1 | GCTCCAGGATGTGTTTCGTGTTGTCCTCCGGGGACCACCCCCTGCTCTATGCCGTCTTCTTCCACGT | SEQ ID NO: 2894 |
| SEMA3F | NM_004186.1 | CGCGAGCCCCTCCATTATACACTGGAGCAGCCTCCCCACAGCCATCGAGGAATGCGTGCTCTCAGGCAAGGATGTCAACGCGCGAGTG | SEQ ID NO: 2895 |
| SEMA4B | NM_020210.1 | TTCCAGCCCAACACAGTGAACACTTTGGCCTGCCAGCCTCCTCCTGCCCTGCGCGACCCGACTC | SEQ ID NO: 2896 |
| SFRP2 | NM_003013.2 | CAAGCTGAACGGTGTGTCCGAAAGGGACCTGAAGAAATCGTGTGGCTCAAAGACAGCTTGCA | SEQ ID NO: 2897 |
| SFRP4 | NM_003014.2 | TACAGGATGAGGCTGGCATTGCCTGGACACCTATGTAAGGCCATGTGTGCTGCCCCTTGCCTAACAAC | SEQ ID NO: 2898 |
| SGCB | NM_000232.1 | CAGTGGAGACCAGTTGGGTAGTGGTGACTGGGTACCGCTACAAGCTCTGCATGTGTCGATGGGACGCTCTTCAAGG | SEQ ID NO: 2899 |
| SHC1 | NM_003029.3 | CCAACACCTTCTTGGCTTCTGGGACCTGTGTTCTTGCTGAGCACCCTCTCCGGTTTGGGTTTGGGATAACAG | SEQ ID NO: 2900 |
| SHH | NM_000193.2 | GTCCAAGGCACACATATCCACTGCTCGTGATGAAAGCAGAGAACTCGGTGCGGCCAAATCGGAGGCTGCTTC | SEQ ID NO: 2901 |
| SI | NM_001041.1 | AACGGACTCCCTCAATTTGTGTCAAGATTTGCATGACCATGACAGAAATATGTCATCATCTTGGACCCTGCAATTTC | SEQ ID NO: 2902 |
| Siah-1 | NM_003031.2 | TTGGCATTGGAACTACATTCAATCCGGGTATCCTCGGATTAGTTCTAGGACCCCCCTTCTCCATACC | SEQ ID NO: 2903 |
| SIAT4A | NM_003033.2 | AACCACAGTTGAGGAGGACCGCAGAGACAGTTCCCTCCCCGCTATACCACCCTTCTTCG | SEQ ID NO: 2904 |

TABLE B-continued

| Gene | Locus Link | Sequence | Sequence ID Number |
|---|---|---|---|
| SIAT7B | NM_006456.1 | TCCAGCCCAAATCCTCCTGGTGGCACATCCTACCCAGATGCTAAAGTGATTCAAGGACTTCCAGGACACC | SEQ ID NO: 2905 |
| SIM2 | NM_005069.2 | GATGGTAGGAGGGATGTGCCCGCCTCTCCACGCACTCAGCTATACCTCAGCTCATTCACAGCTCCTTGTG | SEQ ID NO: 2906 |
| SIN3A | NM_015477.1 | CCAGAGTCATGCTCATCCAGCCCCACCAGTTGCACCAGTGCAGGGACAGCAGCAATTTCAGAGGCTGAAGGTGG | SEQ ID NO: 2907 |
| SIR2 | NM_012238.3 | AGCTGGGGTGTCTGTTTCATGTGGAATACCTGACTTCAGGTCAAGGGATGTATTTATGCTCGCCTTGCTGT | SEQ ID NO: 2908 |
| SKP1A | NM_006930.2 | CCATTGCCTTTGCTTTGTTCATAATTTCAGCAGGGCAGAATAAAAACCATGGAGGCAAAGAAGGAAATCCGGAA | SEQ ID NO: 2909 |
| SKP2 | NM_005983.2 | AGTTGCAGAATCTAAGCCTGGAAGGCCTGCGGCTTTCGGATCCCATTGTCAATACTCTCGCAAAAAACTCA | SEQ ID NO: 2910 |
| SLC25A3 | NM_213611.1 | TCTGCCAGTGCTGAATTCTTTGCTGACATTGCCCTGCCTCCTGGCTCTCACCCAGGCTTCACCTGAAGGTGCTAAGGTTCGAA | SEQ ID NO: 2911 |
| SLC2A1 | NM_006516.1 | GCCTGAGTCTCCTGTGCCACATCCCAGGCTTCACCCAGGCTTCACCCTGAATGGTTCCATGCCTGAGGGTGGAGACT | SEQ ID NO: 2912 |
| SLC31A1 | NM_001859.2 | CCGTTCGAAGAGTCGTGAGGGGGTGAGGGTTAAGATTCGGACGGGTTGAAGATTCAGAGAGAGGTGCTAGTGGCTGGACT | SEQ ID NO: 2913 |
| SLC5A8 | NM_145913.2 | CCTGCTTTCAACCACATTGAATTGAACTCAGATCAGAGTGGCAATGGGACTCGTTTGTGAAGCTGCTCT | SEQ ID NO: 2914 |
| SLC7A5 | NM_003486.4 | GCGCAGAGCCAGTTAAAGTAGAGATCCTCCTCGAACCCACTCCGGTTCCCGCAACCCCAGCTCAGCT | SEQ ID NO: 2915 |
| SLPI | NM_003064.2 | ATGGCCAATGTTTGATGCTTAACCCCCCCCAATTTCTGTGAGATGATGGCCAGTGCAAGCTGACTTGAAGTGT | SEQ ID NO: 2916 |
| SMARCA3 | NM_003071.2 | AGGGACTGTCCTGGCACATTATGCAGATGTCCTGGGTCTTTTGCTTAGACTGCGGCAAATTTGTTG | SEQ ID NO: 2917 |
| SNAI1 | NM_005985.2 | CCCAATCGGAAGCCTAACTACAGCGAGCTGCAGGACTCTAATCCAGAGTTTACCTTCCAGCAGCCCTAC | SEQ ID NO: 2918 |
| SNAI2 | NM_003068.3 | GGCTGGCCAAACATAAGCAGCTGCACTGCGATGCCCAGTCTAGAAAAATCTTTCAGCTGTAAATACTGTGACAAGGA | SEQ ID NO: 2919 |
| SNRPF | NM_003095.1 | GGCTGGTCGGCAGAGAGTAGCCTGCAACATTCGGCCTGCGTGGTTTACCTGGTTTACATGAGTTTACCCCTCAATCCAAACCTTTCCTCA | SEQ ID NO: 2920 |
| SOD1 | NM_000454.3 | TGAAGAGAGGCATGTTGGAGACTTGGGCAATGTGACTGCTGACAAAGATGTGTGGCCGATGTGTCTATT | SEQ ID NO: 2921 |
| SOD2 | NM_000636.1 | GCTTGTCCAAATTCAGGATCCACTGCAAGGAACAACAGGCCTTATTCCACTGCTGGGGATTGATGTGTGGGAGCACGCT | SEQ ID NO: 2922 |
| SOS1 | NM_005633.2 | TCTGACCAAATTCTCCAAGAACACCGTTAACACCTCCGCCTGCTTCTGGTGCTTCCAGTACCAC | SEQ ID NO: 2923 |
| SOX17 | NM_022454.2 | TCGTGTGCAAGCCTGAGATGGGGGCCTCCCCTACCAGGGGCATGACTCCGGTGTGAATCTCCCGACAG | SEQ ID NO: 2924 |
| SPARC | NM_003118.1 | TCTTCCCTGTACACTGCACTTCGGCCAGTTGGACCAGCACCCCATTGACGGGTACCTCTCCCACCGAGCT | SEQ ID NO: 2925 |
| SPINT2 | NM_021102.1 | AGGAATGCAGCGGATTCCTCGTCCCAGAAGCTCCCAGAAGCAGGATTCTGAAGACCACTCCAGCGA | SEQ ID NO: 2926 |

TABLE B-continued

| Gene | Locus Link | Sequence | Sequence ID Number |
|---|---|---|---|
| SPRY1 | AK026960.1 | CAGACCAGTCCCTGGTCATAGGTCTGAAAGGGCAATCCGGACCCAGCCAAGCAACTGATTGTGGATGACTTGAAGG | SEQ ID NO: 2927 |
| SPRY2 | NM_005842.1 | TGTGGCAAGTGCAAATGTAAGGAGTGCACCTACCCAAGGCCTCTGCCATCAGACTGATCTGCGAC | SEQ ID NO: 2928 |
| SR-A1 | NM_021228.1 | AGATGAAGAAGCCAACCTGGCAGCCGAGCGAAGGCGAGCTGATCCAGGCCACCAACCAGATCCTCAGCCACAG | SEQ ID NO: 2929 |
| ST14 | NM_021978.2 | TGACTGCACATGGAACATTGAGGTGCCAACAACCAGCATGTGAAGGTGCGCTTCAAATTCTT | SEQ ID NO: 2930 |
| STAT1 | NM_007315.1 | GGGCTCAGCTTTCAGAAGTGCTGAGTTGGCAGTTTTCTTCTGTCACCAAAAGAGGTCTCAATGTGACCAGCTGAACATGT | SEQ ID NO: 2931 |
| STAT3 | NM_003150.1 | TCACATGCCACTTGGTGTTTCATAATCTCCTGGGAGAGATTGACCAGCAGTATAGCCTTCCTGCAAG | SEQ ID NO: 2932 |
| STAT5A | NM_003152.1 | GAGGCGCTCAACATGAAATTCAAGGCCGAAGTGCAGAGCAACCGGGGCCTGACCAAGGAGAACCTCGTGTTCCTGGC | SEQ ID NO: 2933 |
| STAT5B | NM_012448.1 | CCAGTGTGGTGATCGTTCATGGCCAGCAGGACAACAATGCGACGGCCACTGTTCTGGGACAATGCTTTTGC | SEQ ID NO: 2934 |
| STC1 | NM_003155.1 | CTCCGGAGGTGAGGAGGACTCTCCCCTCCACATCAAACGCACATCCCATGAGAGTGCATAACCAGGAGAGGT | SEQ ID NO: 2935 |
| STK11 | NM_000455.3 | GGACTCGGAGACGCGTGCAGGAGGGCCGTCAAGATCCTCAAGAAGAAGAAGTTGCGAAGGATCCC | SEQ ID NO: 2936 |
| STK15 | NM_003600.1 | CATCTTCCAGGAGGACGCACCACTCTCTGTGGCACACCCTGACTACCTGCCCCCTGAAATGATTGAAGGTCGGA | SEQ ID NO: 2937 |
| STMN1 | NM_005563.2 | AATACCCAACGCACACAAATGACCGCACGTTCTCTGCCCCAGTGTGTTTGCCAATTGTCTCC | SEQ ID NO: 2938 |
| STMY3 | NM_005940.2 | CCTGAGGCTGCAACATACCTCAATCTCGTCTTCCAGGCCGGATCCTCCGAGCCTTTCGCAGCACTGCTATCCTCCAAAGCCATTGTA | SEQ ID NO: 2939 |
| STS | NM_000351.2 | GAAGATCCCTTTCCCTACTGTTCTTTTCGTGGGAAGCCACGAGAGCCACGAAGCATCAAGGCCGAACATCATCC | SEQ ID NO: 2940 |
| SURV | NM_001168.1 | TGTTTTGATTCCCGGGCTTACCAGTTCCTGAAGGCGGCTGAGAAGTGAGGAGGAAGAGGCAGTGTCCTTTTGCTAGAGCTGACAGCTTTG | SEQ ID NO: 2941 |
| TAGLN | NM_003186.2 | GATGGAGCAGGTGGCTCAGTTCTCAGGACTCTGGGGTCATCAAGACTGACATGTTCCAGACT | SEQ ID NO: 2942 |
| TBP | NM_003194.1 | GCCCGAAACGCCGAATATAATCCCAAGCGGTTTGCTGCGGTAATCATGAGGATAAGAGAGCCACG | SEQ ID NO: 2943 |
| TCF-1 | NM_000545.3 | GAGGTCCTGAGCACTGCAGGAGGACAGCCAGGACAAAGGAGCCTGTGAACCAGCCATGGTCCCCACATC | SEQ ID NO: 2944 |
| TCF-7 | NM_003202.2 | GCAGCTGCAGTCAACAGTTCAAAGAAGTCATGGCCCAAATCCAGTGTGCACCCTCCCATTCACAG | SEQ ID NO: 2945 |
| TCF7L1 | NM_031283.1 | CCGGGACACTTTTCAGAAGCCGCGCGGAGACTATTTCGCCGGAAGTGAGAAGGCCTCAGGACAGCGCGTTCT | SEQ ID NO: 2946 |
| TCF7L2 | NM_030756.1 | CCAATCACGACAGGAGATTCAGACACCCCTACCCCACAGCTCTGACCGTCAATGCTTCCGTGTCA | SEQ ID NO: 2947 |
| TCFL4 | NM_170607.2 | CTGACTGCTCTGCTTAAAGGTGAAAGTAGCAGGAAGAACAACCAAAAAGCCAACCAGAAAACAGGTAGCCAGTGCAAGACAT | SEQ ID NO: 2948 |

TABLE B-continued

| Gene | Locus Link | Sequence | Sequence ID Number |
|---|---|---|---|
| TEK | NM_000459.1 | ACTTCGTGCTACTTAACAACTTACATCCCAGGAGCAGTACGTGGTCCGAGTGAGTCAACACCAAGGCCCAGG | SEQ ID NO: 2949 |
| TERC | U86046.1 | AAGAGGAACGAGCGAGTCCCCGCGCGCGCGCGATTCCCTGAGCTGTGGGACGTGCACCCAGGACTCGGCTGCTCACACAT | SEQ ID NO: 2950 |
| TERT | NM_003219.1 | GACATGAGAGAACAAGCTGTTTGCGGGGATTCGCGGGACGGGCTGCTCCTCGCGTTTGGTGATGATGATTTCTTGTTGTGACACCTC | SEQ ID NO: 2951 |
| TFF3 | NM_003226.1 | AGGCACTGTTCATCTCAGTTTTTCTGTCCCCTTTGCTTCCCCGGCAAGCTTTCTGCTGAAAAGTTCATATCTGGAGCCTGATG | SEQ ID NO: 2952 |
| TGFA | NM_003236.1 | GGTGTGCCACAGACCTTCCTACTTGGCCTGTAATCACCTGTGCAGCCTTTTGTGGGCCTTCAAAACTCTGTCAAGAACTCCGT | SEQ ID NO: 2953 |
| TGFB2 | NM_003238.1 | ACCAGTCCCCCAGAAGACTATCCTGAGCCCCGAGGAAGTCCCCCCGAGGAGGTGATTTCCATCTACAACAGCACCAGG | SEQ ID NO: 2954 |
| TGFB3 | NM_003239.1 | GGATCCAGCTCTTCCAGATCCTTCGGCCAGATGAGCACATTGCCAAACAGCGCTATATCGGTGGC | SEQ ID NO: 2955 |
| TGFBI | NM_000358.1 | GCTACAGAGTGCTGTCCTGGATATGAAAAGGTCCCTGGGGAGAAGGGCTGTCCAGCCCCTACCACT | SEQ ID NO: 2956 |
| TGFBR1 | NM_004612.1 | GTCATCACCTGGCCTTGGTCCTGTGGAACTGGCAGCTGTCATTGCTGGACCAGTGTGCTTCGTCTGC | SEQ ID NO: 2957 |
| TGFBR2 | NM_003242.2 | AACACCAATGGGTTCCATCTTTCTGGGCTCCTGATTGCTCAAGCACCAGTTTGGCTGATGAAGAGG | SEQ ID NO: 2958 |
| THBS1 | NM_003246.1 | CATCCCAAAGTGACTGAAGAGTGACAAAGATTGGCCAATGAGCTGAGGCGGCCTCCCCTATGCTATCACAACGAGAGTTCAGTAC | SEQ ID NO: 2959 |
| THY1 | NM_006288.2 | GGACAAGACCCTCTCAGGCGTCCCAAGCTCCCAGATGAGCTTCCAGAGCTCCTCAGACCTGTCCACCCTCCAA | SEQ ID NO: 2960 |
| TIMP1 | NM_003254.1 | TCCCTGCGGTCCCAGATAGCCTGAATCCTGCCCGGAGTGAACTGAAGCCTGCACAGTGTCCACCCTGTTCCCAC | SEQ ID NO: 2961 |
| TIMP2 | NM_003255.2 | TCACCCTCTGTGACTTCATCGTGCCCTGAGCACCCTGAGCACCAGAAGAAGAGCCTGAACCACA | SEQ ID NO: 2962 |
| TIMP3 | NM_000362.2 | CTACCTGCCTTGCTTTGTGACTTCCAAGAACAGAGTGTCTCTGGACCGACATGTCCTCCAATTTCGT | SEQ ID NO: 2963 |
| TJP1 | NM_003257.1 | ACTTTGCTGGGACAAAGGTCAACTGAAGAAGTGGGCAGGCCCGAGGCAGGAGAGATGCTGAGGAGTCCATGTG | SEQ ID NO: 2964 |
| TK1 | NM_003258.1 | GCCGGGAAGACCGTAATTGTGCTGACTGATGGAGACCTTCCAGAGGAGGACCCATTTGGGGCCATCATCCTGAACCTGTGCCCCTG | SEQ ID NO: 2965 |
| TLN1 | NM_006289.2 | AAGCAGAAGGGAGAGCCTAAGATCTTCCAGGCACACAAGAATTGTGGGCAGATGAGTGAGATTGAGGCCAAGG | SEQ ID NO: 2966 |
| TMEPAI | NM_020182.3 | CAGAAGGATGCCTGTGCCCTCGGAGGAGCACAGTGTCAGGCAACGAATCCCAGAGCCGCAGGTCTAC | SEQ ID NO: 2967 |
| TMSB10 | NM_021103.2 | GAAATCGCCAGCTTCGATAAGGCCAAGCTGAAGAAAACGGAGACGCAGGAGAAAAGAACACCCTGCCGAC | SEQ ID NO: 2968 |
| TMSB4X | NM_021109.2 | CACATCAAAGAACTACTGACAACGAAGGCCGCGCCCCTCCCTTTCCCATCTGTCTATCTATCTGGCTGGCAGG | SEQ ID NO: 2969 |
| TNC | NM_002160.1 | AGTCCGGAACCTCACCGTGCCTGGCAGCCTTCGGACACATACCGGGCCTCAAGGCTGCTAC | SEQ ID NO: 2970 |
| TNF | NM_000594.1 | GGAGAAGGGTGACCGACTCAGCGCTGAGATCAATCGCCCGACTATCGACTTTGCCGAGTCTGGGCA | SEQ ID NO: 2971 |

TABLE B-continued

| Gene | Locus Link | Sequence | Sequence ID Number |
|---|---|---|---|
| TNFRSF5 | NM_001250.3 | TCTCACCTCGCTATGGTTCGTCTGCCTCTGCAGTGCGTCCTCTGGGGCTGCTTGCTGTCCATC | SEQ ID NO: 2972 |
| TNFRSF6B | NM_003823.2 | CCTCAGCACCAGGGTACCAGGAGCTGAGGAGTGTGAGCGGTCGCCGTCATCGACTTGTGGCTTTCAGGACA | SEQ ID NO: 2973 |
| TNFSF4 | NM_003326.2 | CTTCATCTTCCCTCTACCCAGATTGTGAAGATGGAAAGGGTCCAACCCCTGAAGAGAATGTGGGAAATGCAGC | SEQ ID NO: 2974 |
| TOP2A | NM_001067.1 | AATCCAAGGGGAGAGTGATGATGCATTCCATATGGACTTTGACTCAGCTGTGCTCCTCGGCAAAATCTGTAC | SEQ ID NO: 2975 |
| TOP2B | NM_001068.1 | TGTGGACATCTTCCCCTCAGACTTCCCTACTGAGCCACCTTCTCTGCCACGAACCGTCGGGCTAG | SEQ ID NO: 2976 |
| TP | NM_001953.2 | CTATATGCAGCCAGCAGATGTGACAGCCACCGTGGACAGCCTGCCACTCATCACAGCCTCCATTCTCAGTAAGAAACTCGTGG | SEQ ID NO: 2977 |
| TP53BP1 | NM_005657.1 | TGCTGTTGCTGAGTCTGTTGCCAGTCCCCAGAAGACCATGTCTGTGTTGAGCTGTATCGTGAAGCCAGGCAAG | SEQ ID NO: 2978 |
| TP53BP2 | NM_005426.1 | GGGCCAAATATTCAGAGAGCTTTTATATCAGAGAGGACCACCATAGCGGCCATGAGACCATCTCTGTCCATCATACCCATCC | SEQ ID NO: 2979 |
| TP53I3 | NM_004881.2 | GCGGACTTAATGCAGAGACAAGGCCAGTATGCAGGTGACCACCTCCAGGAGCCAGCACAACATTTTGGGACTTGA | SEQ ID NO: 2980 |
| TRAG3 | NM_004909.1 | GACGCTGGTCTGGTGAAGATGTCCAGGAAACAACCAGAGCCTCCAGCCCCATTGTCCAACAACCACCA | SEQ ID NO: 2981 |
| TRAIL | NM_003810.1 | CTTCACAGTGCTCCTGCCAGTCTCTGTGTGGCTGTAACTTACGTGTACTTTACCACGAGCTGAAGCAGATG | SEQ ID NO: 2982 |
| TS | NM_001071.1 | GCCTCGGTGCCTGTGCCTTTCAACATCGCCAGCTACGCCCTGCTCACGACGTACATGATTGCCGACATCACG | SEQ ID NO: 2983 |
| TST | NM_003312.4 | GGAGCCGGATGCAGTAGGACTGGACTCGGGCCATATCCGTGTGCCGTCAACATGCCTTTCATGGACTT | SEQ ID NO: 2984 |
| TUBA1 | NM_006000.1 | TGTCACCCCGACTCAACGTCGAGACGCCACCGCCGGACTCGTGATGCATCTCAGTCCACGT | SEQ ID NO: 2985 |
| TUBB | NM_001069.1 | CGAGGACGAGGCTTAAAAACTTCTCAGATCAATGTGCATCCTTAGTGAACTTCGTGTTGTCCTCAAGCATGGT | SEQ ID NO: 2986 |
| TUFM | NM_003321.3 | GTATCACCACATCAATGCGGCTCATGTGGAGTATAGACTGCCCGCCCCACTACGCCCACACAGAGACTG | SEQ ID NO: 2987 |
| TULP3 | NM_003324.2 | TGTGTATAGTCCTGCCCCTCAAGGTGTCACAGTGTCCACAGTGTAAGATGTCGGATAATCCGGATAAAGGGGAATGGATCGGG | SEQ ID NO: 2988 |
| tusc4 | NM_006545.4 | GGAGGAGCTAAATGCCTCAGGCCGGTGCACTCTGCCCATTGATGAGTCCAACCATCCACTTGAAGG | SEQ ID NO: 2989 |
| UBB | NM_018955.1 | GAGTCGACCCTGCACCTGGTCCTGCGTCTGAGAGGTTGGTATGCAGATCTTCGTGAAGACCCGACCGGCAAGAACCATCACCCTGGAAGTGGAGCCCAGTGACCCAGTCCAGTGGTATGCCAAGATCCAAGATGTGAAGGCCAAGATCCAGGATAAAGAAGGCATCCCGCCTGATCAGCAGAGGCTCATCTTTGCGGGCAAGCAGCTGGAAGATGGCCGTACTCTTTCTGACTACAACATCCAGAAGGAGTCGACCCTGCACCTGGTCCTGCGTCTGCGTGGTGGATGAAATGAAGCTGAAGGCCAAGATCCAAGATAAAGAAGGCATCCCGCCTGATCAGCAGCGGCTCATCTTTGCTGGAAAGCAGCTGGAAGATGGCCGTACTCTTTCTGACTACAACATCCAGAAGGAGTCGACCCTGCACCTGGTCCTGCGTCTGCGTGGCGGCATGCAGATCTTCGTGAAGACCCTGACCGGTAAGACCATCACCCTGGAAGTGGAGCCCAGTGACACCATTGAGAATGTGAAGGCCAAGATCCAGGATAAAGAAGGCATCCCACCTGATCAGCAGAGATTGATCTTTGCTGGCAAACAGCTAGAAGATGGTCGTACGCTTTCTGACTACAACATCCAGAAGGAGTCGACCCTGCACCTGGTCCTGCGCCTGAGAGGTGGTATGCAGATCTTCGTGAAGACCCTGACCGGCAAGACCATCACCCTGGAAGTGGAACCCAGTGACACCATCGAGAACGTGAAGGCCAAGATCCAGGACAAGGAGGGCATCCCTCCTGACCAGCAGAGACTGATCTTTGCCGGAAAGCAGCTGGAAGATGGGCGCACGCTTGCCGACTACAACATACAGAAGGAGTCCACCCTGCACTTGGTCCTCCGTCTGCGAGGTGGCTGAGTCGGTGGGAATCATTATCCGAGGGCAGATCACGCATGGCCCTCCCCTCAAGGTGCACACAGTGTCACAGTGTCACAAGCTCTCCAAGGATGTCCGGATAATCCGGGATAAAGGGGAATGGATCGGGTGTTAATTCTTCAGTCATGGCATTCGC | SEQ ID NO: 2990 |
| UBC | NM_021009.2 | ACGCACCCTGTCTGACTACACAACATCCAGAAAAGAGTCCACCCTGCACCTGGTGCTCCGTCTTAGAGGT | SEQ ID NO: 2991 |
| UBE2C | NM_007019.2 | TGTCTGCGATAAAGGGATTTCTGCCTTCCCTGAATCAGACAACCTTTCAAATGGTAGGGACCAT | SEQ ID NO: 2992 |

TABLE B-continued

| Gene | Locus Link | Sequence | Sequence ID Number |
|---|---|---|---|
| UBE2M | NM_003969.1 | CTCCATAATTTATGGCTGCAGTATCTCTTCTTGGAGCCCCTGAGACCCACTGAACAAGGAGGCCG CA | SEQ ID NO: 2993 |
| UBL1 | NM_003352.3 | GTGAAGCCACCGTCATCATGTCTGACCAGGAGGCAAAACCTTCAACTGAGGACTTGGGGATAAGAAGGAA GG | SEQ ID NO: 2994 |
| UCP2 | NM_003355.2 | ACCATGCTCCAGAAGGAGGGCCCCGAGCCTTCTACAAAGGGTTCATGCCCTTCTCCGCTTGGGTT | SEQ ID NO: 2995 |
| UGT1A1 | NM_000463.2 | CCATGCAGCCTGGAATTTGAGGCTACCCAGTGCCCCAACCATTCTCCTACGTGCCCAGGCCTCTC | SEQ ID NO: 2996 |
| UMPS | NM_000373.1 | TGCGGAAATGAGCTCCACCGGCTCCACCCTGGCCACTGGGGACTACACACTAGAGCAGCGTTAGAATGGCTGAGG | SEQ ID NO: 2997 |
| UNC5A | XM_030300.7 | GACAGCTGATCCAGGAGCCACGGGTCCTGCACTTCAAGGACAGTTACCACAACCTGCGCCTATCCAT | SEQ ID NO: 2998 |
| UNC5B | NM_170744.2 | AGAACCGGAGGCCGTGACTGCAGCGGGACGCTGCTCTCAAGAACTGCACAGATGGGCTGTGCATG | SEQ ID NO: 2999 |
| UNC5C | NM_003728.2 | CTGAACACAGTGGAGCTGGTTTGCAAACTCTGTGCGGCAGGTGGAAGGAGAAGGCAGATCTTCCAG | SEQ ID NO: 3000 |
| upa | NM_002658.1 | GTGGATGTGCCCTGAAGGACAAGCCAGGCGTTCTACAACGAAGAGTCTTCACACTTCTTACCCTGGATCCGCAG | SEQ ID NO: 3001 |
| UPP1 | NM_003364.2 | ACGGGTCCTGCCTCAGTTGGCGGAATGGCGGCGAGCCAATGCAGAGAAGCTGAAAGTCACAATG ATTGCCCCG | SEQ ID NO: 3002 |
| VCAM1 | NM_001078.2 | TGGCTTCAGGAGCTGAATACCCTCCCAGGCACACACAGGTGGGACACACAAATAAGGGTTTTGGAACCACTATTTCTCATCACGACAGCA | SEQ ID NO: 3003 |
| VCL | NM_003373.2 | GATACCACAACTCCCATCAAGCTGTTGGCAGTGGCAGCCACCGGCCTCCTGATGCGCCTAACAGGGA | SEQ ID NO: 3004 |
| VCP | NM_007126.2 | GGCTTTGGCAGCTTCAGATTCCCTTCAGGGAACCAGGGTCGGAGCTGAGCCAGTCAGGGCAGTGGAG | SEQ ID NO: 3005 |
| VDAC1 | NM_003374.1 | GCTGCCGACATGGATTTCGACATTGCTGGGCCTTCCATCGGGGTGCTCTGGTGTGCTAGGTTACGAGGGCTGG | SEQ ID NO: 3006 |
| VDAC2 | NM_003375.2 | ACCCAGCGACAGACTTGCGCCGCGTCAAGTGTGTATTCCTCATCATATGCTGACCTTGGCAAAGCT | SEQ ID NO: 3007 |
| VDR | NM_000376.1 | GCCCTGATTTCAGAAAGAGCCAAGTCTGAAAGAGCCAAGTCTGGATCTGGGACCCTTTCCTTCCTCCAGCCTTGTGCCTTTCCTTGTAACT | SEQ ID NO: 3008 |
| VEGF | NM_003376.3 | CTGCTGTCTTGGGTGCATTGGAGCCTTGAGCCTCAAGATCCAAGTGGTCCCAGGCTGC | SEQ ID NO: 3009 |
| VEGF_altsplice1 | AF486837.1 | TGTGAATGCAGACCAACAAATGTGAATGCAGACCAAGACAAGAAATCCCTGTGGGCCTTGCTCAGAGCGGAGAAA GC | SEQ ID NO: 3010 |
| VEGF_altsplice2 | AF214570.1 | AGCTTCCTACAGCACACAACAAATGTGAATGCAGACCAAGAAAGATAGAGCAAGAAAATGTGACAA GCCGAG | SEQ ID NO: 3011 |

TABLE B-continued

| Gene | Locus Link | Sequence | Sequence ID Number |
|---|---|---|---|
| VEGFB | NM_003377.2 | TGACGATGGCCTGGAGTGTGTGCCCACTGGGCAGCACCAAGTCCGATGCAGATCCTCATGATCCGGTACC | SEQ ID NO: 3012 |
| VEGFC | NM_005429.2 | CCTCAGCAAGACGTTATTTGAAATTACAGTGCCTCTCTCTCAAGGCCCCAAACCAGTAACAATCAGTTTTGCCAATCACACTT | SEQ ID NO: 3013 |
| VIM | NM_003380.1 | TGCCCTTAAAGGAACCAATGAGTCCCTGGAACGCCAGATGCGTGAAATGGAAGAGAACTTTGCCGTTGAAGC | SEQ ID NO: 3014 |
| WIF | NM_007191.2 | TACAAGCTGAGTGCCCAGGCGGGTGCCGAAATGGAGGCTTTTGTAATGAAAGACGCATCTGCGAGTG | SEQ ID NO: 3015 |
| WISP1 | NM_003882.2 | AGAGGCATCCATGAACTTCACACTTGCGGGCTGCATCAGCACACGCTCCTATCAACCCAAGTACTGTGGAGTTTG | SEQ ID NO: 3016 |
| Wnt-3a | NM_033131.2 | ACAAAGCTACCAGGGAGTCGGCCTTTGTCCACGCCATTGCCTGCCGGTGTGGCCTTTGCAGTGACACGCTCA | SEQ ID NO: 3017 |
| Wnt-5a | NM_003392.2 | GTATCAGGACCACACATGCAGTACATCGGAGAAGGCGCGAAGACAGGCCATCAAAGAATGCCAGTATCAATTCCGACA | SEQ ID NO: 3018 |
| Wnt-5b | NM_032642.2 | TGTCTTCAGGGTCTTGTCCAGAATGTAGAATGGGTTCCGTAAGAGGCCTGGTGCTCTCTTACTCTTTCATCCACGTGCAC | SEQ ID NO: 3019 |
| WNT2 | NM_003391.1 | CGGTGGAAATCTGGCTCTCTGCCTCCCTCTGCTCTTGGCCTCACCCCGAGGTCAACTCTTCATGG | SEQ ID NO: 3020 |
| WWOX | NM_016373.1 | ATCGCAGCTGTGTGGGGTGTACACACTGCTGTTTACCTTGGCCAGGCCTTTCACCAAGTCCATGCAACAGGGAGCT | SEQ ID NO: 3021 |
| XPA | NM_000380.2 | GGGTAGAGGGAAAAGGGTTCAACAAAGCTGAACTGGATTCTTAACCAAGAAACAAATAATAGCAATGGTGGTGCA | SEQ ID NO: 3022 |
| XPC | NM_004628.2 | GATACATCGTCTGGAGGGAATTCAAAGACGTGCTCTCCTGACTGCCTGGGAAAATGAGGCAGCAGTCATTGAAAG | SEQ ID NO: 3023 |
| XRCC1 | NM_006297.1 | GGAGATGAAGCCCCAAGCTTCCTCAGAAGCCCAGACCAAAACGCCAAAACCACTCAGGCAGTGGAC | SEQ ID NO: 3024 |
| YB-1 | NM_004559.1 | AGACTGTGGAGTTTGATGTTGTTGAAGGAGAAAGGGTGCCGAGGCAGCAAATGTTACAGGTCCTGGTGGTGTTCC | SEQ ID NO: 3025 |
| YWHAH | NM_003405.2 | CATGGCCTCCGCTATGAAGGCGGGTGACAGAGCTGAATGAACCTCTCTCCAATGAGATCGAAATTCC | SEQ ID NO: 3026 |
| zbtb7 | NM_015898.2 | CTGCGTTCACCCCGTCACAGGGCGAGCTGTTCTGGAGAGAAAACCATCTGTCGTGGCTGAG | SEQ ID NO: 3027 |
| ZG16 | NM_152338.1 | TGCTGAGCCCTCCTCCTTGGCAGGGCACTGTGATGAGGAGTAAGAACTCCCTATCACTAACCCCCATCC | SEQ ID NO: 3028 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08198024B2). An electronic copy of the "Sequence Listing" will also be available from the USPTO upon request and payment of the fee set forth in 37 CFR 1.19(b)(3).

What is claimed is:

1. A method of predicting clinical outcome without treatment with chemotherapy for a human subject diagnosed with colorectal cancer following surgical resection of said cancer, comprising:
   determining a normalized expression level of an RNA transcript of EFNB2, or an expression product thereof, in a biological sample comprising cancer cells obtained from said human subject, and;
   predicting the likelihood of a positive clinical outcome without treatment with chemotherapy for said human subject based on said normalized expression level of an RNA transcript of EFNB2, or an expression product thereof, wherein said normalized expression level of an RNA transcript of EFNB2, or an expression product thereof, is negatively correlated with an increased likelihood of a positive clinical outcome without treatment with chemotherapy.

2. The method of claim 1, further comprising determining a normalized expression level of an RNA transcript, or an expression product thereof, of one or more of BGN, Ki-67, CMYC, MYBL2, FAP, INHBA, and GADD45B in the biological sample;
   wherein said normalized expression level of each of BGN, FAP, INHBA, and GADD45B is negatively correlated with an increased likelihood of a positive clinical outcome without treatment with chemotherapy; and
   wherein said normalized expression level of each of Ki-67, CMYC, and MYBL2 is positively correlated with an increased likelihood of a positive clinical outcome without treatment with chemotherapy.

3. The method of claim 1, wherein said normalized expression level of an RNA transcript of EFNB2 is determined using a PCR-based method.

4. The method of claim 1, wherein said normalized expression level of an RNA transcript of EFNB2, or an expression product thereof, is normalized relative to the expression level of an RNA transcript, or an expression product thereof, of at least one reference gene.

5. The method of claim 1, wherein said clinical outcome is expressed in terms of Recurrence-Free Interval (RFI), Overall Survival (OS), Disease-Free Survival (DFS), or Distant Recurrence-Free Interval (DRFI).

6. The method of claim 1, wherein said colorectal cancer is Dukes B (stage II) or Dukes C (stage III) colorectal cancer.

7. The method of claim 1, wherein said colorectal cancer is Dukes B (stage II) or Dukes C (stage III) colon cancer.

8. The method of claim 1, further comprising the step of creating a report summarizing said prediction.

9. A method of predicting in a human subject diagnosed with Dukes B (stage II) or Dukes C (stage III) colorectal cancer a likelihood of recurrence of colorectal cancer without treatment with chemotherapy following surgical resection of said cancer, comprising:
   determining the normalized expression level of an RNA transcript of EFNB2, or an expression product thereof, in a biological sample comprising cancer cells obtained from said human subject, and;
   predicting the likelihood of recurrence of colorectal cancer without treatment with chemotherapy for the human subject based on said normalized expression level of an RNA transcript of EFNB2, or an expression product thereof, wherein said normalized expression level of an RNA transcript of EFNB2, or an expression product thereof, is positively correlated with an increased likelihood of recurrence of colorectal cancer without treatment with chemotherapy.

10. The method of claim 9, further comprising determining a normalized expression level of an RNA transcript, or an expression product thereof, of one or more of BGN, Ki-67, CMYC, MYBL2, FAP, INHBA, and GADD45B in the biological sample;
    wherein said normalized expression level of each of BGN, FAP, INHBA, and GADD45B is positively correlated with an increased likelihood of recurrence of colorectal cancer without treatment with chemotherapy; and
    wherein said normalized expression level of each of Ki-67, CMYC, and MYBL2 is negatively correlated with an increased likelihood of recurrence of colorectal cancer without treatment with chemotherapy.

11. The method of claim 9, wherein said normalized expression level of an RNA transcript of EFNB2 is determined using a PCR-based method.

12. The method of claim 9, wherein if said likelihood of recurrence of colorectal cancer is increased, said human subject is subjected to further therapy following said surgical resection.

13. The method of claim 9, wherein said further therapy is chemotherapy and/or radiation therapy.

14. The method of claim 9, further comprising the step of creating a report summarizing said prediction.

15. The method of claim 9, wherein said normalized expression level of an RNA transcript of EFNB2, or an expression product thereof, is normalized relative to the expression level of an RNA transcript, or an expression product thereof, of at least one reference gene.

16. The method of claim 9, wherein said colorectal cancer is Dukes B (stage II) or Dukes C (stage III) colon cancer.

* * * * *